US011555071B2

(12) United States Patent
Buatois et al.

(10) Patent No.: US 11,555,071 B2
(45) Date of Patent: Jan. 17, 2023

(54) BISPECIFIC ANTIBODIES AGAINST CEACAM5 AND CD47

(71) Applicant: LamKap Bio beta Ltd., Schwyz Pfäffikon (CH)

(72) Inventors: Vanessa Buatois, Contamine-Sarzin (FR); Stefano Majocchi, Grand Lancy (CH); Klaus Strein, Weinheim (DE)

(73) Assignee: LamKap Bio beta Ltd., Schwyz Pfäffikon (CH)

( * ) Notice: Subject to any disclaimer, the term of this patent is extended or adjusted under 35 U.S.C. 154(b) by 541 days.

(21) Appl. No.: 16/428,539

(22) Filed: May 31, 2019

(65) Prior Publication Data
US 2020/0123252 A1    Apr. 23, 2020

(30) Foreign Application Priority Data

| Jun. 3, 2018 | (EP) | 18175655 |
| Jun. 3, 2018 | (EP) | 18175656 |
| Jun. 3, 2018 | (EP) | 18175657 |
| Jun. 3, 2018 | (EP) | 18175658 |
| Aug. 13, 2018 | (EP) | 18188788 |
| Aug. 13, 2018 | (EP) | 18188790 |
| Aug. 13, 2018 | (EP) | 18188792 |
| Aug. 27, 2018 | (EP) | 18190983 |

(51) Int. Cl.
| C07K 16/28 | (2006.01) |
| C12N 15/85 | (2006.01) |
| C07K 16/30 | (2006.01) |
| A61K 39/00 | (2006.01) |

(52) U.S. Cl.
CPC ...... *C07K 16/2803* (2013.01); *C07K 16/2809* (2013.01); *C07K 16/3007* (2013.01); *C12N 15/85* (2013.01); *A61K 2039/505* (2013.01); *C07K 2317/31* (2013.01); *C07K 2317/41* (2013.01); *C07K 2317/52* (2013.01); *C07K 2317/565* (2013.01); *C07K 2317/622* (2013.01); *C07K 2317/732* (2013.01); *C07K 2317/76* (2013.01); *C07K 2317/92* (2013.01); *C12N 2015/8518* (2013.01)

(58) Field of Classification Search
USPC ..................................................... 424/136.1
See application file for complete search history.

(56) References Cited

U.S. PATENT DOCUMENTS

| 6,602,684 B1 | 8/2003 | Umana et al. |
| 6,946,292 B2 | 9/2005 | Kanda et al. |
| 7,425,446 B2 | 9/2008 | Kanda et al. |
| 7,521,051 B2 | 4/2009 | Collins et al. |
| 8,008,449 B2 | 8/2011 | Korman et al. |
| 8,067,232 B2 | 11/2011 | Kanda et al. |
| 8,236,308 B2 | 8/2012 | Kischel et al. |
| 8,354,509 B2 | 1/2013 | Carven et al. |
| 8,383,796 B2 | 2/2013 | Korman et al. |
| 2003/0115614 A1 | 6/2003 | Kanda et al. |
| 2003/0157108 A1 | 8/2003 | Presta |
| 2003/0175884 A1 | 9/2003 | Umana et al. |
| 2004/0013214 A1 | 1/2004 | Katta et al. |
| 2004/0093621 A1 | 5/2004 | Shitara et al. |
| 2004/0110282 A1 | 6/2004 | Kanda et al. |
| 2004/0110704 A1 | 6/2004 | Yamane et al. |
| 2004/0241817 A1 | 12/2004 | Umana et al. |
| 2011/0064653 A1 | 3/2011 | Hansen et al. |
| 2014/0140989 A1 | 5/2014 | Eckelman et al. |
| 2014/0242079 A1 | 8/2014 | Bacac et al. |
| 2014/0303354 A1* | 10/2014 | Masternak ........... C07K 16/461 530/387.3 |
| 2016/0144009 A1 | 5/2016 | Tseng et al. |
| 2016/0333093 A1 | 11/2016 | Weiskopf et al. |
| 2021/0221908 A1* | 7/2021 | Buatois .............. C07K 16/3007 |
| 2022/0195067 A1* | 6/2022 | Buatois .............. C07K 16/3007 |

FOREIGN PATENT DOCUMENTS

| AO | WO-2005063815 A2 | 7/2005 |
| EP | 2681244 B1 | 11/2017 |
| WO | WO-1999054342 | 10/1999 |
| WO | WO-2000041474 A1 | 7/2000 |
| WO | WO-2003056914 A1 | 7/2001 |
| WO | WO-2003099196 A2 | 12/2003 |
| WO | WO-2004024927 A1 | 3/2004 |
| WO | WO-2004057002 A2 | 7/2004 |
| WO | WO-2004063351 A2 | 7/2004 |
| WO | WO-2004065540 A2 | 8/2004 |
| WO | WO-2004099249 A2 | 11/2004 |
| WO | WO-2005018572 A2 | 3/2005 |

(Continued)

OTHER PUBLICATIONS

Www.creative-biolabs.com/car-t/cellrapeutics-phagocytosis-assay (pp. 1-11 (Dec. 1, 2021)).*

(Continued)

*Primary Examiner* — Lynn A Bristol
(74) *Attorney, Agent, or Firm* — Sterne, Kessler, Goldstein & Fox P.L.L.C.

(57) ABSTRACT

The invention provides bispecific antibodies binding to human carcinoembryonic antigen CEACAM5 and human CD47, polynucleotides encoding such bispecific antibodies and vectors and host cells comprising such polynucleotides. The invention further provides methods for selecting and producing such antibodies and methods of using such antibodies in the treatment of diseases in monotherapy as well in combination.

23 Claims, 21 Drawing Sheets

Specification includes a Sequence Listing.

(56) References Cited

FOREIGN PATENT DOCUMENTS

| | | |
|---|---|---|
| WO | WO-2005018669 A1 | 3/2005 |
| WO | WO-2005056759 A2 | 6/2005 |
| WO | WO-2005092925 A2 | 10/2005 |
| WO | WO-2005110474 A2 | 11/2005 |
| WO | WO-2006019447 A1 | 2/2006 |
| WO | WO-2006023420 A2 | 3/2006 |
| WO | WO-2006047350 A2 | 5/2006 |
| WO | WO-2006085967 A2 | 8/2006 |
| WO | WO-2006105338 A2 | 10/2006 |
| WO | WO-2006116260 A2 | 11/2006 |
| WO | WO-2007005874 A2 | 1/2007 |
| WO | WO-2007008943 A2 | 1/2007 |
| WO | WO-2007021841 A2 | 2/2007 |
| WO | WO-2007024249 A2 | 3/2007 |
| WO | WO-2007041635 A2 | 4/2007 |
| WO | WO-2007042261 A2 | 4/2007 |
| WO | WO-2007044616 A2 | 4/2007 |
| WO | WO-2007048077 A2 | 4/2007 |
| WO | WO-2007071426 A1 | 6/2007 |
| WO | WO-2007106707 A2 | 9/2007 |
| WO | WO-2008022152 A2 | 2/2008 |
| WO | WO-2008036688 A2 | 3/2008 |
| WO | WO-2008091798 A2 | 7/2008 |
| WO | WO-2008091954 A2 | 7/2008 |
| WO | WO-2008092117 A2 | 7/2008 |
| WO | WO-2008098115 A2 | 8/2008 |
| WO | WO-2008119565 A2 | 10/2008 |
| WO | WO-2008119566 A2 | 10/2008 |
| WO | WO-2008119567 A2 | 10/2008 |
| WO | WO-2008121160 A2 | 10/2008 |
| WO | WO-2008140603 A2 | 11/2008 |
| WO | WO-20081 50494 A1 | 12/2008 |
| WO | WO-2008156712 A1 | 12/2008 |
| WO | WO-2009101611 A1 | 8/2009 |
| WO | WO-2009114335 A2 | 9/2009 |
| WO | WO-201 0027423 A2 | 3/2010 |
| WO | WO-201 0027827 A2 | 3/2010 |
| WO | WO-201 0027828 A2 | 3/2010 |
| WO | WO-201 0033736 A1 | 3/2010 |
| WO | WO-2010037836 A2 | 4/2010 |
| WO | WO-2010037837 A2 | 4/2010 |
| WO | WO-2010037838 A2 | 4/2010 |
| WO | WO-2012023053 A2 | 2/2012 |
| WO | WO-2012117002 A1 | 9/2012 |
| WO | WO-2013012414 A1 | 1/2013 |
| WO | WO-2013019906 A1 | 2/2013 |
| WO | WO-2013088259 A2 | 6/2013 |
| WO | WO-2013173223 A1 | 11/2013 |
| WO | WO-2014056783 A1 | 4/2014 |
| WO | WO-2014087248 A2 | 6/2014 |
| WO | WO-2014113510 A1 | 7/2014 |
| WO | WO-2015026634 A1 | 2/2015 |
| WO | WO-2015112534 A2 | 7/2015 |
| WO | WO-2016007235 A1 | 1/2016 |
| WO | WO-2016116907 A1 | 7/2016 |
| WO | WO-2016156537 A1 | 10/2016 |
| WO | WO-2017027422 A1 | 2/2017 |
| WO | WO-2017055389 A1 | 4/2017 |
| WO | WO-2017081101 A1 | 5/2017 |
| WO | WO-2017118675 A1 | 7/2017 |
| WO | WO-2017121771 A1 | 7/2017 |
| WO | WO-2017196793 A1 | 11/2017 |
| WO | WO-2018098384 A1 | 5/2018 |
| WO | WO-2019234576 A1 | 12/2019 |

OTHER PUBLICATIONS

Gonzalez-Quintela, A., et al., "Serum levels of immunoglobulins (IgG, IgA, IgM) in a general adult population and their relationship with alcohol consumption, smoking and common metabolic abnormalities," *Clinical and Experimental Immunology* 151(1):42-50, John Wiley & Sons, Inc., on behalf of the British Society for Immunology, United Kingdom (published online Nov. 2007, published in print Jan. 2008).

McKelvey, E. M., and Fahey, J. L., "Immunoglobulin changes in disease: quantitation on the basis of heavy polypeptide chains, IgG (gammaG), IgA (gammaA), and IgM (gammaM), and of light polypeptide chains, type K (I) and type L (II)," *Journal of Clinical Investigation* 44(11):1778-1787, American Society for Clinical Investigation, United States (Nov. 1965).

Preithner, S., et al., "High concentrations of therapeutic IgGl antibodies are needed to compensate for inhibition of antibody-dependent cellular cytotoxicity by excess endogenous immunoglobulin G," *Molecular Immunology* 43(8):1183-1193, Elsevier, Netherlands (published online Aug. 2005, published in print Mar. 2006).

Request for Examination for European Patent Application EP 19 72 8547.1, Munich, Germany, dated Dec. 1, 2020, 5 pages.

Anasetti et al., "Treatment of acute graft-versus-host disease with a nonmitogenic anti-CD3 monoclonal antibody", Transplantation 54: 844-851 (1992).

Bacac et al., "A Novel Carcinoembryonic Antigen T-Cell Bispecific Antibody (CEA TCB) for the Treatment of Solid Tumors", Clin. Cancer Res., 22(13): 3286-97 (2016).

Berinstein. L., "Carcinoembryonic antigen as a target for therapeutic anticancer vaccines: a review", J Clin Oncol., 20:2197-2207 (2002).

Bruhns P. "Specificity and affinity of human Fcgamma receptors and their polymorphic variants for human IgG subclasses", Blood 113: 3716-3725 (2009).

Bruhns P., "Properties of mouse and human IgG receptors and their contribution to disease models", Blood 119: 5640-5649 (2012).

Cassard L. et al., "Fcγ receptors inhibit mouse and human basophil activation", J. Immunol.189: 2995-3006 (2012).

Conaghhan P. J., et al., "Targeted killing of colorectal cancer cell lines by a humanised IgG 1 monoclonal antibody that binds to membrane-bound carcinoembryonic antigen", Br. J. Cancer, 98: 1217-1225 (2008).

Cote, et al., "Generation of human monoclonal antibodies reactive with cellular antigens", Proc Natl Acad Sci USA 80: 2026-2030 (1983).

Dall'Ozzo, "Rituximab-dependent cytotoxicity by natural killer cells: influence of FCGR3A polymorphism on the concentration-effect relationship", Cancer Res. 64(13): 4664-9 (2004).

Davis J. et al.; "Expression of GnTIII in a recombinant anti-CD20 CHO production cell line: Expression of antibodies with altered glycoforms leads to an increase in ADCC through higher affinity for FC gamma RIII",Biotechnol. Bioeng. 74:288-294 (2001).

Dhelly E. et al., "Selective Blockade of the Ubiquitous Checkpoint Receptor CD47 is Enabled by Dual-Targeting Bispecific Antibodies", Mol. Thera. 25: 523-533 (2017).

Durbin H. et al., "An epitope on carcinoembryonic antigen defined by the clinically relevant antibody PR1A3", Proc. Natl. Scad. Sci. USA, 91 :4313-4317 (1994).

Gold and Freedmann, "Demonstration of Tumor-Specific Antigens in Human Colonic Carcinomata by Immunological Tolerance and Absorption Techniques", J Exp. Med., 121:439-462 (1965).

Hammarstroem S., "The carcinoembryonic antigen (CEA) family: structures, suggested functions and expression in normal and malignant tissues", Semin Cancer Biol. 9(2):67-81 (1999).

Hao C., et al., "Serum CEA levels in 49 different types of cancer and noncancer diseases", Prog Mol Biol Transl Sci162:213-227 (2019).

Hoffmann La-Roche: "A Study of the Safety, Pharmacokinetics, and Therapeutic Activity of R06958688 in Combination With Atezolizumab in Participants With Locally Advanced and/or Metastatic Carcinoembryonic Antigen (CEA)-Positive Solid Tumors", ClinicalTrials.gov., Clinical trials, Jan. 6, 2016 (Jan. 6, 2016).

Hohenberger et al., "Pre-and Postoperative Carcinoembryonic Antigen Determinations in Hepatic Resection for Colorectal Metastases", Annals Surgery 219: 135-143 (1994).

Holliger P. et al., "Carcinoembryonic antigen (CEA)-specific T-cell activation in colon carcinoma induced by anti-CD3 x anti-CEA bispecific diabodies and B7 x anti-CEA bispecific fusion proteins", Cancer Res. 59(12):2909-16 (1999).

(56) References Cited

OTHER PUBLICATIONS

Huang Y et al., "Targeting CD47: the achievements and concerns of current studies on cancer immunotherapy", J Thorac Dis.9(2):E168-E174 (2017).
Jurgensmeier et al., Br J Cancer. "Prognostic and predictive value of VEGF, sVEGFR-2 and CEA in mCRC studies comparing cediranib, bevacizumab and chemotherapy", 108(6):1316-23 (2013).
Kanda Y, et al.; "Establishment of a GDP-mannose 4,6-dehydratase (GMD) knockout host cell line: a new strategy for generating completely non-fucosylated recombinant therapeutics", J. Biotechnol. 130: 300-310 (2007).
Kozbor, et al., "The production of monoclonal antibodies from human lymphocytes", Immunol Today 4: 72 (1983).
Lund et al., "Multiple interactions of IgG with its core oligosaccharide can modulate recognition by complement and human Fc gamma receptor I and influence the synthesis of its oligosaccharide chains",J. Immunol. 157: 4963-69 (1996).
Mori K, et al.; "Engineering Chinese hamster ovary cells to maximize effector function of produced antibodies using FUT8 siRNA",Biotechnol. Bioeng; 88:901-908 (2004).
Niwa R et al., "Defucosylated Chimeric Anti-CC Chemokine Receptor 4 IgG1 with Enhanced Antibody-Dependent Cellular Cytotoxicity Shows Potent Therapeutic Activity to T-Cell Leukemia and Lymphoma", Cancer Res, 64: 2127-33 (2004).
Niwa R. et al., "The Current Status and Prospects of Antibody Engineering for Therapeutic Use: Focus on Glycoengineering Technology", Journal of Pharmaceutical Sciences, 104(3): 930-941 (2015).
Okazaki, A., et al., "Fucose depletion from human IgG1 oligosaccharide enhances binding enthalpy and association rate between IgG1 and FcgammaRIIIa", J Mol. Biol. 336:1239-1249 (2004).
Osada T. et al., "CEA/CD3-bispecific T cell-engaging (BiTE) antibody-mediated T lymphocyte cytotoxicity maximized by inhibition of both PD1 and PD-L1", Cancer Immunol Immunother. 64(6):677-88 (2015).
Piccione EC et al. "A bispecific antibody targeting CD47 and CD20 selectively binds and eliminates dual antigen expressing lymphoma cells", mAbs 7: 946-956 (2015).
Richards Jo, et al., "Optimization of antibody binding to FcγRIIa enhances macrophage phagocytosis of tumor cells", Mol. Cancer Ther. 7: 2517-2527 (2008).
Richmann P. I. and Bodmer W. F., "Monoclonal antibodies to human colorectal epithelium: markers for differentiation and tumour characterization", Int. J. Cancer, 39:317-328 (1987).
Ring NG et al., "Anti-SIRPα antibody immunotherapy enhances neutrophil and macrophage antitumor activity", PNAS 114 (49) E10578-E10585; https://doi.org/10.1073/pnas.1710877114 (2017).
Saba JA, et al.; "A study of immunoglobulin G glycosylation in monoclonal and polyclonal species by electrospray and matrix-assisted laser desorption/ionization mass spectrometry", Anal. Biochem. 305:16-31 (2002).
Salmeron et al., "A conformational epitope expressed upon association of CD3-epsilon with either CD3-delta or CD3-gamma is the main target for recognition by anti-CD3 monoclonal antibodies", J. Immunol. 147: 3047-3052 (1991).
Sandler B. et al.,"The role of blood levels of soluble 53 kDa protein and CEA in monitoring colon cancer patients", Anticancer Res, 19(5B): 4229-33 (1999).
Shields, R. L. et al.,, "Lack of fucose on human IgG1 N-linked oligosaccharide improves binding to human Fcgamma RIII and antibody-dependent cellular toxicity", J Biol. Chem. 277: 26733-26740 (2002).
Stewart et al.,"Humanisation and characterisation of PR1A3, a monoclonal antibody specific for cell-bound carcinoembryonic antigen", Cancer Immunol Immunother, 47: 299-06 (1999).
Taberno J. et al., "Phase Ia and Ib studies of the novel carcinoembryonic antigen (CEA) T-cell bispecific (CEA CD3 TCB) antibody as a single agent and in combination with atezolizumab: Preliminary efficacy and safety in patients with metastatic colorectal cancer (mCRC)", Journal of Clinical Oncology 35(15_suppl): 3002 (2017).
Umana, P. et al., "Engineered glycoforms of an antineuroblastoma IgG1 with optimized antibody-dependent cellular cytotoxic activity", Nature Biotechnol. 17:176-180 (1999).
Van Bommel PE et al., "CD20-selective inhibition of CD47-SIRPα "don't eat me" signaling with a bispecific antibody-derivative enhances the anticancer activity of daratumumab, alemtuzumab and obinutuzumab", Oncoimmunol. 7: e386361 (2018).
Wanebo et al., "Preoperative carcinoembryonic antigen level as a prognostic indicator in colorectal cancer", N Engl J Med. 299(9):448-51 (1978).
Wang X. et al., "IgG Fc engineering to modulate antibody effector functions ", Protein and Cell, 9(1):63-73 (2018).
Weiskopf K., "Cancer immunotherapy targeting the CD47/SIRPα axis",European Journal of Cancer 76:100-109(2017).
Wormald MR et al., "Variations in oligosaccharide-protein interactions in immunoglobulin G determine the site-specific glycosylation profiles and modulate the dynamic motion of the Fc oligosaccharides.", Biochemistry 36 (6):1370-1380 (1997).
Xu et al., "Chimeric antigen receptor-T cell therapy for solid tumors require new clinical regimens", Expert Review of Anticancer Therapy, 17:1099-1106 (2017).
Yamane-Ohnuki N. et al., "Establishment of FUT8 knockout Chinese hamster ovary cells: an ideal host cell line for producing completely defucosylated antibodies with enhanced antibody-dependent cellular cytotoxicity", Biotech. Bioeng.; 87: 614-622 (2004).
Yang SJ, "A common pathway for T lymphocyte activation involving both the CD3-Ti complex and CD2 sheep erythrocyte receptor determinants", The Journal of Immunology 137: 1097-1100 (1986).
Yu S. et al., "Recent advances of bispecific antibodies in solid tumors", J Hematol Oncol. 10(1):155. (2017).
International Search Report and Written Opinion for International PCT Application No. PCT/IB2019/054559, dated Aug. 1, 2019, EPO, Netherlands, 19 pages.
Hezareh, M., et al., "Effector Function Activities of a Panel of Mutants of a Broadly Neutralizing Antibody against Human Immunodeficiency Virus Type I," *Journal of Virology* 75:12161-12168, American Society of Microbiology, United States (2001).

\* cited by examiner

SEQUENCE LISTING

```
<160> NUMBER OF SEQ ID NOS: 116

<210> SEQ ID NO 1
<211> LENGTH: 8
<212> TYPE: PRT
<213> ORGANISM: Artificial Sequence
<220> FEATURE:
<223> OTHER INFORMATION: Mab CD47 CDRH1
```

```
<400> SEQUENCE: 1

Gly Phe Thr Phe Ser Ser Tyr Ala
1               5

<210> SEQ ID NO 2
<211> LENGTH: 8
<212> TYPE: PRT
<213> ORGANISM: Artificial Sequence
<220> FEATURE:
<223> OTHER INFORMATION: Mab CD47 CDRH2

<400> SEQUENCE: 2

Ile Ser Gly Ser Gly Gly Ser Thr
1               5

<210> SEQ ID NO 3
<211> LENGTH: 9
<212> TYPE: PRT
<213> ORGANISM: Artificial Sequence
<220> FEATURE:
<223> OTHER INFORMATION: Mab CD47 CDRH3

<400> SEQUENCE: 3

Ala Lys Ser Tyr Gly Ala Phe Asp Tyr
1               5

<210> SEQ ID NO 4
<211> LENGTH: 116
<212> TYPE: PRT
<213> ORGANISM: Artificial Sequence
<220> FEATURE:
<223> OTHER INFORMATION: Mab CD47 VH

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Tyr Gly Ala Phe Asp Tyr Trp Gly Gln Gly Thr Leu Val
            100                 105                 110

Thr Val Ser Ser
        115

<210> SEQ ID NO 5
<211> LENGTH: 445
<212> TYPE: PRT
<213> ORGANISM: Artificial Sequence
<220> FEATURE:
<223> OTHER INFORMATION: Mab CD47 HC

<400> SEQUENCE: 5

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
         20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Tyr Gly Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
```

<210> SEQ ID NO 6
<211> LENGTH: 1338
<212> TYPE: DNA
<213> ORGANISM: Artificial Sequence
<220> FEATURE:
<223> OTHER INFORMATION: Mab CD47 HC

<400> SEQUENCE: 6

```
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtat attactgtgc gaaaagttat     300
ggtgcttttg actactgggg ccagggaacc ctggtcacag tctcgagcgc ctccaccaag     360
ggcccatcgg tcttccccct ggcaccctcc tccaagagca cctctggggg cacagcggcc     420
ctgggctgcc tggtcaagga ctacttcccc gaaccggtga cagtctcgtg gaactcagga     480
gccctgacca gcggcgtgca caccttcccg gctgtcctac agtcctcagg actctactcc     540
ctcagcagcg tggtgactgt gccctccagc agcttgggca cccagaccta catctgcaac     600
gtgaatcaca agcccagcaa caccaaggtg gacaagagag ttgagcccaa atcttgtgac     660
aaaactcaca catgcccacc gtgcccagca cctgaactcc tggggggacc gtcagtcttc     720
ctcttccccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cacgtaccgt     900
gtggtcagcg tcctcaccgt cctgcaccag gactggctga atggcaagga gtacaagtgc     960
aaggtctcca acaaagccct cccagccccc atcgagaaaa ccatctccaa agccaaaggg    1020
cagccccgag aaccacaggt gtataccctg cccccatctc gggaggagat gaccaagaac    1080
caggtcagcc tgacttgcct ggtcaaaggc ttctatccca gcgacatcgc cgtggagtgg    1140
gagagcaacg ggcagccgga gaacaactac aagaccacgc ctcccgtgct ggactccgac    1200
ggctccttct tcctctatag caagctcacc gtggacaagt ccaggtggca gcaggggaac    1260
gtcttctcat gctccgtgat gcatgaggct ctgcacaacc actacacgca gaagagcctc    1320
tccctgtctc cgggttaa                                                  1338
```

<210> SEQ ID NO 7
<211> LENGTH: 6
<212> TYPE: PRT
<213> ORGANISM: Artificial Sequence
<220> FEATURE:
<223> OTHER INFORMATION: Mab CD47 CDRL1

<400> SEQUENCE: 7

Gln Ser Ile Ser Ser Tyr
1               5

<210> SEQ ID NO 8
<211> LENGTH: 4
<212> TYPE: PRT
<213> ORGANISM: Artificial Sequence
<220> FEATURE:
<223> OTHER INFORMATION: MabCd47 CDRL2

```
<400> SEQUENCE: 8

Ala Ala Ser Ser
1

<210> SEQ ID NO 9
<211> LENGTH: 10
<212> TYPE: PRT
<213> ORGANISM: Artificial Sequence
<220> FEATURE:
<223> OTHER INFORMATION: Mab CD47 CDRL3

<400> SEQUENCE: 9

Gln Gln Met His Pro Arg Ala Pro Lys Thr
1               5                   10

<210> SEQ ID NO 10
<211> LENGTH: 108
<212> TYPE: PRT
<213> ORGANISM: Artificial Sequence
<220> FEATURE:
<223> OTHER INFORMATION: Mab CD47 VL

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ala Pro
                85                  90                  95

Lys Thr Phe Gly Gln Gly Thr Lys Val Glu Ile Lys
            100                 105

<210> SEQ ID NO 11
<211> LENGTH: 215
<212> TYPE: PRT
<213> ORGANISM: Artificial Sequence
<220> FEATURE:
<223> OTHER INFORMATION: Mab CD47 LC

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ala Pro
                85                  90                  95

Lys Thr Phe Gly Gln Gly Thr Lys Val Glu Ile Lys Arg Thr Val Ala
            100                 105                 110
```

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
        195                 200                 205

Ser Phe Asn Arg Gly Glu Cys
        210                 215

<210> SEQ ID NO 12
<211> LENGTH: 648
<212> TYPE: DNA
<213> ORGANISM: Artificial Sequence
<220> FEATURE:
<223> OTHER INFORMATION: Mab CD47 LC

<400> SEQUENCE: 12
gacatccaga tgacccagtc tccatcctcc ctgtctgcat ctgtaggaga cagagtcacc       60
atcacttgcc gggcaagtca gagcattagc agctatttaa attggtatca gcagaaacca      120
gggaaagccc ctaagctcct gatctatgct gcatccagtt tgcaaagtgg ggtcccatca      180
aggttcagtg gcagtggatc tgggacagat ttcactctca ccatcagcag tctgcaacct      240
gaagattttg caacttacta ctgtcagcag atgcacccgc gcgccccgaa gaccttcggc      300
caagggacca aggtggaaat caaacgtacg gtggctgcac catctgtctt catcttcccg      360
ccatctgatg agcagttgaa atctggaact gcctctgttg tgtgcctgct gaataacttc      420
tatcccagag aggccaaagt acagtggaag gtggataacg ccctccaatc gggtaactcc      480
caggagagtg tcacagagca ggacagcaag gacagcacct acagcctcag cagcaccctg      540
acgctgagca agcagactac gagaaacac aaagtctacg cctgcgaagt cacccatcag      600
ggcctgagct cgcccgtcac aaagagcttc aacaggggag agtgttaa                  648

<210> SEQ ID NO 13
<211> LENGTH: 116
<212> TYPE: PRT
<213> ORGANISM: Artificial Sequence
<220> FEATURE:
<223> OTHER INFORMATION: Mab CEA CL

<400> SEQUENCE: 13

Phe Gly Gly Gly Thr Lys Leu Thr Val Leu Gly Gln Pro Lys Ala Ala
1               5                   10                  15

Pro Ser Val Thr Leu Phe Pro Pro Ser Ser Glu Glu Leu Gln Ala Asn
                20                  25                  30

Lys Ala Thr Leu Val Cys Leu Ile Ser Asp Phe Tyr Pro Gly Ala Val
            35                  40                  45

Thr Val Ala Trp Lys Ala Asp Ser Ser Pro Val Lys Ala Gly Val Glu
        50                  55                  60

Thr Thr Thr Pro Ser Lys Gln Ser Asn Asn Lys Tyr Ala Ala Ser Ser
65                  70                  75                  80

Tyr Leu Ser Leu Thr Pro Glu Gln Trp Lys Ser His Arg Ser Tyr Ser
            85                  90                  95

Cys Gln Val Thr His Glu Gly Ser Thr Val Glu Lys Thr Val Ala Pro
        100                 105                 110

Thr Glu Cys Ser
        115

<210> SEQ ID NO 14
<211> LENGTH: 24
<212> TYPE: DNA
<213> ORGANISM: Artificial Sequence
<220> FEATURE:
<223> OTHER INFORMATION: Primer

<400> SEQUENCE: 14
gtctgaagca ttatgtgttg aagc                                          24

<210> SEQ ID NO 15
<211> LENGTH: 23
<212> TYPE: DNA
<213> ORGANISM: Artificial Sequence
<220> FEATURE:
<223> OTHER INFORMATION: Primer

<400> SEQUENCE: 15
gtgagtacat tcattgtact gtg                                           23

<210> SEQ ID NO 16
<211> LENGTH: 24
<212> TYPE: DNA
<213> ORGANISM: Artificial Sequence
<220> FEATURE:
<223> OTHER INFORMATION: Primer

<400> SEQUENCE: 16
ttgtgtgact cttaactctc agag                                          24

<210> SEQ ID NO 17
<211> LENGTH: 25
<212> TYPE: DNA
<213> ORGANISM: Artificial Sequence
<220> FEATURE:
<223> OTHER INFORMATION: Primer

<400> SEQUENCE: 17
gaggccactt gtgtagcgcc aagtg                                         25

<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18
gtgagtccat ggctgtcact g                                             21

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
cctgacttgg ctattctcag                                                    20

<210> SEQ ID NO 20
<211> LENGTH: 121
<212> TYPE: PRT
<213> ORGANISM: Artificial Sequence
<220> FEATURE:
<223> OTHER INFORMATION: Mab CEA variable heavy chain

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser
        115                 120

<210> SEQ ID NO 21
<211> LENGTH: 108
<212> TYPE: PRT
<213> ORGANISM: Artificial Sequence
<220> FEATURE:
<223> OTHER INFORMATION: Mab CEA variable light chain

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Lys Ala Ser Ala Ala Val Gly Thr Tyr
            20                  25                  30

Val Ala Trp Tyr Gln Gln Lys Pro Gly Lys Ala Pro Lys Leu Leu Ile
        35                  40                  45

Tyr Ser Ala Ser Tyr Arg Lys Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys
            100                 105

<210> SEQ ID NO 22
<211> LENGTH: 5
<212> TYPE: PRT
<213> ORGANISM: Artificial Sequence
<220> FEATURE:
<223> OTHER INFORMATION: Epitope of CD3 epsilon

<400> SEQUENCE: 22

Gln Asp Gly Asn Glu
1               5

<210> SEQ ID NO 23
<211> LENGTH: 445
<212> TYPE: PRT
<213> ORGANISM: Artificial Sequence
<220> FEATURE:
<223> OTHER INFORMATION: Mab CD47 HC-DE

<400> SEQUENCE: 23

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Tyr Gly Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Asp Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Glu Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365
```

```
Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly
                435                 440                 445

<210> SEQ ID NO 24
<211> LENGTH: 445
<212> TYPE: PRT
<213> ORGANISM: Artificial Sequence
<220> FEATURE:
<223> OTHER INFORMATION: Mab CD47 HC-DEA

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Tyr Gly Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Ala Gly Pro Asp Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285
```

```
Lys Pro Arg Glu Glu Gln Tyr Asn Ser Thr Tyr Arg Val Val Ser Val
            290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Glu Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Glu Glu Met Thr Lys Asn Gln Val Ser Leu Thr Cys Leu Val
            355                 360                 365
Lys Gly Phe Tyr Pro Ser Asp Ile Ala Val Glu Trp Glu Ser Asn Gly
370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly
            435                 440                 445

<210> SEQ ID NO 25
<211> LENGTH: 5
<212> TYPE: PRT
<213> ORGANISM: Artificial Sequence
<220> FEATURE:
<223> OTHER INFORMATION: Mab CD47 CDRH1

<400> SEQUENCE: 25

Ser Tyr Ala Met Ser
1               5

<210> SEQ ID NO 26
<211> LENGTH: 17
<212> TYPE: PRT
<213> ORGANISM: Artificial Sequence
<220> FEATURE:
<223> OTHER INFORMATION: Mab CD47 CHRH2

<400> SEQUENCE: 26

Ala Ile Ser Gly Ser Gly Gly Ser Thr Tyr Tyr Ala Asp Ser Val Lys
1               5                   10                  15
Gly

<210> SEQ ID NO 27
<211> LENGTH: 7
<212> TYPE: PRT
<213> ORGANISM: Artificial Sequence
<220> FEATURE:
<223> OTHER INFORMATION: Mab CD47 CDRH3

<400> SEQUENCE: 27

Ser Tyr Gly Ala Phe Asp Tyr
1               5

<210> SEQ ID NO 28
<211> LENGTH: 11
<212> TYPE: PRT
<213> ORGANISM: Artificial Sequence
<220> FEATURE:
<223> OTHER INFORMATION: Mab CD47 CDRL1; KA3
```

```
<400> SEQUENCE: 28

Arg Ala Ser Gln Ser Ile Ser Ser Tyr Leu Asn
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Mab CD47 CDRL2; KA3

<400> SEQUENCE: 29

Ala Ala Ser Ser Leu Gln Ser
1               5

<210> SEQ ID NO 30
<211> LENGTH: 10
<212> TYPE: PRT
<213> ORGANISM: Artificial Sequence
<220> FEATURE:
<223> OTHER INFORMATION: Mab CD47 CDRL3; KA3

<400> SEQUENCE: 30

Gln Gln Met His Pro Arg Ala Pro Lys Thr
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Mab CEA CDRL1; 1D9 (AC5)

<400> SEQUENCE: 31

Ser Gly Ser Ser Ser Asn Ile Gly Tyr Gly Leu Val Ser
1               5                   10

<210> SEQ ID NO 32
<211> LENGTH: 7
<212> TYPE: PRT
<213> ORGANISM: Artificial Sequence
<220> FEATURE:
<223> OTHER INFORMATION: Mab CEA CDRL2; 1D9 (AC5)

<400> SEQUENCE: 32

Ala Gly Asn Leu Arg Pro Ser
1               5

<210> SEQ ID NO 33
<211> LENGTH: 10
<212> TYPE: PRT
<213> ORGANISM: Artificial Sequence
<220> FEATURE:
<223> OTHER INFORMATION: Mab CEA CDRL3; 1D9 (AC5)

<400> SEQUENCE: 33

Gly Thr Trp Asp Phe Asn Tyr Gly Val Val
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Mab CEA CDRL1; 1G6 (AC22)
```

```
<400> SEQUENCE: 34

Ser Gly Ser Ser Ser Asn Ile Ala Asn Gly Ile Val Ser
1               5                   10

<210> SEQ ID NO 35
<211> LENGTH: 7
<212> TYPE: PRT
<213> ORGANISM: Artificial Sequence
<220> FEATURE:
<223> OTHER INFORMATION: Mab CEA CDRL2; 1G6 (AC22)

<400> SEQUENCE: 35

Phe Asp Asn Leu Arg Pro Ser
1               5

<210> SEQ ID NO 36
<211> LENGTH: 10
<212> TYPE: PRT
<213> ORGANISM: Artificial Sequence
<220> FEATURE:
<223> OTHER INFORMATION: Mab CEA CDRL3; 1G6 (AC22)

<400> SEQUENCE: 36

Gly Thr Trp Asp Phe Ser Tyr Gly Ile Val
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Mab CEA CDRL1; 1D5 (AC10)

<400> SEQUENCE: 37

Thr Gly Ser Ser Ser Asn Ile Tyr Ala Asn Ser Asn Val His
1               5                   10

<210> SEQ ID NO 38
<211> LENGTH: 7
<212> TYPE: PRT
<213> ORGANISM: Artificial Sequence
<220> FEATURE:
<223> OTHER INFORMATION: Mab CEA CDRL2; 1D5 (AC10)

<400> SEQUENCE: 38

Ser Gly Ser Asn Arg Pro Ser
1               5

<210> SEQ ID NO 39
<211> LENGTH: 13
<212> TYPE: PRT
<213> ORGANISM: Artificial Sequence
<220> FEATURE:
<223> OTHER INFORMATION: Mab CEA CDRL3; 1D5 (AC10)

<400> SEQUENCE: 39

Gln Ser Tyr Asp Pro Ala His Asn Leu Leu Thr Ala Val
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Mab CEA CDRL1, 2B8 (AC13)

<400> SEQUENCE: 40
```

```
Thr Gly Thr Ser Ser Asn Val Arg Tyr Ala Ala Gly Val Ser
1               5                   10
```

<210> SEQ ID NO 41
<211> LENGTH: 7
<212> TYPE: PRT
<213> ORGANISM: Artificial Sequence
<220> FEATURE:
<223> OTHER INFORMATION: Mab CEA CDRL2; 2B8 (AC13)

<400> SEQUENCE: 41

```
Glu Val Ser Asn Arg Pro Ser
1               5
```

<210> SEQ ID NO 42
<211> LENGTH: 13
<212> TYPE: PRT
<213> ORGANISM: Artificial Sequence
<220> FEATURE:
<223> OTHER INFORMATION: Mab CEA CDRL3; 2B8 (AC13)

<400> SEQUENCE: 42

```
Ser Ser Trp Asp Phe Glu His Gly Pro Ala Ala Lys Val
1               5                   10
```

<210> SEQ ID NO 43
<211> LENGTH: 11
<212> TYPE: PRT
<213> ORGANISM: Artificial Sequence
<220> FEATURE:
<223> OTHER INFORMATION: Mab CEA CDRL1; 1A2 (AC18)

<400> SEQUENCE: 43

```
Gly Gly Asn Gly Ile Gly Asp Ala Ser Val His
1               5                   10
```

<210> SEQ ID NO 44
<211> LENGTH: 7
<212> TYPE: PRT
<213> ORGANISM: Artificial Sequence
<220> FEATURE:
<223> OTHER INFORMATION: Mab CEA CDRL2; 1A2 (AC18)

<400> SEQUENCE: 44

```
Ser Thr Thr Thr Arg Pro Ser
1               5
```

<210> SEQ ID NO 45
<211> LENGTH: 13
<212> TYPE: PRT
<213> ORGANISM: Artificial Sequence
<220> FEATURE:
<223> OTHER INFORMATION: Mab CEA CDRL3; 1A2 (AC18)

<400> SEQUENCE: 45

```
Gln Val Trp Asp Gly Phe Gly Pro Arg His Arg Ala Val
1               5                   10
```

<210> SEQ ID NO 46
<211> LENGTH: 13
<212> TYPE: PRT
<213> ORGANISM: Artificial Sequence
<220> FEATURE:
<223> OTHER INFORMATION: Mab CEA CDRL1; 1A8 (AC23)

<400> SEQUENCE: 46

```
Ser Gly Ser Ser Ser Asn Ile Gly Tyr Gly Leu Val Asn
1               5                   10
```

<210> SEQ ID NO 47
<211> LENGTH: 7
<212> TYPE: PRT
<213> ORGANISM: Artificial Sequence
<220> FEATURE:
<223> OTHER INFORMATION: Mab CEA CDRL2; 1A8 (AC23)

<400> SEQUENCE: 47

```
Ala Thr Asn Thr Arg Pro Ser
1               5
```

<210> SEQ ID NO 48
<211> LENGTH: 10
<212> TYPE: PRT
<213> ORGANISM: Artificial Sequence
<220> FEATURE:
<223> OTHER INFORMATION: Mab CEA CDRL3; 1A8 (AC23)

<400> SEQUENCE: 48

```
Ala Ala Trp Asp Phe Ser Tyr Lys Val Val
1               5                   10
```

<210> SEQ ID NO 49
<211> LENGTH: 13
<212> TYPE: PRT
<213> ORGANISM: Artificial Sequence
<220> FEATURE:
<223> OTHER INFORMATION: Mab CEA CDRL1; 2F4 (AC25)

<400> SEQUENCE: 49

```
Ser Gly Ser Ser Ser Asn Ile Gly Ile Thr Pro Val Ser
1               5                   10
```

<210> SEQ ID NO 50
<211> LENGTH: 7
<212> TYPE: PRT
<213> ORGANISM: Artificial Sequence
<220> FEATURE:
<223> OTHER INFORMATION: Mab CEA CDRL2; 2F4 (AC25)

<400> SEQUENCE: 50

```
Ser Asn Asn Phe Arg Pro Ser
1               5
```

<210> SEQ ID NO 51
<211> LENGTH: 13
<212> TYPE: PRT
<213> ORGANISM: Artificial Sequence
<220> FEATURE:
<223> OTHER INFORMATION: Mab CEA CDRL3; 2F4 (AC25)

<400> SEQUENCE: 51

```
Gly Thr Trp Asp Arg Thr Gly His Glu Ile Arg Pro Val
1               5                   10
```

<210> SEQ ID NO 52
<211> LENGTH: 14
<212> TYPE: PRT
<213> ORGANISM: Artificial Sequence
<220> FEATURE:
<223> OTHER INFORMATION: Mab CEA CDRL1; 2F7 (AC26)

<400> SEQUENCE: 52

```
Thr Gly Thr Ser Ser Asp Val Lys Tyr Ala Asn Ala Val Ser
```

<210> SEQ ID NO 53
<211> LENGTH: 7
<212> TYPE: PRT
<213> ORGANISM: Artificial Sequence
<220> FEATURE:
<223> OTHER INFORMATION: Mab CEA CDRL2; 2F7 (AC26)

<400> SEQUENCE: 53

Ser Asn Ser Ile Arg Pro Ser
1               5

<210> SEQ ID NO 54
<211> LENGTH: 13
<212> TYPE: PRT
<213> ORGANISM: Artificial Sequence
<220> FEATURE:
<223> OTHER INFORMATION: Mab CEA CDRL3; 2F7 (AC26)

<400> SEQUENCE: 54

Ser Ser Tyr Asp Pro Arg Gly Asn Leu Leu Ile Arg Val
1               5                   10

<210> SEQ ID NO 55
<211> LENGTH: 14
<212> TYPE: PRT
<213> ORGANISM: Artificial Sequence
<220> FEATURE:
<223> OTHER INFORMATION: Mab CEA CDRL1; 2C11 (AC27)

<400> SEQUENCE: 55

Thr Gly Ser Ser Ser Asn Ile Gly Tyr Ala Asp Lys Val His
1               5                   10

<210> SEQ ID NO 56
<211> LENGTH: 7
<212> TYPE: PRT
<213> ORGANISM: Artificial Sequence
<220> FEATURE:
<223> OTHER INFORMATION: Mab CEA CDRL2; 2C11 (AC27)

<400> SEQUENCE: 56

Asn Asn Ser Asp Arg Pro Ser
1               5

<210> SEQ ID NO 57
<211> LENGTH: 12
<212> TYPE: PRT
<213> ORGANISM: Artificial Sequence
<220> FEATURE:
<223> OTHER INFORMATION: Mab CEA CDRL3; 2C11 (AC27)

<400> SEQUENCE: 57

Gln Ser Tyr Asp Gly Tyr Asn Met Leu Thr Ala Val
1               5                   10

<210> SEQ ID NO 58
<211> LENGTH: 13
<212> TYPE: PRT
<213> ORGANISM: Artificial Sequence
<220> FEATURE:
<223> OTHER INFORMATION: Mab CEA CDRL1; C11 (AC28)

<400> SEQUENCE: 58

Thr Arg Ser Ser Gly Ser Ile Asn Asp Ile Thr Val His
1               5                   10

```
<210> SEQ ID NO 59
<211> LENGTH: 7
<212> TYPE: PRT
<213> ORGANISM: Artificial Sequence
<220> FEATURE:
<223> OTHER INFORMATION: Mab CEA CDRL2; C11 (AC28)

<400> SEQUENCE: 59

Gly Tyr Asn Ala Arg Pro Ser
1               5

<210> SEQ ID NO 60
<211> LENGTH: 11
<212> TYPE: PRT
<213> ORGANISM: Artificial Sequence
<220> FEATURE:
<223> OTHER INFORMATION: Mab CEA CDRL3; C11 (AC28)

<400> SEQUENCE: 60

Gln Ser Trp Asp Gly His Gly Ser Ala Tyr Val
1               5                   10

<210> SEQ ID NO 61
<211> LENGTH: 14
<212> TYPE: PRT
<213> ORGANISM: Artificial Sequence
<220> FEATURE:
<223> OTHER INFORMATION: Mab CEA CDRL1; 2B5 (AC29)

<400> SEQUENCE: 61

Thr Gly Thr Ser Ser Asp Val Glu Phe Thr Asn Gly Val Ser
1               5                   10

<210> SEQ ID NO 62
<211> LENGTH: 7
<212> TYPE: PRT
<213> ORGANISM: Artificial Sequence
<220> FEATURE:
<223> OTHER INFORMATION: Mab CEA CDRL2; 2B5 (AC29)

<400> SEQUENCE: 62

Gly Phe Ser Ser Arg Pro Ser
1               5

<210> SEQ ID NO 63
<211> LENGTH: 13
<212> TYPE: PRT
<213> ORGANISM: Artificial Sequence
<220> FEATURE:
<223> OTHER INFORMATION: Mab CEA CDRL3; 2B5 (AC29)

<400> SEQUENCE: 63

Ser Ser Tyr Asp Pro Pro Trp His Leu Leu Ala Arg Val
1               5                   10

<210> SEQ ID NO 64
<211> LENGTH: 215
<212> TYPE: PRT
<213> ORGANISM: Artificial Sequence
<220> FEATURE:
<223> OTHER INFORMATION: Mab CEA 1D9 VLCL2 CEA (AC5)

<400> SEQUENCE: 64

Gln Ser Val Leu Thr Gln Pro Pro Ser Val Ser Ala Ala Pro Gly Gln
1               5                   10                  15
```

```
Lys Val Thr Ile Ser Cys Ser Gly Ser Ser Asn Ile Gly Tyr Gly
            20                  25                  30

Leu Val Ser Trp Tyr Gln Gln Leu Pro Gly Thr Ala Pro Lys Leu Leu
        35                  40                  45

Ile Tyr Ala Gly Asn Leu Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Phe Asn Tyr
                85                  90                  95

Gly Val Val Phe Gly Gly Gly Thr Lys Leu Thr Val Leu Gly Gln Pro
                100                 105                 110

Lys Ala Ala Pro Ser Val Thr Leu Phe Pro Pro Ser Ser Glu Glu Leu
            115                 120                 125

Gln Ala Asn Lys Ala Thr Leu Val Cys Leu Ile Ser Asp Phe Tyr Pro
        130                 135                 140

Gly Ala Val Thr Val Ala Trp Lys Ala Asp Ser Ser Pro Val Lys Ala
145                 150                 155                 160

Gly Val Glu Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
                180                 185                 190

Ser Tyr Ser Cys Gln Val Thr His Glu Gly Ser Thr Val Glu Lys Thr
                195                 200                 205

Val Ala Pro Thr Glu Cys Ser
            210                 215

<210> SEQ ID NO 65
<211> LENGTH: 215
<212> TYPE: PRT
<213> ORGANISM: Artificial Sequence
<220> FEATURE:
<223> OTHER INFORMATION: Mab CEA 1G6 VLCL2 CEA (AC22)

<400> SEQUENCE: 65

Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Ala Asn Gly
            20                  25                  30

Ile Val Ser Trp Tyr Gln Gln Leu Pro Gly Thr Ala Pro Lys Leu Leu
        35                  40                  45

Ile Tyr Phe Asp Asn Leu Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Phe Ser Tyr
                85                  90                  95

Gly Ile Val Phe Gly Gly Gly Thr Lys Leu Thr Val Leu Gly Gln Pro
                100                 105                 110

Lys Ala Ala Pro Ser Val Thr Leu Phe Pro Pro Ser Ser Glu Glu Leu
            115                 120                 125

Gln Ala Asn Lys Ala Thr Leu Val Cys Leu Ile Ser Asp Phe Tyr Pro
        130                 135                 140

Gly Ala Val Thr Val Ala Trp Lys Ala Asp Ser Ser Pro Val Lys Ala
145                 150                 155                 160
```

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 66
<211> LENGTH: 219
<212> TYPE: PRT
<213> ORGANISM: Artificial Sequence
<220> FEATURE:
<223> OTHER INFORMATION: Mab CEA 1D5 VLCL2 CEA (AC10)

<400> SEQUENCE: 66

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Tyr Ala Asn
            20                  25                  30

Ser Asn Val His Trp Tyr Gln Gln Leu Pro Gly Thr Ala Pro Lys Leu
        35                  40                  45

Leu Ile Tyr Ser Gly Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Pro Ala
                85                  90                  95

His Asn Leu Leu Thr Ala Val Phe Gly Gly Gly Thr Lys Leu Thr Val
            100                 105                 110

Leu Gly Gln Pro Lys Ala Ala Pro Ser Val Thr Leu Phe Pro Pro Ser
        115                 120                 125

Ser Glu Glu Leu Gln Ala Asn Lys Ala Thr Leu Val Cys Leu Ile Ser
    130                 135                 140

Asp Phe Tyr Pro Gly Ala Val Thr Val Ala Trp Lys Ala Asp Ser Ser
145                 150                 155                 160

Pro Val Lys Ala Gly Val Glu Thr Thr Thr Pro Ser Lys Gln Ser Asn
                165                 170                 175

Asn Lys Tyr Ala Ala Ser Ser Tyr Leu Ser Leu Thr Pro Glu Gln Trp
            180                 185                 190

Lys Ser His Arg Ser Tyr Ser Cys Gln Val Thr His Glu Gly Ser Thr
        195                 200                 205

Val Glu Lys Thr Val Ala Pro Thr Glu Cys Ser
    210                 215

<210> SEQ ID NO 67
<211> LENGTH: 219
<212> TYPE: PRT
<213> ORGANISM: Artificial Sequence
<220> FEATURE:
<223> OTHER INFORMATION: Mab CEA 2B8 VLCL2 CEA (AC13)

<400> SEQUENCE: 67

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asn Val Arg Tyr Ala
            20                  25                  30

```
Ala Gly Val Ser Trp Tyr Gln Gln His Pro Gly Lys Ala Pro Lys Leu
            35                  40                  45

Met Ile Tyr Glu Val Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Trp Asp Phe Glu
                 85                  90                  95

His Gly Pro Ala Ala Lys Val Phe Gly Gly Gly Thr Lys Leu Thr Val
            100                 105                 110

Leu Gly Gln Pro Lys Ala Ala Pro Ser Val Thr Leu Phe Pro Pro Ser
            115                 120                 125

Ser Glu Glu Leu Gln Ala Asn Lys Ala Thr Leu Val Cys Leu Ile Ser
130                 135                 140

Asp Phe Tyr Pro Gly Ala Val Thr Val Ala Trp Lys Ala Asp Ser Ser
145                 150                 155                 160

Pro Val Lys Ala Gly Val Glu Thr Thr Thr Pro Ser Lys Gln Ser Asn
                165                 170                 175

Asn Lys Tyr Ala Ala Ser Ser Tyr Leu Ser Leu Thr Pro Glu Gln Trp
            180                 185                 190

Lys Ser His Arg Ser Tyr Ser Cys Gln Val Thr His Glu Gly Ser Thr
            195                 200                 205

Val Glu Lys Thr Val Ala Pro Thr Glu Cys Ser
            210                 215

<210> SEQ ID NO 68
<211> LENGTH: 216
<212> TYPE: PRT
<213> ORGANISM: Artificial Sequence
<220> FEATURE:
<223> OTHER INFORMATION: Mab CEA 1A2 VLCL2 CEA (AC18)

<400> SEQUENCE: 68

Ser Tyr Val Leu Thr Gln Pro Pro Ser Val Ser Val Ala Pro Gly Lys
 1               5                  10                  15

Thr Ala Arg Ile Thr Cys Gly Gly Asn Gly Ile Gly Asp Ala Ser Val
                 20                  25                  30

His Trp Tyr Gln Gln Lys Pro Gly Gln Ala Pro Val Leu Val Ile Tyr
            35                  40                  45

Ser Thr Thr Thr Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Gly Phe Gly Pro Arg
                 85                  90                  95

His Arg Ala Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175
```

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 69
<211> LENGTH: 215
<212> TYPE: PRT
<213> ORGANISM: Artificial Sequence
<220> FEATURE:
<223> OTHER INFORMATION: Mab CEA 1A8 VLCL2 CEA (AC23)

<400> SEQUENCE: 69

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Tyr Gly
            20                  25                  30

Leu Val Asn Trp Tyr Gln Gln Leu Pro Gly Thr Ala Pro Lys Leu Leu
        35                  40                  45

Ile Tyr Ala Thr Asn Thr Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Phe Ser Tyr
                85                  90                  95

Lys Val Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 70
<211> LENGTH: 218
<212> TYPE: PRT
<213> ORGANISM: Artificial Sequence
<220> FEATURE:
<223> OTHER INFORMATION: Mab CEA 2F4 VLCL2 CEA (AC25)

<400> SEQUENCE: 70

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Ile Thr
            20                  25                  30

Pro Val Ser Trp Tyr Gln Gln Leu Pro Gly Thr Ala Pro Lys Leu Leu

```
            35                  40                  45
Ile Tyr Ser Asn Asn Phe Arg Pro Ser Gly Ile Pro Asp Arg Phe Ser
 50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Arg Thr Gly
                 85                  90                  95

His Glu Ile Arg Pro Val Phe Gly Gly Gly Thr Lys Leu Thr Val Leu
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys Ser
    210                 215

<210> SEQ ID NO 71
<211> LENGTH: 219
<212> TYPE: PRT
<213> ORGANISM: Artificial Sequence
<220> FEATURE:
<223> OTHER INFORMATION: Mab CEA 2F4 VLCL2 CEA (AC25)

<400> SEQUENCE: 71

Gln Ser Ala Leu Thr Gln Pro Ala Ser Val Ser Gly Ser Pro Gly Gln
  1               5                  10                  15

Ser Ile Thr Ile Ser Cys Thr Gly Thr Ser Ser Asp Val Lys Tyr Ala
                 20                  25                  30

Asn Ala Val Ser Trp Tyr Gln Gln His Pro Gly Lys Ala Pro Lys Leu
             35                  40                  45

Met Ile Tyr Ser Asn Ser Ile Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Asp Pro Arg
                 85                  90                  95

Gly Asn Leu Leu Ile Arg Val Phe Gly Gly Gly Thr Lys Leu Thr Val
            100                 105                 110

Leu Gly Gln Pro Lys Ala Ala Pro Ser Val Thr Leu Phe Pro Pro Ser
        115                 120                 125

Ser Glu Glu Leu Gln Ala Asn Lys Ala Thr Leu Val Cys Leu Ile Ser
    130                 135                 140

Asp Phe Tyr Pro Gly Ala Val Thr Val Ala Trp Lys Ala Asp Ser Ser
145                 150                 155                 160

Pro Val Lys Ala Gly Val Glu Thr Thr Thr Pro Ser Lys Gln Ser Asn
                165                 170                 175

Asn Lys Tyr Ala Ala Ser Ser Tyr Leu Ser Leu Thr Pro Glu Gln Trp
```

180                 185                 190
Lys Ser His Arg Ser Tyr Ser Cys Gln Val Thr His Glu Gly Ser Thr
            195                 200                 205
Val Glu Lys Thr Val Ala Pro Thr Glu Cys Ser
    210                 215

<210> SEQ ID NO 72
<211> LENGTH: 218
<212> TYPE: PRT
<213> ORGANISM: Artificial Sequence
<220> FEATURE:
<223> OTHER INFORMATION: Mab CEA 2C11 VLCL2 CEA

<400> SEQUENCE: 72

Gln Ser Val Leu Thr Gln Pro Pro Ser Val Ser Gly Ala Pro Gly Gln
1               5                   10                  15
Arg Val Thr Ile Ser Cys Thr Gly Ser Ser Asn Ile Gly Tyr Ala
            20                  25                  30
Asp Lys Val His Trp Tyr Gln Gln Leu Pro Gly Thr Ala Pro Lys Leu
        35                  40                  45
Leu Ile Tyr Asn Asn Ser Asp Arg Pro Ser Gly Val Pro Asp Arg Phe
    50                  55                  60
Ser Gly Ser Lys Ser Gly Thr Ser Ala Ser Leu Ala Ile Thr Gly Leu
65              70                  75                  80
Gln Ala Glu Asp Glu Ala Asp Tyr Tyr Cys Gln Ser Tyr Asp Gly Tyr
                85                  90                  95
Asn Met Leu Thr Ala Val Phe Gly Gly Gly Thr Lys Leu Thr Val Leu
            100                 105                 110
Gly Gln Pro Lys Ala Ala Pro Ser Val Thr Leu Phe Pro Pro Ser Ser
        115                 120                 125
Glu Glu Leu Gln Ala Asn Lys Ala Thr Leu Val Cys Leu Ile Ser Asp
    130                 135                 140
Phe Tyr Pro Gly Ala Val Thr Val Ala Trp Lys Ala Asp Ser Ser Pro
145                 150                 155                 160
Val Lys Ala Gly Val Glu Thr Thr Thr Pro Ser Lys Gln Ser Asn Asn
                165                 170                 175
Lys Tyr Ala Ala Ser Ser Tyr Leu Ser Leu Thr Pro Glu Gln Trp Lys
            180                 185                 190
Ser His Arg Ser Tyr Ser Cys Gln Val Thr His Glu Gly Ser Thr Val
        195                 200                 205
Glu Lys Thr Val Ala Pro Thr Glu Cys Ser
    210                 215

<210> SEQ ID NO 73
<211> LENGTH: 218
<212> TYPE: PRT
<213> ORGANISM: Artificial Sequence
<220> FEATURE:
<223> OTHER INFORMATION: Mab CEA C11 VLCL2 CEA (AC28)

<400> SEQUENCE: 73

Asn Phe Met Leu Thr Gln Pro His Ser Val Ser Glu Ser Pro Gly Lys
1               5                   10                  15
Thr Val Thr Ile Ser Cys Thr Arg Ser Ser Gly Ser Ile Asn Asp Ile
            20                  25                  30
Thr Val His Trp Tyr Gln Gln Arg Pro Gly Ser Ser Pro Thr Thr Val
        35                  40                  45

Ile Tyr Gly Tyr Asn Ala Arg Pro Ser Gly Val Pro Asp Arg Phe Ser
 50                  55                  60

Gly Ser Ile Asp Ser Ser Asn Ser Ala Ser Leu Thr Ile Ser Gly
 65                  70                  75                  80

Leu Lys Thr Glu Asp Glu Ala Asp Tyr Tyr Cys Gln Ser Trp Asp Gly
                 85                  90                  95

His Gly Ser Ala Tyr Val Phe Gly Gly Gly Thr Lys Leu Thr Val Leu
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys Ser
210                 215

<210> SEQ ID NO 74
<211> LENGTH: 219
<212> TYPE: PRT
<213> ORGANISM: Artificial Sequence
<220> FEATURE:
<223> OTHER INFORMATION: Mab CEA 2B5 VLCL2 CEA (AC29)

<400> SEQUENCE: 74

Gln Ser Ala Leu Thr Gln Pro Ala Ser Val Ser Gly Ser Pro Gly Gln
1                5                  10                  15

Ser Ile Thr Ile Ser Cys Thr Gly Thr Ser Ser Asp Val Glu Phe Thr
                20                  25                  30

Asn Gly Val Ser Trp Tyr Gln Gln His Pro Gly Lys Ala Pro Lys Leu
            35                  40                  45

Met Ile Tyr Gly Phe Ser Ser Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Asp Pro Pro
                85                  90                  95

Trp His Leu Leu Ala Arg Val Phe Gly Gly Gly Thr Lys Leu Thr Val
            100                 105                 110

Leu Gly Gln Pro Lys Ala Ala Pro Ser Val Thr Leu Phe Pro Pro Ser
        115                 120                 125

Ser Glu Glu Leu Gln Ala Asn Lys Ala Thr Leu Val Cys Leu Ile Ser
    130                 135                 140

Asp Phe Tyr Pro Gly Ala Val Thr Val Ala Trp Lys Ala Asp Ser Ser
145                 150                 155                 160

Pro Val Lys Ala Gly Val Glu Thr Thr Thr Pro Ser Lys Gln Ser Asn
                165                 170                 175

Asn Lys Tyr Ala Ala Ser Ser Tyr Leu Ser Leu Thr Pro Glu Gln Trp
            180                 185                 190

Lys Ser His Arg Ser Tyr Ser Cys Gln Val Thr His Glu Gly Ser Thr
            195                 200                 205

Val Glu Lys Thr Val Ala Pro Thr Glu Cys Ser
    210                 215

<210> SEQ ID NO 75
<211> LENGTH: 648
<212> TYPE: DNA
<213> ORGANISM: Artificial Sequence
<220> FEATURE:
<223> OTHER INFORMATION: Nucleic acid 1D9 VLCL2 CEA (AC5)

<400> SEQUENCE: 75
cagtctgtgt tgacgcagcc gccctcagtg tctgcggccc caggacagaa ggtcaccatc      60
tcctgctctg gaagcagctc aacattggt tatgggcttg tatcctggta ccagcagctc     120
ccaggaacag cccccaaact cctcatttat gctggtaatc ttcgaccctc agggattcct     180
gaccgattct ctggctccaa gtctggcacg tcagccaccc tgggcatcac cggactccag     240 actgggacg aggccgatta ttactgcgga acatgggatt taattatgg ggttgtgttc      300 ggcggaggga ccaagctgac cgtcctaggt cagcccaagg ctgcccctc ggtcactctg      360 ttcccgccct cctctgagga gcttcaagcc aacaaggcca cactggtgtg tctcataagt     420
gacttctacc cgggagccgt gacagtggct tggaaagcag atagcagccc cgtcaaggcg     480
ggagtggaga ccaccacacc ctccaaacaa agcaacaaca gtacgcggc cagcagctat      540 ctgagcctga cgcctgagca gtggaagtcc cacagaagct acagctgcca ggtcacgcat     600
gaagggagca ccgtggagaa gacagtggcc cctacagaat gttcataa              648

<210> SEQ ID NO 76
<211> LENGTH: 648
<212> TYPE: DNA
<213> ORGANISM: Artificial Sequence
<220> FEATURE:
<223> OTHER INFORMATION: Nucleic acid 1G6 VLCL2 CEA (AC22)

<400> SEQUENCE: 76
cagtctgtgt tgacgcagcc gccctcagtg tctgcggccc caggacagaa ggtcaccatc      60
tcctgctctg gaagcagctc aacattgct aatgggattg tatcctggta ccagcagctc     120
ccaggaacag cccccaaact cctcatttat tttgataatc ttcgaccctc agggattcct     180
gaccgattct ctggctccaa gtctggcacg tcagccaccc tgggcatcac cggactccag     240 actgggacg aggccgatta ttactgcgga acatgggatt tagttatgg tattgtgttc      300 ggcggaggga ccaagctgac cgtcctaggt cagcccaagg ctgcccctc ggtcactctg      360 ttcccgccct cctctgagga gcttcaagcc aacaaggcca cactggtgtg tctcataagt     420
gacttctacc cgggagccgt gacagtggct tggaaagcag atagcagccc cgtcaaggcg     480
ggagtggaga ccaccacacc ctccaaacaa agcaacaaca gtacgcggc cagcagctat      540 ctgagcctga cgcctgagca gtggaagtcc cacagaagct acagctgcca ggtcacgcat     600
gaagggagca ccgtggagaa gacagtggcc cctacagaat gttcataa              648

<210> SEQ ID NO 77
<211> LENGTH: 660
<212> TYPE: DNA
<213> ORGANISM: Artificial Sequence
<220> FEATURE:
<223> OTHER INFORMATION: Nucleic acid 1D5 VLCL2 CEA (AC10)

<400> SEQUENCE: 77

```
cagtctgtgc tgacgcagcc gccctcagtg tctggggccc cagggcagag ggtcaccatc      60
tcctgcactg ggagcagctc caacatctat gcgaatagta atgtacactg gtaccagcag     120
cttccaggaa cagcccccaa actcctcatc tattctggta gcaatcggcc ctcaggggtc     180
cctgaccgat tctctggctc caagtctggc acctcagcct ccctggccat cactgggctc     240
caggctgagg atgaggctga ttattactgc cagtcctatg atcccgcgca aacttgctc     300 actgctgtgt tcggcggagg gaccaagctg accgtcctag gtcagcccaa ggctgccccc     360
tcggtcactc tgttcccgcc ctcctctgag gagcttcaag ccaacaaggc cacactggtg     420
tgtctcataa gtgacttcta cccgggagcc gtgacagtgg cttggaaagc agatagcagc     480
cccgtcaagg cgggagtgga gaccaccaca ccctccaaac aaagcaacaa caagtacgcg     540
gccagcagct atctgagcct gacgcctgag cagtggaagt cccacagaag ctacagctgc     600
caggtcacgc atgaagggag caccgtggag aagacagtgg cccctacaga atgttcataa     660

<210> SEQ ID NO 78
<211> LENGTH: 660
<212> TYPE: DNA
<213> ORGANISM: Artificial Sequence
<220> FEATURE:
<223> OTHER INFORMATION: Nucleic acid 2B8 VLCL2 CEA (AC13)

<400> SEQUENCE: 78
cagtctgccc tgactcagcc tgcctccgtg tctgggtctc ctggacagtc gatcaccatc      60
tcctgcactg gaaccagcag taatgttagg tatgctgctg gtgtctcctg gtaccaacag     120
cacccaggca aagcccccaa actcatgatt tatgaggtca gtaatcggcc ctcagggtt     180 tctaatcgct tctctggctc caagtctggc aacacggcct ccctgaccat ctctgggctc     240
caggctgagg acgaggctga ttattactgc agctcatggg attttgagca tggtcctgct     300
gctaaggtgt tcggcggagg gaccaagctg accgtcctag gtcagcccaa ggctgccccc     360
tcggtcactc tgttcccgcc ctcctctgag gagcttcaag ccaacaaggc cacactggtg     420
tgtctcataa gtgacttcta cccgggagcc gtgacagtgg cttggaaagc agatagcagc     480
cccgtcaagg cgggagtgga gaccaccaca ccctccaaac aaagcaacaa caagtacgcg     540
gccagcagct atctgagcct gacgcctgag cagtggaagt cccacagaag ctacagctgc     600
caggtcacgc atgaagggag caccgtggag aagacagtgg cccctacaga atgttcataa     660

<210> SEQ ID NO 79
<211> LENGTH: 651
<212> TYPE: DNA
<213> ORGANISM: Artificial Sequence
<220> FEATURE:
<223> OTHER INFORMATION: Nucleic acid 1A2 VLCL2 CEA

<400> SEQUENCE: 79
tcctatgtgc tgactcagcc accctcagtg tcagtggccc caggaaagac ggccaggatt      60
acctgtgggg gaaacggtat tggagatcgc tctgtgcact ggtaccagca gaagccaggc     120 caggccctg tgctggtcat ctattctact actacgcggc cctcagggat tcctgagcga     180
ttctctggct ccaactctgg gaacacggcc accctgacca tcagcagggt cgaagccggg     240
gatgaggccg actattactg tcaggtgtgg gatgggtttg gtcctaggca tagggctgtg     300
ttcggcggag ggaccaagct gaccgtccta ggtcagccca aggctgcccc ctcggtcact     360
ctgttcccgc cctcctctga ggagcttcaa gccaacaagg ccacactggt gtgtctcata     420
```

```
agtgacttct acccgggagc cgtgacagtg gcttggaaag cagatagcag ccccgtcaag    480
gcgggagtgg agaccaccac accctccaaa caaagcaaca acaagtacgc ggccagcagc    540
tatctgagcc tgacgcctga gcagtggaag tcccacagaa gctacagctg ccaggtcacg    600
catgaaggga gcaccgtgga gaagacagtg gcccctacag aatgttcata a             651
```

<210> SEQ ID NO 80
<211> LENGTH: 648
<212> TYPE: DNA
<213> ORGANISM: Artificial Sequence
<220> FEATURE:
<223> OTHER INFORMATION: Nucleic acid 1A8 VLCL2 CEA (AC23)

<400> SEQUENCE: 80

```
cagtctgtgc tgactcagcc accctcagcg tctgggaccc ccgggcagag ggtcaccatc    60
tcttgttctg gaagcagctc caacatcggg tatgggcttg taaactggta ccagcagctc   120
ccaggaacgg cccccaaact cctcatctat gctactaata cgcggccctc aggggtccct   180
gaccgattct ctggctccaa gtctggcacc tcagcctccc tggccatcag tgggctccag   240
tctgaggatg aggctgatta ttactgtgca gcatgggatt tagttataa ggttgtgttc    300 ggcggaggga ccaagctgac cgtcctaggt cagcccaagg ctgccccctc ggtcactctg   360
ttcccgccct cctctgagga gcttcaagcc aacaaggcca cactggtgtg tctcataagt   420
gacttctacc cgggagccgt gacagtggct tggaaagcag atagcagccc cgtcaaggcg   480
ggagtggaga ccaccacacc tccaaacaa gcaacaaca agtacgcggc cagcagctat     540
ctgagcctga cgcctgagca gtggaagtcc acagaagct acagctgcca ggtcacgcat    600
gaagggagca ccgtggagaa gacagtggcc cctacagaat gttcataa                648
```

<210> SEQ ID NO 81
<211> LENGTH: 657
<212> TYPE: DNA
<213> ORGANISM: Artificial Sequence
<220> FEATURE:
<223> OTHER INFORMATION: Nucleic acid 2F4 VLCL2 CEA (AC25)

<400> SEQUENCE: 81

```
cagtctgtgt tgacgcagcc gccctcagtg tctgcggccc caggacagaa ggtcaccatc    60
tcctgctctg gaagcagctc caacattggt attacgcctg tatcctggta ccagcagctc   120
ccaggaacag cccccaaact cctcatttat tctaataatt ttcgaccctc agggattcct   180
gaccgattct ctggctccaa gtctggcacg tcagccaccc tgggcatcac cggactccag   240
actggggacg aggccgatta ttactgcgga acatgggata ggactggtca tgagattagg   300
cctgtgttcg gcggagggac caagctgacc gtcctaggtc agcccaaggc tgccccctcg   360
gtcactctgt tcccgccctc ctctgaggag cttcaagcca acaaggccac actggtgtgt   420
ctcataagtg acttctaccc gggagccgtg acagtggctt ggaaagcaga tagcagcccc   480
gtcaaggcgg gagtggagac caccacaccc tccaaacaaa gcaacaacaa gtacgcggcc   540
agcagctatc tgagcctgac gcctgagcag tggaagtccc acagaagcta cagctgccag   600
gtcacgcatg aagggagcac cgtggagaag acagtggccc ctacagaatg ttcataa     657
```

<210> SEQ ID NO 82
<211> LENGTH: 660
<212> TYPE: DNA
<213> ORGANISM: Artificial Sequence
<220> FEATURE:
<223> OTHER INFORMATION: Nucleic acid 2F7 VLCL2 CEA

<400> SEQUENCE: 82

```
cagtctgccc tgactcagcc tgcctccgtg tctgggtctc ctggacagtc gatcaccatc    60
tcctgcactg gaaccagcag tgacgttaag tatgcgaatg cggtctcctg gtaccaacag   120
cacccaggca agccccccaa actcatgatt tattctaata gtattcggcc ctcagggggtt  180
tctaatcgct ctctctggctc caagtctggc aacacggcct ccctgaccat ctctgggctc  240
caggctgagg acgaggctga ttattactgc agctcatatg atccccgggg caacctcctg   300
atcagggtgt tcggcggagg gaccaagctg accgtcctag gtcagcccaa ggctgccccc   360
tcggtcactc tgttcccgcc ctcctctgag gagcttcaag ccaacaaggc cacactggtg   420
tgtctcataa gtgacttcta cccgggagcc gtgacagtgg cttggaaagc agatagcagc   480
cccgtcaagg cggagtggga gaccaccaca ccctccaaac aaagcaacaa caagtacgcg   540
gccagcagct atctgagcct gacgcctgag cagtggaagt cccacagaag ctacagctgc   600
caggtcacgc atgaagggag caccgtggag aagacagtgg cccctacaga atgttcataa   660
```

<210> SEQ ID NO 83
<211> LENGTH: 657
<212> TYPE: DNA
<213> ORGANISM: Artificial Sequence
<220> FEATURE:
<223> OTHER INFORMATION: Nucleic acid 2C11 VLCL2 CEA (AC27)

<400> SEQUENCE: 83

```
cagtctgtgc tgacgcagcc gccctcagtg tctggggccc cagggcagag ggtcaccatc    60
tcctgcactg ggagcagctc caacatcggt tatgctgata aggtacactg gtaccagcag   120
cttccaggaa cagccccccaa actcctcatc tataataata gcgatcggcc ctcaggggtc   180
cctgaccgat tctctggctc caagtctggc acctcagcct ccctggccat cactgggctc   240
caggctgagg atgaggctga ttattactgc cagtcctatg atggctacaa catgctgact   300
gctgtgttcg gcggagggac caagctgacc gtcctaggtc agcccaaggc tgccccctcg   360
gtcactctgt tcccgccctc ctctgaggag cttcaagcca acaaggccac actggtgtgt   420
ctcataagtg acttctaccc gggagccgtg acagtggctt ggaaagcaga tagcagcccc   480
gtcaaggcgg gagtggagac caccacaccc tccaaacaaa gcaacaacaa gtacgcggcc   540
agcagctatc tgagcctgac gcctgagcag tggaagtccc acagaagcta cagctgccag   600
gtcacgcatg aagggagcac cgtggagaag acagtggccc ctacagaatg ttcataa     657
```

<210> SEQ ID NO 84
<211> LENGTH: 657
<212> TYPE: DNA
<213> ORGANISM: Artificial Sequence
<220> FEATURE:
<223> OTHER INFORMATION: Nucleic acid C11 VLCL2 CEA (AC28)

<400> SEQUENCE: 84

```
aattttatgc tgactcagcc ccactctgtg tcggagtctc cggggaagac ggtaaccatc    60
tcctgcaccc gcagcagtgg cagcatcaat gatattacgg tgcattggta ccagcagcgc   120
ccgggcagtt ccccccacca ctgtgatctat gggtataacg cgagaccctc tggggtccct   180
gatcggttct ctggctccat cgacagctcc tccaactctg cctccctcac catctctgga   240
ctgaagactg aggacgaggc tgactactac tgtcagtcct gggatgggca tggttctgcg   300
tatgtgttcg gcggagggac caagctgacc gtcctaggtc agcccaaggc tgccccctcg   360
```

| | |
|---|---|
| gtcactctgt tcccgccctc ctctgaggag cttcaagcca acaaggccac actggtgtgt | 420 |
| ctcataagtg acttctaccc gggagccgtg acagtggctt ggaaagcaga tagcagcccc | 480 |
| gtcaaggcgg gagtggagac caccacaccc tccaaacaaa gcaacaacaa gtacgcggcc | 540 |
| agcagctatc tgagcctgac gcctgagcag tggaagtccc acagaagcta cagctgccag | 600 |
| gtcacgcatg aagggagcac cgtggagaag acagtggccc ctacagaatg ttcataa | 657 |

<210> SEQ ID NO 85
<211> LENGTH: 660
<212> TYPE: DNA
<213> ORGANISM: Artificial Sequence
<220> FEATURE:
<223> OTHER INFORMATION: Nucleic acid 2B5 VLCL2 CEA (AC29)

<400> SEQUENCE: 85

| | |
|---|---|
| cagtctgccc tgactcagcc tgcctccgtg tctgggtctc ctggacagtc gatcaccatc | 60 |
| tcctgcactg gaaccagcag tgacgttgag tttacgaatg gtgtctcctg gtaccaacag | 120 |
| cacccaggca aagcccccaa actcatgatt tatggtttta gtagtcggcc ctcaggggtt | 180 |
| tctaatcgct tctctggctc caagtctggc aacacggcct ccctgaccat ctctgggctc | 240 |
| caggctgagg acgaggctga ttattactgc agctcatatg atccccctg gcacctgctg | 300 |
| gctagggtgt tcggcggagg gaccaagctg accgtcctag gtcagcccaa ggctgccccc | 360 |
| tcggtcactc tgttcccgcc ctcctctgag gagcttcaag ccaacaaggc cacactggtg | 420 |
| tgtctcataa gtgacttcta cccgggagcc gtgacagtgg cttggaaagc agatagcagc | 480 |
| cccgtcaagg cgggagtgga gaccaccaca cccctccaaac aaagcaacaa caagtacgcg | 540 |
| gccagcagct atctgagcct gacgcctgag cagtggaagt cccacagaag ctacagctgc | 600 |
| caggtcacgc atgaagggag caccgtggag aagacagtgg cccctacaga atgttcataa | 660 |

<210> SEQ ID NO 86
<211> LENGTH: 2109
<212> TYPE: DNA
<213> ORGANISM: Homo sapiens

<400> SEQUENCE: 86

| | |
|---|---|
| atggagtctc cctcggcccc tccccacaga tggtgcatcc cctggcagag gctcctgctc | 60 |
| acagcctcac ttctaacctt ctggaacccg cccaccactg ccaagctcac tattgaatcc | 120 |
| acgccgttca atgtcgcaga ggggaaggag gtgcttctac ttgtccacaa tctgcccag | 180 |
| catctttttg gctacagctg gtacaaaggt gaaagagtgg atggcaaccg tcaaattata | 240 |
| ggatatgtaa taggaactca acaagctacc ccagggcccg catacagtgg tcgagagata | 300 |
| atataccccaa tgcatcccct gctgatccag aacatcatcc agaatgacac aggattctac | 360 |
| accctacacg tcataaagtc agatcttgtg aatgaagaag caactggcca gttccgggta | 420 |
| tacccggagc tgcccaagcc ctccatctcc agcaacaact ccaaaccegt ggaggacaag | 480 |
| gatgctgtgg ccttcacctg tgaacctgag actcaggacg caacctacct gtggtgggta | 540 |
| aacaatcaga gcctcccggt cagtcccagg ctgcagctgt ccaatggcaa caggaccctc | 600 |
| actctattca atgtcacaag aaatgacaca gcaagctaca atgtgaaaac ccagaaccca | 660 |
| gtgagtgcca ggcgcagtga ttcagtcatc ctgaatgtcc tctatggccc ggatgccccc | 720 |
| accatttccc ctctaaacac atcttacaga tcaggggaaa atctgaacct cctgctgcac | 780 |
| gcagcctcta cccacctgc acagtactct ggtttgtca atgggactt ccagcaatcc | 840 |
| acccaagagc tctttatccc caacatcact gtgaataata gtggatccta acgtgccaa | 900 |

```
gcccataact cagacactgg cctcaatagg accacagtca cgacgatcac agtctatgca    960
gagccaccca aacccttcat caccagcaac aactccaacc ccgtggagga tgaggatgct   1020
gtagccttaa cctgtgaacc tgagattcag aacacaacct acctgtggtg ggtaaataat   1080
cagagcctcc cggtcagtcc caggctgcag ctgtccaatg caacaggac  cctcactcta   1140
ctcagtgtca caaggaatga tgtaggaccc tatgagtgtg aatccagaa  caaattaagt   1200
gttgaccaca cgacccagt  catcctgaat gtcctctatg cccagacga  ccccaccatt   1260
tccccctcat acacctatta ccgtccaggg gtgaacctca gcctctcctg ccatgcagcc   1320
tctaacccac ctgcacagta ttcttggctg attgatggga acatccagca acacacacaa   1380
gagctcttta tctccaacat cactgagaag aacagcggac tctatacctg ccaggccaat   1440
aactcagcca gtggccacag caggactaca gtcaagacaa tcacagtctc tgcggagctg   1500
cccaagccct ccatctccag caacaactcc aaacccgtgg aggacaagga tgctgtggcc   1560
ttcacctgtg aacctgaggc tcagaacaca acctacctgt ggtgggtaaa tggtcagagc   1620
ctcccagtca gtcccaggct gcagctgtcc aatggcaaca ggaccctcac tctattcaat   1680
gtcacaagaa atgacgcaag agcctatgta tgtggaatcc agaactcagt gagtgcaaac   1740
cgcagtgacc cagtcaccct ggatgtcctc tatgggccgg acccccat  catttccccc   1800
ccagactcgt cttaccttc  gggagcgaac ctcaacctct cctgccactc ggcctctaac   1860
ccatccccgc agtattcttg gcgtatcaat gggataccgc agcaacacac acaagttctc   1920
tttatcgcca aaatcacgcc aaataataac gggacctatg cctgttttgt ctctaacttg   1980
gctactggcc gcaataattc catagtcaag agcatcacag tctctgcatc tggaacttct   2040
cctggtctct cagctggggc cactgtcggc atcatgattg gagtgctggt tggggttgct   2100
ctgatataa                                                           2109
```

<210> SEQ ID NO 87
<211> LENGTH: 702
<212> TYPE: PRT
<213> ORGANISM: Homo sapiens

<400> SEQUENCE: 87

```
Met Glu Ser Pro Ser Ala Pro Pro His Arg Trp Cys Ile Pro Trp Gln
1               5                   10                  15

Arg Leu Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Val His Asn Leu Pro Gln His Leu Phe Gly
    50                  55                  60

Tyr Ser Trp Tyr Lys Gly Glu Arg Val Asp Gly Asn Arg Gln Ile Ile
65                  70                  75                  80

Gly Tyr Val Ile Gly Thr Gln Gln Ala Thr Pro Gly Pro Ala Tyr Ser
                85                  90                  95

Gly Arg Glu Ile Ile Tyr Pro Asn Ala Ser Leu Leu Ile Gln Asn Ile
            100                 105                 110

Ile Gln Asn Asp Thr Gly Phe Tyr Thr Leu His Val Ile Lys Ser Asp
        115                 120                 125

Leu Val Asn Glu Glu Ala Thr Gly Gln Phe Arg Val Tyr Pro Glu Leu
    130                 135                 140

Pro Lys Pro Ser Ile Ser Ser Asn Asn Ser Lys Pro Val Glu Asp Lys
```

-continued

```
            145                 150                 155                 160
Asp Ala Val Ala Phe Thr Cys Glu Pro Glu Thr Gln Asp Ala Thr Tyr
                    165                 170                 175
Leu Trp Trp Val Asn Asn Gln Ser Leu Pro Val Ser Pro Arg Leu Gln
                    180                 185                 190
Leu Ser Asn Gly Asn Arg Thr Leu Thr Leu Phe Asn Val Thr Arg Asn
                    195                 200                 205
Asp Thr Ala Ser Tyr Lys Cys Glu Thr Gln Asn Pro Val Ser Ala Arg
            210                 215                 220
Arg Ser Asp Ser Val Ile Leu Asn Val Leu Tyr Gly Pro Asp Ala Pro
225                 230                 235                 240
Thr Ile Ser Pro Leu Asn Thr Ser Tyr Arg Ser Gly Glu Asn Leu Asn
                    245                 250                 255
Leu Ser Cys His Ala Ala Ser Asn Pro Pro Ala Gln Tyr Ser Trp Phe
                    260                 265                 270
Val Asn Gly Thr Phe Gln Gln Ser Thr Gln Glu Leu Phe Ile Pro Asn
                    275                 280                 285
Ile Thr Val Asn Asn Ser Gly Ser Tyr Thr Cys Gln Ala His Asn Ser
            290                 295                 300
Asp Thr Gly Leu Asn Arg Thr Thr Val Thr Thr Ile Thr Val Tyr Ala
305                 310                 315                 320
Glu Pro Pro Lys Pro Phe Ile Thr Ser Asn Asn Ser Asn Pro Val Glu
                    325                 330                 335
Asp Glu Asp Ala Val Ala Leu Thr Cys Glu Pro Glu Ile Gln Asn Thr
                    340                 345                 350
Thr Tyr Leu Trp Trp Val Asn Asn Gln Ser Leu Pro Val Ser Pro Arg
                    355                 360                 365
Leu Gln Leu Ser Asn Asp Asn Arg Thr Leu Thr Leu Leu Ser Val Thr
                    370                 375                 380
Arg Asn Asp Val Gly Pro Tyr Glu Cys Gly Ile Gln Asn Lys Leu Ser
385                 390                 395                 400
Val Asp His Ser Asp Pro Val Ile Leu Asn Val Leu Tyr Gly Pro Asp
                    405                 410                 415
Asp Pro Thr Ile Ser Pro Ser Tyr Thr Tyr Tyr Arg Pro Gly Val Asn
                    420                 425                 430
Leu Ser Leu Ser Cys His Ala Ala Ser Asn Pro Pro Ala Gln Tyr Ser
            435                 440                 445
Trp Leu Ile Asp Gly Asn Ile Gln Gln His Thr Gln Glu Leu Phe Ile
    450                 455                 460
Ser Asn Ile Thr Glu Lys Asn Ser Gly Leu Tyr Thr Cys Gln Ala Asn
465                 470                 475                 480
Asn Ser Ala Ser Gly His Ser Arg Thr Thr Val Lys Thr Ile Thr Val
                    485                 490                 495
Ser Ala Glu Leu Pro Lys Pro Ser Ile Ser Ser Asn Asn Ser Lys Pro
                    500                 505                 510
Val Glu Asp Lys Asp Ala Val Ala Phe Thr Cys Glu Pro Glu Ala Gln
            515                 520                 525
Asn Thr Thr Tyr Leu Trp Trp Val Asn Gly Gln Ser Leu Pro Val Ser
                    530                 535                 540
Pro Arg Leu Gln Leu Ser Asn Gly Asn Arg Thr Leu Thr Leu Phe Asn
545                 550                 555                 560
Val Thr Arg Asn Asp Ala Arg Ala Tyr Val Cys Gly Ile Gln Asn Ser
                    565                 570                 575
```

```
Val Ser Ala Asn Arg Ser Asp Pro Val Thr Leu Asp Val Leu Tyr Gly
            580                 585                 590

Pro Asp Thr Pro Ile Ile Ser Pro Asp Ser Ser Tyr Leu Ser Gly
        595                 600                 605

Ala Asn Leu Asn Leu Ser Cys His Ser Ala Ser Asn Pro Ser Pro Gln
    610                 615                 620

Tyr Ser Trp Arg Ile Asn Gly Ile Pro Gln Gln His Thr Gln Val Leu
625                 630                 635                 640

Phe Ile Ala Lys Ile Thr Pro Asn Asn Gly Thr Tyr Ala Cys Phe
                645                 650                 655

Val Ser Asn Leu Ala Thr Gly Arg Asn Asn Ser Ile Val Lys Ser Ile
                660                 665                 670

Thr Val Ser Ala Ser Gly Thr Ser Pro Gly Leu Ser Ala Gly Ala Thr
            675                 680                 685

Val Gly Ile Met Ile Gly Val Leu Val Gly Val Ala Leu Ile
        690                 695                 700

<210> SEQ ID NO 88
<211> LENGTH: 121
<212> TYPE: PRT
<213> ORGANISM: Artificial Sequence
<220> FEATURE:
<223> OTHER INFORMATION: MAB CEA1 VH

<400> SEQUENCE: 88

Gln Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asp Thr
            20                  25                  30

Tyr Met His Trp Val Arg Gln Ala Pro Gly Gln Gly Leu Glu Trp Met
        35                  40                  45

Gly Arg Ile Asp Pro Ala Asn Gly Asn Ser Lys Tyr Val Pro Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Pro Phe Gly Tyr Tyr Val Ser Asp Tyr Ala Met Ala Tyr Trp Gly
            100                 105                 110

Gln Gly Thr Leu Val Thr Val Ser Ser
        115                 120

<210> SEQ ID NO 89
<211> LENGTH: 111
<212> TYPE: PRT
<213> ORGANISM: Artificial Sequence
<220> FEATURE:
<223> OTHER INFORMATION: MAB CEA1 VL

<400> SEQUENCE: 89

Glu Ile Val Leu Thr Gln Ser Pro Ala Thr Leu Ser Leu Ser Pro Gly
1               5                   10                  15

Glu Arg Ala Thr Leu Ser Cys Arg Ala Gly Glu Ser Val Asp Ile Phe
            20                  25                  30

Gly Val Gly Phe Leu His Trp Tyr Gln Gln Lys Pro Gly Gln Ala Pro
        35                  40                  45

Arg Leu Leu Ile Tyr Arg Ala Ser Asn Arg Ala Thr Gly Ile Pro Ala
```

```
                50                  55                  60
Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Thr Asn
                85                  90                  95

Glu Asp Pro Tyr Thr Phe Gly Gln Gly Thr Lys Leu Glu Ile Lys
            100                 105                 110

<210> SEQ ID NO 90
<211> LENGTH: 125
<212> TYPE: PRT
<213> ORGANISM: Artificial Sequence
<220> FEATURE:
<223> OTHER INFORMATION: MAB CD3 VH

<400> SEQUENCE: 90

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
                20                  25                  30

Ala Met Asn Trp Val Arg Gln Ala Pro Gly Lys Gly Leu Glu Trp Val
                35                  40                  45

Ser Arg Ile Arg Ser Lys Tyr Asn Asn Tyr Ala Thr Tyr Tyr Ala Asp
50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 91
<211> LENGTH: 109
<212> TYPE: PRT
<213> ORGANISM: Artificial Sequence
<220> FEATURE:
<223> OTHER INFORMATION: MAB CD3 VL

<400> SEQUENCE: 91

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
                20                  25                  30

Asn Tyr Ala Asn Trp Val Gln Glu Lys Pro Gly Gln Ala Phe Arg Gly
                35                  40                  45

Leu Ile Gly Gly Thr Asn Lys Arg Ala Pro Gly Thr Pro Ala Arg Phe
50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 92
<211> LENGTH: 232
```

<212> TYPE: PRT
<213> ORGANISM: Artificial Sequence
<220> FEATURE:
<223> OTHER INFORMATION: CD3 VH-CL(CK)

<400> SEQUENCE: 92

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
            85                  90                  95

Tyr Cys Val Arg His Gly Asn Phe Gly Asn Ser Tyr Val Ser Trp Phe
        100                 105                 110

Ala Tyr Trp Gly Gln Gly Thr Leu Val Thr Val Ser Ser Ala Ser Val
    115                 120                 125

Ala Ala Pro Ser Val Phe Ile Phe Pro Pro Ser Asp Glu Gln Leu Lys
130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
            165                 170                 175

Ser Gln Glu Ser Val Thr Glu Gln Asp Ser Lys Asp Ser Thr Tyr Ser
        180                 185                 190

Leu Ser Ser Thr Leu Thr Leu Ser Lys Ala Asp Tyr Glu Lys His Lys
    195                 200                 205

Val Tyr Ala Cys Glu Val Thr His Gln Gly Leu Ser Ser Pro Val Thr
210                 215                 220

Lys Ser Phe Asn Arg Gly Glu Cys
225                 230

<210> SEQ ID NO 93
<211> LENGTH: 449
<212> TYPE: PRT
<213> ORGANISM: Artificial Sequence
<220> FEATURE:
<223> OTHER INFORMATION: CEA VH-CH1(EE)-Fc (hole, P329G LALA)

<400> SEQUENCE: 93

Gln Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asp Thr
            20                  25                  30

Tyr Met His Trp Val Arg Gln Ala Pro Gly Gln Gly Leu Glu Trp Met
        35                  40                  45

Gly Arg Ile Asp Pro Ala Asn Gly Asn Ser Lys Tyr Val Pro Lys Phe
50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
            85                  90                  95

-continued

```
Ala Pro Phe Gly Tyr Tyr Val Ser Asp Tyr Ala Met Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Glu Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Glu Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Asp Glu Leu Thr Lys Asn Gln Val Ser
        355                 360                 365

Leu Ser Cys Ala Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro
```

<210> SEQ ID NO 94
<211> LENGTH: 614
<212> TYPE: PRT
<213> ORGANISM: Artificial Sequence
<220> FEATURE:
<223> OTHER INFORMATION: CEA VH-CH1(EE)-CD3 VL-CH1-Fc (knob, P329G LALA)

<400> SEQUENCE: 94

```
Val Pro Lys Phe Gln Gly Arg Val Thr Ile Thr Ala Asp Thr Ser Thr
  1               5                  10                  15

Ser Thr Ala Tyr Met Glu Leu Ser Ser Leu Arg Ser Glu Asp Thr Ala
             20                  25                  30

Val Tyr Tyr Cys Ala Pro Phe Gly Tyr Val Ser Asp Tyr Ala Met
         35                  40                  45

Ala Tyr Trp Gly Gln Gly Thr Leu Val Thr Val Ser Ser Ala Ser Thr
     50                  55                  60

Lys Gly Pro Ser Val Phe Pro Leu Ala Pro Ser Ser Lys Ser Thr Ser
 65                  70                  75                  80

Gly Gly Thr Ala Ala Leu Gly Cys Leu Val Glu Asp Tyr Phe Pro Glu
                 85                  90                  95

Pro Val Thr Val Ser Trp Asn Ser Gly Ala Leu Thr Ser Gly Val His
            100                 105                 110

Thr Phe Pro Ala Val Leu Gln Ser Ser Gly Leu Tyr Ser Leu Ser Ser
            115                 120                 125

Val Val Thr Val Pro Ser Ser Leu Gly Thr Gln Thr Tyr Ile Cys
            130                 135                 140

Asn Val Asn His Lys Pro Ser Asn Thr Lys Val Asp Glu Lys Val Glu
145                 150                 155                 160

Pro Lys Ser Cys Asp Gly Gly Gly Ser Gly Gly Gly Ser Gln
                165                 170                 175

Ala Val Val Thr Gln Glu Pro Ser Leu Thr Val Ser Pro Gly Gly Thr
            180                 185                 190

Val Thr Leu Thr Cys Gly Ser Ser Thr Gly Ala Val Thr Thr Ser Asn
            195                 200                 205

Tyr Ala Asn Trp Val Gln Glu Lys Pro Gly Gln Ala Phe Arg Gly Leu
        210                 215                 220

Ile Gly Gly Thr Asn Lys Arg Ala Pro Gly Thr Pro Ala Arg Phe Ser
225                 230                 235                 240

Gly Ser Leu Leu Gly Gly Lys Ala Ala Leu Thr Leu Ser Gly Ala Gln
                245                 250                 255

Pro Glu Asp Glu Ala Glu Tyr Tyr Cys Ala Leu Trp Tyr Ser Asn Leu
            260                 265                 270

Trp Val Phe Gly Gly Gly Thr Lys Leu Thr Val Leu Ser Ser Ala Ser
        275                 280                 285

Thr Lys Gly Pro Ser Val Phe Pro Leu Ala Pro Ser Ser Lys Ser Thr
        290                 295                 300

Ser Gly Gly Thr Ala Ala Leu Gly Cys Leu Val Lys Asp Tyr Phe Pro
305                 310                 315                 320

Glu Pro Val Thr Val Ser Trp Asn Ser Gly Ala Leu Thr Ser Gly Val
                325                 330                 335

His Thr Phe Pro Ala Val Leu Gln Ser Ser Gly Leu Tyr Ser Leu Ser
            340                 345                 350

Ser Val Val Thr Val Pro Ser Ser Leu Gly Thr Gln Thr Tyr Ile
            355                 360                 365

Cys Asn Val Asn His Lys Pro Ser Asn Thr Lys Val Asp Lys Lys Val
    370                 375                 380

Glu Pro Lys Ser Cys Asp Lys Thr His Thr Cys Pro Pro Cys Pro Ala
385                 390                 395                 400

Pro Glu Ala Ala Gly Gly Pro Ser Val Phe Leu Phe Pro Pro Lys Pro
                405                 410                 415

Lys Asp Thr Leu Met Ile Ser Arg Thr Pro Glu Val Thr Cys Val Val
```

```
                420             425             430
Val Asp Val Ser His Glu Asp Pro Glu Val Lys Phe Asn Trp Tyr Val
            435             440             445

Asp Gly Val Glu Val His Asn Ala Lys Thr Lys Pro Arg Glu Glu Gln
450             455             460

Tyr Asn Ser Thr Tyr Arg Val Val Ser Val Leu Thr Val Leu His Gln
465             470             475             480

Asp Trp Leu Asn Gly Lys Glu Tyr Lys Cys Lys Val Ser Asn Lys Ala
            485             490             495

Leu Gly Ala Pro Ile Glu Lys Thr Ile Ser Lys Ala Lys Gly Gln Pro
            500             505             510

Arg Glu Pro Gln Val Tyr Thr Leu Pro Pro Cys Arg Asp Glu Leu Thr
            515             520             525

Lys Asn Gln Val Ser Leu Trp Cys Leu Val Lys Gly Phe Tyr Pro Ser
            530             535             540

Asp Ile Ala Val Glu Trp Glu Ser Asn Gly Gln Pro Glu Asn Asn Tyr
545             550             555             560

Lys Thr Thr Pro Pro Val Leu Asp Ser Asp Gly Ser Phe Phe Leu Tyr
            565             570             575

Ser Lys Leu Thr Val Asp Lys Ser Arg Trp Gln Gln Gly Asn Val Phe
            580             585             590

Ser Cys Ser Val Met His Glu Ala Leu His Asn His Tyr Thr Gln Lys
            595             600             605

Ser Leu Ser Leu Ser Pro
    610

<210> SEQ ID NO 95
<211> LENGTH: 218
<212> TYPE: PRT
<213> ORGANISM: Artificial Sequence
<220> FEATURE:
<223> OTHER INFORMATION: CEA VL-CL(RK)

<400> SEQUENCE: 95

Glu Ile Val Leu Thr Gln Ser Pro Ala Thr Leu Ser Leu Ser Pro Gly
1               5                   10                  15

Glu Arg Ala Thr Leu Ser Cys Arg Ala Gly Glu Ser Val Asp Ile Phe
            20                  25                  30

Gly Val Gly Phe Leu His Trp Tyr Gln Gln Lys Pro Gly Gln Ala Pro
        35                  40                  45

Arg Leu Leu Ile Tyr Arg Ala Ser Asn Arg Ala Thr Gly Ile Pro Ala
50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Thr Asn
            85                  90                  95

Glu Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Arg Lys
            115                 120                 125

Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
```

```
                    165                 170                 175
Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 96
<211> LENGTH: 214
<212> TYPE: PRT
<213> ORGANISM: Artificial Sequence
<220> FEATURE:
<223> OTHER INFORMATION: LC CD3 CH2527 Cross Fab VL-CH1

<400> SEQUENCE: 96

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
                20                  25                  30

Asn Tyr Ala Asn Trp Val Gln Glu Lys Pro Gly Gln Ala Phe Arg Gly
            35                  40                  45

Leu Ile Gly Gly Thr Asn Lys Arg Ala Pro Gly Thr Pro Ala Arg Phe
        50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Ser Ser Ala
            100                 105                 110

Ser Thr Lys Gly Pro Ser Val Phe Pro Leu Ala Pro Ser Ser Lys Ser
        115                 120                 125

Thr Ser Gly Gly Thr Ala Ala Leu Gly Cys Leu Val Lys Asp Tyr Phe
    130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Leu Gly Thr Gln Thr Tyr
            180                 185                 190

Ile Cys Asn Val Asn His Lys Pro Ser Asn Thr Lys Val Asp Lys Lys
        195                 200                 205

Val Glu Pro Lys Ser Cys
    210

<210> SEQ ID NO 97
<211> LENGTH: 451
<212> TYPE: PRT
<213> ORGANISM: Artificial Sequence
<220> FEATURE:
<223> OTHER INFORMATION: CEA CH1A10 VH CH1 FC Hole P329G LALA

<400> SEQUENCE: 97

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
                20                  25                  30
```

```
Gly Met Asn Trp Val Arg Gln Ala Pro Gly Gln Gly Leu Glu Trp Met
            35                  40                  45
Gly Trp Ile Asn Thr Lys Thr Gly Glu Ala Thr Tyr Val Glu Glu Phe
 50                  55                  60
Lys Gly Arg Val Thr Phe Thr Thr Asp Thr Ser Thr Ser Thr Ala Tyr
 65                  70                  75                  80
Met Glu Leu Arg Ser Leu Arg Ser Asp Asp Thr Ala Val Tyr Tyr Cys
                85                  90                  95
Ala Arg Trp Asp Phe Ala Tyr Tyr Val Glu Ala Met Asp Tyr Trp Gly
                100                 105                 110
Gln Gly Thr Thr Val Thr Val Ser Ser Ala Ser Thr Lys Gly Pro Ser
            115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Lys Val Glu Pro Lys Ser Cys
    210                 215                 220
Asp Lys Thr His Thr Cys Pro Pro Cys Pro Ala Pro Glu Ala Ala Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Gly Ala Pro Ile
                325                 330                 335
Glu Lys Thr Ile Ser Lys Ala Lys Gly Gln Pro Arg Glu Pro Gln Val
            340                 345                 350
Cys Thr Leu Pro Pro Ser Arg Asp Glu Leu Thr Lys Asn Gln Val Ser
        355                 360                 365
Leu Ser Cys Ala Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Val Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
```

```
                                  450

<210> SEQ ID NO 98
<211> LENGTH: 694
<212> TYPE: PRT
<213> ORGANISM: Artificial Sequence
<220> FEATURE:
<223> OTHER INFORMATION: CEA CH1A1A CD3 CH2527 Cross Fab VH-CK FC Knob
      P329G LALA

<400> SEQUENCE: 98

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Gly Gly Gly Gly Ser Gly Gly Gly Ser Glu Val Gln Leu Leu
225                 230                 235                 240

Glu Ser Gly Gly Gly Leu Val Gln Pro Gly Gly Ser Leu Arg Leu Ser
                245                 250                 255

Cys Ala Ala Ser Gly Phe Thr Phe Ser Thr Tyr Ala Met Asn Trp Val
            260                 265                 270

Arg Gln Ala Pro Gly Lys Gly Leu Glu Trp Val Ser Arg Ile Arg Ser
        275                 280                 285

Lys Tyr Asn Asn Tyr Ala Thr Tyr Tyr Ala Asp Ser Val Lys Gly Arg
    290                 295                 300

Phe Thr Ile Ser Arg Asp Asp Ser Lys Asn Thr Leu Tyr Leu Gln Met
305                 310                 315                 320

Asn Ser Leu Arg Ala Glu Asp Thr Ala Val Tyr Tyr Cys Val Arg His
                325                 330                 335

Gly Asn Phe Gly Asn Ser Tyr Val Ser Trp Phe Ala Tyr Trp Gly Gln
            340                 345                 350
```

```
Gly Thr Leu Val Thr Val Ser Ser Ala Ser Val Ala Ala Pro Ser Val
            355                 360                 365

Phe Ile Phe Pro Pro Ser Asp Glu Gln Leu Lys Ser Gly Thr Ala Ser
370                 375                 380

Val Val Cys Leu Leu Asn Asn Phe Tyr Pro Arg Glu Ala Lys Val Gln
385                 390                 395                 400

Trp Lys Val Asp Asn Ala Leu Gln Ser Gly Asn Ser Gln Glu Ser Val
                405                 410                 415

Thr Glu Gln Asp Ser Lys Asp Ser Thr Tyr Ser Leu Ser Ser Thr Leu
            420                 425                 430

Thr Leu Ser Lys Ala Asp Tyr Glu Lys His Lys Val Tyr Ala Cys Glu
        435                 440                 445

Val Thr His Gln Gly Leu Ser Ser Pro Val Thr Lys Ser Phe Asn Arg
    450                 455                 460

Gly Glu Cys Asp Lys Thr His Thr Cys Pro Pro Cys Pro Ala Pro Glu
465                 470                 475                 480

Ala Ala Gly Gly Pro Ser Val Phe Leu Phe Pro Pro Lys Pro Lys Asp
                485                 490                 495

Thr Leu Met Ile Ser Arg Thr Pro Glu Val Thr Cys Val Val Val Asp
            500                 505                 510

Val Ser His Glu Asp Pro Glu Val Lys Phe Asn Trp Tyr Val Asp Gly
        515                 520                 525

Val Glu Val His Asn Ala Lys Thr Lys Pro Arg Glu Glu Gln Tyr Asn
    530                 535                 540

Ser Thr Tyr Arg Val Val Ser Val Leu Thr Val Leu His Gln Asp Trp
545                 550                 555                 560

Leu Asn Gly Lys Glu Tyr Lys Cys Lys Val Ser Asn Lys Ala Leu Gly
                565                 570                 575

Ala Pro Ile Glu Lys Thr Ile Ser Lys Ala Lys Gly Gln Pro Arg Glu
            580                 585                 590

Pro Gln Val Tyr Thr Leu Pro Pro Cys Arg Asp Glu Leu Thr Lys Asn
        595                 600                 605

Gln Val Ser Leu Trp Cys Leu Val Lys Gly Phe Tyr Pro Ser Asp Ile
    610                 615                 620

Ala Val Glu Trp Glu Ser Asn Gly Gln Pro Glu Asn Asn Tyr Lys Thr
625                 630                 635                 640

Thr Pro Pro Val Leu Asp Ser Asp Gly Ser Phe Phe Leu Tyr Ser Lys
                645                 650                 655

Leu Thr Val Asp Lys Ser Arg Trp Gln Gln Gly Asn Val Phe Ser Cys
            660                 665                 670

Ser Val Met His Glu Ala Leu His Asn His Tyr Thr Gln Lys Ser Leu
        675                 680                 685

Ser Leu Ser Pro Gly Lys
    690

<210> SEQ ID NO 99
<211> LENGTH: 215
<212> TYPE: PRT
<213> ORGANISM: Artificial Sequence
<220> FEATURE:
<223> OTHER INFORMATION: LC CEA 2F1 84

<400> SEQUENCE: 99

Asp Ile Gln Met Thr Gln Ser Pro Ser Ser Leu Ser Ala Ser Val Gly
1               5                   10                  15
```

```
Asp Arg Val Thr Ile Thr Cys Lys Ala Ser Ala Val Gly Thr Tyr
            20                  25                  30

Val Ala Trp Tyr Gln Gln Lys Pro Gly Lys Ala Pro Lys Leu Leu Ile
        35                  40                  45

Tyr Ser Ala Ser Tyr Arg Lys Arg Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
210                 215

<210> SEQ ID NO 100
<211> LENGTH: 106
<212> TYPE: PRT
<213> ORGANISM: Artificial Sequence
<220> FEATURE:
<223> OTHER INFORMATION: VK_SM3E

<400> SEQUENCE: 100

Glu Asn Val Leu Thr Gln Ser Pro Ser Ser Met Ser Val Ser Val Gly
1               5                   10                  15

Asp Arg Val Asn Ile Ala Cys Ser Ala Ser Ser Ser Val Pro Tyr Met
            20                  25                  30

His Trp Leu Gln Gln Lys Pro Gly Lys Ser Pro Lys Leu Leu Ile Tyr
        35                  40                  45

Leu Thr Ser Asn Leu Ala Ser Gly Val Pro Ser Arg Phe Ser Gly Ser
50                  55                  60

Gly Ser Gly Thr Asp Tyr Ser Leu Thr Ile Ser Ser Val Gln Pro Glu
65                  70                  75                  80

Asp Ala Ala Thr Tyr Tyr Cys Gln Gln Arg Ser Ser Tyr Pro Leu Thr
                85                  90                  95

Phe Gly Gly Gly Thr Lys Leu Glu Ile Lys
            100                 105

<210> SEQ ID NO 101
<211> LENGTH: 120
<212> TYPE: PRT
<213> ORGANISM: Artificial Sequence
<220> FEATURE:
<223> OTHER INFORMATION: VH_SM3E

<400> SEQUENCE: 101
```

Gln Val Lys Leu Glu Gln Ser Gly Ala Glu Val Val Lys Pro Gly Ala
1               5                   10                  15

Ser Val Lys Leu Ser Cys Lys Ala Ser Gly Phe Asn Ile Lys Asp Ser
            20                  25                  30

Tyr Met His Trp Leu Arg Gln Gly Pro Gly Gln Arg Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Phe Thr Thr Asp Thr Ser Ala Asn Thr Ala Tyr
65                  70                  75                  80

Leu Gly Leu Ser Ser Leu Arg Pro Glu Asp Thr Ala Val Tyr Tyr Cys
                85                  90                  95

Asn Glu Gly Thr Pro Thr Gly Pro Tyr Tyr Phe Asp Tyr Trp Gly Gln
            100                 105                 110

Gly Thr Leu Val Thr Val Ser Ser
        115                 120

<210> SEQ ID NO 102
<211> LENGTH: 116
<212> TYPE: PRT
<213> ORGANISM: Artificial Sequence
<220> FEATURE:
<223> OTHER INFORMATION: VL_MEDI

<400> SEQUENCE: 102

Gln Ala Val Leu Thr Gln Pro Ala Ser Leu Ser Ala Ser Pro Gly Ala
1               5                   10                  15

Ser Ala Ser Leu Thr Cys Thr Leu Arg Arg Gly Ile Asn Val Gly Ala
            20                  25                  30

Tyr Ser Ile Tyr Trp Tyr Gln Gln Lys Pro Gly Ser Pro Pro Gln Tyr
        35                  40                  45

Leu Leu Arg Tyr Lys Ser Asp Ser Asp Lys Gln Gln Gly Ser Gly Val
    50                  55                  60

Ser Ser Arg Phe Ser Ala Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His Ser Gly Ala Ser Ala Val Phe Gly Gly Gly Thr Lys
            100                 105                 110

Leu Thr Val Leu
        115

<210> SEQ ID NO 103
<211> LENGTH: 121
<212> TYPE: PRT
<213> ORGANISM: Artificial Sequence
<220> FEATURE:
<223> OTHER INFORMATION: VH_MEDI

<400> SEQUENCE: 103

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Val Ser Ser Tyr
            20                  25                  30

Trp Met His Trp Val Arg Gln Ala Pro Gly Lys Gly Leu Glu Trp Val
        35                  40                  45

Gly Phe Ile Arg Asn Lys Ala Asn Gly Gly Thr Thr Glu Tyr Ala Ala

```
                    50                  55                  60
Ser Val Lys Gly Arg Phe Thr Ile Ser Arg Asp Asp Ser Lys Asn Thr
 65                  70                  75                  80

Leu Tyr Leu Gln Met Asn Ser Leu Arg Ala Glu Asp Thr Ala Val Tyr
                     85                  90                  95

Tyr Cys Ala Arg Asp Arg Gly Leu Arg Phe Tyr Phe Asp Tyr Trp Gly
                    100                 105                 110

Gln Gly Thr Thr Val Thr Val Ser Ser
                115                 120

<210> SEQ ID NO 104
<211> LENGTH: 107
<212> TYPE: PRT
<213> ORGANISM: Artificial Sequence
<220> FEATURE:
<223> OTHER INFORMATION: VK_SAR

<400> SEQUENCE: 104

Asp Ile Gln Met Thr Gln Ser Pro Ser Ser Leu Ser Ala Ser Val Gly
 1               5                  10                  15

Asp Arg Val Thr Ile Thr Cys Arg Ala Ser Glu Asn Ile Phe Ser Tyr
                 20                  25                  30

Leu Ala Trp Tyr Gln Gln Lys Pro Gly Lys Ala Pro Lys Leu Leu Ile
             35                  40                  45

Tyr Asn Thr Arg Thr Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln His His Tyr Gly Thr Pro Phe
                     85                  90                  95

Thr Phe Gly Gln Gly Thr Lys Leu Glu Ile Lys
                100                 105

<210> SEQ ID NO 105
<211> LENGTH: 120
<212> TYPE: PRT
<213> ORGANISM: Artificial Sequence
<220> FEATURE:
<223> OTHER INFORMATION: VH_SAR

<400> SEQUENCE: 105

Glu Val Gln Leu Val Glu Ser Gly Gly Leu Val Gln Pro Gly Gly
 1               5                  10                  15

Ser Leu Arg Leu Ser Cys Ala Ala Ser Gly Phe Val Phe Ser Ser Tyr
                 20                  25                  30

Asp Met Ser Trp Val Arg Gln Ala Pro Gly Lys Gly Leu Glu Trp Val
             35                  40                  45

Ser Tyr Ile Ser Ser Gly Gly Gly Ile Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Ala His Tyr Phe Gly Ser Ser Gly Pro Phe Ala Tyr Trp Gly Gln
                100                 105                 110

Gly Thr Leu Val Thr Val Ser Ser
                115                 120
```

```
<210> SEQ ID NO 106
<211> LENGTH: 108
<212> TYPE: PRT
<213> ORGANISM: Artificial Sequence
<220> FEATURE:
<223> OTHER INFORMATION: VK_CH1A1A

<400> SEQUENCE: 106

Asp Ile Gln Met Thr Gln Ser Pro Ser Ser Leu Ser Ala Ser Val Gly
1               5                   10                  15

Asp Arg Val Thr Ile Thr Cys Lys Ala Ser Ala Ala Val Gly Thr Tyr
            20                  25                  30

Val Ala Trp Tyr Gln Gln Lys Pro Gly Lys Ala Pro Lys Leu Leu Ile
        35                  40                  45

Tyr Ser Ala Ser Tyr Arg Lys Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys
            100                 105

<210> SEQ ID NO 107
<211> LENGTH: 121
<212> TYPE: PRT
<213> ORGANISM: Artificial Sequence
<220> FEATURE:
<223> OTHER INFORMATION: VH_ CH1A1A

<400> SEQUENCE: 107

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser
        115                 120

<210> SEQ ID NO 108
<211> LENGTH: 111
<212> TYPE: PRT
<213> ORGANISM: Artificial Sequence
<220> FEATURE:
<223> OTHER INFORMATION: VK_T84.66

<400> SEQUENCE: 108

Glu Ile Val Leu Thr Gln Ser Pro Ala Thr Leu Ser Leu Ser Pro Gly
1               5                   10                  15

Glu Arg Ala Thr Leu Ser Cys Arg Ala Gly Glu Ser Val Asp Ile Phe
```

```
            20                  25                  30
Gly Val Gly Phe Leu His Trp Tyr Gln Gln Lys Pro Gly Gln Ala Pro
        35                  40                  45

Arg Leu Leu Ile Tyr Arg Ala Ser Asn Arg Ala Thr Gly Ile Pro Ala
 50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln Gln Thr Asn
                 85                  90                  95

Glu Asp Pro Tyr Thr Phe Gly Gln Gly Thr Lys Leu Glu Ile Lys
                100                 105                 110

<210> SEQ ID NO 109
<211> LENGTH: 121
<212> TYPE: PRT
<213> ORGANISM: Artificial Sequence
<220> FEATURE:
<223> OTHER INFORMATION: VH_T84.66

<400> SEQUENCE: 109

Gln Val Gln Leu Val Gln Ser Gly Ala Glu Val Lys Lys Pro Gly Ser
 1               5                  10                  15

Ser Val Lys Val Ser Cys Lys Ala Ser Gly Phe Asn Ile Lys Asp Thr
                 20                  25                  30

Tyr Met His Trp Val Arg Gln Ala Pro Gly Gln Gly Leu Glu Trp Met
             35                  40                  45

Gly Arg Ile Asp Pro Ala Asn Gly Asn Ser Lys Tyr Val Pro Lys Phe
 50                  55                  60

Gln Gly Arg Val Thr Ile Thr Ala Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Pro Phe Gly Tyr Tyr Val Ser Asp Tyr Ala Met Ala Tyr Trp Gly
                100                 105                 110

Gln Gly Thr Leu Val Thr Val Ser Ser
        115                 120

<210> SEQ ID NO 110
<211> LENGTH: 106
<212> TYPE: PRT
<213> ORGANISM: Artificial Sequence
<220> FEATURE:
<223> OTHER INFORMATION: VK_LABETUZUMAB

<400> SEQUENCE: 110

Asp Ile Gln Leu Thr Gln Ser Pro Ser Ser Leu Ser Ala Ser Val Gly
 1               5                  10                  15

Asp Arg Val Thr Ile Thr Cys Lys Ala Ser Gln Asp Val Gly Thr Ser
                 20                  25                  30

Val Ala Trp Tyr Gln Gln Lys Pro Gly Lys Ala Pro Lys Leu Leu Ile
             35                  40                  45

Tyr Trp Thr Ser Thr Arg His Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Ser Leu Tyr Arg Ser
                 85                  90                  95
```

Phe Gly Gln Gly Thr Lys Val Glu Ile Lys
            100                 105

<210> SEQ ID NO 111
<211> LENGTH: 119
<212> TYPE: PRT
<213> ORGANISM: Artificial Sequence
<220> FEATURE:
<223> OTHER INFORMATION: VH_LABETUZUMAB

<400> SEQUENCE: 111

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Asp Phe Thr Thr Tyr
            20                  25                  30

Trp Met Ser Trp Val Arg Gln Ala Pro Gly Lys Gly Leu Glu Trp Ile
        35                  40                  45

Gly Glu Ile His Pro Asp Ser Ser Thr Ile Asn Tyr Ala Pro Ser Leu
    50                  55                  60

Lys Asp Arg Phe Thr Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Ser Leu Tyr Phe Gly Phe Pro Trp Phe Ala Tyr Trp Gly Gln Gly
            100                 105                 110

Thr Pro Val Thr Val Ser Ser
        115

<210> SEQ ID NO 112
<211> LENGTH: 13
<212> TYPE: PRT
<213> ORGANISM: Artificial Sequence
<220> FEATURE:
<223> OTHER INFORMATION: Mab CEA 1B2 (AC39) CDRL1

<400> SEQUENCE: 112

Ser Gly Ser Ser Ser Glu Ile Thr Ala Ser Gly Val Ser
1               5                   10

<210> SEQ ID NO 113
<211> LENGTH: 7
<212> TYPE: PRT
<213> ORGANISM: Artificial Sequence
<220> FEATURE:
<223> OTHER INFORMATION: Mab CEA 1B2 (AC39) CDRL2

<400> SEQUENCE: 113

Asp Asn Asn Lys Arg Pro Ser
1               5

<210> SEQ ID NO 114
<211> LENGTH: 11
<212> TYPE: PRT
<213> ORGANISM: Artificial Sequence
<220> FEATURE:
<223> OTHER INFORMATION: Mab CEA 1B2 (AC39) CDRL3

<400> SEQUENCE: 114

Gly Thr Trp Asp Phe Pro Pro Ser Arg Phe Val
1               5                   10

<210> SEQ ID NO 115
<211> LENGTH: 216

```
<212> TYPE: PRT
<213> ORGANISM: Artificial Sequence
<220> FEATURE:
<223> OTHER INFORMATION: Mab CEA 1B2 (AC39) VLCL2

<400> SEQUENCE: 115

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Glu Ile Thr Ala Ser
            20                  25                  30

Gly Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Phe Pro Pro
                85                  90                  95

Ser Arg Phe Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 116
<211> LENGTH: 651
<212> TYPE: DNA
<213> ORGANISM: Artificial Sequence
<220> FEATURE:
<223> OTHER INFORMATION: Mab CEA 1B2 (AC39) VLCL2, nucleic acid

<400> SEQUENCE: 116
cagtctgtgt tgacgcagcc gccctcagtg tctgcggccc caggacagaa ggtcaccatc        60
tcctgctctg gaagcagctc cgagattact gcgtctggtg tatcctggta ccagcagctc       120
ccaggaacag cccccaaact cctcatttat gacaataata agcgaccctc agggattcct       180
gaccgattct ctggctccaa gtctggcacg tcagccaccc tgggcatcac cggactccag       240
actggggacg aggccgatta ttactgcgga acatgggatt tcccgccgtc aggttcgtg        300 ttcggcggag ggaccaagct gaccgtccta ggtcagccca aggctgcccc ctcggtcact       360
ctgttcccgc cctcctctga ggagcttcaa gccaacaagg ccacactggt gtgtctcata       420
agtgacttct acccgggagc cgtgacagtg gcttggaaag cagatagcag ccccgtcaag       480
```

```
gcgggagtgg agaccaccac accctccaaa caaagcaaca acaagtacgc ggccagcagc    540
tatctgagcc tgacgcctga gcagtggaag tcccacagaa gctacagctg ccaggtcacg    600
catgaaggga gcaccgtgga gaagacagtg gcccctacag aatgttcata a             651
```

BISPECIFIC ANTIBODIES AGAINST CEACAM5 AND CD47

REFERENCE TO SEQUENCE LISTING

The content of the electronically submitted sequence listing ("4130_0020009_SeqListing_ST25.txt", 122,773 bytes, created on May 31, 2019) filed with the application is incorporated herein by reference in its entirety.

FIELD OF THE INVENTION

The present invention relates to bispecific antibodies which bind to human carcinoembryonic antigen CEACAM5 (CEA) and human CD47 (CEA×CD47 bispecific antibodies). In addition, the present invention relates to polynucleotides encoding such bispecific antibodies and vectors and host cells comprising such polynucleotides. The invention further relates to methods for selecting and producing such antibodies and to methods of using such antibodies in the treatment of diseases. The invention also relates to the therapeutic use of the CEA×CD47 bispecific antibodies in monotherapy and in combination therapy, especially with CEA×CD3 T-cell bispecific antibodies (TCB) and/or inhibitors of PD-1 or PD-L1.

BACKGROUND OF THE INVENTION

The human CEA family contains 29 genes, of which 18 are expressed: 7 belonging to the CEA subgroup and 11 to the pregnancy-specific glycoprotein subgroup. Several CEA subgroup members are thought to possess cell adhesion properties. CEA is thought to have a role in innate immunity (Hammarström S., Semin Cancer Biol. 9(2):67-81 (1999)). Carcinoembryonic antigen (CEA, CEACAM5 or CD66e; UniProtKB—P06731) is a member of the carcinoembryonic antigen-related cell adhesion molecule (CEACAM) family and a tumor-associated antigen (Gold and Freedman, J Exp. Med., 121:439-462, 1965; Berinstein N. L., J Clin Oncol., 20:2197-2207, 2002). CEACAM6 (CD66c; UniProtKB—P40199) belongs also to the carcinoembryonic antigen (CEA) family. Multiple monoclonal antibodies have been raised against CEA for research purposes, as diagnostic tools, and for therapeutic purposes (see e.g. WO2012117002 (incorporated by reference in its entirety), see also Example 8 f)). Soluble CEA—in this application also called shed CEA or sCEA—is an established tumor marker. Levels in plasma of cancer patients can go in some cases over 1000 ng/ml, whereas plasma concentrations in healthy individuals are below 10 ng/ml (e.g. Sandler B. et al Anticancer Res 1999, 19(5B), 4229-33). Hao C., Zhang G. and L. in Progress in Molecular Biology and Translational Science (2019) report that CEA plasma concentrations between 100 and 250 ng/mL can be found in a significant % of patients in Pancreatic Cancer, Colon- and Rectal Cancer, Lung Cancer and Gastric Cancer. Such high levels are especially observed when these cancers are locally advanced and/or metastatic. According to Wanebo et. al., New Eng. J. Med. (1978) 21% of recurrent/meatastatic colon cancer have sCEA above 100 ng/ml. Hohenberger et. al., Annals Surgery (1994) report in colorectal patients, stage Duke 4 and liver metastasis, that 26% of patients have sCEA over 50 ng/mL. Jurgensmerier et al Br. J. Cancer (2013) report in rather large studies with several hundred of patients suffering from metastatic colorectal cancer sCEA above 225 ng/mL in 24% respectively 25% of these patients. Soluble CEA can compete with therapeutic anti-CEA antibodies for binding to the CEA on the tumor cells potentially causing decreased efficacy of the anti-CEA antibody. This can be avoided in the majority of cancer patients, e.g. colorectal cancer patients, by using anti-CEA antibodies with limited cross-reactivity to soluble CEA up to sCEA plasma concentrations of 100 to 250 ng/ml The mouse monoclonal antibody PR1A3 was raised by fusion of NS1 (P3/NS 1/I-Ag-4-1) myeloma cells with spleen cells from mice immunized with normal colorectal epithelium Richman P. I. and Bodmer W. F., Int. J. Cancer, 39:317-328, 1987 describe mouse monoclonal antibody PR1A3. Epitope mapping of PR1A3 shows that the antibody targets the B3 domain and the GPI anchor of the CEA molecule (Durbin H. et al., Proc. Natl. Scad. Sci. USA, 91:4313-4317, 1994). Consequently, the PR1A3 antibody binds mainly to the membrane-bound CEA, and not the soluble CEA form that can be found in the bloodstreams of cancer patients. The epitope bound by PR1 A3 is a conformational epitope, not a linear epitope (Stewart et al., Cancer Immunol Immunother, 47 (1999) 299-06). Humanized PRI A3 (hPR1 A3) antibodies are described e.g. by Conaghhan P. J., et al., Br. J. Cancer, 98 (2008)1217-1225 and WO2012117002 (incorporated by reference in its entirety).

A method for treating cancer by a combination of a human PD-1 axis antagonist and an anti-CEA/anti-CD3 bispecific antibody is mentioned in US20140242079 and WO2017118657 (each of which is incorporated by reference in its entirety) and clinical results have been published at ASCO conference 2017 (Tabernero et al, J Clin Oncol 35, 2017 (suppl; abstr 3002)). A method of treating tumors by administering immune checkpoint antagonists binding two or more different targets of an immune checkpoint pathway, and a T cell-redirecting agent binding to CEA and a T cell surface antigen is mentioned in WO2015112534. A conjugate consisting of a single domain anti-CEACAM6 antibody and urease is at present in clinical trials (NCT02309892; WO2016116907). A class I antibody binding to CEACAM5, CEACAM6 and granulocytes is mentioned in US20110064653.

An anti CD3ε antibody described in the state of the art is SP34 (Yang S J, The Journal of Immunology (1986) 137; 1097-1100). SP34 reacts with both primate and human CD3. SP34 is available from BD Biosciences. A further anti CD3 antibody described in the state of the art is UCHT-1 (see WO2000041474). A further anti CD3 antibody described in the state of the art is BC-3 (Fred Hutchinson Cancer Research Institute; used in Phase I/II trials of GvHD, Anasetti et al., Transplantation 54: 844 (1992)). SP34 differs from UCHT-1 and BC-3 in that SP-34 recognizes an epitope present on solely the ε chain of CD3 (see Salmeron et al., (1991) J. Immunol. 147: 3047) whereas UCHT-1 and BC-3 recognize an epitope contributed by both the ε and γ chains. Anti CD3 antibodies are also described in WO2007042261, WO2008119565, WO2008119566, WO2008119567, WO2010037836, WO2010037837, WO2010037838, and U.S. Pat. No. 8,236,308 (each of which is incorporated by reference in its entirety). A bispecific antibody comprising a binding part specific for CEA and a binding part specific for CD3ε is described in US20140242079A1 (incorporated by reference in its entirety).

Human CD47 (UniProtKB—Q08722 (CD47_HUMAN; IAP) is a transmembrane protein that binds the ligands thrombospondin-1 (TSP-1) and signal-regulatory protein alpha (SIRPα; CD172a; UniProtKB P78324) and can act as a "don't eat me" signal to the immune system, especially for macrophages. CD47 is involved in a range of cellular processes, including apoptosis, proliferation, adhesion, and migration. Furthermore, it plays a key role in immune and angiogenic responses. CD47 is overexpressed in different tumor cells. Antibodies against CD47 are described in the state of the art and some are in clinical trials as therapeutic agents for tumor treating (Weiskopf K. European Journal of Cancer 76 (2017) 100-109; Huang Y et al., J Thorac Dis 2017; 9(2):E168-E174. Antibodies of the IgG1 subclass that bind CD47 can result in the depletion of platelets and reduction of red blood cells RBC of hemoglobin in a Fc-dependent manner (see e.g. US20140140989). For avoiding this adverse effect, in WO2017196793 there is described a mutant form of the IgG4 subclass of an anti-CD47 antibody (IgG4PE, with the S228P mutation as well as a L235E mutation to reduce FcγR binding). Such anti-CD47 antibody with severely reduced FcγR binding and effector function does not result in such platelet depletion. A single domain bispecific antibody against CD47 and CD20 was described by von Bommel P E et al., Oncoimmunol. 7 (2018) e386361 and Piccione E C et al. mAbs 7 (2015)946-956. Dheilly E. et al., Mol. Thera. 25 (2017) 523-533 (see also WO2014087248) describe a bispecific antibody against CD19 and CD47. A bispecific antibody against CD19 and CD47 comprising a common heavy chain of SEQ ID NO:5 and a variable light domain VL of SEQ ID NO:10 is described in WO2014087248 (incorporated by reference in its entirety).

Human FcRI (CD64) is restricted to monocytes/macrophages and dendritic cells (DCs) and, inducibly expressed on neutrophils and mast cells; hFc RIIA (CD32A) is expressed on all myeloid cells but not on lymphocytes; hFc RIIB (CD32B) is highly expressed only on circulating B cells and basophils (L. Cassard, F. Joensson, S. Arnaud, M. Dacron, J. Immunol. 189 (2012(2995-3006), poorly expressed on 20% of the monocytes and 4% of the neutrophils, and expressed on tissue macrophages and DCs, but not on mast cells hFc RUC (CD32C) is expressed on NK cells, monocytes, and neutrophils. hFc RIIIA (CD16A) is expressed on NK cells and monocytes/macrophages; hFcRIIIB CD16B) is expressed on neutrophils and, as recently demonstrated, on subsets of basophils. These expression patterns highlight that hFc RIIA is the only activating IgG receptor constitutively expressed by mast cells, basophils, neutrophils and eosinophils (Bruhns P., Blood 119 (2012) 5640). The biological activities of each subclass of IgG are poorly known. IgG receptors (FcγRs) are strikingly numerous in humans. They comprise high-affinity and low-affinity receptors. Both high-affinity and low-affinity FcγRs bind IgG-immune complexes with a high avidity, but only high-affinity FcγRs bind monomeric IgG. There is one high-affinity IgG receptor in humans, hFcγRI (CD64), and two families of low-affinity IgG receptors, hFcγ RIIA, IIB, and IIC (CD32), and hFcγRIIIA and IIIB (CD16). hFcγRI and hFcγRIIIA are FcγR associated activating receptors, hFcγRIIA and hFcγRIIC are single-domain activating receptors, hFcγRIIB are single-domain inhibitory receptors, and hFcγRIIIB are GPI-anchored receptors whose function is uncertain (Bruhns P. Blood 113 (2009) 3716). Several research groups have demonstrated that antibodies, lacking the 1,6-fucose on their heavy chain glycosylation, have enhanced binding affinity to the FcγRIII receptor and increased ADCC activity (Shields, R. L., et al., (2002) J Biol. Chem. 277, 26733-26740; (2002) J Biol. Chem. 8, 8). In addition, a correlation between binding affinity to the FcγRIII receptor and ADCC activity has been established (Okazaki, A., et al., (2004) J Mol. Biol. 336, 1239-1249; Dall'Ozzo, 2004). An IgG molecule carries two N-linked oligosaccharides in its Fc region, one on each heavy chain. As any glycoprotein, an antibody is produced as a population of glycoforms which share the same polypeptide backbone but have different oligosaccharides attached to the glycosylation sites. The oligosaccharides normally found in the Fc region of serum IgG are of complex bi-antennary type (Wormald et al., Biochemistry 36: 130-38 (1997), with a low level of terminal sialic acid and bisecting N-acetylglucosamine (GlcNAc), and a variable degree of terminal galactosylation and core fucosylation. Some studies suggest that the minimal carbohydrate structure required for FcγR binding lies within the oligosaccharide core. Lund et al., J. Immunol. 157:4963-69 (1996). Antibodies with a reduced fucose content in glycan moieties exhibit higher antibody dependent cellular cytotoxicity (ADCC) activity compared to a normally fucosylated antibody (Niwa R et al., Cancer Res, 64, 2127-33, 2004). The mechanism behind the enhanced ADCC of a low/no-fucose antibody is its increased affinity to FcγRIIIa (CD16). A cell line with knockout of both alleles for the gene responsible for fucose addition (α1,6-fucosyltransferase; FUT8) is described in U.S. Pat. Nos. 6,946,292, 7,425,446, 8,067,232 (each of which is incorporated by reference in its entirety), and under. Overexpression in Chinese hamster ovary (CHO) cells of β(1, 4)-N-acetylglucosaminyltransferase III (GnTIII), a glycosyltransferase catalyzing the formation of bisected oligosaccharides, significantly increases the in vitro ADCC activity of antibodies produced by the engineered CHO cells. (Umaña, P. et al., Nature Biotechnol. 17:176-180 (1999), WO199954342, US20030175884 (each of which is incorporated by reference in its entirety)). Mutations within the Fc domain can also alter binding properties of the Fc domain to the different Fc receptors (WO2004063351, WO2004099249; WO2005018669, WO2005063815, WO2005110474, WO2005056759, WO2005092925, WO2005018572, WO2006019447, WO2006116260, WO2006023420-, WO2006047350, WO2006085967, WO2006105338, WO2007021841, WO2007008943, WO2007024249, WO2007041635, WO2007048077, WO2007044616, WO2007106707, WO2008022152, WO2008140603, WO2008036688, WO2008091798, WO2008091954, WO2008092117, WO2008098115, WO2008121160, WO2008150494, WO2010033736, WO2014113510 (each of which is incorporated by reference in its entirety)).

Considerable progress has been made in the treatment of hematological malignancies. That is in contrast to the progression made in the treatment of several types of advanced solid tumors. Progression free survival (PFS) and overall survival (OS) of those advanced tumor types, many of those rather frequent, was to some extent improved by new chemotherapy schemes with and w/o monoclonal antibodies against e.g. VEGFR or ERGFR as combination partner to chemotherapy. But in the past years for many of the advanced/metastatic solid tumors the progress of drug therapy was limited. Much hope has been put into cancer immunotherapy and there are certain, but limited, successes. Tumors develop measures to protect their cells from destruction by T-effector cells and other immune cells like macrophages. Cancer immunotherapy in the last decade(s) had certainly quite some focus and success on making T-cells fit again and to re-direct them against cancer cells. The most prominent examples are inhibitors/activators of certain immune checkpoints. E. g. checkpoint inhibitors like PD-1 axis antagonists have shown to re-activate T-effector cells to fight certain solid cancers. But not all solid tumor types are responsive and even in those responsive, it is often much less than 50% of patients having a relevant benefit from e.g. treatment with an anti-PD-1 or PD-L1 antibody.

Adoptive T-cell therapy with CAR T-cells and also therapy with T-cell bispecific antibodies delivered promising clinical results in hematological malignancies. But clinical studies with adoptive T-cell therapies, e.g. CAR T-cells, in various solid tumors mostly showed no or only minor response rates (e.g. Xu et. al. Expert Review of Anticancer Therapy 2017, 17, 1099-1106).

US20140242079 and WO2017055389 (each of which is incorporated by reference in its entirety) describe CEA× CD3 T-cell bispecific antibodies. One antibody from US20140242079 and one from WO2017055389 are both in clinical development (see RO6958688 in NCT3866239 and RO7172508 in NCT03539484). These T-cell bispecific antibodies bind to different epitopes of CEA×CD3 and have different tumor cell killing potency. Regarding tumor cell killing in an in vitro assay with human T-cells, most potent CEA×CD3 T-cell bispecific antibodies described in WO201705389 are by a factor of 10 to 100 or more potent than RO6958688/cibisatamab (CEA-TCB).

Until recently results of clinical trials with T-cell bispecific antibodies TAA×CD3 (TAA=Tumor Associated Antigen) in patients with advanced solid tumors were disappointing. But preliminary phase 1 results have been published at ASCO 2017 for the CEA×CD3 T-cell bispecific antibody CEA-TCB (RO6958688/cibisatamab, see for example Bacac et al Clin. Cancer Res., 22(13), 3286-97 (2016); and US20140242079) showing in advanced colorectal cancer patients in monotherapy partial responses and stable disease (J. Tabernero et. al., J. Clin. Oncol. 35, 2017 (suppl. Abstr. 3002)). At clinically active doses plasma concentrations of e.g. 300 Nm have been reached for cibisatamab. More partial responses and stable disease occurred when CEA-TCB was combined with a PD-L1 inhibiting antibody. These data show that efficacy can be achieved with CEA-TCB in advanced solid tumors. But in monotherapy and also in the combination with a PD-L1 inhibitor, most of the patients were still progressing and those reacting showed at best partial responses and stable disease, but no complete responses have been achieved. One approach to get better results could be to add to T-cell bispecific antibodies not only an inhibitor of PD-1 checkpoint axis, but to add further checkpoint inhibitors or agonists. But so far, to the best of our knowledge, there are no promising clinical data for such a combination approach available. Limited availability of T-cells within advanced solid tumors is certainly an important mechanism limiting the efficacy achievable with T-cell bispecific antibodies plus PD-1 axis inhibitors and/or other checkpoint inhibitors or agonists for T-cells.

Instead of adding to the combination of a T-cell bispecific antibody and a PD-1 axis inhibitor another therapeutic agent aiming to re-direct T-cells against tumor cells of advanced solid tumors, it may be more successful to add a therapeutic agent re-directing to the tumor cells other immune cells, especially macrophages or macrophages and natural killer NK-cells. This invention deals with bispecific antibodies re-directing macrophages and also NK-cells against CEA expressing solid tumors as a monotherapy or in combination with e.g. T-cell bispecific antibodies and/or PD-1/PD-L1 inhibiting antibodies.

The disappointing results with CAR T-cells in solid tumors may have a simple explanation—the number of CAR T-cells penetrating the solid tumor and distributed in it are just not sufficient. This is certainly different in the majority of haematological malignancies; CAR T-cells can well access the tumor cells, explaining the difference of high efficacy in these malignancies compared to disappointing efficacy in solid tumors. In addition, CAR T-cells may be heavily suppressed by the tumor microenvironment (TME) which is mostly strongly immune suppressive.

Monoclonal antibodies and also bispecific antibodies used in therapy can cause a variety of adverse effects. An important toxicity issue is the cytokine-release syndrome (CRS), which was for example found in therapy with alemtuzumab, muromonab-CD3, rituximab, and CD19×CD3 bispecific antibody blinatumomab. It was also found that treatment with anti-CD47 antibodies induce increased amounts of pro-inflammatory cytokines after anti-CD47 antibody mediated phagocytosis (see e.g. US20160144009). Known adverse events of anti-CD47 monoclonal antibodies with wt IgG1 Fc are increased red blood cell RBC phagocytosis/lysis and platelet activation (see e.g. in FIGS. 8 and 10 RBC phagocytosis and platelet activation induced by the anti-CD47 antibody B6H12.2 carrying a wt IgG1 Fc).

The present invention provides bispecific antibodies specifically binding to human CEACAM5 and human CD47 designated for the treatment of solid tumors. These bispecific antibodies combine high efficacy with low toxicity, low immunogenicity and favourable pharmacokinetic properties. The bispecific antibodies according to this invention induce their anti-tumor cells effects mainly via optimized ADCP (antibody dependent cellular phagocytosis) and ADCC (antibody dependent cellular cytotoxicity) due to involvement of immune cells especially macrophages and NK-cells. The present invention also provides bispecific antibodies specifically binding to human CEACAM5 and human CD47 designated for the combination treatment with CEA×CD3 T-cell bispecific antibodies like RO6958688, RO7172508 and other CEA×CD3 T-cell bispecific antibodies e.g. as described below and showing strong phagocytosis of tumor cells like MKN-45 in the presence of human macrophages.

SUMMARY OF THE INVENTION

In one embodiment, the invention relates to a bispecific antibody (further named also as "Mab CEA×CD47" or "CEA×CD47 bispecific antibody") comprising a first binding part specifically binding to human CEACAM5 (further named also as "CEA") and a second binding part specifically binding to human CD47 (further named also as "CD47").

In one embodiment, the invention relates to a bispecific antibody specifically binding to human CEACAM5 and human CD47 characterized in that the Fc region has been glycoengineered to have a reduced number of fucose residues as compared to the same but non-glycoengineered bispecific antibody.

In one embodiment, the present invention provides a bispecific antibody, characterized in specifically binding to human CEACAM5 and CEACAM6 in the first binding part and to human CD47 in the second binding part. In one embodiment the invention relates to a bispecific antibody CEA×CD47 specifically binding in a balanced manner to human CEACAM5 and human CEACAM6. In one embodiment the bispecific antibody is characterized in binding to human recombinant CEACAM5 and CEACAM6, characterized in that the EC50 values of binding to CEACAM5 and CEACAM6 differing by less than a factor of 3 (balanced binding, binding in balanced manner, see table 5). Binding is measured in a streptavidin/biotin-based ELISA (see example 80.

In one embodiment the present invention provides a bispecific antibody, specifically binding to human CEACAM5 and CEACAM6 in the first binding part and human CD47 in the second binding part, characterized in a) that the first binding part comprises a heavy chain variable region comprising as CDRs a CDRH1 of SEQ ID NO:25, CDRH2 of SEQ ID NO:26 and CDRH3 of SEQ ID NO:27 and a light chain variable region comprising as CDRs a CDRL1 of SEQ ID NO: 112, a CDRL2 of SEQ ID NO: 113, and a CDRL3 of SEQ ID NO: 114, and
b) that the second binding part comprises a heavy chain variable region comprising as CDRs a CDRH1 of SEQ ID NO:25, CDRH2 of SEQ ID NO:26 and CDRH3 of SEQ ID NO:27 and a light chain variable region comprising as CDRs a CDRL1 of SEQ ID NO:28, CDRL2 of SEQ ID NO:29, and CDRL3 of SEQ ID NO:30.

In one embodiment, the invention relates to a bispecific antibody specifically binding to human CEACAM5 and human CD47, the bispecific antibody comprising a first binding part, specifically binding to human CEACAM5 and a second binding part, specifically binding to human CD47, characterized in that the first binding part binds to the Ig-like V-type domain of CEACAM5 of amino acids 35-144.

In one embodiment, the invention relates to a bispecific antibody specifically binding to human CEACAM5 and human CD47, the bispecific antibody comprising a first binding part, specifically binding to human CEACAM5 and a second binding part, specifically binding to human CD47, characterized in that said bispecific antibody competes with the anti-CEA antibody SM3E, comprising as VK and VH domains VK and VH of sequences SEQ ID NO:100 and 101, for binding to CEACAM5.

In one embodiment, the invention relates to a bispecific antibody specifically binding to human CEACAM5 and human CD47, the bispecific antibody comprising a first binding part, specifically binding to human CEACAM5 and a second binding part, specifically binding to human CD47, characterized in that said bispecific antibody does not compete with anti-CEA antibodies SM3E, MEDI, comprising as VL and VH domains VL and VH of sequences SEQ ID NO:102 and 103, Labetuzumab (Lab), comprising as VK and VH domains VK and VH of sequences SEQ ID NO:110 and 111, SAR, comprising as VK and VH domains VK and VH of sequences SEQ ID NO:104 and 105, T86.66, comprising as VK and VH domains VK and VH of sequences SEQ ID NO:108 and 109, CH1A1A, comprising as VK and VH domains VK and VH of sequences SEQ ID NO:106 and 107 for binding to CEACAM5.

In one embodiment, the invention relates to a bispecific antibody specifically binding to human CEACAM5 and human CD47, the bispecific antibody comprising a first binding part, specifically binding to human CEACAM5 and a second binding part, specifically binding to human CD47, characterized in that the EC50 value of phagocytosis index curve of said bispecific antibody is in the range of 0.1 to 3 times of the E50 value of reference antibody K2AC22 under the same experimental conditions and in the presence or without of 1 mg/ml human IgG. In further embodiments the range is 0.2 to 3.0, 0.3 to 3.0, 0.5 to 2.5 or 1.0 to 2.5. EC50 values of phagocytosis are measured as EC50 values of the phagocytosis index curve (imaging-based phagocytosis assay, see Example 9 and FIG. 12 and Table 3).

In one embodiment, the invention relates to a bispecific antibody specifically binding to human CEACAM5 and human CD47, the bispecific antibody comprising a first binding part, specifically binding to human CEACAM5 and a second binding part, specifically binding to human CD47, characterized in that in presence of 1 mg/ml human IgG the maximal phagocytosis index (see example 9.2; CellInsight™ based assay) of said bispecific antibody is not decreased for 30% or more in comparison to the maximal phagocytosis index measured under the same experimental conditions but without addition of human IgG (see e.g. FIG. 17).

In one embodiment the bispecific antibody is characterized in comprising a first binding part, specifically binding to human CEACAM5 and a second binding part, specifically binding to human CD47, characterized in that:
a) the first binding part comprises a heavy chain variable region comprising a CDRH1 of SEQ ID NO:1, a CDRH2 of SEQ ID NO:2 and a CDRH3 of SEQ ID NO:3 and a light chain constant domain of human lambda type and of SEQ ID NO:13, and
the second binding part comprises a heavy chain variable region comprising a CDRH1 of SEQ ID NO:1, CDRH2 of SEQ ID NO:2 and CDRH3 of SEQ ID NO:3 and a light chain variable region comprising a CDRL1 of SEQ ID NO:7, CDRL2 of Ala Ala Ser, included in SEQ ID NO:8, and CDRL3 of SEQ ID NO:9, or
b) the first binding part comprises a heavy chain variable region comprising as CDRs a CDRH1 of SEQ ID NO:25, CDRH2 of SEQ ID NO:26 and CDRH3 of SEQ ID NO:27 and a light chain constant domain of human lambda type and of SEQ ID NO:13 and the second binding part comprises a heavy chain variable region comprising as CDRs a CDRH1 of SEQ ID NO:25, CDRH2 of SEQ ID NO:26 and CDRH3 of SEQ ID NO:27 and a light chain variable region comprising a CDRL1 of SEQ ID NO:28, CDRL2 of SEQ ID NO:29, and CDRL3 of SEQ ID NO:30.

In one embodiment the bispecific antibody is characterized in comprising a first binding part, specifically binding to human CEACAM5 and a second binding part, specifically binding to human CD47, characterized in that:
a) the first binding part comprises a heavy chain variable region comprising as CDRs a CDRH1 of SEQ ID NO:25, a CDRH2 of SEQ ID NO:26 and a CDRH3 of SEQ ID NO:27 and a light chain variable region comprising a combination of CDRL1, CDRL2 and CDRL3 selected from the group consisting of:
SEQ ID NO:31, 32 and 33; SEQ ID NO:34, 35, and 36, SEQ ID NO:37, 38, and 39, SEQ ID NO:40, 41, and 42, SEQ ID NO:43, 44, and 45, SEQ ID NO:46, 47, and 48, SEQ ID NO:49, 50, and 51, SEQ ID NO:52, 53, and 54, SEQ ID NO:55, 56, and 57, SEQ ID NO:58, 59, and 60, SEQ ID NO:61, 62, and 63, SEQ ID NO: 112, 113, and 114, and
b) the second binding part comprises a heavy chain variable region comprising as CDRs a CDRH1 of SEQ ID NO:25, CDRH2 of SEQ ID NO:26 and CDRH3 of SEQ ID NO:27 and a light chain variable region comprising as CDRs a CDRL1 of SEQ ID NO:28, CDRL2 of SEQ ID NO:29, and CDRL3 of SEQ ID NO:30.

In one embodiment the bispecific antibody is characterized in comprising in the first binding part as light chain constant domain a human lambda type domain of SEQ ID NO:13 In one embodiment the bispecific antibody is characterized in comprising a first binding part, specifically binding to human CEACAM5 and a second binding part, specifically binding to human CD47, characterized in that:
a) the first binding part comprises a heavy chain variable region (VH) of SEQ ID NO:4 and a light chain variable region selected from the group of VLs included in the VLCL regions consisting of: SEQ ID NO:64, SEQ ID NO:65, SEQ ID NO:66, SEQ ID NO:67, SEQ ID NO:68, SEQ ID NO:69, SEQ ID NO:70; SEQ ID NO:71, SEQ ID NO:72, SEQ ID NO:73, SEQ ID NO:74, and SEQ ID NO:115; and b) the second binding part comprises a heavy chain variable region of SEQ ID NO:4 and a light chain variable region of SEQ ID NO:10.

In one embodiment the bispecific antibody is characterized in comprising a first binding part, specifically binding to human CEACAM5 and a second binding part, specifically binding to human CD47, characterized in that:
a) the first binding part comprises a heavy chain of SEQ ID NO:5 and a light chain selected from the group consisting of: SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, and SEQ ID NO:115
b) the second binding part comprises a heavy chain variable region of SEQ ID NO:5 and a light chain variable region of SEQ ID NO:11.

In one embodiment the bispecific antibody is characterized in being monovalent for the first binding part and monovalent for the second binding part.

In one embodiment, the constant and variable framework region sequences are human.

In one embodiment, the bispecific antibody is characterized in that each of the first and second binding part comprises an immunoglobulin heavy chain and an immunoglobulin light chain. In one embodiment the bispecific antibody is characterized in being of human IgG1 type. In one embodiment the bispecific antibody is a full-length antibody.

In one embodiment the bispecific antibody according to the invention is characterized in comprising a first binding part specifically binding to CEA, comprising a kappa light chain variable domain and a lambda light chain constant domain and a second binding part specifically binding to CD47, comprising a kappa light chain variable domain and a kappa light chain constant domain (i bispecific antibody, κλ Body, type 1).

In one embodiment the bispecific antibody according to the invention is characterized in comprising a first binding part specific for CEA, comprising a lambda light chain variable domain and a lambda light chain constant domain and a second binding part specific for CD47, comprising a kappa light chain variable domain and a kappa light chain constant domain (κλ bispecific antibody, κλ Body, type 2). In one embodiment the bispecific antibody according to the invention is of fully human bispecific IgG (especially IgG1) format and in addition a κλ bispecific antibody of type 1 or type 2.

In one embodiment the bispecific antibody according to the invention is characterized in being κλ, bispecific antibody of type 1 or type 2 and comprising a common heavy chain (cHC).

In one embodiment the bispecific antibody is characterized in binding to human CD47 with a binding affinity of 100 nM to 600 nM, in one embodiment with a binding affinity of 100 nM to 500 nM. In one embodiment the bispecific antibody is characterized in binding to MKN-45 cells with an EC50 value of 1 to 200 nM. In one embodiment the bispecific antibody is characterized in binding to MKN-cells with an EC50 value of 1 to 50 nM. In one embodiment the bispecific antibody is characterized in binding to MKN-45 cells with an EC50 value of 50 to 100 nM. In one embodiment the bispecific antibody is characterized in binding to MKN-45 cells with an EC50 value of 100 to 200 nM.

In one embodiment the bispecific antibody according to the invention is characterized in that the maximal achievable phagocytosis index for the phagocytosis of MKN-45 cells in the presence of human macrophages, by said bispecific antibody is not reduced by more than 20% in the presence of 5000 ng/ml soluble CEA compared to the phagocytosis index measured without soluble CEA.

In one embodiment the bispecific antibody according to the invention is characterized in that the EC50 for the phagocytosis index curve of MKN-45 cells in the presence of human macrophages, by said bispecific antibody is not shifted by more than a factor 4 towards higher concentrations in the presence of 200 ng/ml soluble CEA compared to the EC50 measured without soluble CEA and/or that the maximum of the phagocytosis index curve is not reduced by 10% or more, 15% or more, or 20% or more by addition of 200 ng/mL sCEA (see e.g. FIG. 20B).

In one embodiment the bispecific antibody according to the invention is characterized in that the EC50 for the binding curve to MKN-45 cells of said bispecific antibody is not shifted by more than a factor 2 towards higher concentrations in the presence of 200 ng/ml soluble CEA compared to the EC50 measured without soluble CEA (sec e.g. FIG. 20A).

In one embodiment the bispecific antibody is characterized in that it does not cross-react with human CEACAM1.

In one embodiment the bispecific antibody is characterized in binding to human CEACAM6 expressed on recombinant CHO cells CHO-K1 (ATCC® CCL-61™) with an EC50 value of 1 to 50 nM (CEACAM6 negative CHO cells are transfected with a vector containing cDNA of human CEACAM6 to get CEACAM6 protein expressed).

In one embodiment the bispecific antibody according to the invention is characterized in that a monoclonal antibody specifically binding to human CEACAM5 (further named also as MAB CEA), comprising a heavy chain variable region of SEQ ID NO:20 and a light chain variable region of SEQ ID NO:21 in a concentration of 300 nM do not shift the EC50 of the binding curve of the bispecific antibody of the invention to MKN-45 cells by more than a factor of 3, in one embodiment towards higher concentrations. In one embodiment the bispecific antibody according to the invention is characterized in that a bispecific antibody specifically binding to human CEACAM5 and CD3ε (further named also as CEA-TCB), comprising as heavy chains the heavy chains of SEQ ID NO:97 and 98 and as light chains the light chains of SEQ ID NO: 96 and 99 in a concentration of 300 nM does not shift the EC50 of the binding curve of the bispecific antibody of the invention to MKN-45 cells by more than a factor of 3, in one embodiment towards higher concentrations. In such case the bispecific antibody according to the invention and CEA-TCB are defined as "not competitive" and considered able to bind simultaneously to CEA without significantly interfering in binding to said CEA.

In one embodiment the bispecific antibody according to the invention is characterized that a bispecific antibody specifically binding to human CEACAM5 and CD3ε(further named also as CEA-TCB1), comprising as heavy and light chains the chains of amino acid sequences SEQ ID NO: 92 to 95 in a concentration of 30 nM does not shift the EC50 of the binding curve of the bispecific antibody of the invention to MKN-45 cells by more than a factor of 3, in one embodiment towards higher concentrations. In such case the bispecific antibody according to the invention and CEA-TCB1 are defined as "not competitive" and considered able to bind simultaneously to CEA without significantly interfering in binding to said CEA. In such case the bispecific antibody according to the invention and MAB CEA, CEA-TCB and/or CEA-TCB1 are defined as "not competitive"

and considered able to bind simultaneously to CEA without significantly interfering in their binding to said CEA.

In one embodiment the bispecific antibody according to the invention is characterized in that a bispecific antibody specifically binding to human CEACAM5 and CD3ε (further named also as CEA-TCB1), comprising as heavy and light chains the chains of amino acid sequences SEQ ID NO: 92 to 95, in a concentration of 30 nM does not shift the EC50 of the phagocytosis index curve of the bispecific antibody of the invention to MKN-45 cells by more than a factor of 3, in one embodiment towards higher concentrations. In such case the bispecific antibody according to the invention and CEA-TCB1 are defined as "not competitive" and considered able to bind simultaneously to CEA without significantly interfering in their binding to said CEA, and can therefore develop its effect on phagocytosis (CEAxCD47) undisturbed and also its effect on T-cell activation (CEAxTCB1) undisturbed, even if therapeutic levels of both drugs are simultaneously present in the tumor tissue (see FIG. 18).

In one embodiment the bispecific antibody according to the invention is characterized that a bispecific antibody specifically binding to human CEACAM5 and CD3ε(further named also as CEA-TCB), comprising as heavy and light chains the chains of amino acid sequences SEQ ID NO: 96 to 99 in a concentration of 300 nM does not shift the EC50 of the phagocytosis index curve of the bispecific antibody of the invention to MKN-45 cells by more than a factor of 3, in one embodiment towards higher concentrations. In such case the bispecific antibody according to the invention and CEA-TCB are defined as "not competitive" and considered able to bind simultaneously to CEA without significantly interfering in their binding to said CEA and can therefore develop its effect on phagocytosis (CEAxCD47) undisturbed and also its effect on T-cell activation (CEA-TCB) undisturbed, even if therapeutic levels of both drugs are simultaneously present in the tumor tissue (see FIG. 18). This facilitates combination treatment of CEA-TCB/TCB1 with CEAxCD47 of this invention (see FIG. 18).

The sequences of SEQ ID NO 88 to 99 are according to US20140242079 respectively WO2017055389.

In one embodiment the CEAxCD47 bispecific antibodies of the invention combined with CEAxCD3 bispecific antibodies like CEA-TCB and CEA-TCB1 show at least additive or even synergistic % killing of tumor cells in an assay containing e.g. MKN-45 tumor cells and human macrophages and T-cells derived from the same volunteer human donor (see FIGS. 19A and B).

In one embodiment, the bispecific antibody is characterized in comprising a common heavy chain (cHC) as heavy chain of the first binding part and as heavy chain of the second binding part. In one embodiment, the bispecific antibody is characterized in that said common heavy chain of each binding part comprises as CDRs CDRH1 of SEQ ID NO:1, CDRH2 of SEQ ID NO:2 and CDRH3 of SEQ ID NO:3 or a CDRH1 of SEQ ID NO:25, CDRH2 of SEQ ID NO:26 and CDRH3 of SEQ ID NO:27. In one embodiment, the bispecific antibody is characterized in that said common heavy chain of each binding part comprises as common variable heavy domain (cVH) SEQ ID NO:4. In one embodiment the bispecific antibody according to the invention is characterized in comprising a common heavy chain (cHC) selected of the group consisting of SEQ ID NO:5, SEQ ID NO:23, and SEQ ID NO:24. In one embodiment the common heavy chain of SEQ ID NO:5 is encoded by the nucleic acid sequence shown in SEQ ID NO:6.

In one embodiment the bispecific antibody according to the invention is characterized in comprising as second binding part specific for CD47, a common heavy chain comprising as CDRs CDRH1 of SEQ ID NO:1, CDRH2 of SEQ ID NO:2 and CDRH3 of SEQ ID NO:3 and a light chain (LC) comprising as CDRs CDRL1 of SEQ ID NO:7, CDRL2 of Ala Ala Ser, included in SEQ ID NO:8, and CDRL3 of SEQ ID NO:9, or a common heavy chain comprising as CDRs CDRH1 of SEQ ID NO:25, CDRH2 of SEQ ID NO:26 and CDRH3 of SEQ ID NO:27 and a light chain (LC) comprising as CDRs CDRL1 of SEQ ID NO:28, CDRL2 of SEQ ID NO:29, and CDRL3 of SEQ ID NO:30.

In one embodiment the bispecific antibody according to the invention is characterized in comprising as second binding part a heavy chain comprising as variable heavy domain (cVH) SEQ ID NO:4 and a variable light domain (VL) of SEQ ID NO:10.

In one embodiment the bispecific antibody according to the invention is characterized in comprising as second binding part a heavy chain (cHC) comprising of SEQ ID NO:5 and a light chain (CL) of SEQ ID NO:11. In one embodiment the bispecific antibody according to the invention is characterized in comprising as second binding part a heavy chain (cHC) comprising of SEQ ID NO:23 and a light chain (CL) of SEQ ID NO:11. In one embodiment the bispecific antibody according to the invention is characterized in comprising as second binding part a heavy chain (cHC) comprising of SEQ ID NO:24 and a light chain (CL) of SEQ ID NO:11. In one embodiment the light chain (LC) of SEQ ID NO:11 is encoded by the nucleic acid sequence shown in SEQ ID NO:12.

In one embodiment, the bispecific antibody is characterized in specifically binding to CEA and comprising a light chain constant domain of SEQ ID NO:13.

In one embodiment, the bispecific antibody according to the invention is characterized in inhibiting the interaction between CD47 on MKN-45 cells with an IC50 of 0.1 to 10 nM. SIRPα (SIRPα, CD172a; UniProtKB P78324) is used in a concentration of 200 ng/ml (His tagged soluble SIRPαalpha). Details of the assay are described in example 8 (SIRPα Blocking Activity of CD47 Antibodies), and results are shown in Table 2.

In one embodiment the bispecific antibody of the invention is characterized in a concentration dependent phagocytosis (ADCP) of CEA expressing tumor cell lines like MKN-45 cells by human macrophages at an EC50 of the bispecific antibody below 10 nM. ADCP is measured according to the invention as phagocytosis index (EC50 or maximum) by imaging, usually with an E:T ratio of 1:3 (human macrophages:target cells (tumor cells); see e.g. FIGS. 12, 15, and 16). Results in FIG. 3B have been obtained with E:T of 1:1. Details of the assay are described in example 9.2.

For further information, phagocytosis (ADCP) of CEA expressing tumor cell lines like MKN-45 cells by human macrophages at an EC50 of the bispecific antibody below 10 nM. ADCP can be also measured by Flow Cytometry with an E:T ratio of e.g. 3:1 (human macrophages:target cells (tumor cells); see e.g. FIG. 3A). Details of the assay are described in example 9 (1. Flow cytometry based ADCP assay).

In one embodiment, the bispecific antibody is characterized in specifically binding to CEACAM5 but is not competing for binding to CEACAM5 on tumor cells like MKN-45 with MAB CEA, CEA-TCB and/or CEA-TCB1.

In one embodiment, the bispecific antibody according to the invention is characterized in that the EC50 value for the binding to MKN-45 cells (EC50 between 1 and 200 nM) is increased by less than a factor of three by addition of MAB CEA or CEA-TCB at a concentration of 300 nM respectively by addition of CEA-TCB1 at a concentration of 30 nM (no competition).

In one embodiment, the CEA×CD47 antibodies of the invention show a 100 or more times higher EC50 for RBC phagocytosis compared to the EC50 measured in the same assay (Example 15) with B6H12.2.

In one embodiment, the CEA×CD47 antibodies of the invention (carrying wt IgG1 Fc w/o or with afucosylation) do not show significant platelet activation in concentrations up to 200 µg/mL (see Example 15 and results mentioned in Example 15 for CEA×CD47 bispecific antibodies K2AC5 and K2AC22).

In another embodiment, the present invention relates to a bispecific antibody according to the invention that has been glycoengineered to have an Fc region with modified oligosaccharides. It was surprisingly found, that such a glycoengineered bispecific antibody according to the invention is characterized in an at least 3 times lower EC50 value for the phagocytosis index curve measured by the imaging based assay) as the same not glycoengineered (parent) bispecific antibody if measured under the same experimental conditions. In one embodiment EC50 for the phagocytosis index is 5 to 10 times lower, or 10 to 30 times lower). In one embodiment, the Fc region has been modified to have a reduced number of fucose residues as compared to the same but non-glycoengineered bispecific antibody. In another embodiment, the Fc region has an increased proportion of bisected oligosaccharides as compared to the non-glycoengineered bispecific antibody. In yet another embodiment, the bisected oligosaccharides are predominantly bisected complex. In another embodiment, the glycoengineered antigen binding molecules of the invention have an increased proportion of bisected, nonfucosylated oligosaccharides in the Fc region of said bispecific antibody as compared to the non-glycoengineered bispecific antibody. Alternatively, the bispecific antibodies of the invention may have an increased ratio of GlcNAc residues to fucose residues in the Fc region compared to the non-glycoengineered bispecific antibody. In one embodiment, the bisected, nonfucosylated oligosaccharides are predominantly in hybrid form. Alternatively, the bisected, nonfucosylated oligosaccharides are predominantly complex type.

In one embodiment the bispecific antibody according to the invention is characterized in that 50% to 100% of the N-linked oligosaccharides in the Fc region are nonfucosylated.

In one embodiment the bispecific antibody is characterized in that 50% to 100% of the N-linked oligosaccharides in the Fc region are bisected.

In one embodiment the bispecific antibody is characterized that 80% to 100% of the N-linked oligosaccharides in the Fc region are bisected and nonfucosylated.

In one embodiment the bispecific antibody is characterized in that concentration/ADCC curve (decrease of EC50 or increase of maximum of ADCC (see FIGS. 13 and 14) induced by said glycoengineered antibody is increased by at least a factor of 1.2 compared to the ADCC induced by the same but non-glycoengineered bispecific antibody. In one embodiment ADCC is increased by a factor of 1.2 to 2.0.

In one embodiment the bispecific antibody is characterized in an at least 3 times lower EC50 value for the phagocytosis index curve measured by the imaging based assay as compared to the same but not glycoengineered (parent) bispecific antibody if measured under the same experimental conditions. In one embodiment EC50 for the phagocytosis index is 5 to 10 times lower, or 10 to 30 times lower. In one embodiment the bispecific antibody is characterized in that the maximal phagocytosis index induced by said glycoengineered antibody and measured by flow cytometry is increased by at least a factor of 1.2 compared to the maximal phagocytosis index induced by the same but non-glycoengineered bispecific antibody. In one embodiment maximal phagocytosis index is increased by a factor of 1.2 to 2.0.

In one embodiment the bispecific antibody is characterized in that the maximal phagocytosis index induced by said glycoengineered antibody and measured by imaging is increased by at least a factor of 1.2 compared to maximal phagocytosis index induced by the same but non-glycoengineered bispecific antibody. In one embodiment maximal phagocytosis index is increased by a factor of 1.2 to 2.0.

In one embodiment the bispecific antibody according to the invention is characterized in comprising one, two or three amino acid substitutions in the Fc region ("Fc amino acid substitution") selected from the group consisting of mono-substitutions S239D, I332E, G236A, of bi-substitutions I332E and G236A, S239D and I332E, S239D and G236A, and of triple-substitution S329D and I332E and G236A.

In one embodiment the bispecific antibody according to the invention is characterized in comprising one, two or three amino acid substitutions in the Fc region selected from the group consisting of mono-substitutions S239D, I332E, G236A, of bi-substitutions I332E and G236A, S239D and I332E, S239D and G236A, and triple-substitution S329D and I332E and G236A and a Fc region which has been glycoengineered to have a reduced number of fucose residues as compared to the same but non-glycoengineered bispecific antibody.

In one embodiment the bispecific antibody comprising said substitutions in the Fe region is characterized in that concentration/ADCC curve (decrease of EC50 or increase of maximum of ADCC) induced by said amino acid substituted antibody is increased by at least a factor of 1.2 compared to the ADCC induced by said antibody comprising none of said amino acid substitutions in the Fc region. In one embodiment ADCC is increased by a factor of 1.2 to 2.0.

In one embodiment the bispecific antibody comprising said substitutions in the Fc region is characterized in an at least 3 times lower EC50 value for the phagocytosis index curve measured by the imaging based assay as compared to the same (parent) bispecific antibody comprising none of said amino acid substitutions in Fc region, if measured under the same experimental conditions. In one embodiment EC50 for the phagocytosis index is 5 to 10 times lower, or 10 to 30 times lower In one embodiment the bispecific antibody comprising said substitutions in the Fc region is characterized in that flow cytometry determined maximal phagocytosis (ADCP) induced by said amino acid substituted antibody is increased by at least a factor of 1.2 compared to the ADCP induced by said antibody comprising none of said amino acid substitutions in the Fc region. In one embodiment ADCP is increased by a factor of 1.2 to 2.0. In one embodiment the bispecific antibody comprising said substitutions in the Fc region is characterized in that by imaging determined maximal phagocytosis index induced by said amino acid substituted antibody is increased by at least a factor of 1.2 compared to the ADCP induced by said antibody comprising none of said amino acid substitutions in the Fc region. In one embodiment ADCP is increased by a factor of 1.2 to 2.0.

In one embodiment, the bispecific antibody according to the invention is characterized in that 50% to 100%, 60% to 100%, 70% to 100% or 80% to 100% of the N-linked oligosaccharides in the Fc region are non-fucosylated. In one embodiment, the bispecific antibody according to the invention is characterized in 50% to 100%, 60% to 100%, 70% to 100% or 80% to 100% of the N-linked oligosaccharides in the Fc region are bisected. In one embodiment, the bispecific antibody according to the invention is characterized in that 50% to 100%, 60% to 100%, 70% to 100% or 80% to 100% of the N-linked oligosaccharides in the Fc region are bisected, nonfucosylated.

In one embodiment, the glycoengineered bispecific antibody comprises increased effector functions compared to the non-glycoengineered bispecific antibody comprising as common heavy chain SEQ ID NO:5 (parent bispecific antibody, produced in a CHO K1 cell line CHO-K1 (ATCC® CCL-61™ at standard conditions as defined below).

In one embodiment, the bispecific antibody according to the invention is characterized in that said glycoengineered bispecific antibody comprises one or more increased effector functions such as those from the group consisting of increased binding affinity to FcγRs, increased binding of macrophages (increased antibody dependent cellular phagocytosis; ADCP), increased binding of NK cells (increased antibody-mediated cellular cytotoxicity; ADCC), and increased binding to monocytes.

The concentration/phagocytosis index curve measured for the anti-CD47 monoclonal antibody hu5F9-G4 (tested in clinical trials since 2014) is strongly reduced by the addition of huIgG added in physiological concentrations of 1 mg/mL to the assay (increase of EC50 and decrease of the maximum of the phagocytosis curve measured in imaging based assay, sec e.g. FIG. 17).

Surprisingly the CEAxCD47 antibodies of the invention show only a small shift below a factor of 3 of EC50 and no significant decrease of the maximum of the concentration/phagocytosis index curve if human IgG is added (see Table 4).

In one embodiment the CEAxCD47 antibodies of the invention are characterized in that addition of 1 mg/mL of hu IgG to the imaging based phagocytosis assay causes a less than a factor of 0.9 reduction of the maximum of the concentration/phagocytosis index curve and/or a less than a factor of 3 shift of the EC50 towards higher concentrations (see Table 4)

A further embodiment of the invention is an isolated polynucleotide characterized in encoding a bispecific antibody according to the invention.

A further embodiment of the invention is an expression vector comprising the polynucleotide according to the invention.

A further embodiment of the invention is a host cell comprising the expression vector according to the invention.

A further embodiment of the invention is a method for the production of a bispecific antibody according to the invention, characterized in comprising:
a) culturing a host cell comprising an expression vector encoding said bispecific antibody under conditions which permit the production of said antibody of the invention, and
b) isolating said antibody wherein said antibody is capable of specifically binding to CEA and CD47.

In one embodiment, the invention is characterized in comprising a method for producing a glycoengineered bispecific antibody according to the invention in a host cell, said method comprising:
a) culturing a host cell glycoengineered to express at least one nucleic acid encoding a polypeptide having β(1,4)-N-acetylglucosaminyltransferase III activity under conditions which permit the production of said bispecific antibody of the invention, and which permit the modification of the oligosaccharides present on the Fc region of said bispecific antibody; and
b) isolating said glycoengineered bispecific antibody wherein said glycoengineered bispecific antibody is capable of specifically binding to CEA and CD47.

In one embodiment, the invention is characterized in comprising a method for producing a glycoengineered bispecific antibody in a host cell, said method comprising:
a) culturing a host cell glycoengineered by targeted disruption of the FUT8 gene under conditions which permit the production of said bispecific antibody of the invention, and which permit the modification of the oligosaccharides present on the Fc region of said bispecific antibody, and
b) isolating said glycoengineered bispecific antibody wherein said glycoengineered bispecific antibody is capable of specifically binding to CEA and CD47.

In one embodiment, the invention is characterized in comprising a method for producing a Fc substituted bispecific antibody according to the invention in a host cell, said method comprising:
a) culturing a host cell comprising an expression vector encoding a Fc substituted, bispecific antibody of the invention under conditions which permit the production of said bispecific antibody, and
b) isolating said Fc substituted bispecific antibody wherein said bispecific antibody is capable of specifically binding to CEA and CD47.

A further embodiment of the invention is a method of inducing cell lysis of a tumor cell comprising contacting the tumor cell with a bispecific antibody according to the invention. The tumor cell is a human tumor cell, preferably in a patient.

A further embodiment of the invention is a method according to the invention, characterized in that the tumor cell is a colorectal cancer cell, NSCLC (non-small cell lung cancer) cell, gastric cancer cell, pancreatic cancer cell, breast cancer cell, or another tumor cell expressing CEA.

A further embodiment of the invention is a method of treating a subject having a cancer that expresses CEA, the method comprising administering to the subject a therapeutically effective amount of a bispecific antibody according to the invention.

A further embodiment of the invention is a method of increasing survival time in a subject having a cancer that expresses CEA, said method comprising administering to said subject a therapeutically effective amount of a bispecific antibody according to the invention.

A further embodiment of the invention is a method according to the invention, characterized in that the cancer is colorectal cancer, non-small cell lung cancer (NSCLC), gastric cancer, pancreatic cancer or breast.

A further embodiment of the invention is a method according to the invention, characterized in that a bispecific antibody according to the invention is administered in combination with chemotherapy or radiation therapy to a human subject.

A further embodiment of the invention is a method of treating a subject having a cancer that expresses CEA, the method comprising administering to the subject a therapeutically effective amount of a bispecific antibody according to the invention, characterized in that the EC50 value of phagocytosis of said bispecific antibody is in the range of 0.1 to 3 times of the E50 value of reference antibody K2AC22 under the same experimental conditions and in the presence and/or without of 1 mg/ml human IgG. In further embodiments the range is 0.2 to 3.0, 0.3 to 3.0, 0.5 to 2.5 or 1.0 to 2.5. In one embodiment the bispecific antibody is characterized in binding to human CD47 with a binding affinity of 100 nM to 600 nM, in one embodiment with a binding affinity of 100 nM to 500 nM.

A further embodiment of the invention is the use of a bispecific antibody according to the invention in a method of treating a subject having a cancer that expresses CEA, the method comprising administering to the subject a therapeutically effective amount of a bispecific antibody according to the invention, characterized in that the EC50 value of phagocytosis of said bispecific antibody is in the range of 0.1 to 3 times of the E50 value of reference antibody K2AC22 under the same experimental conditions and in the presence and/or without of 1 mg/ml human IgG. In further embodiments the range is 0.2 to 3.0, 0.3 to 3.0, 0.5 to 2.5 or 1.0 to 2.5. In one embodiment the bispecific antibody is characterized in binding to human CD47 with a binding affinity of 100 nM to 600 nM, in one embodiment with a binding affinity of 100 nM to 500 nM.

As can be seen from FIGS. 13 to 17, ADCC and ADCP/phagocytosis index values of antibodies according to the invention are not or only to a low extend affected by human IgG in a concentration of 1 mg/ml (1 mg/ml or even higher human IgG is present in most patients), whereas for an anti-CD47 antibody of the state of the art (hu5F9-G4), ADCC and ADCP values are strongly reduced in the presence of 1 mg/mL human IgG.

A further embodiment of the invention is the use of the bispecific antibody according to the invention in the manufacture of a medicament for treating a subject having a cancer that expresses CEA.

A further embodiment of the invention is the use of the bispecific antibody according to the invention in the manufacture of a medicament according to the invention, characterized in that the cancer is selected from the group consisting of colorectal cancer, non-small cell lung cancer (NSCLC), gastric cancer, pancreatic cancer and breast cancer.

A further embodiment of the invention is a bispecific antibody according to the invention, for use in simultaneous, separate, or sequential combination with a second bispecific antibody comprising a third binding part specifically binding to human CEACAM5, and a fourth binding part specifically binding to human CD3ε in the treatment of a subject having a cancer that expresses CEA. A further embodiment of the invention is a bispecific antibody according to the invention, for use in simultaneous, separate, or sequential combination with a second bispecific antibody comprising a third binding part specifically binding to human CEACAM5 and a fourth binding part specifically binding to an epitope of human CD3ε, said epitope comprising the amino acid sequence of SEQ ID NO:22 in the treatment of a subject having a cancer that expresses CEA.

A further embodiment of the invention is a bispecific antibody according to the invention, for use in simultaneous, separate, or sequential combination with CEA-TCB and/or CEA/TCB1 in the treatment of a subject having a cancer that expresses CEA.

A further embodiment of the invention is a bispecific antibody according to the invention, for use in simultaneous, separate, or sequential combination with a second bispecific antibody comprising a third binding part specifically binding to human CEACAM5, comprising a heavy chain variable region of SEQ ID NO:20 and a light chain variable region of SEQ ID NO:21 and a fourth binding part specifically binding to an epitope of human CD3ε, said epitope comprising the amino acid sequence of SEQ ID NO:22 in the treatment of a subject having a cancer that expresses CEA.

A further embodiment of the invention is a bispecific antibody according to the invention, characterized in not competing with said second bispecific antibody for use in simultaneous, separate, or sequential combination with said second bispecific antibody in the treatment of a subject having a cancer that expresses CEA.

A further embodiment of the invention is a bispecific antibody according to the invention, characterized in not competing with CEA-TCB or CEA-TCB1 for use in simultaneous, separate, or sequential combination with said CEA-TCB or CEA-TCB1 in the treatment of a subject having a cancer that expresses CEA.

A further embodiment of the invention is a bispecific antibody according to the invention, characterized in competing with CEA-TCB or CEA-TCB1 for use in simultaneous, separate, or sequential combination with said CEA-TCB or CEA-TCB1 in the treatment of a subject having a cancer that expresses CEA.

A further embodiment of the invention is a bispecific antibody according to the invention, for use in simultaneous, separate, or sequential combination with a second bispecific antibody comprising a third binding part specifically binding to human CEACAM5, comprising a heavy chain variable region of SEQ ID NO:88 and a light chain variable region of SEQ ID NO:89 and a fourth binding part specifically binding to human CD3ε, comprising a heavy chain variable region of SEQ ID NO:90 and a light chain variable region of SEQ ID NO:91.

A further embodiment of the invention is a bispecific antibody according to the invention, for use according to the invention, characterized in that the bispecific antibody according to the invention and the second bispecific antibody are administered to said subject alternately in 6 to 15 day intervals.

A further embodiment of the invention is a bispecific antibody according to the invention, for use according to the invention, characterized in that the bispecific antibody according to the invention and the second bispecific antibody are administered to said subject simultaneously in 6 to 15 day intervals.

A further embodiment of the invention is a first bispecific antibody according to the invention, comprising a first binding part, specifically binding to human CEACAM5 and a second binding part, specifically binding to human CD47, for use in simultaneous, separate, or sequential combination in the treatment of a subject having a cancer that expresses CEA, with a second bispecific antibody, comprising a third binding part specifically binding to human CEACAM5, comprising a heavy chain variable region of SEQ ID NO:20 and a light chain variable region of SEQ ID NO:21 and a fourth binding part specifically binding to an epitope of human CD3ε, comprising the amino acid sequence of SEQ ID NO:22, whereby said second bispecific antibody in a concentration of 300 nM does not shift the EC50 value of the phagocytosis index curve to MKN-45 cells of the bispecific antibody according to the invention by more than a factor of 3, in one embodiment towards higher concentrations.

A further embodiment of the invention is a first bispecific antibody according to the invention, comprising a first binding part, specifically binding to human CEACAM5 and a second binding part, specifically binding to human CD47, for use in simultaneous, separate, or sequential combination in the treatment of a subject having a cancer that expresses CEA, with a second bispecific antibody comprising a third binding part specifically binding to human CEACAM5, comprising a heavy chain variable region of SEQ ID NO:88 and a light chain variable region of SEQ ID NO:89 and a fourth binding part specifically binding to human CD3ε, comprising a heavy chain variable region of SEQ ID NO:90 and a light chain variable region of SEQ ID NO:91, whereby said second bispecific antibody in a concentration of 30 nM does not shift the EC50 of the binding curve to MKN-45 cells of the bispecific antibody according to the invention by more than a factor of 3, in one embodiment towards higher concentrations.

A further embodiment of the invention is a first bispecific antibody according to the invention, for use in simultaneous, separate, or sequential combination in the treatment of a subject having a cancer that expresses CEA, with CEA-TCB or CEA-TCB1, whereby said CEA-TCB in a concentration of 300 nM or CEA-TCB1 in a concentration of 30 nM do not shift the EC50 of the binding curve to MKN-45 cells of the bispecific antibody according to the invention by more than a factor of 3, in one embodiment towards higher concentrations.

A further embodiment of the invention is a first bispecific antibody according to the invention, comprising a first binding part, specifically binding to human CEACAM5 and a second binding part, specifically binding to human CD47 according to the invention, for use according to the invention, characterized in that said cancer is colorectal cancer, non-small cell lung cancer (NSCLC), gastric cancer, pancreatic cancer and breast cancer.

A further embodiment of the invention is a composition comprising a bispecific antibody according to the invention, characterized in not competing with said second bispecific antibody as defined above for use in the treatment of a subject having a cancer that expresses CEA.

A further embodiment of the invention is a composition comprising a bispecific antibody according to the invention, characterized in not competing with a second bispecific antibody comprising a third binding part specifically binding to human CEACAM5, comprising a heavy chain variable region of SEQ ID NO:20 and a light chain variable region of SEQ ID NO:21 and a fourth binding part specifically binding to an epitope of human CD3ε, comprising the amino acid sequence of SEQ ID NO:22, for use in the treatment of a subject having a cancer that expresses CEA.

A further embodiment of the invention is a composition comprising a bispecific antibody according to the invention, characterized in not competing with a second bispecific antibody comprising a third binding part specifically binding to human CEACAM5, comprising a heavy chain variable region of SEQ ID NO:88 and a light chain variable region of SEQ ID NO:89 and a fourth binding part specifically binding to human CD3ε, comprising a heavy chain variable region of SEQ ID NO:90 and a light chain variable region of SEQ ID NO:91, for use in the treatment of a subject having a cancer that expresses CEA. A further embodiment of the invention is a composition comprising a bispecific antibody according to the invention, characterized in not competing with CEA-TCB and/or CEA-TCB1.

A further embodiment of the invention is a method for the treatment of a human patient diagnosed with a tumor (cancer), especially a solid tumor, especially a solid cancer that expresses CEA, especially colorectal cancer, non-small cell lung cancer (NSCLC), gastric cancer, pancreatic cancer and breast cancer, comprising administering an effective amount of an bispecific antibody according to the invention and a second bispecific antibody as described above, against CEA and CD3 (in one embodiment CEA-TCB or CEA-TCB1), to the human patient, the method comprising subsequently:
administering to the patient a dose of 0.1 to 10 mg/kg, in a further embodiment of 0.5 to 10 mg/kg, in a further embodiment of 1 to 2 mg/kg of said second anti CEA×CD3 antibody, e.g. weekly over 4 to 12 weeks.
administering to the patient said second antibody q1, q2w, q3w or optionally q4w,
administering after these 4 to 12 weeks and after additional 2 or 3 or 4 elimination half-lives of said anti CEA×CD3 antibody to the patient a dose of 0.1 to 20 mg/kg of an antibody according to the invention,
administering to the patient said antibody according to the invention q1, q2w, q3w or optionally q4w, waiting 2 or 3 or 4 elimination half-lives of said antibody according to the invention and then optionally repeating said cycle of CEA× CD3 bispecific antibody administration followed by CEA× CD47 bispecific antibody administration and optionally repeat again that cycle.

This "alternating" method is applied if the antibody of the invention and the second bispecific antibody are competitive.

In case said CEA×CD3 bispecific antibody and the CEA× CD47 bispecific antibody according to this invention are not competitive, the two bispecific antibodies can also be administered in a manner ("simultaneous manner") that the patient experiences therapeutically effective plasma and tissue concentrations of both bispecific antibodies in parallel, e.g. by administration to the patient at about the same time a dose of 0.1 to 10 mg/kg, in a further embodiment of 0.5 to 10 mg/kg, in a further embodiment of 1 to 2 mg/kg of the CEA×CD3 bispecific antibody and 1 to 20 mg/kg of the CEA×CD47 bispecific antibody of this invention, followed by one or more of these combined administrations at a frequency of q1w or q2w or q3w or optionally q4w.

The term "Q1w" means administration once a week; q2w means administration every two weeks etc.

A further embodiment of the invention is a pharmaceutical composition comprising an antibody according to the invention and a pharmaceutically acceptable excipient or carrier.

A further preferred embodiment of the invention is a pharmaceutical composition comprising an antibody according to the invention for use as a medicament.

A further preferred embodiment of the invention is a pharmaceutical composition comprising an antibody according to the invention for use as a medicament in the treatment of solid tumor disorders.

A further preferred embodiment of the invention is a pharmaceutical composition comprising an antibody according to the invention for use as a medicament in the treatment of colorectal cancer, NSCLC (non-small cell lung cancer), gastric cancer, pancreatic cancer or breast cancer.

A further embodiment of the invention is a composition comprising a bispecific antibody according to the invention, for use in simultaneous, separate, or sequential combination in the treatment of a subject having a cancer that expresses CEA, with a second bispecific antibody, comprising a third binding part specifically binding to human CEACAM5, comprising a heavy chain variable region of SEQ ID NO:20 and a light chain variable region of SEQ ID NO:21 and a fourth binding part specifically binding to an epitope of human CD36, comprising the amino acid sequence of SEQ ID NO:22, whereby said second bispecific antibody in a concentration of 300 nM does not shift the EC50 of the binding curve to MKN-45 cells of the bispecific antibody according to the invention by more than a factor of 3, in one embodiment towards higher concentrations.

A further embodiment of the invention is a composition comprising a bispecific antibody according to the invention, for use in simultaneous, separate, or sequential combination in the treatment of a subject having a cancer that expresses CEA, with a second bispecific antibody comprising a third binding part specifically binding to human CEACAM5, comprising a heavy chain variable region of SEQ ID NO 88 and a light chain variable region of SEQ ID NO:89 and a fourth binding part specifically binding to human CD3ε, comprising a heavy chain variable region of SEQ ID NO:90 and a light chain variable region of SEQ ID NO:91, whereby said second bispecific antibody in a concentration of 30 nM does not shift the EC50 of the binding curve to MKN-45 cells of the bispecific antibody according to the invention by more than a factor of 3, towards higher concentrations.

A further embodiment of the invention is a composition according to the invention, characterized in that the cancer is colorectal cancer, non-small cell lung cancer (NSCLC), gastric cancer, pancreatic cancer, or breast cancer.

A further embodiment of the invention is the use of an antibody according to the invention for the manufacture of a pharmaceutical composition.

A further embodiment of the invention is the use of an antibody according to the invention and a pharmaceutically acceptable excipient or carrier for the manufacture of a pharmaceutical composition.

A further embodiment of the invention is the use of an antibody according to the invention for the manufacture of a medicament in the treatment of solid tumor disorders.

A further embodiment of the invention is the use of an antibody according to the invention in the treatment of colorectal cancer, NSCLC (non-small cell lung cancer), gastric cancer, pancreatic cancer or breast cancer.

Another aspect of the invention provides a method of inducing cell lysis of a tumor cell comprising contacting the tumor cell with the bispecific antibody of any of above described embodiments. In some embodiments, the tumor cell is a colorectal cancer cell, NSCLC (non-small cell lung cancer), gastric cancer cell, pancreatic cancer cell or breast cancer cell.

In one embodiment, the cell lysis is induced by antibody dependent cellular phagocytosis and/or antibody dependent cellular cytotoxicity of the bispecific antibody.

Another aspect of the invention provides a method of treating a subject having a cancer that abnormally expresses CEA, the method comprising administering to the subject a therapeutically effective amount of the bispecific antibody of any of above described embodiments.

Another aspect of the invention provides a method of treating a subject having a cancer that abnormally expresses CEA, the method comprising administering to the subject a therapeutically effective amount of the bispecific antibody of any of above described embodiments in combination with a bispecific antibody binding to human CEA and human CD3. If the CEA×CD47 antibody and the CEA×CD3 antibody are competing they will compete for the CEA receptors on the surface of the tumor cell and the receptor occupancy and efficacy for each combination partner depends on their binding affinity and their plasma concentrations and is therefore difficult to predict and also variable over time if the concentrations of the two drugs have a different elimination half-life respectively clearance from the body. Therefore, competing CEA×CD3 and CEA×CD47 bispecific antibodies should be given sequentially (alternating). If the CEA×CD3 and CEA×CD47 bispecific antibodies are not or only minimally competing they can be not only given sequentially but also in parallel (simultaneously) which may well be an advantage because tumor cell killing via engagement of T-cells by the CEA×CD3 bispecific antibody and at the same time via engagement of macrophages by the CEA×CD47 bispecific antibody is additive or may be even synergistic, which means efficacy is increased if both drugs are given in parallel.

Another aspect of the invention provides a method of increasing progression free survival and/or overall survival time in a subject having a cancer that abnormally expresses CEA, said method comprising administering to said subject a therapeutically effective amount of the bispecific antibody of any of above described embodiments. In one embodiment, the cancer is colorectal cancer, non-small cell lung cancer (NSCLC), gastric cancer, pancreatic cancer or breast cancer or another cancer expressing CEA.

In certain embodiments of these methods, the bispecific antibody is administered in combination with chemotherapy or radiation therapy. In one embodiment, the subject is a patient suffering from colorectal cancer or lung cancer or gastric cancer or pancreatic cancer or breast cancer or another cancer expressing CEA.

Another aspect of the invention provides a method of treating a subject having a cancer that abnormally expresses CEA, the method comprising administering to the subject a therapeutically effective amount of the bispecific antibody of any of above described embodiments in combination with a bispecific antibody against human CEA and human CD3epsilon.

Another aspect of the invention provides a method of increasing progression free survival time and/or overall survival time in a subject having a cancer that abnormally expresses CEA, said method comprising administering to said subject a therapeutically effective amount of the bispecific antibody of any of above described embodiments. In one embodiment, the cancer is colorectal cancer, non-small cell lung cancer (NSCLC), gastric cancer, pancreatic cancer or breast cancer.

In certain embodiments of these methods, the bispecific antibody is administered in combination with chemotherapy or radiation therapy. In one embodiment, the subject is a cancer patient with colorectal cancer or lung cancer or gastric cancer or pancreatic cancer or breast cancer or another CEA expressing cancer.

Another embodiment of the invention provides the use of a bispecific antibody according to the invention for any of the above described methods of treatment. In one embodiment, the cancer is selected from the group consisting of colorectal cancer, non-small cell lung cancer (NSCLC), gastric cancer, pancreatic cancer and breast cancer.

BRIEF DESCRIPTION OF THE FIGURES

FIG. 11A shows antibodies classified in bin 1, binding to MKN-45 cells inhibited by SM3E antibody by more than 80%; FIG. 11B shows antibodies classified in bins 2, binding to MKN-45 cells not inhibited by anti-CEA antibodies SM3E, MEDI, T84.66, SAR, Lab, and CH1A1A (by less than 20%).

DETAILED DESCRIPTION OF THE INVENTION

Figure 1A:
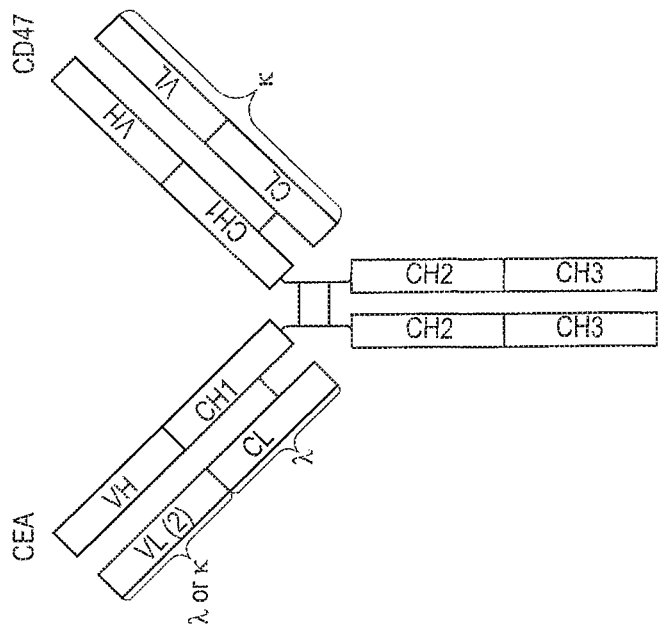
FIGS. 1A and 1B show the general molecular format of the CEA×CD47 bispecific antibodies of this invention; fully human IgG1 structure undistinguishable from IgG monoclonal antibody and with no aa bridges to minimize immunogenicity and anti-drug antibody ADA formation; common heavy chain (see sequence list); kappa light chain (CL and VL) in the CD47 binding part (see sequence list); lambda CL in the CEA binding part (see sequence list) and lambda or kappa VL in the CEA binding part (1A); Glycoengineering (low fucose) of the Fc or aa mutation(s) or both to increase ADCP, and ADCC (1B).
Figure 1B:
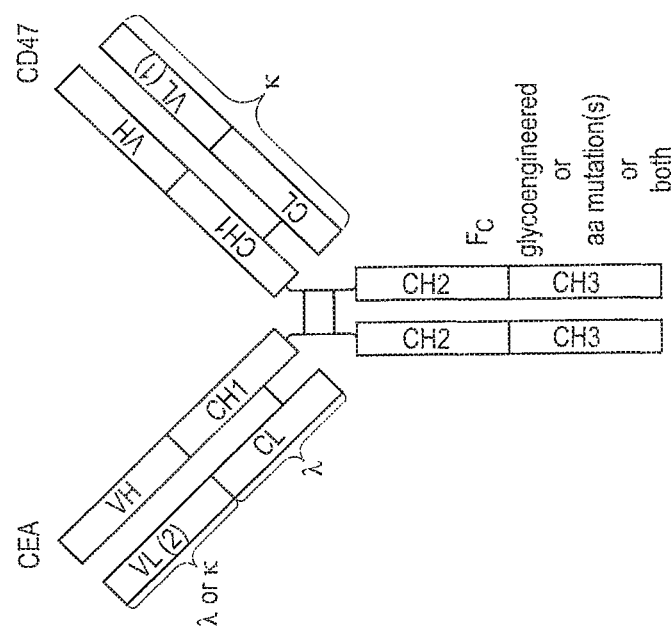

Terms are used herein as generally used in the art, unless otherwise defined as follows.

As used herein, the term "antigen binding part, binding part" refers in its broadest sense to a part of an antibody that specifically binds an antigenic determinant such as CEA, CD47 and CD3.

More specifically, as used herein, a binding part that binds membrane-bound human carcinoembryonic antigen (CEA, same as CEACAM5) or to CD47 specifically binds to CEA or CD47, more particularly to cell surface or membrane-bound CEA or CD47. Therefore, each binding part binds either to CEA or CD47. By "specifically binding, specific for, binding to" is meant that the binding is selective for the antigen and can be discriminated from unwanted or non-specific interactions. In some embodiments, the extent of binding of an anti-target antibody to an unrelated, non-target protein is about 10-fold preferably >100-fold less than the binding of the antibody to said target as measured, e.g., by surface plasmon resonance (SPR) e.g. Biacore®, enzyme-linked immunosorbent (ELISA) or flow cytometry (FACS). Targets are the proteins discussed herein—e.g. CEA, CD47, and CD3ε. In one embodiment the CEA binding part binds in addition to CEACAM6.

"Specifically binding to CEA, CD47, binding to CEA, CD47, specific for CEA, CD47" refers in one embodiment to an antibody, e.g., bispecific antibody, that is capable of binding to the targets CEA and. CD47 with sufficient affinity such that the antibody is useful as a therapeutic agent in targeting tumor cells expressing CEA and CD47. The term "binding to MKN-45 cells with an EC50 value of refers to assay conditions whereby the bispecific antibody concentrations tested are between 0.1 and 1000 nM in the presence of anti-CD47 antibody B6H12.2 (ATCC® HB-9771™, also named B6H12 herein) in a concentration of 300 nM.

In one embodiment the bispecific antibody according to the invention binds to cynomolgus CEACAM5 as well as human CEACAM5.

As used herein, the term "antibody" refers to an antibody comprising two heavy chains and two light chains. In one embodiment the antibody is a full-length antibody. As used herein, the term "antibody heavy chain" refers to an antibody heavy chain, consisting of a variable region and a constant region as defined for a full-length antibody. As used herein, the term "antibody light chain" refers to an antibody light chain, consisting of a variable region and a constant region as defined for a full-length antibody.

The term "full-length antibody" denotes an antibody consisting of two "full-length antibody heavy chains" and two "full-length antibody light chains" A "full-length antibody heavy chain" is a polypeptide consisting in N-terminal to C-terminal direction of an antibody heavy chain variable domain (VH), an antibody constant heavy chain domain 1 (CH1), an antibody hinge region (HR), an antibody heavy chain constant domain 2 (CH2), and an antibody heavy chain constant domain 3 (CH3), abbreviated as VH-CH1-HR-CH2-CH3. A "full-length antibody light chain" is a polypeptide consisting in N-terminal to C-terminal direction of an antibody light chain variable domain (VL), and an antibody light chain constant domain (CL), abbreviated as VL-CL. The antibody light chain constant domain (CL) can be κ (kappa) or λ (lambda). The two full-length antibody domains are linked together via inter-polypeptide disulphide bonds between the CL domain and the CH1 domain and between the hinge regions of the full-length antibody heavy chains. Examples of typical full-length antibodies are natural antibodies like IgG (e.g. IgG 1 and IgG2), IgM, IgA, IgD, and IgE. The full-length antibody according to the invention is in one embodiment of human IgG1 type, in one further embodiment comprising one or more amino acid substitutions in the Fc part as defined below and/or being glycoengineered at Asn297. The full-length antibody according to the invention comprise two binding parts each formed by a pair of VH and VL, one binding to CEA and the other binding to CD47.

As used herein "Complementarity determining region(s)" ("CDR") describe the non-contiguous antigen combining sites (also known as antigen binding regions) found within the variable region of both heavy and light chain polypeptides. CDRs are also referred to as "hypervariable regions" and that term is used interchangeably herein with the term "CDR" in reference to the portions of the variable region that form the antigen binding regions. This particular region has been described by Kabat et al., U.S. Dept. of Health and Human Services, "Sequences of Proteins of Immunological Interest" (1983) and by Chothia et al., J. Mol. Biol. 196: 901-917 (1987), which are incorporated herein by reference, where the definitions include overlapping or subsets of amino acid residues when compared against each other. The definition of the FR-IMGT and CDR-IMGT regions of IG and TR is based on the "IMGT unique numbering for all IG and TR V-REGIONs of all species: interest for structure and evolution" (Lefranc, M.-P. et al., Dev. Comp. Immunol., 27, 55-77 (2003) and, for rearranged CDR3-IMGT and for FR4-IMGT, on the "IMGT unique numbering for V-DOMAIN and V-LIKE-DOMAIN" (Lefranc, M.-P. et al., Dev. Comp. Immunol., 27, 55-77 (2003)). Nevertheless, application of either definition to refer to a CDR of an antibody or variants thereof is intended to be within the scope of the term as defined and used herein. The appropriate amino acid residues which encompass the CDRs as defined by IMGT and Kabat are set forth below in the sequence list table. The exact residue numbers which encompass a particular CDR will vary depending on the sequence and size of the CDR. Those skilled in the art can routinely determine which residues comprise a particular CDR given the variable region amino acid sequence of the antibody. As used herein the term "comprising a CDRL1 of SEQ ID NO:x" refers to that the CDRL1 part of the referred variable light chain is of SEQ ID NO:x (comprising as CDRL1 a CDRL1 of SEQ ID NO:x). This is true also for the other CDRs.

As used herein, the term "Fc region; Fc domain" refers to a C-terminal region of an IgG heavy chain; in case of an IgG1 antibody, the C-terminal region comprises —CH2-CH3 (see above). Although the boundaries of the Fc region of an IgG heavy chain might vary slightly, the human IgG heavy chain Fc region is usually defined to stretch from the amino acid residue at position Cys226 to the carboxyl-terminus.

Constant regions are well known in the state of the art and e.g. described by Kabat, E. A., (see e.g. Johnson, G., and Wu, T. T., Nucleic Acids Res. 28 (2000) 214-218; Kabat. E. A., et al, Proc. Natl. Acad. Sci. USA 72 (1975) 2785-2788).

The term "epitope" includes any polypeptide determinant capable of specific binding to an antibody. In certain embodiments, "epitope" includes chemically active surface groupings of molecules such as amino acids, sugar side chains, phosphoryl, or sulfonyl, and, in certain embodiments, may have specific three dimensional structural characteristics, and or specific charge characteristics. An epitope is a region of a target that is bound by an antibody. In one embodiment the bispecific antibody of the invention binds to the N-terminal domain of CEACAM5 (Ig-like V-type domain of amino acids 35-144, UniProtKB—P06731). Binding location of the CEA×CD47 bispecific antibodies to CEACAM5 is achieved via epitope binning. In epitope binning, antibodies are tested in a pairwise combinatorial manner, and antibodies that compete for the same binding region are grouped together into bins. Competition testing is performed herein with anti-CEA antibodies according to the state of the art and as described herein. In one embodiment the bispecific antibody of the invention competes for binding to CEACAM5 with reference antibody SM3E (bin 1). In one embodiment the bispecific antibody of the invention does not compete for binding to CEACAM5 with reference antibodies SM3E, MEDI, T84.66, SAR, Lab, and CH1A1A (bin 2). Competition is measured by an assay wherein biotinylated human CEACAM5 in a concentration of 0.5 µg/ml is immobilized and incubated with 10 µg/ml of the reference. CEACAM5 antibodies comprising the CEACAM5 binding part of the CEA×CD47 bispecific antibody of the present invention are added at 0.2 µg/ml for 1 hour at room temperature. The plate is washed and the bound CEACAM5 mAbs are detected.

In one embodiment the bispecific antibody of the invention binds to the B3 domain and the GPI anchor of CEACAM5. In one embodiment of the invention the antibody of the invention binds to the same epitope as an anti-CEA antibody (MAB CEA), which comprises a heavy chain variable region of SEQ ID NO:20 and a light chain variable region of SEQ ID NO:21.

As used herein, the term "a common heavy chain (cHC)" refers to a polypeptide consisting in N-terminal to C-terminal direction of an antibody heavy chain variable domain (VH), an antibody constant heavy chain domain 1 (CH1), an antibody hinge region (HR), an antibody heavy chain constant domain 2 (CH2), and an antibody heavy chain constant domain 3 (CH3), abbreviated as VH-CH1-HR-CH2-CH3. Common heavy chains suitable for the bispecific antibodies according to the invention are heavy chains of an anti-CD47 antibody as described in WO2012023053, WO2013088259, WO2014087248, and WO2016156537 (each of which is incorporated by reference in its entirety). In one embodiment the cHC of the bispecific antibody according to the invention comprises as light chain CDRs a CDRL1 of SEQ ID NO:1, a CDRL2 of SEQ ID NO:2, and a CDRL3 of SEQ ID NO:3, and as heavy chain CDRs a CDRH1 of SEQ ID NO:25, a CDRH2 of SEQ ID NO:26 and a CDRH3 of SEQ ID NO:27. In one embodiment the cHC of the bispecific antibody according to the invention comprises as heavy chain variable region VH a VH region of SEQ ID NO:4. In one embodiment the cHC of the bispecific antibody according to the invention is of SEQ ID NO:5.

In one embodiment the antibody according to the invention is a κλ bispecific antibody comprising a cHC (κλ Body).

"The κλ Body format allows the affinity purification of bispecific antibodies which are undistinguishable from a standard IgG molecule and with characteristics that are undistinguishable from a standard monoclonal antibody (see e.g. WO2013088259, WO2012023053), promising no or low immunogenicity potential in patients.

Bispecific antibodies of the invention, comprising a common heavy chain, can be made for example according to WO2012023053 (incorporated by reference in its entirety). The methods described in WO2012023053 generate bispecific antibodies that are identical in structure to a human immunoglobulin. This type of molecule is composed of two copies of a unique heavy chain polypeptide, a first light chain variable region fused to a constant Kappa domain and second light chain variable region fused to a constant Lambda domain. One binding site displays specificity to CEA and the other site displays specificity to CD47, wherein to each the heavy and the respective light chain contribute. The light chain variable regions can be of the Lambda or Kappa family and are preferably fused to a Lambda and Kappa constant domains, respectively. This is preferred in order to avoid the generation of non-natural polypeptide junctions. However, it is also possible to obtain bispecific antibodies of the invention by fusing a Kappa light chain variable domain to a constant Lambda domain for a first specificity or fusing a Lambda light chain variable domain to a constant Kappa domain for the second specificity. The other light chain is then always fully kappa (VL and CL) or fully lambda (VL and CL). The bispecific antibodies described in WO 2012023053 are "κλ Bodies". This κλ-Body format allows the affinity purification of a bispecific antibody that is undistinguishable from a standard IgG molecule with characteristics that are undistinguishable from a standard monoclonal antibody and, therefore, favourable as compared to previous formats including e.g. amino acid bridges or other unnatural elements.

An essential step of the method is the identification of two antibody Fv regions (each composed by a variable light domain and variable heavy domain) having different antigen specificities that share the same heavy chain variable domain. Numerous methods have been described for the generation of monoclonal antibodies and fragments thereof. (see, e.g., Antibodies: A Laboratory Manual, Harlow E, and Lane D, 1988, Cold Spring Harbor Laboratory Press, Cold Spring Harbor, N.Y.). Fully human antibodies are antibody molecules in which the sequence of both the light chain and the heavy chain, including the CDRs 1 and 2, arise from human genes. The CDR3 region can be of human origin or designed by synthetic means. Such antibodies are termed "human antibodies", or "fully human antibodies". Human monoclonal antibodies can be prepared by using the trioma technique; the human B-cell hybridoma technique (see Kozbor, et al., 1983 Immunol Today 4: 72); and the EBV hybridoma technique to produce human monoclonal antibodies (see Cole, et al., 1985 In: Monoclonal Antibodies and Cancer Therapy, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., supra). As used herein, the term "CEA, CEACAM5" refers to human carcinoembryonic antigen (CEA, CEACAM-5 or CD66e; UniProtKB—P06731) which is a cell surface glycoprotein and a tumor-associated antigen (Gold and Freedman, J Exp. Med., 121:439-462, 1965; Berinstein N L, J Clin Oncol., 20:2197-2207, 2002). As used herein, the term "CEACAM6" refers to human CEACAM6 (CD66c; UniProtKB—P40199), which is also a member of the carcinoembryonic antigen-related cell adhesion molecule (CEACAM) family. As used herein, the term "CEACAM1" refers to human CEACAM1 (UniProtKB—P13688 (CEAM1_HUMAN) which is also a member of the carcinoembryonic antigen-related cell adhesion molecule (CEACAM) family.

As used herein, the term "MAB CEA" refers to a monoclonal antibody specifically binding to human CEACAM5, comprising a heavy chain variable region of SEQ ID NO:20 and a light chain variable region of SEQ ID NO:21. As used herein, the term "MAB CEA1" refers to a monoclonal antibody specifically binding to human CEACAM5, comprising a heavy chain variable region of SEQ ID NO:88 and a light chain variable region of SEQ ID NO:89. In one embodiment the bispecific antibody according to the invention is competitive with MAB CEA, MAB CEA1, CEA-TCB, or CEA-TCB1; in a further embodiment the bispecific antibody according to the invention is not competitive with MAB CEA, MAB CEA1, CEA-TCB, or CEA-TCB1. MAB CEA and said variable chains are described in US20140242079 (SEQ ID NO:21 and 27 of US20140242079 (incorporated by reference in its entirety)). A bispecific anti-CEA×anti-CD3ε antibody (CEA-TCB) comprising the VH and VL of MAB CEA is described in Bacac et al Clin. Cancer Res., 22(13), 3286-97 (2016)). A further bispecific CEA×CD3 Mab comprising the VH and VL of MAB CEA1 (CEA-TCB1) is described in WO2017055389 as molecule B "2+1 IgG CrossFab, inverted" with charge modifications (VH/VL exchange in CD3 binder, charge modification in CEA binder, humanized CEA binder) (see FIG. 3B and SEQ ID NOs 34, 36-38 of WO2017055389 (incorporated by reference in its entirety)).

As used herein in one embodiment "bispecific CEA×CD3 antibody" refers to antibody CEA-TCB or antibody CEA-TCB1.

"As used herein, the terms "specifically binding to CD47, binding to CD47, CD47 binding part" refer in the context of the bispecific antibodies according to the invention to specificity for CD47. CD47 is a multi-pass membrane protein and comprises three extracellular domains (amino acids 19-141, 198-207, and 257-268; see UniProtKB—Q08722). As used herein the term "binding affinity to CD47" is measured by SPR.

In one embodiment binding of the bispecific antibody according to the invention to CD47 occurs via one or more of said extracellular domains. In one embodiment, the bispecific antibodies according to the invention inhibit the interaction between human CD47 and human SIRPα.

As used herein, the terms "specifically binding to CEA, binding to CEA, CEA binding part" refer in the context of the bispecific antibodies according to the invention to specificity for CEACAM5 on the surface of a cell. Binding to CEA (CEACAM5) on cells is preferably measured with gastric adenocarcinoma MKN-45 cells comprising 200.000 to 600.000 CEA copies per cell. The concentration of the antibody according to the invention is varied in an appropriate range in regard to a resulting EC50 value for binding to MKN-45 cells as defined above. The bispecific antibodies according to the invention are specifically binding to such cell membrane-bound CEACAM5 and do not or only minimally bind in a further embodiment to soluble CEACAM5, in concentrations like found in the blood/plasma of patients, i.e. soluble CEA in such concentrations, does not or only minimally influence the efficacy of a bispecific antibody of the invention. This is measured by influence of soluble CEA on the phagocytosis of MIKN-45 cells by the bispecific antibodies of this invention as described.

As used herein, the term "membrane-bound human CEA" refers to human carcinoembryonic antigen (CEA) that is bound to a membrane-portion of a cell or to the surface of a cell, in particular, the surface of a tumor cell. The term "membrane-bound human CEA" may, in certain circumstances, refer to CEA which is not bound to the membrane of a cell, but which has been constructed so as to preserve the membrane bound CEA epitope to which the antibody according to the invention binds.

Figure 20A:
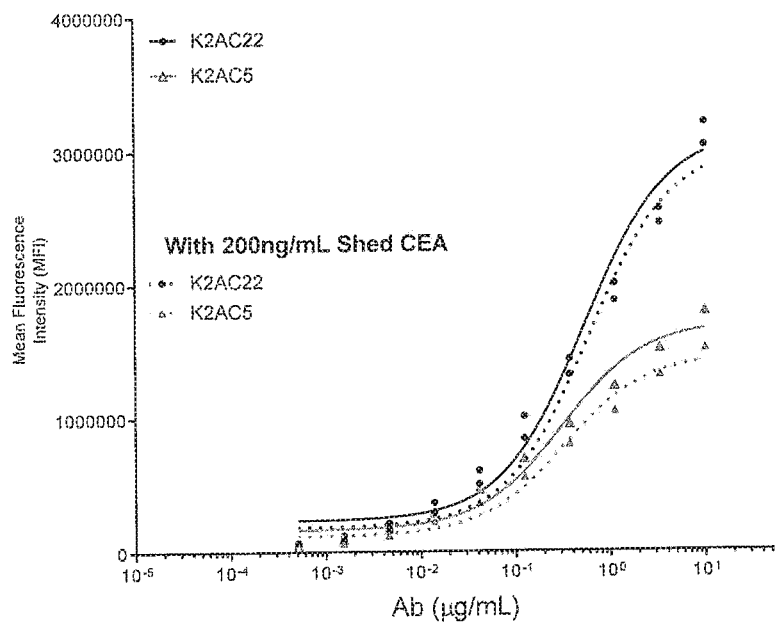
FIGS. 20A and 20B shows the concentration dependent effects of the CEA×CD47 antibodies K2AC5 and 22 on binding (FIG. 20A) and phagocytosis (FIG. 20B) (assessed with imaging based assay (CellInsight) and expressed as phagocytosis index) in presence or not of 200 ng/mL of shed CEA. No significant influence of 200 ng/mL soluble CEA on the binding curves of both CEA×CD47 antibodies. No significant effect of soluble CEA on the maximal phagocytosis, EC50 are shifted by less than a factor of 4.
Figure 20B:
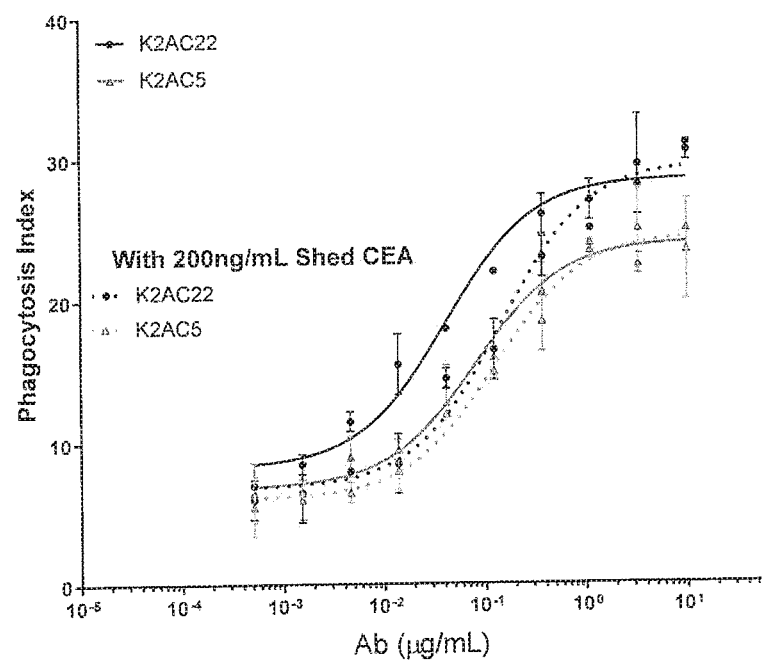
Figure 21A:
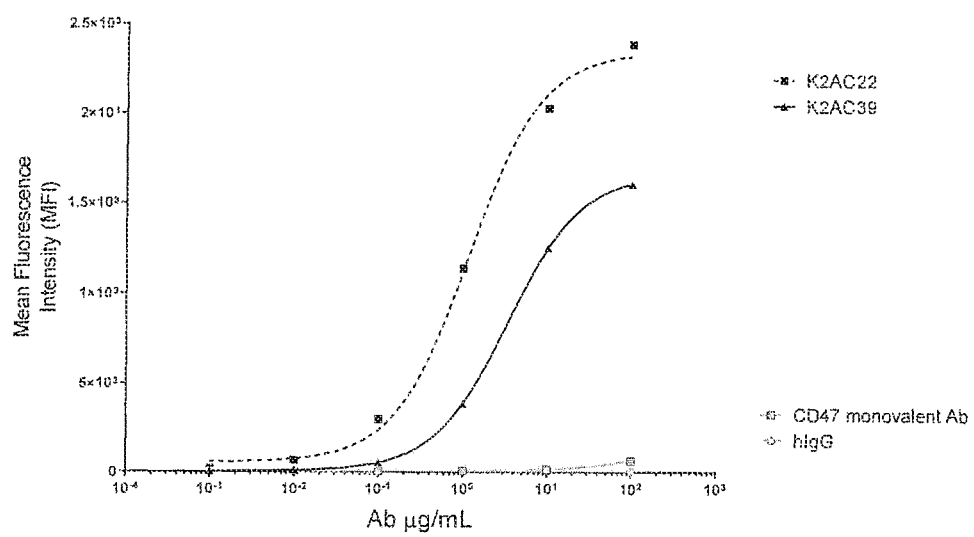
FIG. 21A shows the concentration dependent binding of CD47×CEA bispecific antibodies of the invention to MKN-45 cells as compared to the corresponding anti-CD47 monovalent antibody and an irrelevant hIgG1 control. K2AC39 is a CD47×CEA bispecific antibody candidate cross-reactive to human CEACAM5 and human CEACAM6; while K2AC22 does not cross-react to CEACAM6. Binding to target cells (MKN-45) expressing CD47, CEACAM5 and CEACAM6 was assessed by FACS.
Figure 21B:
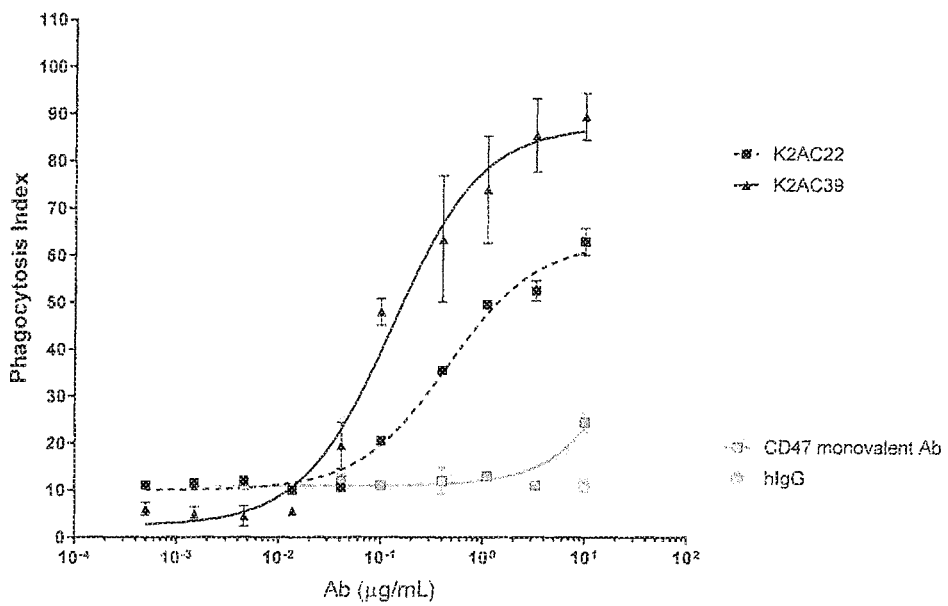
FIG. 21B shows the concentration dependent increase of phagocytosis (assessed by the imaging based assay (CellInsight™) and expressed as phagocytosis index) of MKN-45 cells induced by 2 different CD47×CEA bispecific antibodies (K2AC22 and K2AC39) as compared to the corresponding anti-CD47 monovalent antibody and an irrelevant hIgG1 control. K2AC39 is CD47×CEA bispecific candidate cross-reactive to human CEACAM5 and human CEACAM6; while K2AC22 does not cross-react to CEACAM6. 1 mg/mL of human IgG is added in this experiment. K2AC39 exhibits higher phagocytosis of MKN45 cells as compared to K2AC22.

As used herein, the term "no substantial cross-reactivity against soluble CEACAM5, non-binding to soluble CEACAM5" refer in the context of the bispecific antibodies according to the invention that such antibodies do not show relevant binding to soluble CEACAM5, particularly when compared to membrane-bound CEACAM5. Such non-binding can be indirectly determined by low influence of the soluble CEA on the phagocytosis activity of the bispecific antibody in a phagocytosis assay with MKN-45 cells as described below, preferably imaging based measurement of phagocytosis index, see Example 9). No substantial cross-reactivity against soluble CEACAM5 means therefore that the maximum achievable phagocytosis index (typical concentration-phagocytosis index curves of the bispecific antibody CEA×CD47 and maximal achievable phagocytosis index are shown e.g. in FIGS. 12, 15, 16, 17, 20A the assay is explained in Example 9.2) for the phagocytosis of MKN-45 cells in the presence of human macrophages, by said bispecific antibody is not reduced by more than 20% if 200 ng/ml soluble CEA are added to the phagocytosis assay. Alternatively, the shift of the EC50 for the concentration—phagocytosis index curve can be determined. Addition of 200 ng/ml soluble CEA will not shift this EC50 by more than a factor of 3, in one embodiment towards higher concentrations. Alternatively, no or minimal influence of soluble CEA on binding of a bispecific antibody of this invention to CEA on cells is expected by the influence of the soluble CEA on the binding curve measured by flow cytometry (such a binding curve is shown in FIG. 20B). Addition of 200 ng/ml soluble CEA to the flow cytometry assay will not shift the binding curve respectively the EC50 by more than a factor of 3, in one embodiment towards higher concentrations The term "soluble CEA, shed CEA, sCEA" refers to CEACAM5 that is not bound to or is cleaved from a cell membrane or cell surface (e.g., a tumor cell surface). Soluble CEA can, for example, be found in the blood stream of a subject with cancer. When CEA is shed from the cell membrane, it is assumed that the GPI anchor is disrupted, and CEACAM5 undergoes a conformational change that can prevent or at least weaken the binding of soluble CEA to the antibody according to the invention.

As used herein, the terms "cross-reactivity against CEACAM6, specifically binding to CEACAM6, binding to CEACAM6, CEACAM6 binding part" refer in the context of the bispecific antibodies according to the invention that the bispecific antibody according to the invention recognizes specifically CEACAM5 and CEACAM6 on the surface (membrane) of a cell. In one embodiment the bispecific antibodies according to the invention are specifically binding to membrane-bound CEACAM6, when compared to binding to membrane-bound CEA. The ratio of the occupancy of CEACAM5 to CEACAM6 receptors on a cell surface by a given bispecific antibody of the invention is dependent on the binding affinities to CEACAM5 respectively CEACAM6 and can be easily calculated if these binding affinities have been measured, e.g. by SPR.

In certain embodiments, an antibody that specifically binds to CEACAM5 does not bind to carcinoembryonic antigen-related cell adhesion proteins such as, CEACAM1, CEACAM3, CEACAM4, CEACAM6, CEACAM7 and CEACAM8. In certain embodiments, an antibody that specifically binds to CEACAM5 also binds to CEACAM6 at similar EC50.

As used herein, the terms "no substantial cross-reactivity against CEACAM1 and/or CEACAM3, CEACAM4, CEACAM6, CEACAM7 and CEACAM8, non-binding to said CEACAM" refer in the context of the bispecific antibodies according to the invention that such antibodies do not show any relevant binding to said membrane-bound CEACAM at therapeutic plasma concentrations (1 to 1000 nM), when compared to membrane-bound CEACAM5. Non-binding to CEACAM1 and/or CEACAM5, CEACAM6 and CEACAM8 can be determined by flow cytometry based measurement of the binding curve to recombinant CHO cells expressing said CEACAM and to CEACAM3 and/or CEACAM4, and CEACAM7 by measurement of the binding curve to recombinant PEAK cells expressing said CEACAM or by an ELISA assay measuring the binding to the recombinant CEACAM proteins. As used herein, the terms "does not bind, no binding to" a compound mentioned herein (e.g. human IgG), refer also to such non-relevant binding or non crossreactivity. E.g. in an ELISA, OD values for such unrelated compounds will be about equal to that of the limit of detection.

As used herein, the term "bispecific antibody binding to human CEA and human CD3, CEA×CD3 Mab" means a bispecific antibody binding to human CEACAM5 and CD3ε. Such antibodies are for example "CEA-TCB" and "CEA-TCB1". As used herein "CEA-TCB" refers to a bispecific antibody binding to CEA and CD3 as described in US20140242079 (incorporated by reference in its entirety) as SEQ ID NO:1, 2, 21, and 22. The amino acid sequences of CEA-TCB are also described as SEQ ID NO:96 to 99 of the present invention. As used herein "CEA-TCB1" refers to molecule B in the "2+1 IgG CrossFab, inverted" format with charge modifications (VH/VL exchange in CD3 binder, charge modification in CEA binder, humanized CEA binder): FIG. 3B, SEQ ID NOs 34, 36-38 of WO2017055389 (incorporated by reference in its entirety)). The amino acid sequences of CEA-TCB1 are described as SEQ ID NO:92 to 95 of the present invention. Further CEA×CD3 Mabs are described in WO2007071426, WO2013012414, WO2015112534, WO2017118675, US20140242079 and WO2017055389 (each of which is incorporated by reference in its entirety). A further CEA×CD3 Mab is RO6958688 (see e.g. Bacac et al Clin. Cancer Res., 22(13), 3286-97 (2016). In one embodiment said CEA×CD3 Mab is competitive and/or binds to the same epitope of human CEACAM5 as MAB CEA. In one embodiment said CEA×CD3 Mab is competitive and/or binds to the same epitope of human CEACAM5 as MAB CEA1.

As used herein "CD3 Mab, antibody against CD3" refers to human CD3ε(UniProtKB—P07766 (CD3E_HUMAN). The term "antibody against CD3ε, anti CD3ε antibody" relates to an antibody specifically binding to CD3ε. In one embodiment, the antibody against CD3ε is specifically binding to the same epitope as anti-CD3 antibody SP34 (BD Biosciences Catalog No. 565983). In one embodiment, the antibody against CD3ε is specifically binding to an epitope of human CD3ε, comprising the amino acid sequence of SEQ ID NO:22. In one embodiment, the antibody against CD3ε is specifically binding to human CD3ε and comprises a heavy chain variable region of SEQ ID NO:90 and a light chain variable region of SEQ ID NO:91.

In one embodiment the bispecific antibody of the invention does not compete with CEA-TCB and/or CEA-TCB1 for binding on CEA as presented on MKN-45 cells. Therefore CEA-TCB in a concentration of 300 nM (CEA-TCB) or 30 nM (CEA-TCB1) do not shift the EC50 of the phagocytosis index curve of said the bispecific antibody of the invention for MKN-45 cells by more than a factor of 3, in one embodiment towards higher concentrations.

300 nM are a concentration measured in patient plasma at therapeutically effective doses of CEA-TCB ((J. Tabernero et. al., J. Clin. Oncol. 35, 2017 (suppl. Abstr. 3002)). CEA-TCB1 is in preclinical investigations approx. 10 to 100 times more potent than CEA-TCB (binding affinity, tumor cell lysis, WO2017055389), therefore the shift of the EC50 is tested at 30 nM.

Figure 2:
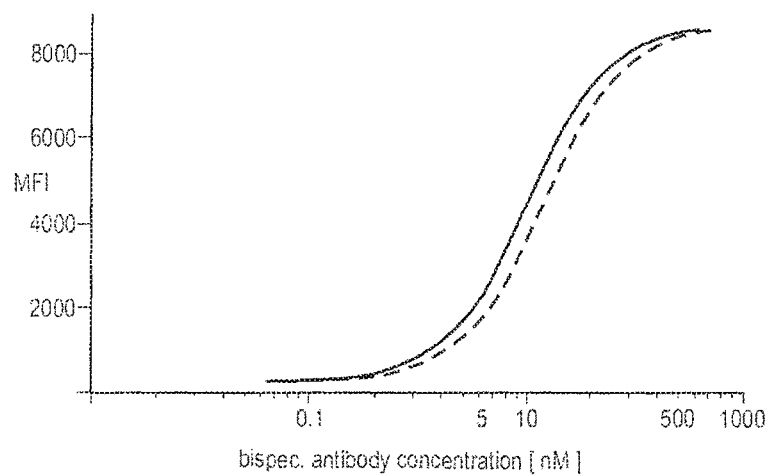
FIG. 2 shows the binding of a TAA×CD47 bispecific antibody to tumor cells carrying on the surface the TAA as well as CD47. Binding of the TAA×CD47 with an EC50 between 1 and 50 nM (solid line, see also FIG. 11 for binding curves of various CEA×CD47 antibodies of the invention); the broken line shows exemplary and schematic a potential shift of the binding curve by e.g. soluble CEA, for concrete data see FIG. 20A showing e.g. the influence of 200 ng/mL soluble CEA on the binding curve to MKN-45 cells of CEA×CD47 bispecific antibodies of the invention like K2AC5 and 22.
Figure 11A:
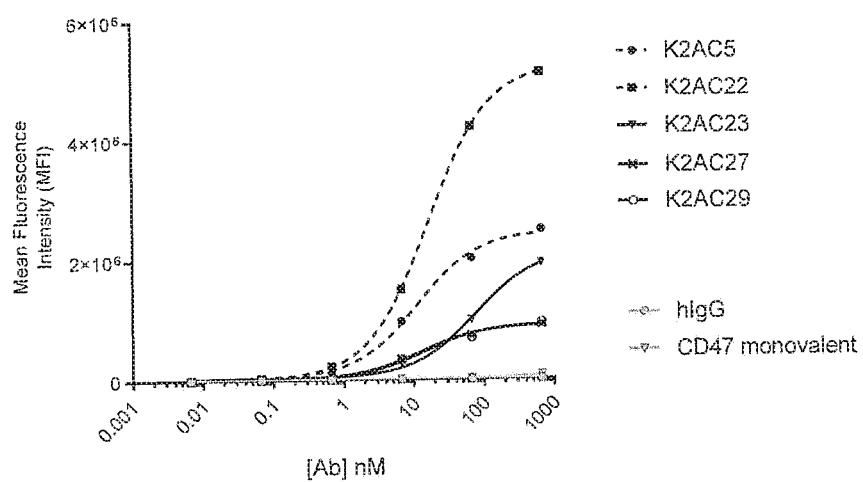
FIGS. 11A and 11B show concentration dependent binding of CD47×CEA bispecific antibodies of the invention as compared to the corresponding anti-CD47 monovalent antibody. Binding to target cells (MKN-45) expressing CD47 and CEA was assessed by FACS.
Figure 11B:
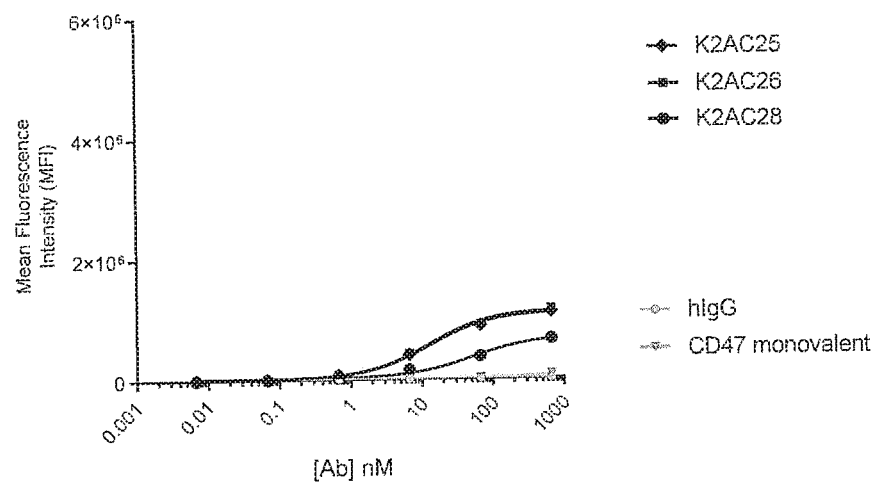

Competition in binding can be determined by flow cytometry based measurement of the binding curve to MKN-45 cells and determination of the EC50 of this binding curve (see e.g. FIG. 2 and FIG. 11 for such a binding curves). Non-competition means that EC50 is shifted by less than a factor of 3, in one embodiment to towards higher concentrations, if 300 nM of MAB CEA or CEA-TCB are added to the assay. 300 nM are a concentration in the range of therapeutically active doses/plasma-concentrations of CEA×CD3 bispecific antibody (CEA-TCB) (J. Tabernero et. al., J. Clin. Oncol. 35, 2017 (suppl. Abstr. 3002)). Non-competition by MAB CEA1 or CEA-TCB1 means that EC50 is shifted by less than a factor of 3 if 30 nM of MAB CEA1 respectively CEA-TCB1 are added to the assay.

Competition in binding can be determined by flow cytometry based measurement of the binding curve to MKN-45 cells and determination of the EC50 of this binding curve (see FIG. 2 and FIG. 11 for such binding curves). Non-competition means that EC50 is changed by less than a factor of 3 if 300 nM of MAB CEA, or CEA-TCB are added to the assay. 300 nM are a concentration in the range of therapeutically active doses/plasma-concentrations of CEA×CD3 bispecific antibody (CEA-TCB) (J. Tabernero et. al., J. Clin. Oncol. 35, 2017 (suppl. Abstr. 3002)). Non-competition by MAB CEA1 or CEA-TCB1 means that EC50 is changed by less than a factor of 3 if 30 nM of MAB CEA1 respectively CEA-TCB1 are added to the assay.

As used herein, the term "noncompetitive" means that a second antibody (MAB CEA, MAB CEA1 or a bispecific antibody against CEA×CD3ε, like CEA-TCB or CEA-TCB1) in a concentration of 300 nM (MAB-CEA, CEA-TCB) or 30 nM (MAB CEA1, CEA-TCB1) does not shift the EC50 of the binding curve of the bispecific antibody of the invention to MKN-45 cells by more than a factor of 3, in one embodiment towards higher concentrations. As used herein, the term "competitive" means that a second antibody (MAB CEA, MAB CEA1 or bispecific antibody against CEA×CD3ε, like CEA-TCB or CEA-TCB1) in a concentration of 300 nM respectively 30 nM (MAB CEA1 or CEA-TCB1) shifts the EC50 of the binding curve of the bispecific antibody of the invention to MKN-45 cells by more than a factor of 3, preferably by more than a factor of 5 towards higher concentrations.

As used herein the term "complementarity determining region" ("CDR") describes the non-contiguous antigen combining sites (also known as antigen binding regions) found within the variable region of both heavy and light chain polypeptides. CDRs are also referred to as "hypervariable regions" and that term is used interchangeably herein with the term "CDR" in reference to the portions of the variable region that form the antigen binding regions. This particular region has been described by Kabat et al., U.S. Dept. of Health and Human Services, "Sequences of Proteins of Immunological Interest" (1983) and by Chothia et al., J. Mol. Biol. 196:901-917 (1987). Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in bispecific antibody according to the invention are according to the Kabat numbering system.

As used herein the term "ADCP" refers to antibody-dependent cell-mediated phagocytosis.

Figure 12:
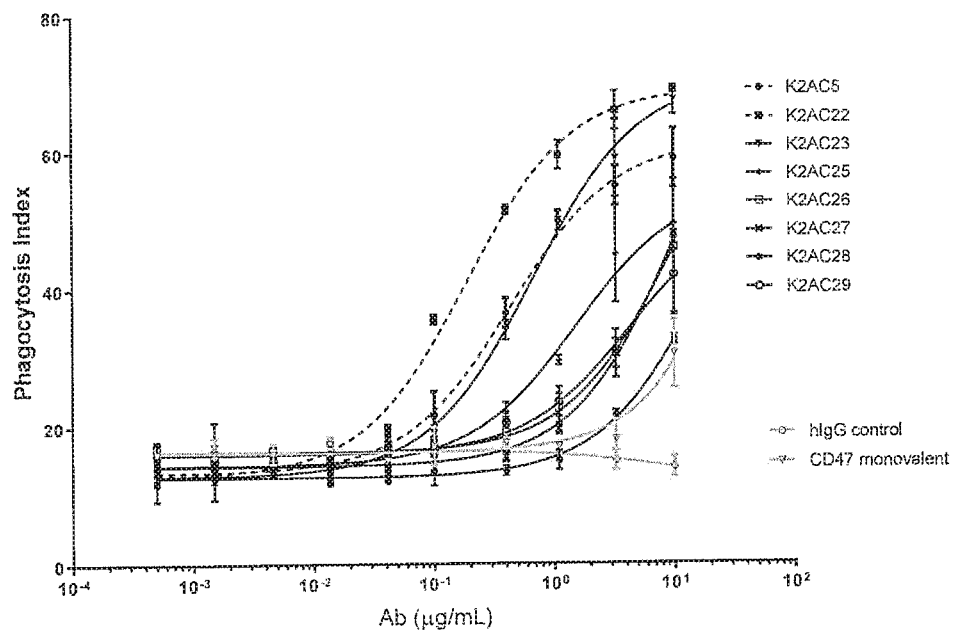
FIG. 12 shows the concentration dependent increase of phagocytosis (assessed by the CellInsight™ assay and expressed as phagocytosis index) of MKN-45 cells induced by different CD47×CEA bispecific antibodies at different concentrations (K2AC5, K2AC22, K2AC23, K2AC25, K2AC26, K2AC27, K2AC28 and K2AC29) as compared to the corresponding anti-CD47 monovalent antibody. 1 mg/mL of hIgG (human immunoglobulin) is added in this experiment for each tested antibody. EC50 values established in this experiment are comprised between 0.2 and 20 µg/ml and the maximal phagocytosis index (at 10 µg/mL) ranges between 32.5% and 69% (see Table 3 in the Examples Chapter for summary of data for each individual CD47×CEA bispecific antibody tested).
Figure 15:
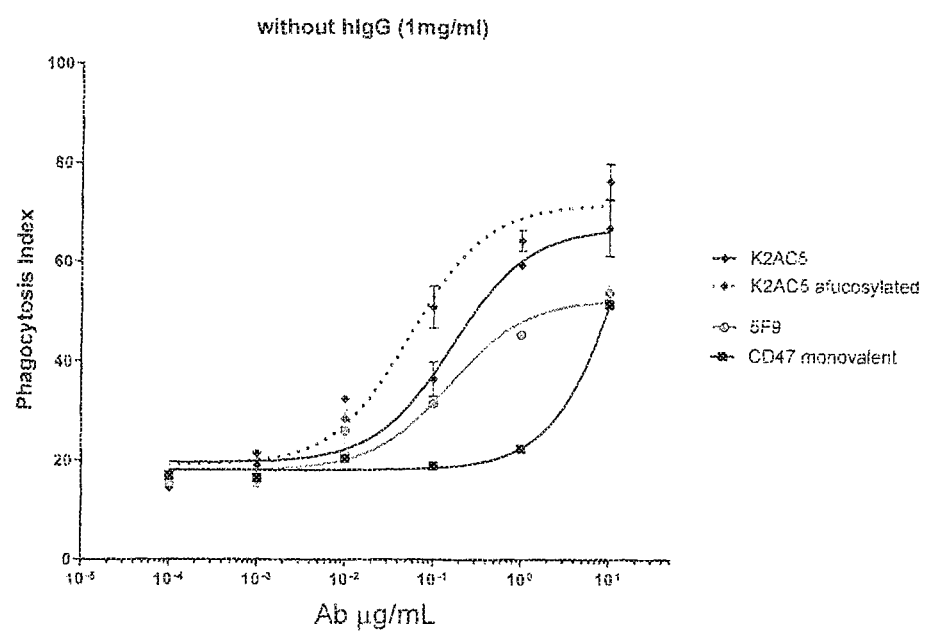
FIGS. 15A and 15B and FIGS. 16A and 16B show the concentration dependent increase of phagocytosis (assessed with imaging based assay CellInsight and expressed as phagocytosis index) induced by K2AC5 and K2AC22 CD47×CEA bispecific antibodies bearing either a wild-type human IgG1 Fc portion or an afucosylated Fc portion. The corresponding CD47 monovalent antibody (with wild-type hIgG1 Fc) and the sequence-identical analogue of the anti-CD47 antibody Hu5F9-G4 (5F9 bearing a human IgG4 Fc) were run for comparison. The experiments were performed either in the absence (FIGS. 15A and 15B) or in the presence (FIGS. 16A and 16B) of 1 mg/ml human IgG. In both experimental conditions, bispecific antibody versions with afucosylated Fc show a higher phagocyte potency as compared to the corresponding wild-type Fc-bearing versions (3-10 fold lower EC50 for afucosylated K2AC5 and K2AC22 bispecific antibodies as compared to the wt version).
Figure 15:
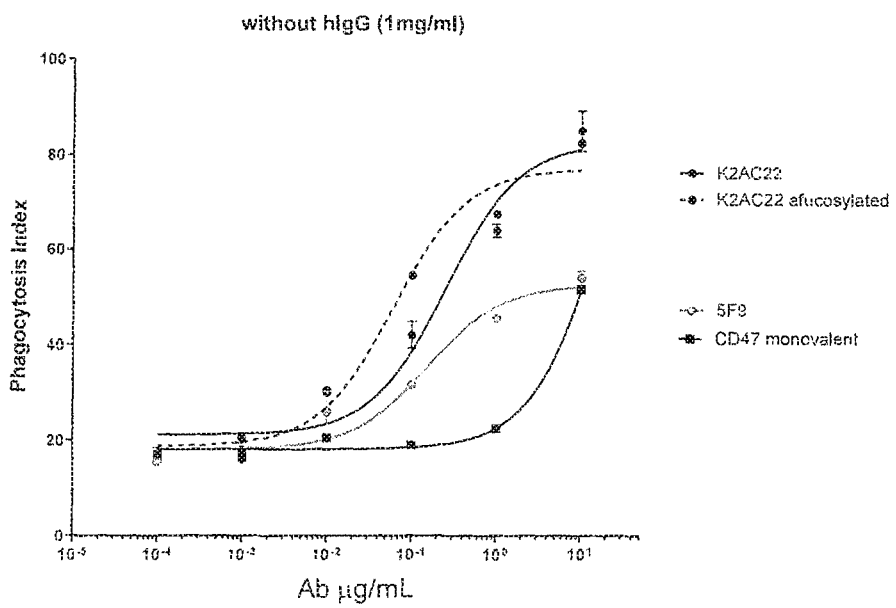
Figure 16:
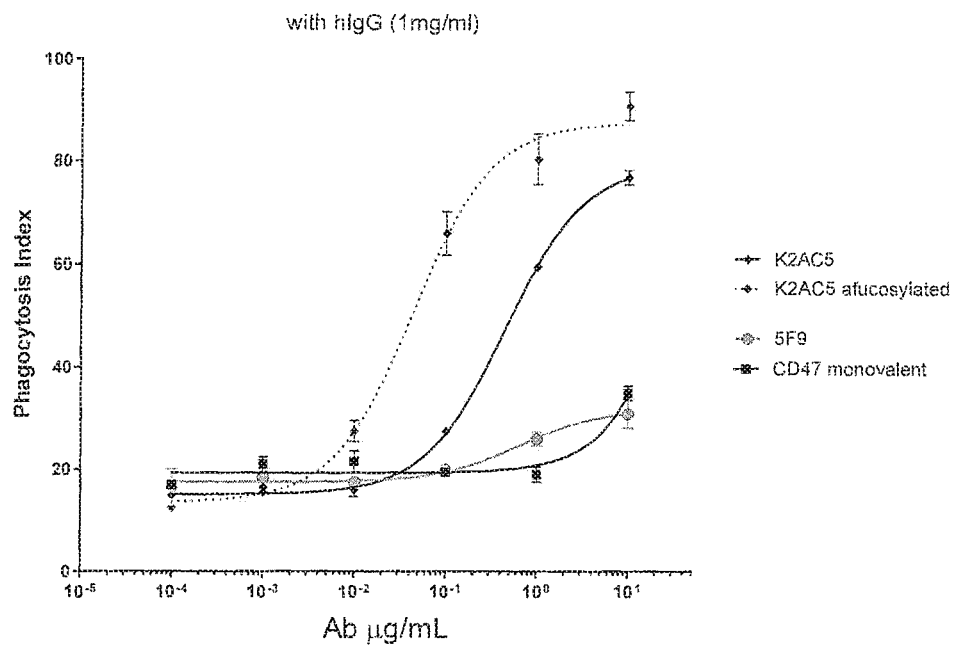
Figure 16:
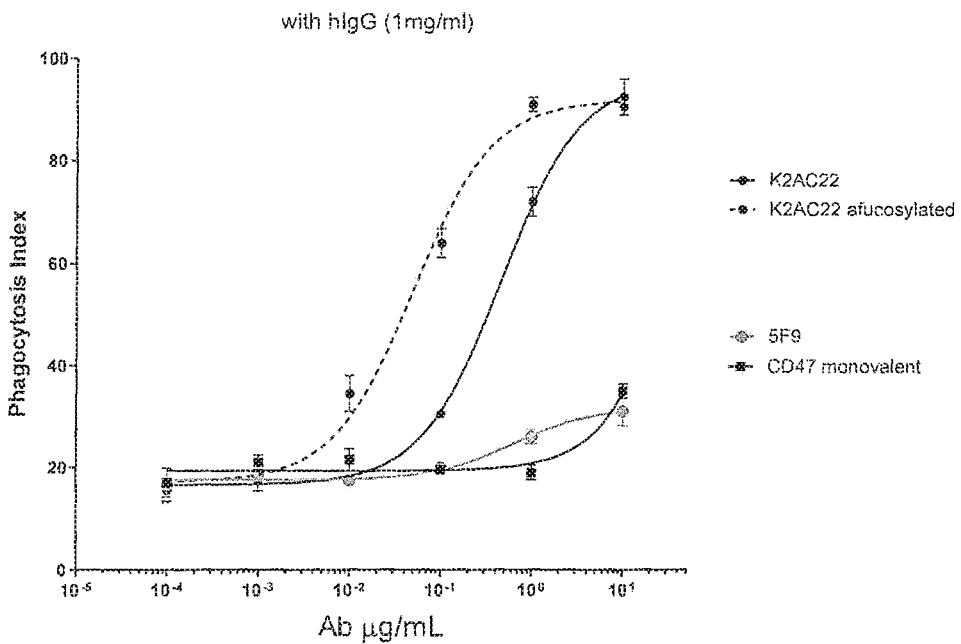

As used herein "phagocytosis, EC50 value of phagocytosis, maximum of phagocytosis, phagocytosis index" according to the invention refer to phagocytosis measured with MKN-45 cells by "imaging". An appropriate imaging method, with incubation at an effector (macrophages):target (tumor) cell ratio of e.g. 1:1 or 1:3 and with the "phagocytosis index" as readout (Imaging determined ADCP") is described in Example 9. FIG. 3B shows the maximal achievable phagocytosis index as determined in tested concentration range of 0.1 or even lower to approx. 500 nM of bispecific TAA×CD47 antibodies. FIGS. 12, 15 and 16 show the ADCP results for bispecific antibodies according to the invention K2AC5 and K2AC22. As used herein "phagocytosis of said bispecific antibody" means phagocytosis caused/induced by said antibody. Antibody K2AC22 comprises a first binding part, specifically binding to human CEACAM5 and a second binding part, specifically binding to human CD47, whereby the first binding part comprises a heavy chain of SEQ ID NO:5 and a light chain of SEQ ID NO:65, and that the second binding part comprises a heavy chain of SEQ ID NO:5 and a light chain of SEQ ID NO:11. Antibody K2AC5 comprises a first binding part, specifically binding to human CEACAM5 and a second binding part, specifically binding to human CD47, whereby the first binding part comprises a heavy chain of SEQ ID NO:5 and a light chain of SEQ ID NO:64, and that the second binding part comprises a heavy chain of SEQ ID NO:5 and a light chain of SEQ ID NO:11. Antibodies K2AC10, K2AC13 K2AC18, K2AC23, K2AC25, K2AC26, K2AC27, K2AC28, K2AC29 comprise the same heavy chains and second binding part light chain, but differ in the first binding part light chain (see table 1, sequence list).

For further information on phagocytosis in the field, phagocytosis can also be measured by a flow cytometry based method as % phagocytosis (see Example 9 and FIG. 3A for dependency of % phagocytosis from the concentrations of monovalent TAA and CD47 antibodies and TAA× CD47 bispecific antibody) and at a ratio of e.g. 3 human macrophages to 1 target/tumor-cell ("flow cytometry determined ADCP").

The terms "human IgG, hIgG" refers to a commercially available clinical-grade homogeneous preparation of human immunoglobulin IgG that does not bind specifically to CD47 and CEACAM5.

Antibodies produced in CHO cells typically have complex biantennary structures with very low or no bisecting-N-acetylglucosamine (bisecting GlcNAc) and high levels of core fucosylation. Overexpression of N-acetylglucosaminyl-transferase III has been used to increase the fraction of bisecting GlcNAc that resides on antibodies to improve antibody-dependent cellular cytotoxicity (ADCC). RNAi and gene deletion technologies have also been used to decrease or eliminate the fucose on antibodies to dramatically increase ADCC activity (Davis J. et al.; Biotechnol. Bioeng. 2001; 74:288-294; Saba J A, et al.; Anal. Biochem. 2002; 305:16-31; Kanda Y, et al.; J. Biotechnol. 2007; 130:300-310; Mori K, et al.; Biotechnol. Bioeng. 2004; 88:901-908).

In one embodiment, the bispecific antibody according to the invention is glycoengineered. In one embodiment the glycoengineered bispecific antibody according to the invention has increased ADCC and/or ADCP activity (decreased EC50 and/or higher maximum of phagocytosis index) compared to the bispecific antibody comprising an Fc part included in SEQ ID NO:5 (parent antibody), comprising glycosylation according to a production in a CHO K1 cell line (ATCC® CCL-61™) at standard conditions (1000 ml vessel, temperature 37° C., pH 7.0, impeller speed 80 rpm, minimum dissolved oxygen 30%; cultivation time 14 days).

Figure 13:
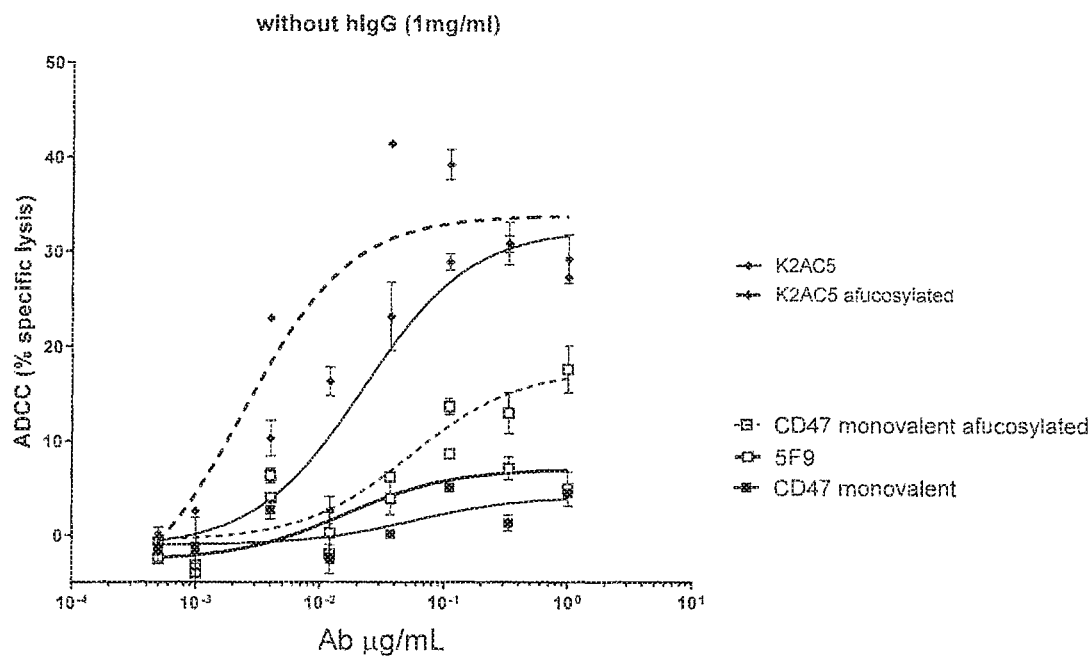
FIGS. 13A and 13B and 14A and 14B show the concentration dependent increase of ADCC (assessed using the LDH release assay and expressed as % specific lysis of MKN45 cancer cells) induced by two selected CD47×CEA bispecific antibodies (K2AC5 and K2AC22) of the invention, and the corresponding CD47 monovalent antibody, either bearing a wild-type human IgG1 Fc part or an afucosylated Fc part. The sequence-identical analogue of the anti-CD47 antibody Hu5F9-G4 (5F9 bearing a human IgG4 Fc portion, described in US20160333093) was run for comparison. The experiments were performed in the absence (FIGS. 13A and 13B) or in the presence (FIGS. 14A and 14B) of 1 mg/ml human IgG. In both experimental conditions, antibody versions with afucosylated Fc induce a higher lysis/killing activity as compared to the corresponding wild-type Fc-bearing versions (5-9 fold lower EC50 for afucosylated K2AC5 and K2AC22 bispecific antibodies as compared to the wt version).
Figure 13:
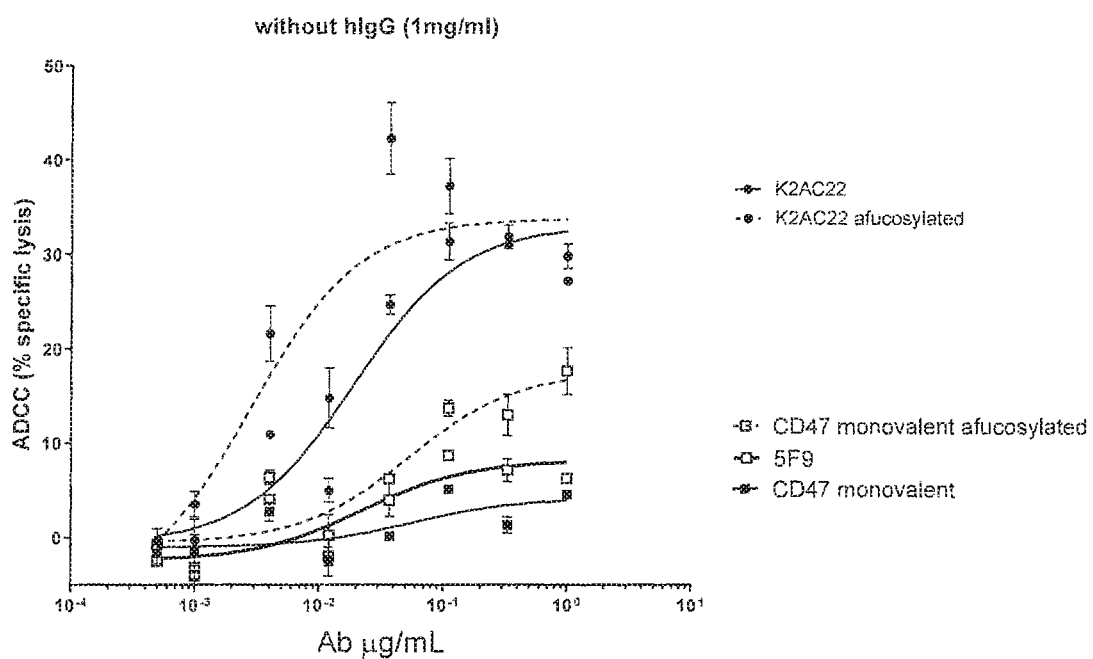
Figure 14:
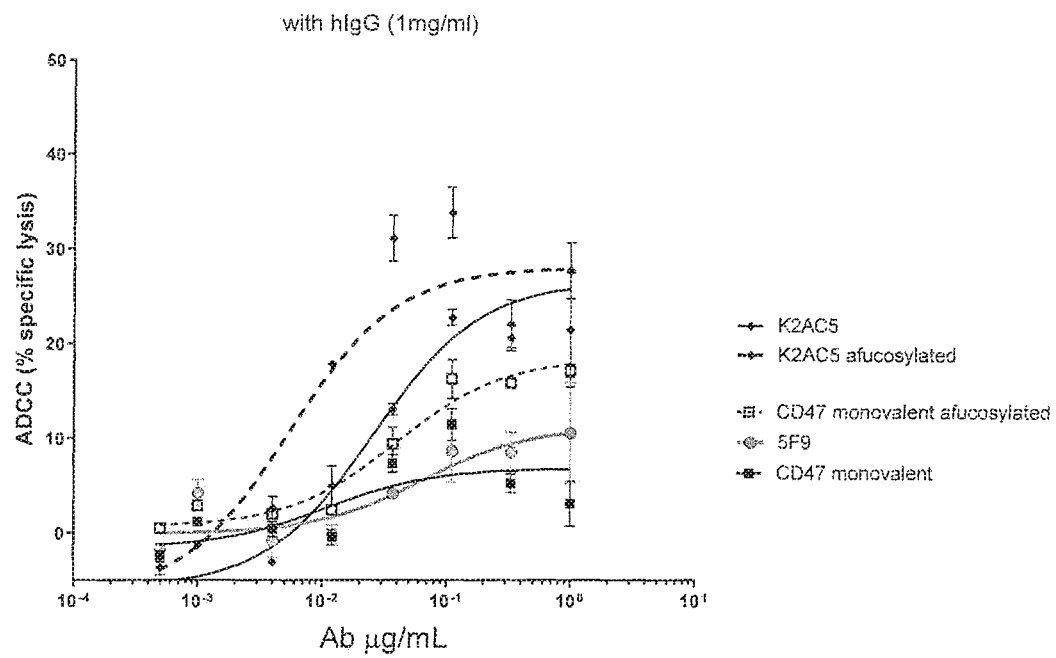
Figure 14:
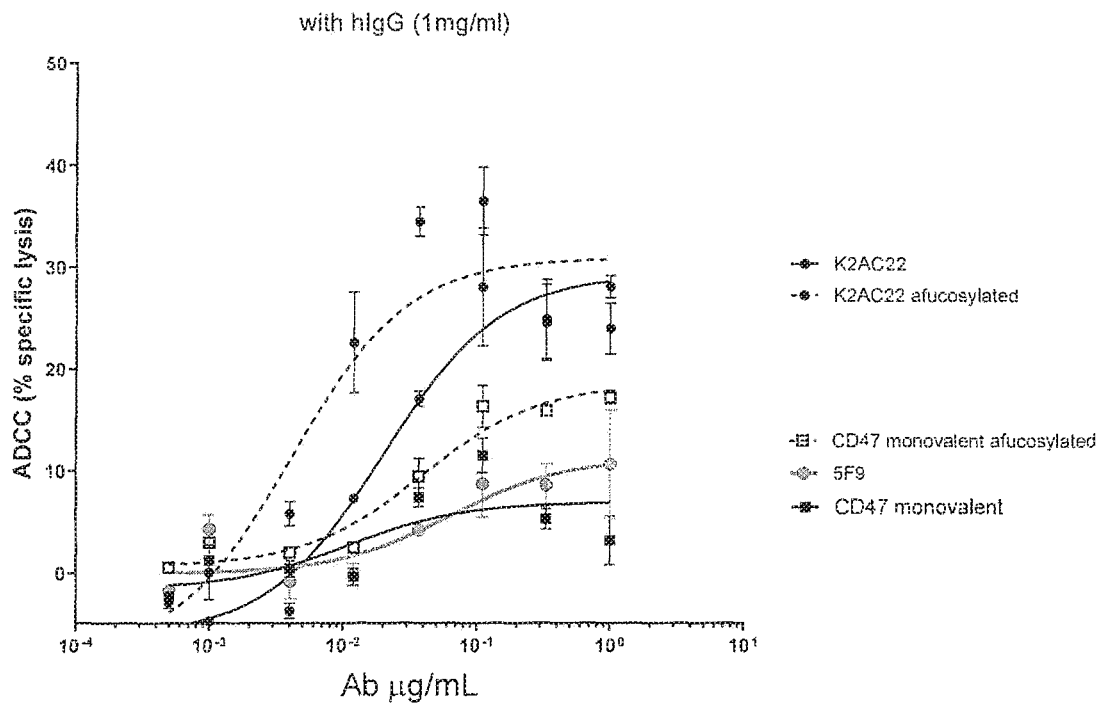

In a more particular embodiment, the increase in ADCC (decrease of EC50 and/or increase of maximum) is by a factor of 1.2 to 2.0 or even at least 2.0 as compared to said parent antibody see e.g. FIGS. 13 and 14).

In a more particular embodiment, the increase in ADCP (decrease of EC50 of the phagocytosis index curve) is by a factor of at least 3 or even 5 or more as compared to said parent antibody (see e.g. FIGS. 15 and 16).

As used herein the term "polypeptide having GnTIII activity, GnTIII" refers to polypeptides that are able to catalyze the addition of a N-acetylglucosamine (GlcNAc) residue in β-1-4 linkage to the β-linked mannoside of the trimannosyl core of N-linked oligosaccharides, eg. ß-1,4-mannosyl-glycoprotein4-ß-N-acetylglucosaminyl-transferase (EC 2.4.1.144).

As used herein the term "FUT8" refers to α1,6-fucosyl-transferase (EC:2.4.1.68).

As used herein, the term "effector function, Fc-mediated cellular cytotoxicity" refers to those biological activities attributable to the Fc region (a native sequence Fc region or amino acid sequence variant Fc region) of an antibody. Examples of antibody effector functions include, but are not limited to, Fc receptor binding affinity, antibody-dependent cellular cytotoxicity (ADCC), antibody-dependent cellular phagocytosis (ADCP), cytokine secretion, immune-complex-mediated antigen uptake by antigen-presenting cells, down-regulation of cell surface receptors, etc. Such immune mechanism is leading to the lysis of "targeted cells" by "human immune effector cells."

As used herein, the term "glycoengineered antibody" refers to a bispecific antibody according to the invention which comprises a reduced amount of fucosylated and/or bisecting oligosaccharides attached to the Fc region of said antibody, usually at amino acid Asn297, compared to a parent antibody.

As used herein, the term "parent antibody, parent bispecific antibody" in the context of glycoengineering refers to a bispecific antibody according to the invention which comprises the same amino acid composition as the glycoengineered antibody but is non-glycoengineered. For such comparison the parent antibody and the glycoengineered antibody are produced in the same host cell, but in the first case in the host cell without glycoengineering, and in the second case in the same host cell but engineered by targeted disruption of the FUT8 gene or engineered by expressing a polynucleotide encoding a polypeptide having GnTIII activity under standard conditions (see above).

As used herein, the term "human immune effector cells" refers to a population of leukocytes that display Fc receptors on their surfaces, through which they bind to the Fc-region of antigen binding molecules or of Fc-fusion proteins and perform effector functions. Such a population may include, but is not limited to, peripheral blood mononuclear cells (PBMC) and/or natural killer (NK) cells and/or macrophages.

As used herein, the term "increased Fc-mediated cellular cytotoxicity" is defined as either an increase in the number of "targeted cells" that are lysed in a given time, at a given concentration of the bispecific antibody of the invention in the medium surrounding the target cells, by the mechanism of Fc-mediated cellular cytotoxicity defined above, and/or a reduction in the concentration of the bispecific antibody of the invention, in the medium surrounding the target cells, required to achieve the lysis of a given number of "targeted cells" in a given time, by the mechanism of Fc-mediated cellular cytotoxicity. The increase in Fc-mediated cellular cytotoxicity is relative to the cellular cytotoxicity mediated by the same bispecific antibody of the invention produced by the same type of host cells, using the same standard conditions, but that has not been produced by host cells engineered to have an altered pattern of glycosylation (e.g., to express the glycosyltransferase, GnTIII, or other glycosyl-transferases or FUT8 disruption) by the methods described herein.

As used herein the term "expression vector" refers to one or more vectors which comprise the heavy and light chains of the antibody according to the invention in an appropriate manner as known from the state of the art.

As used herein "host cells engineered by targeted disruption of the FUT8 gene" refers to host cells capable of expressing an antibody according to the invention and being in addition glycoengineered by targeted disruption of the FUT8 gene as described e.g. in U.S. Pat. Nos. 8,067,232; 7,425,446, 6,946,292 (each of which is incorporated by reference in its entirety), and Yamane-Ohnuki N. et al., Biotech. Bioeng.; 87 (2004) 614-622. An antibody according to the invention expressed in such host cell comprises a Fc region comprising complex N-glycoside-linked sugar chains bound to the Fc region, which comprise a reducing end which contains an N-acetylglucosamine, wherein the sugar chains do not contain fucose bound to the 6 position of N-acetylglucosamine in the reducing end of the sugar chains.

The present invention is further directed to a method for the production of a bispecific antibody according to the present invention characterized in comprising nonfucosylation of 50% to 100%, 60% to 100%, 70% to 100%, 80% to 100%, or 90% to 100%, that are produced by a host cell, comprising expressing in said host cell a nucleic acid encoding a bispecific antibody of the invention and a nucleic acid encoding a polypeptide with a glycosyltransferase activity, or a vector comprising such nucleic acids. Genes with glycosyltransferase activity include (1,4)-N-acetylglucosaminyltransferase III (GnTIII), a-mannosidase II (Man11), (1,4)-galactosyltransferase (GalT), (1,2)-N-acetylglucosaminyltransferase I (GnTI), and β(1,2)-N-acetylglucosaminyltransferase II (GnTII). In one embodiment, a combination of genes with glycosyltransferase activity is expressed in the host cell (e.g., GnTIII and Man II). Likewise, the method also encompasses expression of one or more polynucleotide(s) encoding the bispecific antibody in a host cell in which a glycosyltransferase gene has been disrupted or otherwise deactivated (e.g., a host cell in which the activity of the gene encoding al-6 core fucosyltransferase has been knocked out). In another embodiment, the bispecific antibodies of the present invention can be produced in a host cell that further expresses a polynucleotide encoding a polypeptide having GnTIII activity to modify the glycosylation pattern. In a specific embodiment, the polypeptide having GnTIII activity is a fusion polypeptide comprising the Golgi localization domain of a Golgi resident polypeptide. In another preferred embodiment, the expression of the bispecific antibodies of the present invention in a host cell that expresses a polynucleotide encoding a polypeptide having GnTIII activity results in bispecific antibodies with increased Fc receptor binding affinity and increased effector function.

The present invention is further directed to a method for the production of a bispecific antibody according to the present invention characterized in comprising non-fucosylation of 50% to 100%, 60% to 100%, 70% to 100%, 80% to 100%, or 90% to 100%, that are produced by a host cell, comprising expressing in said host cell a nucleic acid encoding a bispecific antibody of the invention and a disrupted FUT8 gene.

In one embodiment the bispecific antibodies with altered glycosylation produced by the host cells of the invention exhibit increased Fc receptor binding affinity and/or increased effector function as a result of the modification of the host cell (e.g., by expression of a glycosyltransferase gene).

Preferably, the increased Fc receptor binding affinity is increased binding to a Fcγ activating receptor, such as the FcγRIIIa receptor.

In one embodiment, the percentage of nonfucosylated oligosaccharides is 50% to 100%, specifically 60% to 100%, 70% to 100%, and more specifically, 80% to 100%. The nonfucosylated oligosaccharides may be of the hybrid or complex type. In yet another embodiment, the bispecific antibody produced by the methods of the invention has an increased proportion of bisected oligosaccharides in the Fc region as a result of the modification of its oligosaccharides by the methods of the present invention. In one embodiment, the percentage of bisected oligosaccharides is 50% to 100%, specifically 50%, 60% to 70%, and more specifically, 80%. In a particularly preferred embodiment, the bispecific antibody produced by the host cells and methods of the invention has an increased proportion of bisected, nonfucosylated oligosaccharides in the Fc region. The bisected, nonfucosylated oligosaccharides may be either hybrid or complex.

As used herein, the term "host cell" covers any kind of cellular system which can be engineered to generate the bispecific antibodies of the present invention. In one embodiment, the host cell is engineered to allow the production of an antigen binding molecule with modified glycoforms. In certain embodiments, the host cells have been further manipulated to express increased levels of one or more polypeptides having GnTIII activity. Host cells include cultured cells, e.g., mammalian cultured cells, such as CHO cells (see above), BHK cells, NSO cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue. Host cells for the production of glycoengineered bispecific antibodies of the present invention have been described e.g. in U.S. Pat. No. 6,602,684, US20040241817, US20030175884; and WO 2004065540. The bispecific antibodies of the present invention can alternatively be glycoengineered to have reduced fucose residues in the Fc region according to the techniques disclosed in US2003/0157108, EP1176195, WO2003084570, WO2003085119 and US2003/0115614, US2004/093621, US2004/110282, US2004/110704, US2004/132140 (each of which is incorporated by reference in its entirety). Glycoengineered bispecific antibodies of the invention may also be produced in expression systems that produce modified glycoproteins, such as those described in WO2003/056914, WO2004/057002, and WO2004/024927 (each of which is incorporated by reference in its entirety).

In a further embodiment of the invention the antibody according to the invention comprises one or two or three amino acid substitutions in the Fc region ("Fc amino acid substitution") selected from the group consisting of mono-substitutions S239D, I332E, G236A, of bi-substitutions I332E and G236A, S239D and I332E ("DE substitution"), S239D and G236A, and triple-substitution S329D and I332E and G236A ("DEA substitution"); (Richards J O, et al., Mol. Cancer Ther. 7 (2008) 2517-2527). Due to different counting of a heavy chain, these amino acid numbers can be different for +/−one, two or three amino acids, but with the same shift for all three. In case of the heavy chain of SEQ ID NO:5 there is a one amino acid shift and S329D and I332E and G236A therefore denotes S328D and I331E and G235A. SEQ ID: NO:5 with DE substitution is shown in SEQ ID NO:23 and SEQ ID: NO:5 with DEA substitution is shown in SEQ ID NO:24. ADCC and/or ADCP activity of the bispecific antibody can be increased by such amino acid modification of the Fc part.

As used herein, the term "parent antibody, parent bispecific antibody" in the context of Fc substitution refers to a bispecific antibody according to the invention which comprises the same amino acid composition as the Fc substituted antibody, but without said substitution(s). For such comparison the parent antibody and the Fc substituted antibody are produced—as in the case of glycoengineered antibodies—in the same host cell under the same conditions, but in the first case in the host cell without Fc substitution, and in the second case in the same host cell but with such Fc substitution(s). A useful host cell line is e.g. CHO-K1.

As used herein, the term "parent antibody, parent bispecific antibody" in the context of a bispecific antibody according to the invention which comprises Fc substitution and is glycoengineered, such parent antibody therefore is the respective bispecific antibody which comprises the same amino acid composition as the Fc substituted antibody, but without said substitution(s) and is not glycoengineered.

In a further embodiment of the invention ADCC and/or ADCP activity of the bispecific antibody is increased by amino acid substitution of the Fc part in combination with glycoengineering of the Fc part compared ADCC and/or ADCP activity of the respective parent antibody.

The invention comprises therefore in one embodiment a bispecific antibody specifically binding to human CEACAM5 and human CD47, characterized in comprising one or two or three amino acid substitutions in the Fc region ("Fc amino acid substitution") selected from the group consisting of mono-substitutions S239D, I332E, G236A, of bi-substitutions I332E and G236A, S239D and I332E, of triple-substitutions S329D and I332E and G236A and comprising non-fucosylation of the Fc part of 50% to 100%, 60% to 100%, 70% to 100%, 80% to 100%, or 90% to 100%.

Example 9 describes assays used for the determination of ADCC activity and also of ADCP activity ADCC can be measured by an in vitro ADCC assay as follows:
1) the assay uses target cells that are known to express CEA recognized by the CEA-binding region of the bispecific antibody;
2) the assay uses human peripheral blood mononuclear cells (PBMCs), isolated from blood of a randomly chosen healthy donor, as effector cells;
3) the assay is carried out according to following protocol:
i) the PBMCs are isolated using standard density centrifugation procedures and are suspended at $6.25 \times 10^6$ cells/ml in RPMI cell culture medium;
ii) the target cells are grown by standard tissue culture methods, harvested from the exponential growth phase with a viability higher than 90%, washed in RPMI cell culture medium, labelled with 100 micro-Curies of 51Cr for $1 \times 10^6$ cells, washed twice with cell culture medium, and resuspended in cell culture medium at a density of $0.25 \times 10^6$ cells/ml;
iii) 20 microliters of the final target cell suspension above are transferred to each well of a 96-well microtiter plate;
iv) the bispecific antibody is serially-diluted from 4000 ng/ml to 0.12 ng/ml in cell culture medium and microliters of the resulting antibody solutions are added to the target cells in the 96-well microtiter plate, testing in triplicate various antibody concentrations covering the whole concentration range above;
v) for the maximum release (MR) controls, 3 additional wells in the plate containing the labelled target cells, receive 50 microliters of a 5% (VN) aqueous solution of non-ionic detergent (Triton™, Sigma, St. Louis), instead of the bispecific antibody solution (point iv above);
vi) for the spontaneous release (SR) controls, 3 additional wells in the plate containing the labelled target cells, receive 20 microliters of RPMI cell culture medium instead of the bispecific antibody solution (point iv above);
vii) the 96-well microtiter plate is then centrifuged at 50×g for 1 minute and incubated for 1 hour at 4° C.;
viii) 40 microliters of the PBMC suspension (point i above) are added to each well to yield an effector:target (E:T) cell ratio of 50:1 and the plates are placed in an incubator under 5% $CO_2$ atmosphere at 37° C. for 4 hours;
ix) the cell-free supernatant from each well is harvested and the experimentally released radioactivity (ER) is quantified using a gamma counter;
x) the percentage of specific lysis is calculated for each bispecific antibody concentration according to the formula (ER-MR)/(MR-SR)×100, where ER is the average radioactivity quantified (see point ix above) for that antibody concentration, MR is the average radioactivity quantified (see point ix above) for the MR controls (see point v above), and SR is the average radioactivity quantified (see point ix above) for the SR controls (see point vi above);

As used herein "increased ADCC" is defined as either an increase in the maximum percentage of specific lysis observed within the bispecific antibody concentration range tested above, and/or a reduction in the concentration of bispecific antibody required to achieve one half of the maximum percentage of specific lysis (EC50) observed within the bispecific antibody concentration range tested above. The increase in ADCC is relative to the ADCC, measured with the above assay, mediated by the same bispecific antibody, produced by the same type of host cells, using the same standard production, purification, formulation and storage methods, but that has not been produced by host cells engineered to overexpress GnTIII or by host cells engineered by targeted disruption of the FUT8 gene ("parent antibody"). In case of amino acid substitutions in the Fc, the increase in ADCC is relative to the ADCC measured with the parent bispecific antibody not carrying the substitution(s). In case of a bispecific antibody comprising amino acid substitutions in the Fc part and being glycoengineered, the increase in ADCC is relative to the ADCC measured with the parent non glycoengineered, bispecific antibody not carrying the substitution(s).

Therapeutic Applications and Methods of Using Anti-CEA Antigen Binding Molecules The CEACAM×CD47 bispecific antibodies according to the invention are optimized for treatment of solid tumors mainly by macrophages mediated phagocytosis of the tumor cells, either in monotherapy or in combination therapy especially together with a CEA×CD3 T-cell bispecific antibody like CEA-TCB or CEA-TCB1 and/or PD-1 axis antagonist. The antibody according to the invention and the CEA×CD3 T-cell bispecific antibody can be administered as described below.

In a particular embodiment, the disease resp. solid tumor is a cancer that expresses or even overexpresses CEA, including but not limited to the group of colorectal tumors, non-small cell lung tumors, gastric tumors, pancreatic tumors and breast tumors. In a particular embodiment, the tumor is a colorectal tumor. All therapeutic applications methods of use, uses, combinations, etc. described herein are especially embodiments for the treatment of these tumors/diseases.

The inventors recognize that the antibodies according to the invention show low or no ADA formation potential respectively loss of exposure due to neutralizing ADA respectively loss of efficacy.

In one embodiment, the invention provides a method of treating carcinomas (cancer, tumors, for example, human carcinomas), especially CEA expressing tumors, in vivo. This method comprises administering to a subject a pharmaceutically effective amount of a composition containing a bispecific antibody of the invention. By "subject" is meant a human subject, in one embodiment a patient suffering from cancer/tumor/carcinoma.

CEA expression in various tumor entities is generally very high, especially in colorectal carcinoma, pancreatic adenocarcinoma, gastric cancer, non-small cell lung cancer, breast cancer, head and neck carcinoma, uterine and bladder cancers among others. In healthy, normal glandular epithelia in the gastrointestinal tract, CEA is mainly expressed in a polarized pattern on the apical surface of the cells. This polarized expression pattern limits the accessibility by anti-CEA mono or bispecific antibodies which are administered systemically and therefore potential toxicity. Together with the low affinity CD47 binding of the antibody of the invention this leads to no or limited phagocytosis of such normal cells by the antibody of the invention. This polarized expression pattern gets lost in the cells of gastrointestinal and other malignant tumors. CEA is expressed equally over the whole cell surface of the cancer cells that means cancer cells are much better accessible to an antibody of the invention than normal, healthy cells and can be selectively killed by the CEAxCD47 bispecific antibodies of the invention respectively by the combinations mentioned above.

In one embodiment the bispecific antibodies of this invention can be used in monotherapy for the treatment of advanced solid tumors, in one embodiment CEA expressing tumors. In one embodiment a bispecific antibody according to the invention is used in combination with a CEAxCD3 Mab in simultaneous, separate, or sequential combination. In one embodiment a bispecific antibody according to the invention is used in combination with a CEAxCD3 Mab and/or a PD-1 axis antagonist in simultaneous, separate, or sequential combination. In one embodiment a bispecific antibody according to the invention is used in combination with a PD-1 axis antagonist in simultaneous, separate, or sequential combination. Such PD-1 axis antagonists are described e.g. in WO2017118675. Such combinations attack the solid cancer by macrophages and T-cells. Two CEAx CD3 Mabs are in clinical development (CEA-TCB and CEA-TCB1; RO6958688 in NCT3866239 and RO7172508 in NCT03539484). MEDI-565 was in clinical development but no active clinical trial could be identified. In one embodiment as bispecific antibody against CEA and CD3, antibody CEA-TCB or CEA-TCB1 is used.

The binder to CEA used in CEA-TCB has been derived from anti-CEA antibody PR1A3 (see e.g. EP2681244B1). This antibody binds to the so called B3 domain of CEA. CEA-TCB has a low nM binding affinity to CEA and shows efficacy in high doses (between 40 and 600 mg per dose and patient; (see e.g. J. Tabernero et. al., J. Clin. Oncol. 35, 2017 (suppl. Abstr. 3002)). At these doses nearly all CEA targets on the cell surfaces are occupied by the CEA-TCB. Combination of CEA-TCB or CEA-TCB1 and CEAxCD47 generates therapeutic plasma levels of both drugs at the same time and achieves best results (additive or even synergistic), if both drugs are non-competitive for the CEA antigen.

As used herein the terms "combination, simultaneous, separate, or sequential combination" of a an antibody according to the invention and a second bispecific antibody, binding to human CEA and human CD3ε refer to any administration of the two antibodies (or three antibodies in case of the combination of an antibody of the invention, a CEAxCD3 Mab and a PD-1 axis antagonist), either separately or together, where the two or three antibodies are administered as part of an appropriate dose regimen designed to obtain the benefit of the combination therapy, for example in separate, sequential, simultaneous, concurrent, chronologically staggered or alternating administration. Thus, the two or three antibodies can be administered either as part of the same pharmaceutical composition or in separate pharmaceutical compositions. The antibody according to the invention can be administered prior to, at the same time as, or subsequent to the administration of the second bispecific antibody, or in some combination thereof. Where the antibody according to the invention is administered to the patient at repeated intervals, e.g., during a standard course of treatment, the second bispecific antibody can be administered prior to, at the same time as, or subsequent to, each administration of the antibody of the invention or some combination thereof, or at different intervals in relation to the treatment with the antibody of the invention, or in a single dose prior to, at any time during, or subsequent to the course of treatment with the antibody of the invention. In one embodiment the antibody according to the invention and the second bispecific antibody are administered in alternating administration, in one embodiment in intervals of 6 to 15 days between administration of the antibody of the invention and the second antibody. In such alternating administration the first dose can be the antibody of the invention or the second antibody.

The term "PD-1 axis antagonist" refers to an anti-PD-1 antibody or an anti-PD-L1 antibody. Anti-PD-1 antibodies are e.g. pembrolizumab (Keytruda®, MK-3475), nivolumab, pidilizumab, lambrolizumab, MEDI-0680, PDR001, and REGN2810. Anti-PD-1 antibodies are described e.g. in 5 WO200815671, WO2013173223, WO2015026634, U.S. Pat. Nos. 7,521,051, 8,008,449, 8,354,509, WO20091 14335, WO2015026634, WO2008156712, WO2015026634, WO2003099196, WO2009101611, WO2010/027423, WO2010/027827, WO2010/027828, WO2008/156712, and WO2008/156712 (each of which is incorporated by reference in its entirety).

Anti-PD-L1 antibodies are e.g. atezolizumab, MDX-1105, durvalumab and avelumab. Anti-PD-L1 antibodies are e.g. described in WO2015026634, WO2013/019906, WO2010077634, U.S. Pat. No. 8,383,796, WO2010077634, WO2007005874, and WO2016007235 (each of which is incorporated by reference in its entirety).

With regard to combined administration of the antibody according to the invention and the second bispecific antibody, both compounds may be present in one single dosage form or in separate dosage forms, for example in two different or identical dosage forms.

If the antibody of the invention and the second antibody are not competing in regard to CEACAM5, in one embodiment both antibodies if desired by the physician, can be administered simultaneously. If the antibody of the invention and the second antibody are competing in regard to CEACAM5, in one embodiment both antibodies are administered in alternating administration.

The antibody of the invention will typically be administered to the patient in a dose regimen that provides for the most effective treatment of the cancer (from both efficacy and safety perspectives) for which the patient is being treated, as known in the art. Preferably tumor cells are attacked at the same time by T-cells and macrophages, to achieve full therapeutic potential of this approach, CEA-CD3 and CEAxCD47 bispecific antibody have to be non-competitive regarding binding to CEA on cell surface.

As discussed above, the amount of the antibody administered and the timing of the administration of the antibody of the invention can depend on the type (e.g. gender, age, weight) and condition of the patient being treated, the severity of the disease or condition being treated, and on the route of administration. For example, the antibody of the invention and the second antibody can be administered to a patient in doses ranging from 0.1 to 100 mg/kg of body weight per day or per week in single or divided doses, or by continuous infusion. In one embodiment each of the antibodies of the invention and the second antibody is administered to a patient in doses ranging from 0.1 to 20 mg/kg. In some instances, dosage levels below the lower limit of the aforesaid range may be adequate, while in other cases still larger doses may be employed without causing any harmful side effect.

As used herein, the term "half-life of the antibody" refers to the half-life of said antibody as measured in a usual pharmacokinetic assay, e.g. as described in example 17. An antibody according to the invention and the second bispecific antibody against CEA and CD3 have elimination half-life of 3-14 days.

In another aspect, the invention is also directed to use of the bispecific antibody according to the invention in the treatment of disease, particularly cell proliferation disorders wherein CEA is expressed, particularly wherein CEA is abnormally expressed (e.g., overexpressed or expressed in a different pattern on the cell surface) compared to normal tissue of the same cell type. Such disorders include, but are not limited to colorectal cancer, NSCLC (non-small cell lung cancer), gastric cancer, pancreatic cancer and breast cancer. CEA expression levels may be determined by methods known in the art (e.g., via immunohistochemistry assay, immunofluorescence assay, immunoenzyme assay, ELISA, flow cytometry, radioimmunoassay etc.).

In one aspect, bispecific antibodies of the present invention can be used for targeting cells in vivo or in vitro that expresses CEA. The bispecific antibodies of the invention are particularly useful in the prevention of tumor formation, eradication of tumors and inhibition of tumor growth or metastasis via the induction of ADCP and ADCC of tumor cells. The bispecific antibodies of the invention can be used to treat any tumor expressing CEA. Particular malignancies that can be treated with the bispecific antibodies of the invention include, but are not limited to, colorectal cancer, non-small cell lung cancer, gastric cancer, pancreatic cancer and breast cancer.

The bispecific antibodies of the invention are administered to a mammal, preferably a human, in a pharmaceutically acceptable dosage form such as those discussed below, including those that may be administered to a human intravenously as a bolus or by continuous infusion over a period of time, by intramuscular, intraperitoneal, intra-cerebrospinal, subcutaneous, intra-articular, intrasynovial, intrathecal, oral, topical, or inhalation routes. The bispecific antibodies of the invention also are suitably administered by intra tumoral, peritumoral, intralesional, or perilesional routes, to exert local as well as systemic therapeutic effects.

For the treatment of disease, the appropriate dosage of bispecific antibodies of the invention will depend on the type of disease to be treated, the severity and course of the disease, previous therapy, the patient's clinical history and response to the antibody, and the discretion of the attending physician. The bispecific antibody of the invention is suitably administered to the patient at one time or over a series of treatments. The present invention provides a method for selectively killing tumor cells expressing CEA.

This method comprises interaction of the bispecific antibodies of the invention with said tumor cells. These tumor cells may be from a human carcinoma including colorectal carcinoma, non-small cell lung carcinoma (NSCLC), gastric carcinoma, pancreatic carcinoma and breast carcinoma.

In another aspect, the invention is directed to the use of the bispecific antibodies of the invention for the manufacture of a medicament for treating a disease related to abnormal CEA expression. In a particular embodiment, the disease is a cancer that expresses or even overexpresses CEA, including but not limited to colorectal tumor, non-small cell lung tumor, gastric tumor, pancreatic tumor and breast tumor. In a particular embodiment, the tumor is a colorectal tumor.

Compositions, Formulations. Dosages, and Routes of Administration

In one aspect, the present invention is directed to pharmaceutical compositions comprising the bispecific antibodies of the present invention and a pharmaceutically acceptable carrier. The present invention is further directed to the use of such pharmaceutical compositions in the method of treatment of disease, such as cancer, or in the manufacture of a medicament for the treatment of disease, such as cancer. Specifically, the present invention is directed to a method for the treatment of disease, and more particularly, for the treatment of cancer, the method comprising administering a therapeutically effective amount of the pharmaceutical composition of the invention.

In one aspect, the present invention encompasses pharmaceutical compositions, combinations and methods for treating human carcinomas, tumors, as defined above. For example, the invention includes pharmaceutical compositions for use in the treatment of human carcinomas comprising a pharmaceutically effective amount of an antibody of the present invention and a pharmaceutically acceptable carrier.

The bispecific antibody compositions of the invention can be administered using conventional modes of administration including, but not limited to, intravenous, intraperitoneal, oral, intralymphatic or direct intratumoral administration. Intravenous administration or subcutaneous administration are preferred.

In one aspect of the invention, therapeutic formulations containing the bispecific antibodies of the invention are prepared for storage by mixing an antibody having the desired degree of purity with optional pharmaceutically acceptable carriers, excipients or stabilizers (Remington's Pharmaceutical Sciences 16th edition, Osol, A. Ed. (1980)), in the form of lyophilized formulations or liquid formulations. Acceptable carriers, excipients, or stabilizers are nontoxic to recipients at the dosages and concentrations employed. The formulations to be used for in vivo administration must be sterile. This is readily accomplished by filtration through sterile filtration membranes. The most effective mode of administration and dosage regimen for the pharmaceutical compositions of this invention depends upon the severity and course of the disease, the patient's condition and response to treatment and the judgment of the treating physician. Accordingly, the dosages of the compositions may be flat doses or may be adapted to the individual patient, e.g. the body weight. Nevertheless, an effective dose of the compositions of this invention will generally be in a range from 0.1 to 20 mg/kg.

The bispecific antibodies of this invention have a molecular weight in a magnitude of 150 kD per Mol. They carry in one embodiment a Fc part. The elimination half-life in patients is in a range of 3 to 14 days. This half-life allows for, but not limited to administration once a day, once a week, or once every two weeks.

The bispecific antibodies of the present invention and their respective compositions may be in a variety of dosage forms which include, but are not limited to, liquid solutions or suspensions, tablets, pills, powders, suppositories, polymeric microcapsules or microvesicles, liposomes, and injectable or infusible solutions. The preferred form depends upon the mode of administration and the therapeutic application.

The composition comprising a bispecific antibody of the present invention will be formulated, dosed, and administered in a fashion consistent with good medical practice. Factors for consideration in this context include the particular disease or disorder being treated, the particular mammal being treated, the clinic condition of the individual patient, the cause of the disease or disorder, the site of delivery of the agent, the method of administration, the scheduling of administration, and other factors known to medical practitioners.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is a bispecific antibody of the invention. The label or package insert indicates that the composition is used for treating the condition of choice. Moreover, the article of manufacture may comprise (a) a first container with a composition contained therein, wherein the composition comprises a bispecific antibody of the invention; and (b) a second container with a composition contained therein; wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

FURTHER EMBODIMENTS OF THE INVENTION

In the following embodiments of a bispecific antibody specifically binding to human CEACAM5 and human CD47 are described.

1. A bispecific antibody comprising a first binding part, specifically binding to human CEACAM5 and a second binding part, specifically binding to human CD47.

2. The bispecific antibody according to embodiment 1, characterized in that the Fc region has been glycoengineered to have a reduced number of fucose residues as compared to the same but non-glycoengineered bispecific antibody.

3. The bispecific antibody according to embodiment 1 or 2, characterized in that the first binding part binds to the Ig-like V-type domain of CEACAM5 of amino acids 35-144.

4. The bispecific antibody according to any one of embodiments 1 to 3, characterized in that said bispecific antibody competes with antibody SM3E for binding to CEACAM5.

5. The bispecific antibody according to any one of embodiments 1 to 3, characterized in that said bispecific antibody does not compete with antibodies SM3E, MEDI, LAB, SAR, T86.66, CH1A1A.

6. The bispecific antibody according to any one of embodiments 1 to 5, characterized in that the EC50 value of phagocytosis of said bispecific antibody is in the range of 0.1 to 10 times of the E50 value of reference antibody K2AC22 under the same experimental conditions and in the presence or without of 1 mg/ml human IgG.

7. The bispecific antibody according to any one of embodiments 1 to 6, characterized in that in presence of 1 mg/ml human IgG maximum of phagocytosis index measured in imaging based assay is not decreased by more than 30% in comparison to phagocytosis without human IgG under the same experimental conditions.

8. The bispecific antibody according to any one of embodiments 1 to 7, characterized in being monovalent for the first binding part and monovalent for the second binding part.

9. The bispecific antibody according to any one of embodiments 1 to 8, characterized in that each of the first and second binding part comprises an immunoglobulin heavy chain and an immunoglobulin light chain.

10. The bispecific antibody according to any one of embodiments 1 to 9, characterized in being of human IgG1 type.

11. The bispecific antibody according to any one of embodiments 1 to 10, characterized in that the constant and variable framework region sequences are human or of human origin.

12. The bispecific antibody according to any one of embodiments 1 to 11, characterized in that the bispecific antibody is a full-length antibody.

13. The bispecific antibody according to any one of embodiments 1 to 12, characterized in comprising a first binding part specifically binding to human CEACAM5, comprising a kappa light chain variable domain and a lambda light chain constant domain and a second binding part specifically binding to human CD47, comprising a kappa light chain variable domain and a kappa light chain constant domain.

14. The bispecific antibody according to any one of embodiments 1 to 12, characterized in comprising a first binding part specifically binding to human CEACAM5, comprising a lambda light chain variable domain and a lambda light chain constant domain and a second binding part specifically binding to human CD47, comprising a kappa light chain variable domain and a kappa light chain constant domain.

15. The bispecific antibody according to any one of embodiments 13 or 14, characterized in comprising a common heavy chain.

16. The bispecific antibody according to any one of embodiments 1 to 15, characterized in
a) that the first binding part comprises a heavy chain variable region comprising a CDRH1 of SEQ ID NO:1, a CDRH2 of SEQ ID NO:2 and a CDRH3 of SEQ ID NO:3 and a light chain constant domain of human lambda type and of SEQ ID NO:13, and that the second binding part comprises a heavy chain variable region comprising a CDRH1 of SEQ ID NO:1, CDRH2 of SEQ ID NO:2 and CDRH3 of SEQ ID NO:3 and a light chain variable region comprising a CDRL1 of SEQ ID NO:7, CDRL2 of Ala Ala Ser, included in SEQ ID NO:8, and CDRL3 of SEQ ID NO:9, or b) that the first binding part comprises a heavy chain variable region comprising as CDRs a CDRH1 of SEQ ID NO:25, CDRH2 of SEQ ID NO:26 and CDRH3 of SEQ ID NO:27 and a light chain constant domain of human lambda type and of SEQ ID NO:13, and that the second binding part comprises a heavy chain variable region comprising as CDRs a CDRH1 of SEQ ID NO:25, CDRH2 of SEQ ID NO:26 and CDRH3 of SEQ ID NO:27 and a light chain variable region comprising as CDRs a CDRL1 of SEQ ID NO:28, CDRL2 of SEQ ID NO:29, and CDRL3 of SEQ ID NO:30.

17. The bispecific antibody according to any one of embodiments 1 to 16, characterized in comprising a first binding part, specifically binding to human CEACAM5 and a second binding part, specifically binding to human CD47, characterized in a) that the first binding part comprises a heavy chain variable region comprising as CDRs a CDRH1 of SEQ ID NO:25, a CDRH2 of SEQ ID NO:26 and a CDRH3 of SEQ ID NO:27 and a light chain variable region comprising a combination of CDRL1, CDRL2 and CDRL3 selected from the group consisting of:
SEQ ID NO:31, 32 and 33; SEQ ID NO:34, 35 and 36, SEQ ID NO:37, 38 and 39, SEQ ID NO:40, 41 and 42, SEQ ID NO:43, 44 and 45, SEQ ID NO:46; 47 and 48, SEQ ID NO:49, 50 and 51, SEQ ID NO:52, 53 and 54, SEQ ID NO:55, 56 and 57, SEQ ID NO:58, 59 and 60, SEQ ID NO:61, 62 and 63, and SEQ ID NO: 112, 113, and 114, and
b) that the second binding part comprises a heavy chain variable region comprising as CDRs a CDRH1 of SEQ ID NO:1, CDRH2 of SEQ ID NO:2 and CDRH3 of SEQ ID NO:3 and a light chain variable region comprising as CDRs a CDRL1 of SEQ ID NO:7, CDRL2 of Ala Ala Ser, included in SEQ ID NO:8, and CDRL3 of SEQ ID NO:9, or
that the second binding part comprises a heavy chain variable region comprising as CDRs a CDRH1 of SEQ ID NO:25, CDRH2 of SEQ ID NO:26 and CDRH3 of SEQ ID NO:27 and a light chain variable region comprising as CDRs a CDRL1 of SEQ ID NO:28, CDRL2 of SEQ ID NO:29, and CDRL3 of SEQ ID NO:30 and optionally a light chain constant domain of human lambda type and of SEQ ID NO:13

18. The bispecific antibody according to any one of embodiments 1 to 17, characterized in comprising a first binding part, specifically binding to human CEACAM5 and a second binding part, specifically binding to human CD47, characterized in
a) that the first binding part comprises a heavy chain variable region of SEQ ID NO:4 and a light chain variable region selected from the group of VLs included in the VLCL regions consisting of:
SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, and SEQ ID NO:115, and
b) that the first binding part comprises a heavy chain variable region of SEQ ID NO:4 and a light chain variable region of SEQ ID NO:10.

19. The bispecific antibody according to any one of embodiments 1 to 18, characterized in comprising a first binding part, specifically binding to human CEACAM5 and a second binding part, specifically binding to human CD47, characterized in
a) that the first binding part comprises a heavy chain of SEQ ID NO:5 and a light chain selected from the group consisting of:
SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, and SEQ ID NO:115, and
b) that the second binding part comprises a heavy chain variable region of SEQ ID NO:5 and a light chain variable region of SEQ ID NO:11.

20. The bispecific antibody according to any one of embodiments 1 to 19, characterized in being a full-length bispecific antibody of human IgG1 type and being monovalent for the first binding part and monovalent for the second binding part, and comprising a first binding part specifically binding to human CEACAM5, comprising a kappa light chain variable domain and a lambda light chain constant domain and a second binding part specifically binding to human CD47, comprising a kappa light chain variable domain and a kappa light chain constant domain or comprising a first binding part specifically binding to human CEACAM5, comprising a lambda light chain variable domain and a lambda light chain constant domain and a second binding part specifically binding to human CD47, comprising a kappa light chain variable domain and a kappa light chain constant domain.

21. The bispecific antibody according to any one of embodiments 1 to 20, characterized in binding to human CD47 with a binding affinity of 100 nM to 600 nM, preferably 100 to 500 nM.

22. The bispecific antibody according to any one of embodiments 1 to 21, characterized in binding to MKN-45 cells with an EC50 value of 1 to 200 nM.

23. The bispecific antibody according to any one of embodiments 1 to 22, characterized in binding to human CD47 with a binding affinity of 100 nM to 500 nM, and binding to MKN-45 cells with an EC50 value of 1 to 200 nM.

24. The bispecific antibody according to any one of embodiments 1 to 23, characterized in that
a) the EC50 for the phagocytosis index curve of MKN-45 cells in the presence of human macrophages, by said bispecific antibody is not shifted by more than a factor 4 towards higher concentrations in the presence of 200 ng/ml soluble CEA compared to the EC50 measured without soluble CEA and/or that the maximum of the phagocytosis index curve is not reduced by 10% or more, 15% or more, or 20% or more by addition of 200 ng/mL soluble CEA, and/or
b) the EC50 for the binding curve to MKN-45 cells of said bispecific antibody is not shifted by more than a factor 2 towards higher concentrations in the presence of 200 ng/ml soluble CEA compared to the EC50 measured without soluble CEA.

25. The bispecific antibody according to any one of embodiments 1 to 24, characterized in binding to human recombinant CEACAM5 and CEACAM6, whereby the EC50 values of binding to recombinant CEACAM5 and CEACAM6 differing by less than a factor of 3.

26. The bispecific antibody according to embodiments 25, characterized in a) that the first binding part comprises a heavy chain variable region comprising as CDRs a CDRH1 of SEQ ID NO:25, CDRH2 of SEQ ID NO:26 and CDRH3 of SEQ ID NO:27 and a light chain variable region comprising as CDRs a CDRL1 of SEQ ID NO: 112, a CDRL2 of SEQ ID NO: 113, and a CDRL3 of SEQ ID NO: 114, and b) that the second binding part comprises a heavy chain variable region comprising as CDRs a CDRH1 of SEQ ID NO:25, CDRH2 of SEQ ID NO:26 and CDRH3 of SEQ ID NO:27 and a light chain variable region comprising as CDRs a CDRL1 of SEQ ID NO:28, CDRL2 of SEQ ID NO:29, and CDRL3 of SEQ ID NO:30.

27. The bispecific antibody according to any one of embodiments 1 to 26, characterized that a bispecific antibody specifically binding to human CEACAM5 and CD3ε, comprising as heavy chains the heavy chains of SEQ ID NO:97 and 98 and as light chains the light chains of SEQ ID NO: 96 and 99 in a concentration of 300 nM does not shift the EC50 of the binding curve of the bispecific antibody of the invention to MKN-45 cells by more than a factor of 3, in one embodiment towards higher concentrations.

28. The bispecific antibody according to any one of embodiments 1 to 27, characterized that a bispecific antibody specifically binding to human CEACAM5 and CD3ε (further named also as CEA-TCB1), comprising as heavy and light chains the chains of amino acid sequences SEQ ID NO: 92 to 95 in a concentration of 30 nM does not shift the EC50 of the binding curve of the bispecific antibody of the invention to MKN-45 cells by more than a factor of 3, in one embodiment towards higher concentrations.

29. The bispecific antibody according to any one of embodiments 1 to 28, characterized in that the Fc region has been glycoengineered to have a reduced number of fucose residues as compared to the respective parent bispecific antibody.

30. The bispecific antibody according to embodiment 29, characterized in that 50% to 100% of the N-linked oligosaccharides in the Fc region are nonfucosylated.

31. The bispecific antibody according to any one of embodiments 29 or 30, characterized in that 50% to 100% of the N-linked oligosaccharides in the Fc region are bisected.

32. The bispecific antibody according to any one of embodiments 29 to 31, characterized that 80% to 100% of the N-linked oligosaccharides in the Fc region are bisected and nonfucosylated.

33. The bispecific antibody according to any one of embodiments 29 to 32, characterized in that EC50 value of ADCC and/or ADCC maximum induced by said antibody is increased by a factor of 1.2 to 2.0 or a factor of at least 2.0 and/or EC50 value of the phagocytosis index curve is decreased by at least a factor of 1.2 to 2.0 or a factor of at least 2.0 compared to the maximum of ADCC and/or EC50 value induced by the respective parent bispecific antibody.

34. The bispecific antibody according to any one of embodiments 29 to 33, characterized in that by imaging determined maximum of the phagocytosis index induced by said antibody is increased by at least a factor of 3 and/or EC50 value of the phagocytosis index curve is decreased by at least a factor of 3 or a factor of at least 5 compared to the maximum of the phagocytosis index respectively the EC50 value induced by the respective parent bispecific antibody.

35. A method for the production of a bispecific antibody according to any one of embodiments 29 to 34 and 30, characterized in comprising:
a) culturing a host cell engineered to express at least one nucleic acid encoding a polypeptide having β(1,4)-N-acetyl-glucosaminyltransferase III activity under conditions which permit the production of said bispecific antibody, and which permit said glycoengineered modification of the oligosaccharides present on the Fc region of said bispecific antibody; and
b) isolating said glycoengineered bispecific antibody wherein said antibody is capable of specifically binding to human CEACAM5 and human CD47.

36. A method for the production of a bispecific antibody according to any one of embodiments 29 to and 33 to 34, characterized in comprising:
a) culturing a host cell glycoengineered by targeted disruption of the FUT8 gene under conditions which permit the production of said glycoengineered bispecific antibody of the invention, and which permit the said glycoengineered modification of the oligosaccharides present on the Fc region of said bispecific antibody, and
b) isolating said glycoengineered bispecific antibody wherein said antibody is capable of specifically binding to human CEACAM5 and human CD47.

37. An isolated polynucleotide characterized in encoding a bispecific antibody according to any one of embodiments 1 to 34.

38. A vector comprising the polynucleotide according to embodiment 37.

39. A host cell comprising the vector according to embodiment 38.

40. A composition comprising a bispecific antibody according to any one of embodiments 1 to 34 and a pharmaceutically acceptable carrier.

41. A method of inducing cell lysis of a tumor cell comprising contacting the tumor cell with a bispecific antibody according to any one of embodiments 1 to 34.

42. A method according to embodiment 41, characterized in that the tumor cell is a colorectal cancer cell, NSCLC (non-small cell lung cancer), gastric cancer cell, pancreatic cancer cell, breast cancer cell, or another tumor cell expressing human CEACAM5.

43. A method of treating a subject having a cancer that expresses CEA, the method comprising administering to the subject a therapeutically effective amount of a bispecific antibody according to any one of embodiments 1 to 34.

44. A method of increasing survival time in a subject having a cancer that expresses CEA, said method comprising administering to said subject a therapeutically effective amount of a bispecific antibody according to any one of embodiments 1 to 34.

45. The method according to embodiment 43 or 44, characterized in that the cancer is colorectal cancer, non-small cell lung cancer (NSCLC), gastric cancer, pancreatic cancer or breast cancer.

46. The method according to any one of embodiments 43 to 45, characterized in that a bispecific antibody according to any one of embodiments 1 to 34 is administered in combination with chemotherapy or radiation therapy to a human subject.

47. The bispecific antibody according to any one of embodiments 1 to 34 for use in the manufacture of a medicament for treating a subject having a cancer that expresses CEA.

48. The bispecific antibody for use according to embodiment 47, characterized in that the cancer is selected from the group consisting of colorectal cancer, non-small cell lung cancer (NSCLC), gastric cancer, pancreatic cancer and breast cancer.

49. The bispecific antibody according to any one of embodiments 1 to 34 for use in a method of treating a subject having a cancer that expresses CEA, the method comprising administering to the subject a therapeutically effective amount of a said bispecific antibody, characterized in that the EC50 value of phagocytosis of said bispecific antibody is in the range of 0.1 to 10 times of the E50 value of reference antibody K2AC22, which comprises a first binding part, specifically binding to human CEACAM5 and a second binding part, specifically binding to human CD47, whereby the first binding part comprises a heavy chain of SEQ ID NO:5 and a light chain of SEQ ID NO:65, and that the second binding part comprises a heavy chain of SEQ ID NO:5 and a light chain of SEQ ID NO:11, under the same experimental conditions and in the presence and/or without of 1 mg/ml human IgG.

50. A first bispecific antibody comprising a first binding part, specifically binding to human CEACAM5 and a second binding part, specifically binding to human CD47, for use in simultaneous, separate, or sequential combination with a second bispecific antibody comprising a third binding part specifically binding to human CEACAM5 and a fourth binding part specifically binding to human CD3ε, in the treatment of a human subject having a cancer that expresses CEA.

51. The first bispecific antibody for use according to embodiment 50, characterized in that said fourth binding part of the second bispecific antibody binds to an epitope of human CD3ε which comprises the amino acid sequence of SEQ ID NO:22.

52. The first bispecific antibody for use according to embodiment 50 or 51, characterized in that said second antibody comprises as heavy and light chains the chains of SEQ ID NO:96 to 99 or comprises as heavy and light chains the chains of amino acid sequences SEQ ID NO: 92 to 95 and that said second antibody in a concentration of 300 nM or 30 nM does not shift the EC50 of the binding curve of said first bispecific antibody to MKN-45 cells by more than a factor of 3, in one embodiment towards higher concentrations.

53. The bispecific antibody according to any one of embodiments 1 to 34, for use in simultaneous, separate, or sequential combination with a second bispecific antibody comprising as heavy and light chains the chains of SEQ ID NO:96 to 99 or comprising as heavy and light chains the chains of amino acid sequences SEQ ID NO: 92 to 95 in the treatment of a subject having a cancer that expresses CEA.

54. The bispecific antibody according to any one of embodiments 1 to 34 and 50 to 53, characterized in not competing with a second bispecific antibody comprising as heavy and light chains the chains of SEQ ID NO:96 to 99 or comprising as heavy and light chains the chains of amino acid sequences SEQ ID NO: 92 to 95 for use in simultaneous, separate, or sequential combination with said second bispecific antibody in the treatment of a subject having a cancer that expresses human CEACAM5.

55. The bispecific antibody according to any one of embodiments 1 to 34 and 50 to 53, for use in simultaneous, separate, or sequential combination in the treatment of a subject having a cancer that expresses human CEACAM5, with a second bispecific antibody comprising a) a third binding part specifically binding to human CEACAM5, comprising a heavy chain variable region of SEQ ID NO:20 and a light chain variable region of SEQ ID NO:21 and a fourth binding part specifically binding to, an epitope of human CD3ε, said epitope comprising the amino acid sequence of SEQ ID NO:22 or b) as heavy and light chains the chains of SEQ ID NO:96 to 99 or as heavy and light chains the chains of amino acid sequences SEQ ID NO: 92 to 95 respectively, in the treatment of a subject having a cancer that expresses human CEACAM5, whereby said second bispecific antibody in a concentration of 300 nM (SEQ ID NO:96 to 99) or 30 nM (SEQ ID NO 92 to 95) does not shift the EC50 of the phagocytosis index curve of MKN-45 cells of the bispecific antibody according to any one of the embodiments 1 to 34 by more than a factor of 3 to higher concentrations.

56. The bispecific antibody for use according to any one of embodiments 50 to 55, characterized in that said cancer is colorectal cancer, non-small cell lung cancer (NSCLC), gastric cancer, pancreatic cancer and breast cancer.

57. The bispecific antibody for use according to any one of embodiments 50 to 56, characterized in that the bispecific antibody according to any one of embodiments 1 to 34 and the second bispecific antibody are administered to said subject alternately or simultaneously in 6 to 15 day intervals.

58. A composition comprising a bispecific antibody according to any one of embodiments 1 to 34, characterized in not cross reacting with a second bispecific antibody comprising a) a third binding part specifically binding to human CEACAM5, comprising a heavy chain variable region of SEQ ID NO:20 and a light chain variable region of SEQ ID NO:21 and a fourth binding part specifically binding to, an epitope of human CD3ε, comprising the amino acid sequence of SEQ ID NO:22, orb) as heavy and light chains the chains of SEQ ID NO:96 to 99 or as heavy and light chains the chains of amino acid sequences SEQ ID NO: 92 to 95, for use in the treatment of a subject having a cancer that expresses human CEACAM5.

59. A composition comprising a bispecific antibody according to any one of embodiments 1 to 34, for use in simultaneous, separate, or sequential combination in the treatment of a subject having a cancer that expresses human CEACAM5, with a second bispecific antibody comprising a) a third binding part specifically binding to human CEACAM5, comprising a heavy chain variable region of SEQ ID NO:20 and a light chain variable region of SEQ ID NO:21 and a fourth binding part specifically binding to, an epitope of human CD3ε, comprising the amino acid sequence of SEQ ID NO:22, or b) as heavy and light chains the chains of SEQ ID NO:96 to 99 or as heavy and light chains the chains of amino acid sequences SEQ ID NO: 92 to 95, whereby said second bispecific antibody in a concentration of 300 nM respectively 30 nM (SEQ ID NO: 92 to 95) does not shift the EC50 of the phagocytosis index curve of MKN-45 cells of the bispecific antibody according to any one of the embodiments 1 to 34 by more than a factor of 3, in one embodiment towards higher concentrations.

60. The composition according to embodiment 58 or 59, characterized in that the cancer is colorectal cancer, non-small cell lung cancer (NSCLC), gastric cancer, pancreatic cancer and breast cancer.

61. A bispecific antibody according to any one of embodiments 1 to 34, for use in a method of treating a subject having a cancer that expresses CEA, the method comprising administering to the subject a therapeutically effective amount of said bispecific antibody.

62. A bispecific antibody according to any one of embodiments 1 to 34, for use in a method of increasing survival time in a subject having a cancer that expresses CEA, said method comprising administering to said subject a therapeutically effective amount of said bispecific antibody.

63. The bispecific antibody according to any one of embodiments 61 or 62, characterized in that said bispecific antibody is administered in combination with chemotherapy or radiation therapy to a human subject.

64. The bispecific antibody according to any one of embodiments 60 or 62, characterized in that said cancer is colorectal cancer, non-small cell lung cancer (NSCLC), gastric cancer, pancreatic cancer or breast cancer.

TABLE 1

SEQUENCE LIST

| Sequence Number | Relates to |
|---|---|
| SEQ ID NO: 1 | Mab CD47 CDRH1 (IMGT) |
| SEQ ID NO: 2 | Mab CD47 CDRH2 (IMGT) |
| SEQ ID NO: 3 | Mab CD47 CDRH3 (IMGT) |
| SEQ ID NO: 4 | Mab CD47 VH |
| SEQ ID NO: 5 | Mab CD47 heavy chain |
| SEQ ID NO: 6 | Mab CD47 heavy chain (nucleic acid) |
| SEQ ID NO: 7 | Mab CD47 CDRL1 (IMGT) |
| SEQ ID NO: 8 | Mab CD47 CDRL2 (only Ala Ala Ser; IMGT)) |
| SEQ ID NO: 9 | Mab CD47 CDRL3 (IMGT) |
| SEQ ID NO: 10 | Mab CD47 VL |
| SEQ ID NO: 11 | Mab CD47 light chain; KA3 (K2) |
| SEQ ID NO: 12 | Mab CD47 light chain (nucleic acid); KA3 (K2) |
| SEQ ID NO: 13 | First binding part CL |
| SEQ ID NO: 14 | Primer example 12 |
| SEQ ID NO: 15 | Primer example 12 |
| SEQ ID NO: 16 | Primer example 12 |
| SEQ ID NO: 17 | Primer example 12 |
| SEQ ID NO: 18 | Primer example 12 |
| SEQ ID NO: 19 | Primer example 12 |
| SEQ ID NO: 20 | MAB CEA variable heavy chain |
| SEQ ID NO: 21 | MAB CEA variable light chain |
| SEQ ID NO: 22 | Epitope of CD3 epsilon |
| SEQ ID NO: 23 | Mab CD47 heavy chain, DE substitution |
| SEQ ID NO: 24 | Mab CD47 heavy chain, DEA substitution |
| SEQ ID NO: 25 | Mab CD47 CDRH1 (Kabat) |
| SEQ ID NO: 26 | Mab CD47 CDRH2 (Kabat) |
| SEQ ID NO: 27 | Mab CD47 CDRH3 (Kabat) |
| SEQ ID NO: 28 | Mab CD47 CDRL1 (Kabat); KA3 |
| SEQ ID NO: 29 | Mab CD47 CDRL2 (Kabat); KA3 |
| SEQ ID NO: 30 | Mab CD47 CDRL3 (Kabat); KA3 |
| SEQ ID NO: 31 | Mab CEA CDRL1; 1D9 (AC5) |
| SEQ ID NO: 32 | Mab CEA CDRL2; 1D9 (AC5) |
| SEQ ID NO: 33 | Mab CEA CDRL3; 1D9 (AC5) |
| SEQ ID NO: 34 | Mab CEA CDRL1; 1G6 (AC22) |
| SEQ ID NO: 35 | Mab CEA CDRL2; 1G6 (AC22) |
| SEQ ID NO: 36 | Mab CEA CDRL3; 1G6 (AC22) |
| SEQ ID NO: 37 | Mab CEA CDRL1; 1D5 (AC10) |
| SEQ ID NO: 38 | Mab CEA CDRL2; 1D5 (AC10) |
| SEQ ID NO: 39 | Mab CEA CDRL3; 1D5 (AC10) |
| SEQ ID NO: 40 | Mab CEA CDRL1; 2B8 (AC13) |
| SEQ ID NO: 41 | Mab CEA CDRL2; 2B8 (AC13) |
| SEQ ID NO: 42 | Mab CEA CDRL3; 2B8 (AC13) |
| SEQ ID NO: 43 | Mab CEA CDRL1; 1A2 (AC18) |
| SEQ ID NO: 44 | Mab CEA CDRL2; 1A2 (AC18) |
| SEQ ID NO: 45 | Mab CEA CDRL3; 1A2 (AC18) |
| SEQ ID NO: 46 | Mab CEA CDRL1; 1A8 (AC23) |
| SEQ ID NO: 47 | Mab CEA CDRL2; 1A8 (AC23) |
| SEQ ID NO: 48 | Mab CEA CDRL3; 1A8 (AC23) |
| SEQ ID NO: 49 | Mab CEA CDRL1; 2F4 (AC25) |
| SEQ ID NO: 50 | Mab CEA CDRL2; 2F4 (AC25) |
| SEQ ID NO: 51 | Mab CEA CDRL3; 2F4 (AC25) |
| SEQ ID NO: 52 | Mab CEA CDRL1; 2F7 (AC26) |
| SEQ ID NO: 53 | Mab CEA CDRL2; 2F7 (AC26) |
| SEQ ID NO: 54 | Mab CEA CDRL3; 2F7 (AC26) |
| SEQ ID NO: 55 | Mab CEA CDRL1; 2C11 (AC27) |
| SEQ ID NO: 56 | Mab CEA CDRL2; 2C11 (AC27) |
| SEQ ID NO: 57 | Mab CEA CDRL3; 2C11 (AC27) |
| SEQ ID NO: 58 | Mab CEA CDRL1; C11 (AC28) |
| SEQ ID NO: 59 | Mab CEA CDRL2; C11 (AC28) |
| SEQ ID NO: 60 | Mab CEA CDRL3; C11 (AC28) |
| SEQ ID NO: 61 | Mab CEA CDRL1; 2B5 (AC29) |
| SEQ ID NO: 62 | Mab CEA CDRL2; 2B5 (AC29) |
| SEQ ID NO: 63 | Mab CEA CDRL3; 2B5 (AC29) |
| SEQ ID NO: 64 | Mab CEA 1D9 VLCL2 CEA (AC5) |
| SEQ ID NO: 65 | Mab CEA 1G6 VLCL2 CEA (AC22) |
| SEQ ID NO: 66 | Mab CEA 1D5 VLCL2 CEA (AC10) |
| SEQ ID NO: 67 | Mab CEA 2B8 VLCL2 CEA (AC13) |
| SEQ ID NO: 68 | Mab CEA 1A2 VLCL2 CEA (AC18) |
| SEQ ID NO: 69 | Mab CEA 1A8 VLCL2 CEA (AC23) |
| SEQ ID NO: 70 | Mab CEA 2F4 VLCL2 CEA (AC25) |

TABLE 1-continued

SEQUENCE LIST

| Sequence Number | Relates to |
|---|---|
| SEQ ID NO: 71 | Mab CEA 2F7 VLCL2 CEA (AC26) |
| SEQ ID NO: 72 | Mab CEA 2C11 VLCL2 CEA (AC27) |
| SEQ ID NO: 73 | Mab CEA C11 VLCL2 CEA (AC28) |
| SEQ ID NO: 74 | Mab CEA 2B5 VLCL2 CEA (AC29) |
| SEQ ID NO: 75 | Nucleic acid 1D9 VLCL2 CEA (AC5) |
| SEQ ID NO: 76 | Nucleic acid 1G6 VLCL2 CEA (AC22) |
| SEQ ID NO: 77 | Nucleic acid1D5 VLCL2 CEA (AC10) |
| SEQ ID NO: 78 | Nucleic acid 2B8 VLCL2 CEA (AC13) |
| SEQ ID NO: 79 | Nucleic acid 1A2 VLCL2 CEA (AC18) |
| SEQ ID NO: 80 | Nucleic acid 1A8 VLCL2 CEA (AC23) |
| SEQ ID NO: 81 | Nucleic acid 2F4 VLCL2 CEA (AC25) |
| SEQ ID NO: 82 | Nucleic acid 2F7 VLCL2 CEA (AC26) |
| SEQ ID NO: 83 | Nucleic acid 2C11 VLCL2 CEA (AC27) |
| SEQ ID NO: 84 | Nucleic acid C11 VLCL2 CEA (AC28) |
| SEQ ID NO: 85 | Nucleic acid 2B5 VLCL2 CEA (AC29) |
| SEQ ID NO: 86 | Human CEA (CEACAM5); full-length DNA |
| SEQ ID NO: 87 | Human CEA (CEACAM5); full-length protein |
| SEQ ID NO: 88 | MAB CEA1 VH (SEQ31) and part of CEA VH-CH1(EE)-Fc (hole, P329G LALA) [SEQ ID 36] aa TCB WO2017055389) and SEQ37 |
| SEQ ID NO: 89 | MAB CEA1 VL (SEQ32) and part of Hum. CEA VL-CL(RK) [SEQ ID 38] aa TCB WO201705538 |
| SEQ ID NO: 90 | MAB CD3 VH (SEQ33) and part of CD3 VH-CL(CK)) aa TCB WO2017055389 [SEQ ID 34]) |
| SEQ ID NO: 91 | MAB CD3 VL, (SEQ 34) and part of CEA VH-CH1(EE)-CD3 VL-CH1-Fc 9G LALA) [SEQ ID 37] aa TCB WO2017055389) |
| SEQ ID NO: 92 | CD3 VH-CL(CK) |
| SEQ ID NO: 93 | CEA VH-CH1(EE)-Fc (hole, P329G LALA) |
| SEQ ID NO: 94 | CEAVH-CH1(EE)-CD VL-CH1-Fc (knob, P329G) |
| SEQ ID NO: 95 | CEA VL-CL(RK) |
| SEQ ID NO: 96 | CD3 CH2527 Cross Fab VL-CH1 |
| SEQ ID NO: 97 | CH1A10 VH CH1 FC Hole P329G LALA |
| SEQ ID NO: 98 | CH1A1A CD3 CH2527 Cross Fab VH-CK FC Knob P329G LALA |
| SEQ ID NO: 99 | LC CEA |
| SEQ ID NO: 100 | VK_SM3E |
| SEQ ID NO: 101 | VH_SM3E |
| SEQ ID NO: 102 | VL_MEDI |
| SEQ ID NO: 103 | VH_MEDI |
| SEQ ID NO: 104 | VK_SAR |
| SEQ ID NO: 105 | VH_SAR |
| SEQ ID NO: 106 | VK_CH1A1A |
| SEQ ID NO: 107 | VH_CH1A1A |
| SEQ ID NO: 108 | VK_T84.66 |
| SEQ ID NO: 109 | VH_T84.66 |
| SEQ ID NO: 110 | VK_LABETUZUMAB |
| SEQ ID NO: 111 | VH_LABETUZUMAB |
| SEQ ID NO: 112 | Mab CEA 1B2 (AC39) CDRL1 |
| SEQ ID NO: 113 | Mab CEA 1B2 (AC39) CDRL2 |
| SEQ ID NO: 114 | Mab CEA 1B2 (AC39) CDRL3 |
| SEQ ID NO: 115 | Mab CEA 1B2 (AC39) VLCL2 |
| SEQ ID NO: 116 | Mab CEA 1B2 (AC39) VLCL2, nucleic acid |

SEQ ID NO: 92 to 95 refers to CEA-TCB1 and SEQ 96 to 99 refers to CEA-TCB.
Ala: alanine;
Ser: serine

EXAMPLES

Example 1 Cloning, Expression and Purification of Human CD47

Cloning

The sequence corresponding to the extracellular domain of human CD47 (hCD47), is amplified from human cDNA by polymerase chain reaction (PCR) using specific oligonucleotides. The amplification product is gel-purified and cloned into the pEAK8 mammalian expression vector (Edge Biosystems, Gaithersburg, Md.). The vector is further modified to introduce an Avitag™ (Avidity, Denver Colo.) and a hexa-histidine tag at the C-terminus allowing for single site biotinylation of the protein and purification by IMAC (Immobilized Metal Ion Affinity Chromatography), respectively. The constructs are verified by DNA sequencing.

Expression

The plasmid is then transfected into mammalian cells using a liposome-based transfection reagent such as Lipofectamine® 2000 (Thermofisher Scientific). The transfection step requires only small quantities of DNA and cells, typically $2 \times 10^5$ cells and 2 µg of plasmid DNA per well and the transfection carried out in a 6-well plate. Although different mammalian cell lines can be used, in the examples given below, transformed human embryo kidney monolayer epithelial cells (PEAK cells) are transfected. These cells stably express the EBNA-1 gene, further supporting the episomal replication process, are semi-adherent and can be grown under standard cell culture conditions (5% $CO_2$; 37° C. in DMEM medium supplemented with 10% fetal calf serum). After 24 h, cells are placed under selective conditions by adding medium containing 0.5-2 µg/mL puromycin: cells harboring the episomal vector are resistant to this antibiotic.

Two to three weeks after transfection, amplified and selected cells were injected in disposable CELLine™ bioreactors for the production step. The CELLine™ is a two-compartment bioreactor that can be used in a standard cell culture incubator. The smaller compartment (15 ml) contains the cells and is separated from a larger (one liter) medium containing compartment by a semi-permeable membrane with a cut-off size of 10 kDa (Bruce et al. 2002, McDonald et al. 2005). This system allows for the diffusion of nutrients, gazes and metabolic waste products, while retaining cells and secreted proteins in the smaller compartment. The culture is maintained for 7-10 days before harvest of the supernatant. As the medium contains serum, the cells maintain good viability and several production runs can be generated using the same cells and containers.

Purification

After harvest, the cell culture supernatants are clarified by centrifugation. The supernatant is then supplemented with 100 mM imidazole and loaded on Ni-NTA affinity chromatography resin (Qiagen). The relatively high concentration of imidazole minimizes binding of contaminants to the resin. After washing of the column, proteins are eluted at a flow rate of 2 mL/min using a 30 mL imidazole gradient (20-400 mM imidazole) on an AKTA Prime chromatography system (Amersham Pharmacia Biotech). The elution gradient further improves the purity of the recombinant protein but can be replaced by a step elution approach if a chromatography system is not available. The eluted fractions can be analyzed by SDS-PAGE or ELISA to determine their content in recombinant protein. The fractions of interest are pooled and desalted on Amicon 10KD columns (Millipore) equilibrated with phosphate buffered saline or another appropriate buffer. The desalted proteins can then be quantified using various techniques and their purity analyzed by SDS-PAGE. Recombinant CD47 is biotinylated in vitro using biotin ligase (Avidity, Denver Colo.) according to manufacturer's instructions. After desalting the biotinylation level is evaluated by pull-down assays using streptavidin magnetic beads and SDS-PAGE analysis.

Example 2 Cloning, Expression and Purification of Human CEACAM Family Members

Cloning

The sequence corresponding to the complete extracellular domain (ECD) and A3-B3 domains of CEACAM5 were synthesized by Eurofins and Twist Bioscience. These synthetic genes were subcloned into the pEAK8 mammalian expression vector (Edge Biosystems, Gaithersburg, Md.). The vectors were modified to introduce an Avitag™ (Avidity, Denver Colo.) and either a hexa-histidine tag, a human FC region or a mouse FC region at the C-terminus. Constructs were verified by DNA sequencing. Purification of recombinant soluble protein was carried out by IMAC (Immobilized Metal Ion Affinity Chromatography), FcXL or CaptureSelect™ IgG-Fc (ms) Affinity Matrix (Thermofisher Scientific).

Vectors encoding for the full-length version of human CEACAM 1, 3, 4, 5, 6, 7, 8, 18, 19, 20, 21 and cynomolgus CEACAM5 were also generated for expression at the cell surface of PEAK and/or CHO cells. The soluble, full-length human CEACAM16 was also similarly cloned.

Expression and Purification

The expression, purification and biotinylation of the above-mentioned recombinant proteins was carried out as detailed in Example 1.

Example 3 Phage Display Selection of CEACAM5 Fvs Using Human scFv Libraries Containing Fixed Variable Heavy Domain General procedures for construction and handling of human scFv libraries displayed on M13 bacteriophage are described in Vaughan et al., (Nat. Biotech. 1996, 14:309-314), hereby incorporated by reference in its entirety. The libraries for selection and screening encode scFv that all share the same VH domain and are solely diversified in the VL domain. Methods for the generation of fixed VH libraries and their use for the identification and assembly of bispecific antibodies are described in US 2012/0184716 and WO 2012/023053, each of which is hereby incorporated by reference in its entirety. The procedures to identify scFv binding to human CECAM5 are described below.

Protein Selections

Aliquots of scFv phage libraries ($10^{12}$ Pfu) are blocked with PBS containing 3% (w/v) skimmed milk for one hour at room temperature on a rotary mixer. Blocked phage is deselected on streptavidin magnetic beads (Dynabeads™ M-280) for one hour at room temperature on a rotary mixer. Deselected phage is incubated with 100 nM of either biotinylated human CEACAM5 or the A3-B3 domain captured on streptavidin magnetic beads for two hours at room temperature on a rotary mixer. Beads are captured using a magnetic stand followed by five washes with PBS/0.1% Tween® 20 and two washes with PBS. Phage is eluted with 100 nM TEA for 30 minutes at room temperature on a rotary mixer. Eluted phage and beads are neutralized with Tris™-HCl 1M pH 7.4 and directly added to 10 ml of exponentially growing TG1 cells and incubated for one hour at 37° C. with slow shaking (90 rpm). An aliquot of the infected TG1 is serial diluted to titer the selection output. The remaining infected TG1 are spun at 3800 rpm for 10 minutes and resuspended in 2 ml 2×TY and spread on 2×TYAG (2×TY medium containing 100 µg/ml ampicillin and 2% glucose) agar Bioassay plates. After overnight incubation at 30° C., 10 ml of 2×TY is added to the plates and the cells are scraped from the surface and transferred to a 50 ml polypropylene tube. 50% glycerol solution is added to the cell suspension to obtain a final concentration of 17% glycerol. Aliquots of the selection rounds are kept at −80° C.

Phage Rescue

50 µl of cell suspension obtained from previous selection rounds are added to 50 ml of 2×TYAG and grown at 37° C. with agitation (240 rpm) until an $OD_{600}$ of 0.3 to 0.5 is reached. The culture is then super-infected with $1.2 \times 10^{11}$ M13K07 helper phage and incubated for one hour at 37° C. (90 rpm). The medium is changed by centrifuging the cells at 3800 rpm for 10 minutes, removing the medium and resuspending the pellet in 50 ml of 2×TYAK (2×TY medium containing 100 µg/ml ampicillin; 50 µg/ml kanamycin). The culture is then grown overnight at 30° C. (240 rpm). The next day, the phage containing supernatant is used for the next round of selection.

Cell Surface Selections

Phage containing supernatants are blocked with PBS containing 3% (w/v) skimmed milk for one hour at room temperature on a rotary mixer. Blocked phage is then deselected for one hour on MKN45 $CEACAM5^{KO}$ that do not express human CEACAM5. Deselected phage is incubated with $2 \times 10^7$ MKN45 cells expressing CEACAM5 (blocked in PBS 3% BSA 0.1% $NaN_3$) for two hours at room temperature with gentle shaking. Cells are pelleted and washed six times with PBS. Bound phage is eluted with 76 mM citric acid and shaking for 10 minutes. After neutralization with Tris-HCl 1M pH 8 the cells are added directly to 10 ml of exponentially growing TG1 and incubated for one hour at 37° C. with slow shaking. An aliquot of the infected TG1 is serial diluted to titer the selection output. Infected TG1 are spun at 3800 rpm for 10 minutes and resuspended in 2 ml 2×TY medium and spread on a 2×TYAG agar Bioassay plate. After overnight incubation at 30° C. 10 ml of 2×TY is added to the plate and the cells are scraped from the surface and transferred to a 50 ml polypropylene tube. 50% glycerol solution is added to the cell suspension to obtain a final concentration of 17% glycerol. Aliquots of the selection rounds are kept at −80° C.

Example 4 Screening for scFv Binding/Non-binding to Soluble CEACAM5, CEACAM6, and CEACAM1 scFv Periplasmic Preparation for Binding and Functional Tests

Individual clones are inoculated into a deep-well microtiter plate containing 0.9 ml per well of 2×TYAG medium (2×TY medium containing 100 µg/ml ampicillin, 0.1% glucose) and grown at 37° C. for 5-6 hours (240 rpm). 100 µl per well of 0.2 mM IPTG in 2×TY medium are then added to give a final concentration of 0.02 mM IPTG. The plate is incubated overnight at 30° C. with shaking at 240 rpm. The deep-well plate is centrifuged at 3200 rpm for 10 minutes at 4° C. and the supernatant carefully removed. The pellets are resuspended in 150 µl TES buffer (50 mM Tris-HCl (pH 8), 1 mM EDTA (pH 8), 20% sucrose, complemented with Complete protease inhibitor, Roche). A hypotonic shock is produced by adding 150 µl of diluted TES buffer (1:5 TES:water dilution) and incubation on ice for 30 minutes. The plate is centrifuged at 4000 rpm for 10 minutes at 4° C. to pellet cells and debris. The supernatants are carefully transferred into another microtiter plate and kept on ice for immediate testing in functional assays or binding assays.

Binding

Screening of scFv for binding to CEACAM5 is tested in a homogenous assay using CellInsight™ technology. The following reagents are mixed in each well of a 384 clear bottom well plate (Corning): 30 µl of a streptavidin polystyrene bead suspension (Polysciences; 3000 beads/well) coated with either biotinylated CEACAM5, biotinylated domain A3-B3 or biotinylated NusA for a control protein; 60 µl of blocked scFv periplasmic preparation; 10 µl of detection buffer (PBS containing mouse anti-c-myc antibody at 5 µg/ml; anti-mouse Fc AlexaFluor® 647 diluted 1:200). After mixing at 600 rpm for 5 minutes, the 384-well plate is incubated at room temperature and read after 2 hours on a CellInsight™ CX5 High-Content Screening platform (ThermoFisher Scientific). Clones expressing scFv giving a specific signal for CEACAM5 and not NusA are selected for further analysis or sequencing. Binding to CEACAM1, CEACAM6 and other CEACAMs can be measured in the same manner.

Phage Clone Sequencing

Single clones are inoculated into a 96-deep-well microtiter plate containing 1 ml LBAG medium (LB medium with 100 µg/ml ampicillin and 2% glucose) per well and grown overnight at 37° C., 240 rpm. DNA is extracted using the Zyppy®-96 Plasmid Miniprep kit (Zymo Research) and sequenced.

Example 5 Fixed VII Candidates Reformatting into IgG and Transient Expression in Mammalian Cells After screening and sequencing, scFv candidates with the desired binding properties are reformatted into IgG and expressed by transient transfection into PEAK cells. The VH and VL sequences of selected scFv are amplified with specific oligonucleotides and cloned into an expression vector containing the heavy and light chain constant regions and the constructions are verified by sequencing. The expression vectors are transfected into mammalian cells using Lipofectamine® 2000 (Thermofisher Scientific) according to manufacturer's instructions. Briefly, $3.5 \times 10^6$ PEAK cells are cultured in T75 flasks in 25 ml culture media containing fetal bovine serum. Transfected cells are cultured for 5-6 days at 37° C., IgG production is quantified by Octet®RED96 instrument. The supernatant is harvested for IgG purification on FcXL affinity resin (Thermofisher Scientific) according to manufacturer's instructions. Briefly, supernatants from transfected cells are incubated overnight at 4° C. with an appropriate amount of FcXL resin. After resin wash by PBS, samples are loaded on Amicon Pro column and the IgG consequently eluted in 50 mM Glycine pH3.5. The eluted IgG fraction is then dialyzed by Amicon 50 kDa against Histidine NaCl pH6.0 buffer and the IgG content is quantified by absorption at 280 nm. Purity and IgG integrity are verified by Agilent Bioanalyzer manufacturer (Agilent Technologies, Santa Clara, Calif., USA).

Example 6 Characterization of CEACAM5 Antibodies a) Binding of CEACAM5 Antibodies to Cells Transfected with Different Members of the CEACAM Family According to the knowledge of the inventors specificity of CEACAM5 monoclonal antibodies (mAbs) can be shown by flow cytometry using PEAK and/or CHO cells transfected with different members of the CEACAM family. Vectors encoding the full-length version of human CEACAM 1, 3, 4, 5, 6, 7, 8, 18, 19, 20 and 21 and 20 are used to express these proteins at the surface of PEAK and/or CHO cells as described in Example 2. Non-transfected PEAK and/or CHO cells are used as negative control. Cells are harvested, counted, checked for viability and resuspended at $3 \times 10^6$ cells/ml in FACS buffer (PBS 2% BSA, 0.1% $NaN_3$). 100 µl of the cell suspension are distributed in V-bottom 96-well plates ($3 \times 10^5$ cells/well). The supernatant is removed by centrifugation 3 minutes at 4° C., 1300 rpm and the cells incubated for 15 minutes at 4° C. with increasing concentrations of the antibody according to the invention. The antibodies are diluted in FACS buffer and the concentration range is 30 pM-500 nM. Cells are washed twice with cold FACS buffer and re-incubated for further 15 minutes at 4° C. with the PE (R-phycoerythrin)-conjugated mouse anti-human IgG Fc secondary antibody (SouthernBiotech, pre-diluted 1:100 in FACS buffer). Cells are washed twice with cold FACS buffer and resuspended in 300 µl FACS buffer with 1:1500-diluted TOPRO®-3 (Invitrogen). Fluorescence is measured using a FACSCalibur™ (BD Biosciences). Dose-response binding curves are fitted using GraphPad Prism7 software. In the same manner, CEACAM1, CEACAM6 and other CEACAMs can be characterized. In brief, purified Mabs are incubated with cells expressing one of the CEACAM family proteins at a final concentration of 10 µg/ml for 30 minutes. After two washes, bound antibodies are detected using a Cy-conjugated anti-human Fc secondary antibody (BD biosciences).

An antibody according to the invention is found as non-binding to said CEACAM, if no bound antibody is detected by the PE-conjugated anti-human IgG Fc secondary antibody.

b) Cross-Reactivity of CEACAM5 Antibodies with Cynomolgus CEACAM5

According to the knowledge of the inventors the ability of CEACAM5 monoclonal antibodies of the present invention to cross-react with cynomolgus monkey CEACAM5 can be tested by flow cytometry using PEAK CHO cells transfected with a vector expressing full-length cynomolgus CEACAM5. Flow cytometry allows detecting if the said antibody is binding to the PEAK CHO cells expressing cynoCEACAM5 or if the said antibody is not binding to the PEAK CHO cells respectively non-binding to said CEACAM.

Example 7 Expression and Purification of Bispecific Antibodies Carrying a Lambda and a Kappa Light Chain The simultaneous expression of one heavy chain and two lights chain in the same cell can lead to the assembly of three different antibodies. Simultaneous expression can be achieved in different ways such as that the transfection of multiple vectors expressing one of the chains to be co-expressed or by using vectors that drive multiple gene expression. The vector encoding the different anti-CEACAM5 antibodies are co-transfected with another vector expressing the heavy and light chain of anti-CD47 antibody Ka3 (SEQ ID NO:5 and 11), an anti-CD47 antibody bearing the same common heavy chain and that is described in US 2014/0303354. Alternatively, the two light chains are cloned into the vector pNovi κHλ that is previously generated to allow for the co-expression of one heavy chain, one Kappa light chain and one Lambda light chain as described in US 2012/0184716 and WO 2012/023053, each of which is hereby incorporated by reference in its entirety. The expression of the three genes is driven by human cytomegalovirus promoters (hCMV) and the vector also contains a glutamine synthetase gene (GS) that enables the selection and establishment of stable cell lines. The common VH and the VL genes of the anti-CEACAM5 IgG and of the anti-CD47 IgG are cloned in the vector pNovi κHλ, for transient expression in mammalian cells. Peak cells are cultured in appropriate Flask with suitable cells number and culture medium volume (containing fetal bovine serum). Plasmid DNA is transfected into the cells using Lipofectamine® 2000) according to manufacturer's instructions. Antibody concentration in the supernatant of transfected cells is measured during the production using Octet®RED96. According to antibody concentration, supernatants are harvested 5 to 7 days after transfection and clarified by centrifugation at 1300 g for 10 min. The purification process is composed of three affinity steps. First, the CaptureSelect™ FcXL affinity matrix (Thermofisher Scientific) is washed with PBS and then added in the clarified supernatant. After incubation overnight at +4° C., supernatants are centrifuged at 2000 g for 10 min, flow through is stored and resin washed twice with PBS. Then, the resin is transferred on Amicon Pro columns and a solution containing 50 mM glycine at pH 3.0 is used for elution. Several elution fractions are generated, pooled and desalted against PBS using 50 kDa Amicon™ Ultra Centrifugal filter units (Merck KGaA, Darmstadt, Germany). The elueted product, containing total human IgGs from the supernatant, is quantified using a NanoDrop™ spectrophotometer (NanoDrop Technologies, Wilmington, Del.) and incubated for 15 min at RT and rpm with the appropriate volume of KappaSelect affinity matrix (GE Healthcare). Incubation, resin recovery, elution and desalting steps are performed as described previously. The last affinity purification step is performed using the lambda FabSelect affinity matrix (GE Healthcare) applying the same process as for the two previous purifications. The final product is quantified using the Nanodrop. Purified bispecific antibodies are analyzed by electrophoresis in denaturing and reducing conditions. The Agilent 2100 Bioanalyzer is used with the Protein 80 kit as described by the manufacturer (Agilent Technologies, Santa Clara, Calif., USA). 4 µL of purified samples are mixed with sample buffer supplemented with dithiothreitol (DTT; Sigma Aldrich, St. Louis, Mo.). Samples are heated at 95° C. for 5 min and then loaded on the chip. All samples are tested for endotoxin contamination using the Limulus Amebocyte Lysate test (LAL; Charles River Laboratories, Wilmington, Mass.).

Example 8: Characterization of Monovalent and Bispecific Antibodies a) Dual-Targeting Bispecific Antibodies Bind to Two Different Antigens on the Surface of the Same Cell.

According to the knowledge of the inventors simultaneous binding of the two antibody arms to two antigens on the surface of the cell (termed co-engagement) may result in additive or synergistic increase of affinity due to avidity mechanism. As a consequence, co-engagement confers high selectivity towards cells expressing both antigens as compared to cells that express just one single antigen. In addition, the affinities of the two arms of a bispecific antibody to their respective targets can be set up in a way that binding to target cells is principally driven by one of the antibody arms. For instance, a dual targeting κλ antibody composed of one arm binding with high affinity to CEACAM5 or to CEACAM5 and CEACAM6, and a second arm binding with lower affinity to CD47-but sufficient to inhibit CD47/SIRPα upon CEACAM5 or CEACAM5 and CEACAM6 co-engagement with CD47 should allow preferential inhibition of CD47 in cancer versus normal cells.

b) Affinity Measurement to Human CD47

According to the knowledge of the inventors the binding affinity of the antibodies according to the invention to human CD47 can be evaluated by surface plasmon resonance technology using a Biacore® T200 instrument. The biotinylated human CD47 soluble recombinant protein can be captured on a streptavidin coated sensor chip (Series S Sensor Chip SA). Then a concentration series of the test antibody can be injected over the surface, with regeneration of the surface between each injection.

Figure 6:
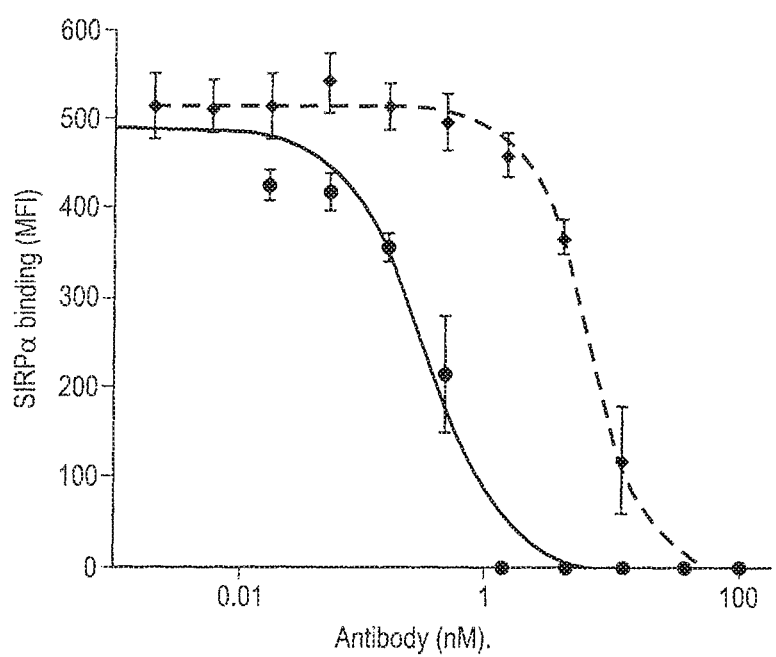
FIG. 6 shows concentration dependent blockade of soluble SIRPαalpha binding to CD47 expressed on MKN-45 cells co-expressing CEA (the TAA) by a TAA×CD47 bispecific antibody (solid line) and the corresponding anti-CD47 monovalent antibody (dashed line). Higher blocking potency of the bispecific antibody is due to more potent binding to target cells and TAA co-engagement-dependent blockade of CD47.

Such measurements were performed with a CD19×CD47 κλ bispecific antibody. The binding affinity measured in repeated determinations was between 400 and 500 nM. The CD47 binding arm of this antibody is the same as the CD47 binding arm of the CEA×CD47 bispecific antibodies of this invention. According to the knowledge of the inventors that same experiments performed with the CEA×CD47 bispecific antibodies of the invention will provide similar results within the standard deviation of such experiments.

c) SIRPα Blocking Activity of Monovalent and Bispecific Antibodies to Demonstrate Co-Engagement of CEACAM5 and CD47 on Surface of Target Tumor Cells According to the knowledge of the inventors another series of experiments can be performed which can provide a proof of co-engagement of TAA (like CEACAM5) and CD47 on the surface of the target cell are experiments showing that the neutralization of CD47-SIRPα interaction by CD47×CEACAM5 κλ antibodies is CEACAM5 dependent. In such experiments, the activity of CD47× CEACAM5 κλ bodies and the corresponding monovalent antibodies can be tested in the CD47-SIRPα inhibition assay. FIG. 6 shows results with a TAA×CD47 bispecific antibody (TAA is not CEA) containing the same CD47 binding arm than the bispecific antibodies of this invention in comparison to the corresponding monovalent anti-CD47 antibody.

d) SIRPα Blocking Activity of CD47 Antibodies

Experimental set-up for the measurement of the SIRPα inhibition potency data shown for bispecific antibodies of this invention (results see table 2):

The detection of bound SIRPα cell-based assay monitoring the interaction of soluble SIRPα with human CD47 expressed at the surface of MKN45 is used for the detection of the blocking activity. Dose-response experiments with bispecific antibodies according to the invention allow determination of an IC50 value.

MKN45 cancer cells, expressing both CD47 and CEACAM5, are stained with CFSE violet to allow the imaging system (CX5) to detect the cells. Briefly, 3'000 stained MKN45 cells per well are seeded in a 384 optical well plate (Costar) and incubated for 50 minutes with increased concentrations of bispecific antibodies of the invention (1.9 pM to 333 nM, in quadruplicates). Then, a fixe concentration of SIRPα-mouseFc premixed with anti-mouse IgG-Fc AF647 coupled antibody (Jackson ImmunoResearch diluted 1:2000) is added at 50 ng/mL final. After an incubation of 3H30 plates are acquired with the imaging system (CX5, Thermofisher) and fluorescence signals emitted by the detected bound SIRPα is recorded by the software dedicated to the imaging system. Fluorescence signals are plotted according to the dose range tested and IC50 are calculated by the software (Prism, Graphpad).

Table 2 shows the potency of several CEA×CD47 bispecific antibodies at inhibiting CD47/SIRPα binding displaying a range of IC50, from 0.22 nM to 7 nM.

e) Epitope Binning of CEACAM5 Antibodies by Competition with Reference Antibodies Epitope binning is a competitive immunoassay used to characterize the binding of antibodies according to the invention or e.g. the binding of the related anti-CEA (target protein) antibodies of the first binding part. A competitive blocking profile of an antibody binding to the target protein is created against antibodies also binding to this target protein and for which the binding epitope has already been established/published. Competition to one of these reference antibodies indicate that the antibody has the same or a closely located epitope and they are "binned" together. The ability of CEACAM5 mAbs, which are part of the bispecific antibodies of the present invention to compete with CEACAM5 reference antibodies is tested by ELISA on recombinant human CEACAM5 with the following reference antibodies carrying a mouse Fc region: SM3E, sequences of mAb derived from SM3E described in patent US20050147614A1, mAb produced using standard methods; MEDI, mAb derived from MEDI-565 described in patent WO2016036678A1; SAR, mAb derived from Mab2_VLg5VHg2 described in patent EP3199552A1; CH1A1A, mAb derived from CH1A1A-2F1 described in patent US20120251529 and by Klein et al in Oncoimmunology, 2017 Jan. 11; 6(3); humanized T84.66 mAb derived from variant 1 described in patent WO2017055389; LAB mAb derived from hMN14 described in patent US 2002/0165360 A1. SM3E binds e.g. more to the N-terminal, cell membrane distal part of CEA, MEDI to the middle part and CH1A1A binds close to the membrane.

Biotinylated human CEACAM5 is coated at 0.5 μg/ml in a Streptavidin-coated 96-well plate and incubated with 10 μg/ml of the reference mAbs or an irrelevant mAb carrying a mouse Fc region for 1 hour. The CEACAM5 mAbs (as bivalent monoclonal anti-CEA antibodies and not as respective CEA×CD47 bispecific antibodies) are added at 0.2 μg/ml for 1 hour at room temperature. The plate is washed and the bound CEACAM5 mAbs are detected with an anti-human IgG(Fc)-HRP (Jackson ImmunoResearch). After washing, the plate is revealed with Amplex Red reagent. The fluorescence signal is measured on a Synergy HT plate reader (Biotek™).

Results are shown in table 2. Bin 1 means that the respective antibody competes with SM3E for binding to CEACAM5. Bin 2 means, that the respective antibody does not compete with any of the tool antibodies mentioned above. The competition experiments were for all of the CEA×CD47 bispecific antibodies listed in Table 2 performed with the respective anti-CEA bivalent monoclonal antibodies. In case binding of such a monoclonal antibody to CEACAM5 was reduced by the respective tool antibody by 80% or more, it was concluded that the CEA×CD47 bispecific antibody is classified to bind competitively with the tool antibody. A CEA×CD47 antibody is identified as non-competitive with a tool antibody in case binding of the respective anti-CEA bivalent mAb to CEACAM5 is reduced by 20% or less if the results with and w/o addition of a tool antibody are compared.

Bin 1: K2AC13, K2AC18, K2AC23, K2AC27, K2AC29

Bin 2: K2AC10, K2AC25, K2AC28 K2AC26

Results for Bin characterization, EC50 values of binding to CEA, SIRPα inhibition potency, and EC50 as well as maximal. index of phagocytosis for bispecific antibodies according to the invention are shown in tables 2, 3 and 4

TABLE 2

In vitro characteristics of CEAxCD47 bispecific antibodies

| Antibody name | Bins characterization | EC50 binding (nM)[#] | SIRPα inhibition potency (nM)[#] |
|---|---|---|---|
| K2AC5 | Bin 1 | 11.3 | 0.4 |
| K2AC10 | Bin 2 | 1.15 | 0.22 |
| K2AC13 | Bin 1 | 190 | 4 |
| K2AC18 | Bin 1 | 131.8 | 7 |
| K2AC22 | Bin 1 | 16.5 | 0.37 |
| K2AC23 | Bin 1 | 76.8 | 1.6 |
| K2AC25 | Bin 2 | 13 | 0.22 |
| K2AC26 | Bin 1 | 12.7 | 0.32 |
| K2AC27 | Bin 1 | 12.5 | 0.86 |
| K2AC28 | Bin 2 | 52.5 | 0.95 |
| K2AC29 | Bin 1 | 14.5 | 0.72 |

[#]using MKN45 CEA[+] cancer cells

TABLE 3

In vitro functional activity CEAxCD47 bispecific antibodies*

| Antibody name | EC50 (μg/mL) | Max index of phagocytosis |
|---|---|---|
| K2AC5 | 0.44 | 59 (±4.2) |
| K2AC22 | 0.19 | 69 |
| K2AC23 | 0.68 | 67.5 (±2.1) |
| K2AC25 | 1.54 | 48 (±1.4) |
| K2AC26 | >9.9 | 46 (±9.9) |
| K2AC27 | >11.7 | 47 (±1.4) |
| K2AC28 | >19.8 | 32.5 (±0.7) |
| K2AC29 | >4.4 | 42 (±5.6) |

TABLE 4

EC50 and maximum index of phagocytosis for two CD47xCEA bispecific antibodies in presence or not of 1 mg/mL of hIgG1 using MKN45 cells.

| Antibody name | EC50 phagocytosis (μg/mL) - w/o hIgG1 | EC50 phagocytosis (μg/mL) - with hIgG1 | Max. Phagocytosis Index - w/o hIgG1 | Max. Phagocytosis Index - with hIgG1 |
|---|---|---|---|---|
| K2AC5 | 0.16 | 0.44 | 67 (±5.7) | 77 (±1.4) |
| K2AC22 | 0.25 | 0.45 | 85 (±4.2) | 92.5 (±3.5) |
| 5F9 hIgG4 | 0.15 | 0.62 | 54 (±1.4) | 31 (±2.8) | max. = maximum;
max. index phagocytosis assessed at 10 μg/ml;
[#]using MKN45 CEA[+] cancer cells

TABLE 5

EC50 binding on human CEACAM5 or human CEACAM6 by ELISA using recombinant proteins by ELISA.

| Antibody name | EC50 binding to CEACAM5 | EC50 binding to CEACAM6 |
|---|---|---|
| AC22 | 0.015 | No binding |
| AC39 | 0.22 | 0.17 | f) Binding of Anti-CEA Antibodies to Human CEACAM5 and Human CEACAM6

Biotinylated recombinant human CEACAM5 or CEACAM6 proteins are captured at 0.5 μg/mL in a streptavidin coated 96-well microplate. The plate is washed and monoclonal anti-CEA bivalent antibodies of the present invention are added as a broad concentration-range (e.g. from $5 \times 10^{-4}$ to 1 μg/mL) and incubated during 1 hr. The plate is washed and bound antibodies are detected with an anti-human IgG(Fc)-HRP (Jackson ImmunoResearch). After washing, the plate is revealed with Amplex™ Red reagent (Molecular Probes). The fluorescence signal is measured on a Synergy HT plate reader (Biotek™).

Results obtained for the monoclonal antibody AC39 are contained in table 5; this antibody shows balanced CEACAM5 and CEACAM6 binding, that means EC50 for binding to CEACAM5 and CEACAM6 are similar (range of the ratio of the EC50 for CEACAM5 binding to CEACAM6 binding of balanced antibodies from 0.33 to 3). Antibodies with a ratio outside this range are considered as not balanced.

Example 9: ADCC and ADCP Mediated by Bispecific Antibodies a) ADCP and ADCC Mediated by TAAxCD47 Bispecific Antibodies is TAA Dependent The ability of dual targeting TAAxCD47 κλ antibodies to co-engage CD47 and TAA results in a significant increase in the affinity of binding to TAA-positive cells as compared to TAA-negative cells and in TAA-dependent neutralization of the CD47-SIRPα interaction. This, in turn, could translate into efficient and selective cancer cell killing mediated by CEAxCD47 κλ antibodies.

Figure 3A:
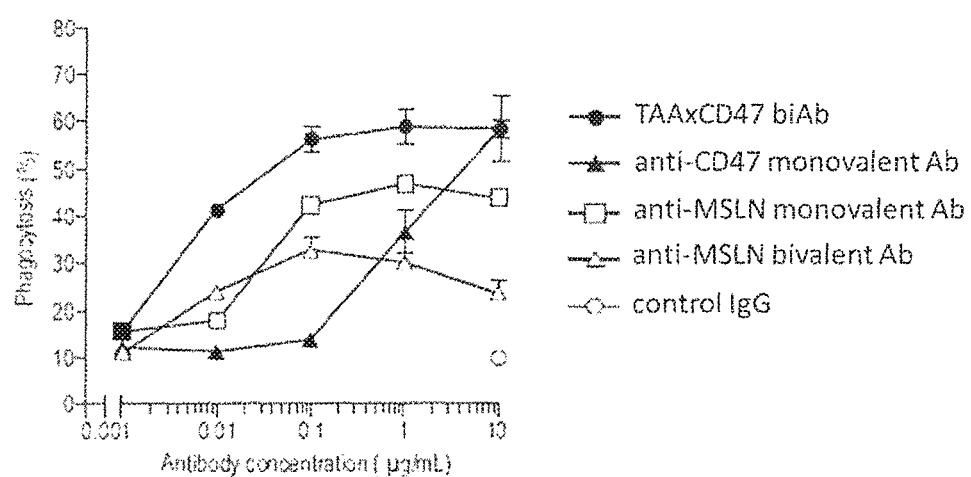
FIG. 3A shows the concentration dependent increase of phagocytosis (assessed by flow cytometry and expressed as % of phagocytosis) of human pancreatic cancer cell line HPAC (expresses CEA and other TAAs like mesothelin MSLN) with a TAA×CD47 bispecific antibody carrying the CD47 binding arm of the invention, the corresponding CD47 and TAA monovalent antibody as well as the high-affinity anti-TAA (MSLN) monoclonal antibody, Amatuximab. All antibodies bear wild-type IgG1 Fc portions. The bispecific antibody shows the highest phagocytosis.
Figure 3B:
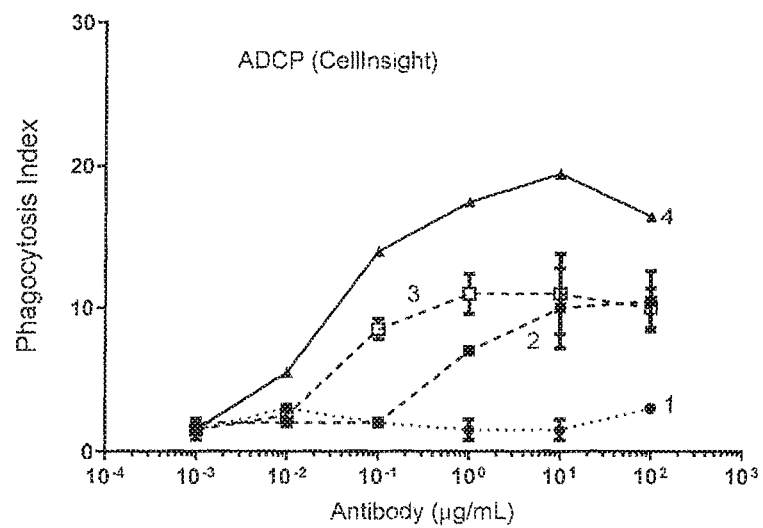
FIG. 3B shows the concentration dependent increase of phagocytosis (assessed with the CellInsight assay and expressed as phagocytosis index) induced by various antibodies; curve 1: control hIgG1 not binding to TAA or CD47; curve 2: TAA×CD47 bispecific antibody with wild type hIgG1 Fc; curve 3: anti CD47 antibody B6H12.2 with wild type hIgG1; curve 4: TAA×CD47 bispecific antibody with DEA aa substitutions (S329D, I332E and G236A) in the hIgG1 Fc part. The strongest phagocytosis was achieved with TAA×CD47 with DEA mutated Fc.
Figure 4:
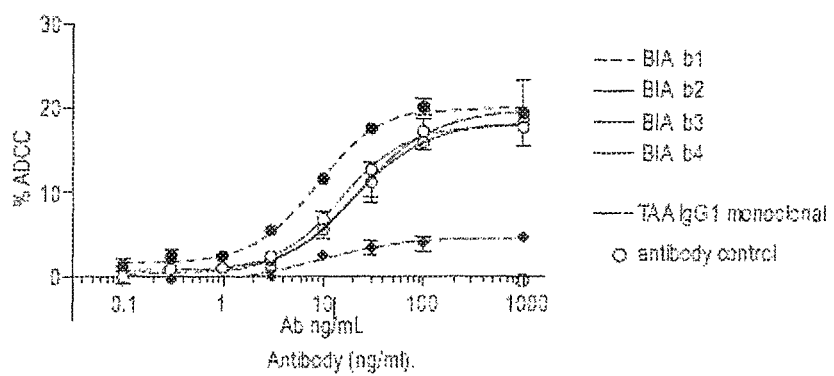
FIG. 4 shows an example of ADCC dose response curves (assessed with the Cr51+ assay and expressed as % specific killing) for various TAA×CD47 bispecific antibodies (TAA is mesothelin MSLN), all carrying the same CD47 binding arm of this invention, using lung cancer NCI-H226 cancer cells as target cells (hu volunteer PBMC to tumor cells 50:1). All bispecific antibodies show stronger ADCC than the high-affinity anti-TAA monoclonal antibody, Amatuximab, an anti-MSLN mAb.

Results as demonstrated from ADCP experiments (flow cytometry based assay) shown in FIG. 3A demonstrate higher ADCP of bispecific TAAxCD47 antibody compared to the corresponding monovalent TAA as well as the monovalent CD47 antibody. FIG. 4 is showing higher ADCC (Cr51 based assay) of four bispecific TAAxCD47 antibodies (TAA is mesothelin MSLN) compared to the high affinity anti-TAA monoclonal antibody Amatuximab (TAA is MSLN) (lung cancer NCI-H226 tumor cells carrying MSLN are used.

b) Cr51[+] Release Assay, Measured with TAAxCD47 Antibodies

Healthy PBMC were activated overnight at 37° C. with RPMI/10% heat inactivated FCS supplemented with 10 ng/mL of recombinant hIL-2. The next day, targets cells (i.e. cancer cells expressing the TAA) were incubated with 100 μCi Cr51 (Perkin Elmer, 37° C., 1 h). After washing, cells were opsonized with test antibodies (30 min, 37° C.). Cr51-loaded cancer cells were then mixed with PBMC cells to obtain the final 80:1 or 50:1 ratio between effector (PBMC) and target cells (TAA-expressing cells). The cell mixture was incubated for 4 h at 37° C. before being centrifuged for 10 min at 1500 rpm. Supernatant was transferred into a LumaPlate™ (coated with scintillant) and counted in a γ-counter. Negative controls (spontaneous Cr51 release) consisted of Cr51-loaded target cells incubated with medium in the absence of effector cells. Total lysis control consisted of Cr51-loaded target cells incubated with 5 μL of cell lysis solution (Triton™ X-100). Nonspecific lysis control (baseline) consisted of Cr51-loaded target cells incubated with effector cells, without Ab. The ADCC percentage was calculated using the following formula: % specific ADCC=((sample counts per minute (cpm)−nonspecific lysis control cpm)/(total lysis control cpm−negative control cpm))×100%.

Figure 5:
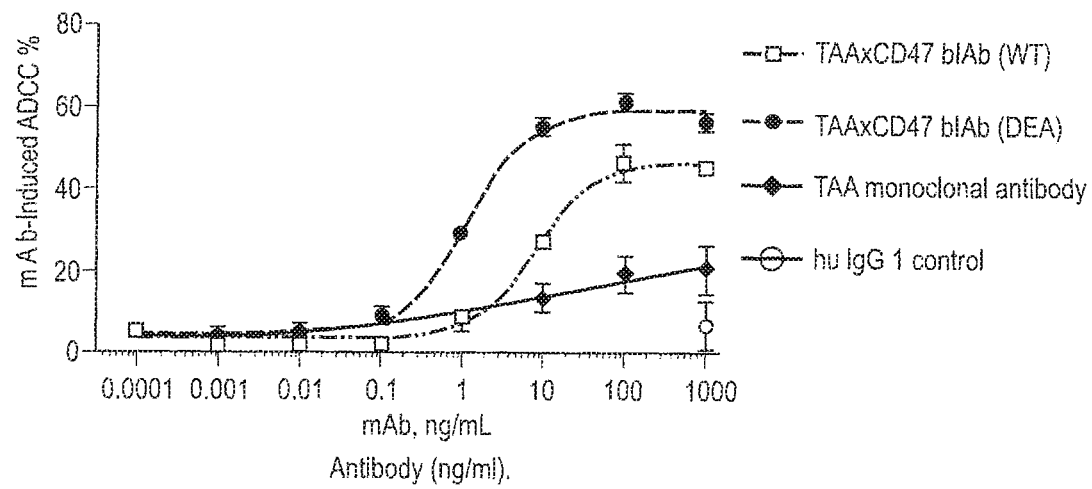
FIG. 5 shows ADCC dose response curves (assessed using the Cr51+ assay and expressed as % specific killing) for a TAA×CD47 bispecific antibody with wildtype Fc, the corresponding TAA×CD47 bispecific antibody with Fc carrying DEA mutations, a high-affinity anti-TAA monoclonal antibody (TAA in this figure is not CEA), and a human IgG1 control antibody; using lung cancer NCl-H226 cancer cells as target cells (effector to tumor cells 50:1). The strongest ADCC was observed with the bispecific antibody carrying the DEA mutations.

FIG. 5 shows the results for ADCC (Cr 51 based assay) of comparison experiment between the wt IgG1 Fc version versus the additionally DEA mutated Fc version of a CD47× TAA bispecfic antibody (TAA not CEA) carrying the same CD47 arm as the CEA×CD47 antibodies of the invention. Also, the results for a high affinity anti-TAA bivalent mAb are shown. Highest ADCC of the TAA×CD47 bispecific antibody carrying IgG1 Fc with DEA mutations, followed by CEA×CD47 biAb with IgG1 Fc and by the bivalent mAb with the wt IgG1 Fc.

c) ADCC Measured by LDH Release Assay

ADCC of the CEA×CD47 bispecific antibodies was tested in the following assay: Healthy PBMC were activated overnight at 37° C. with RPMI/10% heat inactivated FCS supplemented with 10 ng/mL of recombinant hIL-2. The next day, target cells (e.g. MKN45 cancer cells) are opsonized with different concentrations of tested antibodies. The PBMCs and the opsonized target cells are co-incubated at a ratio effector/target 50/1 in round bottom plates for 6 hours at 37° c. in a cell culture incubator. After this incubation, supernatants are transferred into optical flat bottom plate and the LDH release is quantified with a commercial kit from Roche by measuring OD with a microplate reader. The % of specific lysis is calculated with the following formula:

$$\text{Specific lysis} = \left( \frac{LDH \text{ Sample} - (LDH \text{ Effector} + \text{Target cells})}{\text{Maximum } LDH - LDH \text{ Target cells alone}} \right) \times 100$$

FIG. 13 shows the results of comparison experiments between bispecific antibodies of the invention with their glycoengineered forms and with antibody 5F9. FIG. 14 shows the results of comparison experiments between bispecific antibodies of the invention with their glycoengineered forms and with antibody 5F9 in the presence of 1 mg/ml human Immunoglobulin (IgG).

d) ADCP Assay

Figure 17:
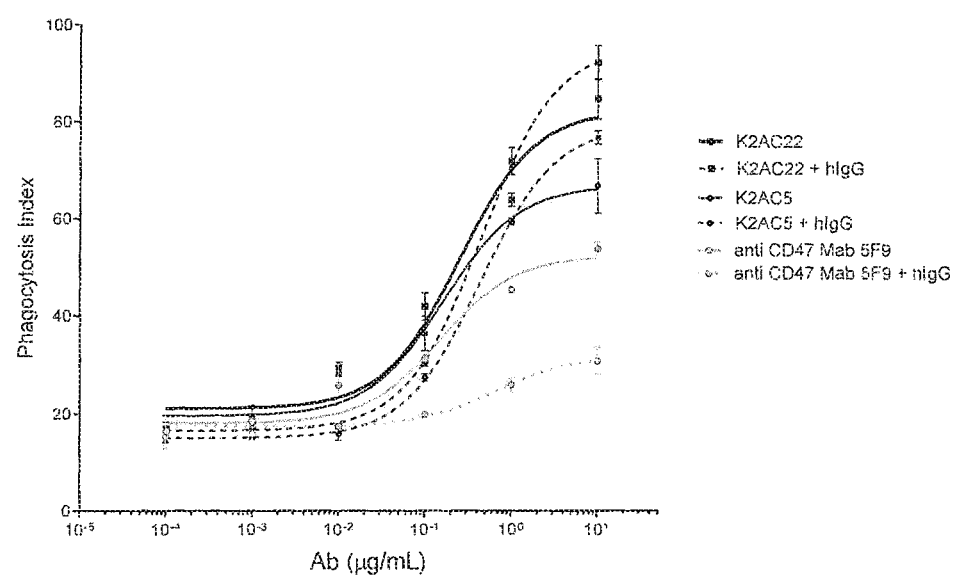
FIG. 17 shows the concentration dependent increase of phagocytosis (assessed with imaging based (CellInsight) and expressed as phagocytosis index) induced by two selected CD47×CEA bispecific antibodies, i.e. K2AC5 and K2AC22, in presence or not of 1 mg/ml of human IgG. The sequence-identical analogue of the anti-CD47 antibody Hu5F9-G4 (5F9 bearing a human IgG4 Fc portion, described in US20160333093) was run for comparison. The addition of 1 mg/mL human IgG (this is even below the physiological plasma concentrations of IgG in men) slightly impacts the potency (i.e. EC50) of the CD47×CEA bispecific antibodies while the activity driven by the mAb 5F9 is drastically impaired (EC50 and maximal phagocytosis).
Figure 18:
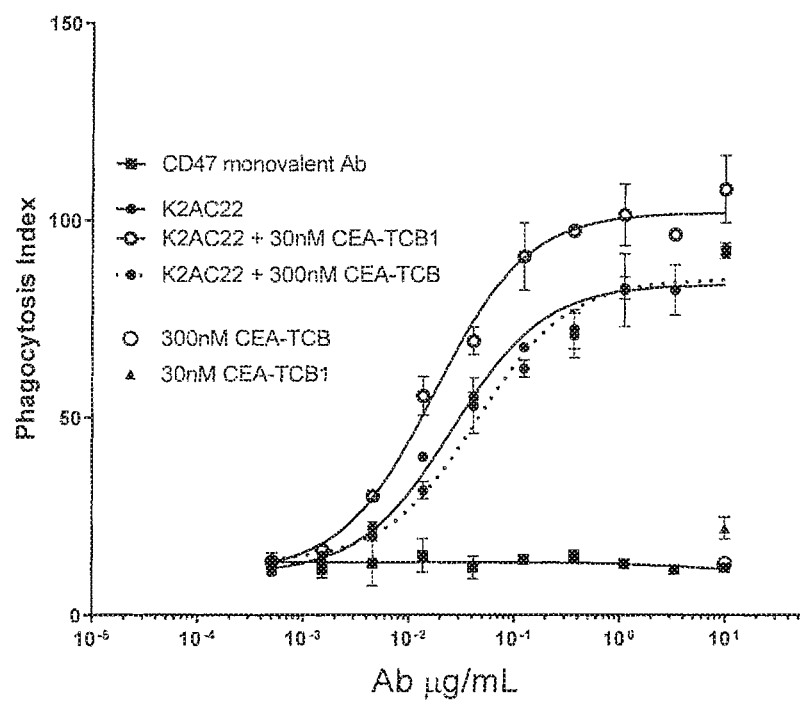
FIG. 18 shows the effect of T-cell retargeting CEA-TCB1 (30 nM) and CEA-TCB (300 nM) bispecific antibodies (CEA×CD3 bispecific antibodies CEA-TCB: RO6958688/cibisatamab, see for example Bacac et al Clin. Cancer Res., 22(13), 3286-97 (2016) and US20140242079; CEA-TCB1: from WO2017055389) on phagocytosis (assessed with imaging based assay (CellInsight) and expressed as phagocytosis index) induced by the K2AC22 CEA×CD47 bispecific antibody. The T cell retargeting bispecific antibodies, the CD47×CEA bispecific antibody and the corresponding CD47 monovalent antibody were tested alone for comparison. Neither CEA-TCB nor CEA-TCB1 impairs the concentration dependent activity in phagocytosis of K2AC22.

Two methods are used. In the FACS based method the percentage of phagocytosis (representing the percentage of macrophages which have engulfed at least one tumor cell) is determined. FIG. 3A shows results obtained with this FACS based assay for a TAA×CD47 antibody carrying the CD47 binding arm also used in the CEA×CD47 antibodies. With the imaging-based method, which makes use of the CellInsight CX5 High Content Screening Platform, the phagocytosis index, defined as the average number of target cells engulfed by 100 macrophages, is determined. FIG. 3B shows results obtained with a TAA×CD47 bispecific antibody (TAA not CEA) carrying the CD47 binding arm of the CEA×CD47 antibodies. FIGS. 12, 15, 16, 17, 18, 20B, and 21B show results obtained with CEA×CD47 bispecific antibodies of the invention. FIG. 15 shows the results of comparison experiments between bispecific antibodies of the invention with their glycoengineered forms and with anti-CD47 antibody 5F9. FIG. 16 shows the results of comparison experiments between bispecific antibodies of the invention with their glycoengineered forms and with antibody 5F9 in the presence of 1 mg/ml human Immunoglobulin (IgG) as usually present in patients. FIG. 17 shows the results of comparison experiments between bispecific antibodies of the invention in presence or not of 1 mg/ml human Immunoglobulin (huIgG, 1 mg/mL or even higher are present in patients). FIG. 18 shows the concentration/phagocytosis index curves of K2AC22 in presence or not of 30 nM of CEA-TCB1 or 300 nM CEA-TCB.

e) Phagocytosis Assays: 1. Imaging Assay Based on CellInsight CX5 High Content Screening Platform and 2. Flow Cytometry Based Assay Preparation of the macrophages: Human peripheral blood mononuclear cells (PBMCs) are isolated from buffy coats by Ficoll gradient. Macrophages are generated by culturing PBMCs for 7 days in complete medium (RPMI 1640, 10% heat-inactivated fetal calf serum [Invitrogen]), 2 mM L-glutamine, 1 mM sodium pyruvate, 10 mM HEPES buffer, 25 mg/mL gentamicin (all from Sigma-Aldrich), and 50 mM 2-mercaptoethanol (Thermo Fisher Scientific) in the presence of 20 ng/mL of human macrophage colony-stimulating factor (M-CSF) (PeproTech). Non-adherent cells are subsequently eliminated in the differentiation phase (day +1) by exchanging the cell culture medium, and adherent cells representing macrophages are detached using cell dissociation buffer (Sigma-Aldrich) and washed in complete medium the day of use (day 8 or day 9) for ADCP experiment based on cytometry. For ADCP based on cell imaging, macrophages are detached at day 6 using cell dissociation buffer and seeded at 30'000 per well in 96 optical plate (costar).

1. CellInsight™ Based Assay

Macrophages (stained with calcein red orange) adhering to microplate wells are co-incubated with Calccin AM-labeled target tumor cells at an effector:target cells ratio of 1:3 for 2.5 hours at 37 degree C. in the presence of different concentrations of the to be tested antibody. At the end of the incubation period, supernatants are replaced by complete culture medium and the microplates are imaged with the CellInsight™ CX5 High Content Screening Platform. 1500 macrophages are acquired and analyzed per well. Phagocytosis is evidenced as double-positive events (macrophage+ target tumor cell) and the phagocytosis indexes are calculated by the CellInsight™ manufacturers' software.

All the results in the FIGS. 12, 15, 16, 17, 18, 20B, and 21B as well as the EC50 and max. phagocytosis index values shown in tables 3 and 4 are obtained with MKN-45 cells expressing CEA and with an effector cell to target/tumor cell ratio of 1:3. The data in FIG. 3B are obtained with NCI-N87 cells carrying the TAA (which is not CEA) and with an effector to target/tumor cell ratio of 1:1. The more tumor cells are offered per macrophage the higher the expected phagocytosis index, this is probably the main reason for the overall lower phagocytosis index and also background signal shown in FIG. 3 B for TAA×CD47 bispecific antibody (TAA not CEA) compared to the other figures demonstrating the result for bispecific antibodies according to the invention.

All ADCP (phagocytosis) values, ranges and the like in the present invention are based on the imaging based assay if not otherwise and explicitly stated (data in FIG. 3A are obtained with flow based assay).

2. Flow Cytometry Based ADCP Assay

According to the knowledge of the inventors ADCP can also be measured by a method as described as follows: The macrophages are co-incubated with CSFE-labeled target tumor cells (e.g. MKN-45, LS174T or HPAC tumor cells) at an effector:target cells ratio of e.g. 3:1 for 2.5 hours at 37 degree C. in the presence of different concentrations of to be tested antibody. At the end of the incubation period, biotinylated anti-human CD14 antibody and Strep-Cy5 are added to label the macrophages. The cells are then washed and subjected to flow cytometry analysis. Phagocytosis is evidenced by double-positive events CD14+ and CFSE+. Percentage of phagocytosis is presented as the ratio between CD14+/CSFE+ double positive events and total target cells multiplied by 100. The data in FIG. 3A are obtained with HPAC cells carrying the TAA (which is not CEA) and with an effector to target/tumor cell ratio of 1:1. Flow cytometry based assay has been used. The data in FIG. 3B are obtained with NCI-N87 cells carrying the TAA (which is not CEA) and with an effector to target/tumor cell ratio of 1:1. Imaging based assay was used.

Example 10: Binding of CEA×CD47 and CEA×CD3 to MNK-45 Cells; Competition of Binding with CEA×CD3 a) The binding of CD47×CEACAM5 bispecific antibody is tested on e.g. CEA-expressing human gastric adenocarcinoma cells (MKN-45, DSMZ ACC 409).

Cells are harvested, counted, checked for viability and resuspended at $3\times10^6$ cells/ml in FACS buffer (PBS 2% BSA, 0.1% NaN3). 100 μl of the cell suspension are distributed in V-bottom 96-well plates ($3\times10^5$ cells/well). The supernatant is removed by centrifugation 3 minutes at 4° C., 1300 rpm. Increasing concentrations of the antibody according to the invention are then added into the wells and incubated for 15 minutes at 4° C. Cells are washed twice with cold FACS buffer and re-incubated for further 15 minutes at 4° C. with the PE (R-phycoerythrin)-conjugated mouse anti-human IgG Fc secondary antibody (SouthernBiotech, pre-diluted 1:100 in FACS buffer). Cells are washed twice with cold FACS buffer and resuspended in 300 μl FACS buffer with 1:15000-diluted Sytox™Blue (Life Technologies). Fluorescence is measured using a Cytoflex (Millipore). Binding curves and EC50 values are obtained and calculated using GraphPad Prism™7 software. In the same manner binding of MAB CEA or MAB CEA1 to MKN-45 cells can be tested. FIG. 11 shows the binding curves of several CEA×CD47 bispecific antibodies to MKN-45 cells.

b) Shift of binding curve of a CEA×CD47 antibody to CEA positive tumor cell-line (MKN-45) by addition of a CEA×CD3 T-cell bispecific antibody.

According to the knowledge of the inventors for competition experiments of CD47×CEACAM5 bispecific antibody according to the invention and CEA×CD3 T-cell bispecific antibodies like CEA-TCB or CEA-TCB1, the binding of the CEACAM5×CD47 to MKN-45 cells can be determined as described above, but with and w/o addition of the CEA×CD3 T-cell bispecific antibody to study if a CEA×CD3 T-cell bispecific antibody as combination partner for the CEA×CD47 bispecific antibodies of this invention is competitive for binding to CEA or not.

Example 11: Production and Purification of Fucosylated and Afucosylated K2AC5 and K2AC22 Bispecific Antibodies Production of Fucosylated and Afucosylated K2AC5 and K2AC22 Bispecific Antibodies:

CHO pool (one for K2AC5 and one for K2AC22) is inoculated at a viable cell concentration of $0.3\times10^6$ cells/mL in a Thomson erlen device with a working volume of 700 mL or 100 mL for the production of fucosylated and afucosylated antibodies, respectively. All the pools are operated in a 15 days duration fed-batch mode using CDACF medium CDCHO and an adapted feeding regime. For the production of afucosylated antibodies, bolus of 200 nM fucose inhibitor (1,3,4-Tri-O-acetyl-2-deoxy-2-fluoro-L-fucose) are added at day 0, 5, 8 and 11 during the fed batch process based on afucosylation strategy described by Rillahan et al. Nature Chem. Biol. 2012 July; 8(7):661-8 and based on EP2282773. Harvest of the K2AC5 and K2AC22 pools supernatants containing fucosylated or afucosylated antibodies is performed after 15 days of Fed batch culture. Harvests of CHO pools supernatants are clarified using the Sartoclear Dynamics® Lab V Cell Harvesting Sartorius system (see supplier instructions).

Purification of Fucosylated and Afucosylated K2AC5 and K2AC22 Bispecific Antibodies Purification of fucosylated and afucosylated K2AC5 and K2AC22 bispecific antibodies is a three affinity step purification process. Before starting purification, antibody concentration in the supernatant of K2AC5 and K2AC 22 pools is measured using OctetRED®96 in order to use columns with appropriate volume of affinity matrix. Each clarified CHO pool supernatant containing fucosylated or afucosylated bispecific antibodies, is loaded onto a MabSelect™ SuRe™ (MSS) column (GE Healthcare) without prior adjustment, to remove a major part of cell culture contaminants. The MSS eluate is then treated by low pH hold to inactivate viruses, and neutralized at pH 6 with Tris 1M pH9. The MSS eluate's is then loaded onto the LambdaFabSelect™ (LFS) column (GE Healthcare) to remove monospecific κ (mono κ). The LFS eluate is then pH adjusted at pH 6. The LFS is loaded onto the Capto L (CL) column (GE Healthcare) to remove monospecific λ (mono λ). The CL Eluate is pH adjusted before storage. The final material is then concentrated and diafiltered into the final formulation buffer, its concentration adjusted using the Nanodrop. Fucosylated and afucosylated K2AC5 and K2AC22 bispecific antibodies are aliquoted and stored at −80° C. until delivery. Purified bispecific antibodies are analyzed for sizing by electrophoresis in denaturing and reducing conditions with the Agilent 2100 Bioanalyzer using the Protein 80 kit as described by the manufacturer (Agilent Technologies, Santa Clara, Calif., USA). Aggregation level is assessed by size exclusion chromatography (SEC-UPLC) using the ACQUITY UPLC H-Class Bio System (Waters™). Charge variant analysis of purified bispecific antibodies is achieved by isoelectric focusing technique (IEF) using the Multiphor™ II Electrophoresis System (GE Healthcare). The relative distribution of N-linked complex biantennary glycoforms of fucosylated and afucosylated K2AC5 and K2AC22 antibodies is determined using the throughput microchip-CE method on the LabChip® GXII Touch (Perkin Elmer).

All antibodies are tested for endotoxin contamination using the Limulus Amebocyte Lysate test (LAL; Charles River Laboratories, Wilmington, Mass.). Glycoengineered K2AC5 shows an afucosylation of 79.68% and glycoengineered K2AC22 shows an afucosylation of 89.13%.

These afucosylated CEA×CD47 bispecific antibodies have been used to obtain the results shown in FIGS. 13, 14, 15 and 16.

Example 12: Expression and Purification in FUT8(-) Cell Line

Alternatively, and according to the knowledge of the inventors, afucosylated bispecific antibodies according to the invention can be produced also according to the method as follows:

Material and Methods are according to Naoko Yamane-Ohnuki et al., Biotech. Bioeng.; 87 (2004) 614-622.

Isolation of Chinese Hamster FUT8 cDNA

Total RNA is isolated from CHO/DG44 cells using the RNeasy® Mini Kit (Qiagen, Hilden, Germany) and reverse transcribed with oligo-dT using a Superscript first-strand synthesis system for reverse transcript-polymerase chain reaction (RT-PCR) (Invitrogen, Carlsbad, Calif.). A Chinese hamster FUT8 cDNA is amplified from single-stranded CHO/DG44 cell cDNAs by PCR using primers 5V-GTCT-GAAGCATTATGTGTTGAAGC-3V (SEQ ID NO:14) and 5V-GTGAGTACATTCATTGTACTGTG-3V (SEQ ID NO:15), designed from the murine FUT8 cDNA (Hayashi, 2000; DNA Seq 11:91-96).

Targeting Construct of FUT8 Locus

The targeted disruption of the FUT8 gene in CHO/DG44 cells is carried out using two replacement vectors, pKOFUT8Neo and pKOFUT8Puro. The 9.0-kb fragment of the FUT8 gene including the first coding exon is isolated by screening the CHO-K1 cell E-genomic library (Stratagene, La Jolla, Calif.) with the Chinese hamster FUT8 cDNA as a probe to establish the targeting constructs. A 234-bp segment containing the translation initiation site is replaced with the neomycin-resistance gene (Neor) cassette or the puromycin-resistance gene (Puror) cassette from plasmid pKOSelect-Neo or pKOSelectPuro (Lexicon, Tex.), respectively, flanked by loxP sites. The diphtheria toxin gene (DT) cassette from plasmid pKOSelectDT (Lexicon) is inserted at the 5V homologous region. The resulting targeting constructs, pKOFUT8Neo and pKOFUT8Puro, included the 1.5-kb 5V homologous sequence and the 5.3-kb 3V homologous sequence. Before transfection, the targeting constructs are linearized at a unique SalI site.

Transfection and Screening for Homologous Recombinants

Subconfluent CHO/DG44 cells (1.6 106) are electroporated with 4 Ag of linearized pKOFUT8Neo at 350 V and 250 AF using a Bio-Rad GenePulser® II. After electroporation, transfectants are selected with 600 Ag/mL G418 (Nacalai Tesque, Kyoto, Japan). Genomic PCR is performed in 96-well plates by the modified microextraction method reported previously (Ramirez-Solis et al., 1992; Anal Biochem 201:331-335) using the following primers:

```
                                   (SEQ ID NO: 16)
5V-TTGTGTGACTCTTAACTCTCAGAG-3V
and
                                   (SEQ ID NO: 17)
5V-GAGGCCACTTGTGTAGCGCCAAGTG-3V.
```

Homologous recombinants are identified by the 1.7-kb fragment obtained using genomic PCR and confirmed by Southern blot analysis using the 221-bp fragment amplified with the following primers:

```
                                   (SEQ ID NO: 218)
5V-GTGAGTCCATGGCTGTCACTG-3V
and
                                   (SEQ ID NO: 19)
5V-CCTGACTTGGCTATTCTCAG-3V.
```

The hemizygous clone is subject to a second round of homologous recombination using linearized pKOFUT8Puro and drug selection with 15 Ag/mL puromycin (Sigma-Aldrich, St. Louis, Mo.) as described earlier. The identified homozygous disruptants are electroporated with the Cre-recombinase expression vector pBS185 (Invitrogen) to remove drug-resistance gene cassettes from both FUT8 alleles.

Monoclonal Antibody Production by FUT8(-) Cells

FUT8(-) cell lines are electroporated with an expression vector encoding an bispecific antibody according to the invention and selected in media lacking hypoxanthine and thymidine. The confluent transfectants are cultured in Ex-Cell® 301 Medium (JRH Biosciences, Lenexa, Kans.) for 1 week. The antibody is purified from culture supernatants using MabSelect™ (Amersham Biosciences, Piscataway, N.J.). Further purification steps can be anion/cation exchange chromatography, size exclusion chromatography and especially purification using kappa respectively lambda selective resins as described above.

Example 13: In Vivo Antitumor Activity of Bispecific Antibodies

According to the knowledge of the inventors the antitumor activity of a bispecific antibody according to the invention can be evaluated in Xenograft models, e.g. by the following model: 1 or $2\times10^6$ CEA positive tumor cells like MKN-45 or LS174T cells are implanted subcutaneously in NOD/SCID mice. Tumor volumes are measured 3 times per week. After the tumor graft reached approx. 0.1 cm$^3$, mice are randomized into groups (e.g. 4 to 6 mice per group) and the antibody treatment is initiated. This experiment could e.g. compare the effect of the bispecific antibody according to the invention and positive control Mabs, e.g. the CD47 Mab B6H12.2 Antibody is injected e.g. i.v. every week until the end of the experiment (d25). Antibodies are administered at e.g. 50 to 1200 µg per mouse per injection. Combinations of a bispecific antibody of this invention with a CEAxCD3 bispecific antibody can be tested in an appropriate model. Models, in which the combination of an antibody according to the invention together with MAB CEA, MAB CEA1 or CEA-TCB CEA-TCB1 can be tested, are e.g. described by Bacac et al (Clin. Cancer Res., 22(13); 3286-97; 2016) and are also used, especially for combination studies of CEACAM5xCD47 and CEA-TCB or CEA-TCB1.

Example 14: Cytokine Release Tested in Whole Blood and PBMCs from Healthy Human Donors Human Blood According to the knowledge of the inventors an in vitro cytokine release assay can be performed using whole blood (WB CRA) with minimal dilution by the test antibodies (95% v/v blood) in aqueous presentation. This assay format is considered to mimic more closely the in vivo environment, containing factors at physiological concentrations that may influence mechanisms of cytokine release. However, this format is thought to be poorly predictive of T cell-mediated cytokine release (e.g., anti-CD28).

The assay can be also performed using peripheral blood mononuclear cells (PBMCs) from healthy human donors and with an immobilized mAb (Solid Phase, SP) presentation to assess T cell-mediated cytokine release (PBMC SP CRA). This assay format simulates cross-linking and high density presentation of mAbs, which may occur in vivo (e.g. clustering of the target via the interaction of the Fc part of the antibody with Fcγ receptors on other immune cells or the cross-linking of mAbs by anti-drug antibodies). This format is predictive of T cell-mediated cytokine release.

Figure 7A:
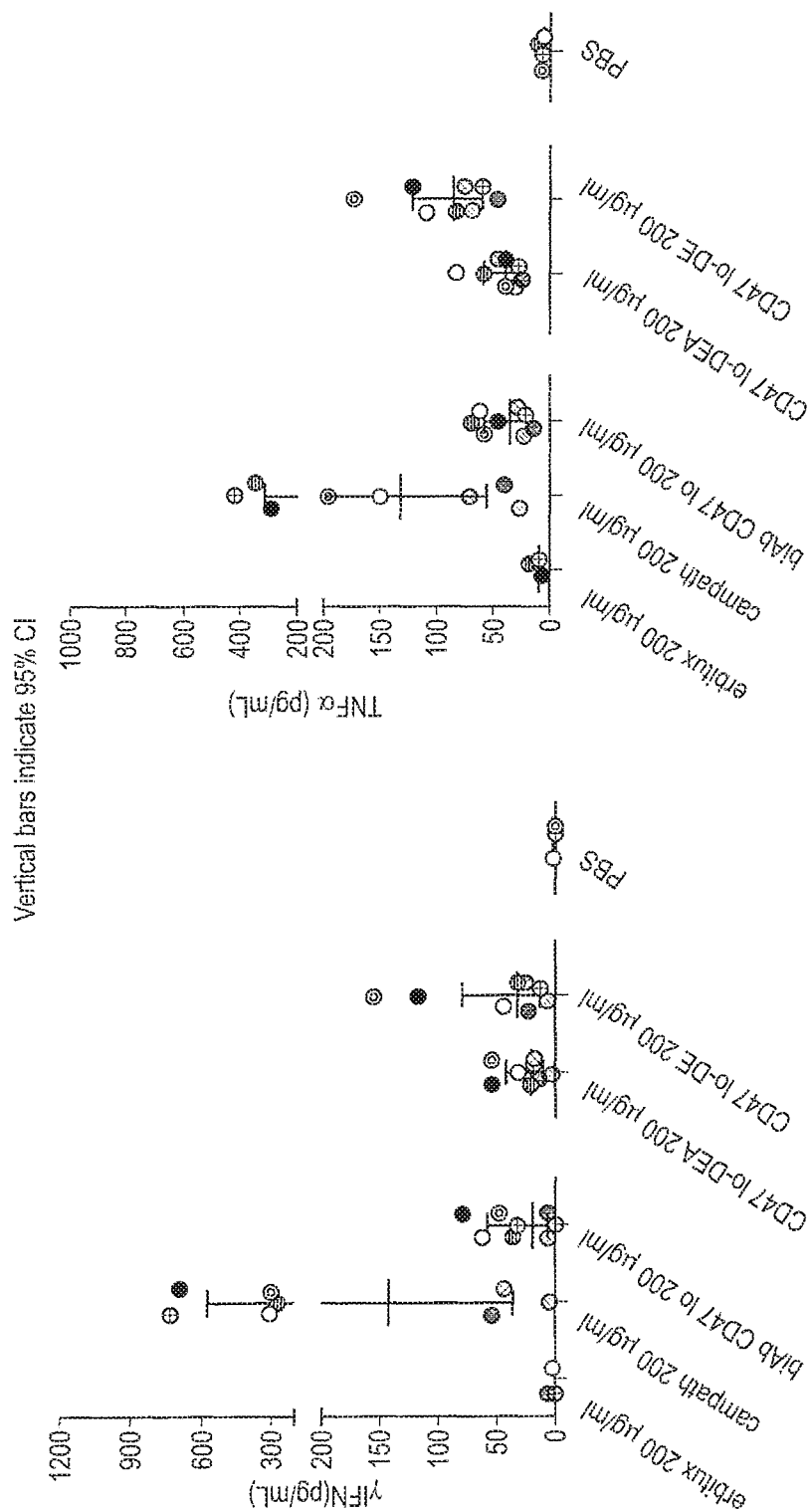
FIG. 7A shows the release of cytokines IFNγ and TNFα in whole human blood incubated with 200 µg/mL of the following antibodies: Erbitux as negative control, anti-CD52 antibody Campath as positive control, and three bispecific antibodies having identical antigen binding regions but different Fc regions (from left to right): wildtype human IgG1 Fc, IgG1 Fc with DEA mutations (S329D and I332E), IgG1 Fe with DE mutations. biAb CD4710 and CD4710 refers to the same CD47×TAA bispecific antibody. IFNγ and TNFα release observed with the bispecific antibody carrying DEA mutations is no higher than with the bispecific antibody with wildtype Fc.
Figure 7B:
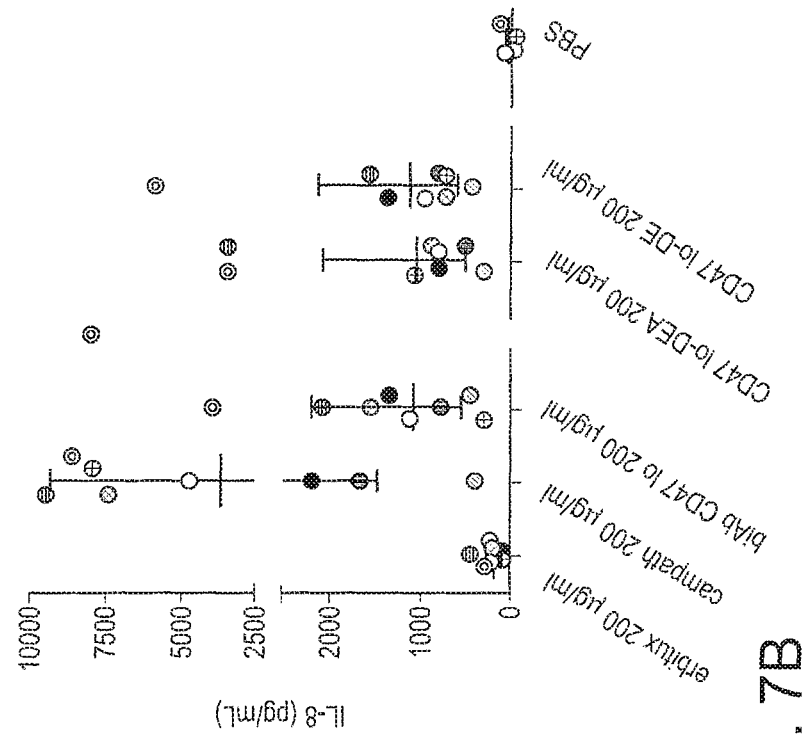
FIG. 7B shows the release of cytokines IL-6 and IL-8 in whole human blood incubated with 200 µg/mL of the following antibodies: Erbitux as negative control; anti-CD52 antibody Campath as positive control, and three bispecific antibodies having identical antigen binding regions but different Fc regions (from left to right): wildtype human IgG1 Fc, IgG1 Fc with DEA mutations, IgG1 Fc with DE mutations. biAb CD4710 and CD4710 refers to the same CD47×TAA bispecific antibody. IL-6 and IL-8 release observed with the bispecific antibodies carrying DE or DEA mutations is no higher than with the bispecific antibody with wildtype Fc.
Figure 7B:
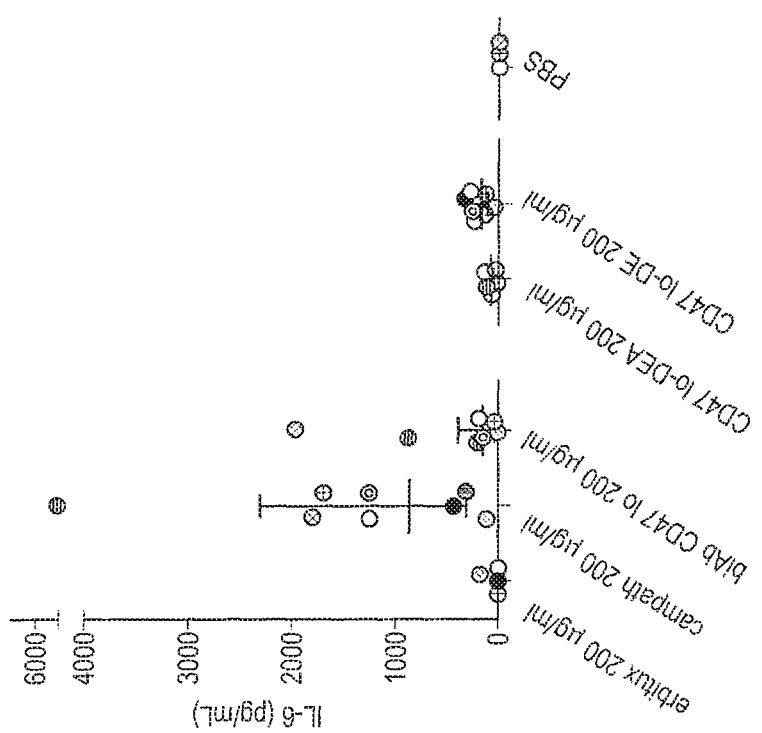

Negative controls as well as specific positive controls for each assay format can be tested in parallel to a TAAxCD47 antibody like a CD47xCEA bispecific antibody. see FIGS. 7A and B.

Example 15: Antibody Binding to Erythrocytes, Phagocytosis of Erythrocytes, and Platelet Activation and Aggregation Whole Blood Binding According to the knowledge of the inventors human whole blood samples collected from healthy donors in citrate can be mixed with 3 µg/mL of AF488-coupled CEA×CD47 bispecific antibodies of this invention, B6H12.2 or isotype control and surface staining antibodies (PE-Cy7 anti-hCD45 and PE anti-hCD41a, for platelets only) for 30 min at 4° C. After the incubation, whole blood is divided in two samples: 5 µL are diluted and washed in PBS for erythrocyte analysis while 150 µL are incubated with erythrocyte lysing solution and washed for platelet analysis. Samples are acquired on a CytoFLEX instrument and analyzed with the FlowJo software to determine MFI values.

Erythrophagocytosis

According to the knowledge of the inventors human red blood cells (RBCs) can be isolated from human whole blood by centrifugation at 300×g, washed twice in PBS, labeled with CFSE-(Carboxyfluorescein succinimidyl ester) and pre-incubated with the test antibody for 1 hour at 37° C. before the addition of macrophages. Labeled RBCs can be cultured with human macrophages in the presence of an antibody according to the invention or control (non-binding IgG1 antibody) for one hour at a target-to-effector ratio of 200:1. After culture, cells are stained with anti-CD14-APC and analyzed by flow cytometry. Phagocytosis was quantitated as the percent of CD14+ events (macrophages) that are also CFSE+ and had therefore engulfed at least one RBC (events are gated on singlets). Phagocytosis and FACS analysis is done as described in example 9, except that the erythrocytes were lysed with FACS lysing solution after macrophage staining.

Figure 8:
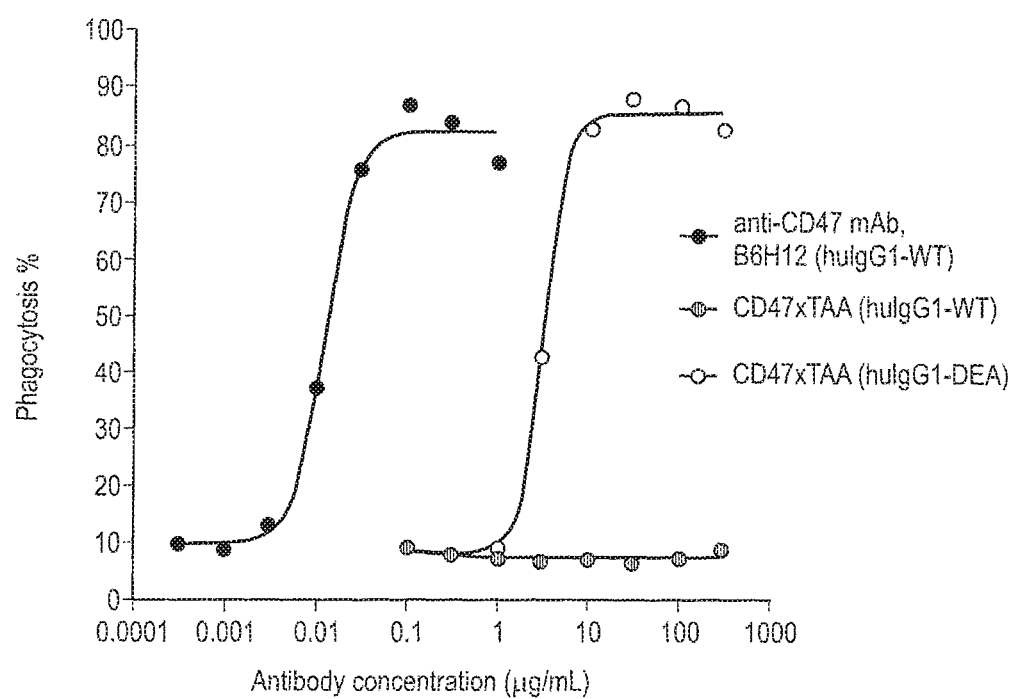
FIG. 8 shows concentration dependent phagocytosis of red blood cells (RBC), a major "antigen sink" for monoclonal anti-CD47 antibodies (every RBC expressing between 20'000 and 25'000 CD47 molecules on the cell surface) induced by various antibodies: the anti-CD47 huIgG1 antibody B6H12.12 with wildtype Fc, a CD47×TAA bispecific antibody with wildtype Fe and the same CD47×TAA bispecific antibody with Fc carrying DEA mutations. B6H12 shows RBC phagocytosis at concentrations of 10 to 100 ng/ml (approx. 0.07 to 0.7 nM) while a TAA×CD47 bispecific antibody with wildtype huIgG1 Fc shows no RBC phagocytosis at concentrations up to 200 000 ng/ml (approx. 1350 nM); The same bispecific antibody but with an Fc portion carrying DEA mutations shows increased phagocytosis of RBC as compared to wild-type Fc, at concentrations above 1000 ng/ml, (approx 7 nM), which is still 2-2.5 logs higher than with the anti CD47 huIgG1 antibody B6H12.

FIG. 8 shows that RBC phagocytosis for the IgG1 anti-CD47 monoclonal antibody B6H12.2 is much more potent than for an IgG1 TAA×CD47 (not CEA×CD47) κλ bispecific antibodies containing the CD47 binding arm of the CEA×CD47 bispecific antibodies of this invention. TAA×CD47 bispecific antibody with wildtype Fc showed no phagocytosis in the tested concentration range, if Fc carries the aa mutations DEA (S329D and I332E and G236A), phagocytosis is detected but at higher concentrations as for B6H12.2 antibody.

In Vitro Platelet Activation and Aggregation

In a standard flow cytometry experiment the ability of TAA×CD47 and CEA×CD47 bispecific antibodies to induce human platelet activation in whole blood of seven human healthy donors was measured by the upregulation of surface marker CD62P. Briefly, 5 µL of whole blood is incubated with 10 µL of each sample (prepared at 2×) for 15 minutes at room temperature. Each tested antibody is added at different concentrations (0, 0.02, 0.2, 2, 20 and 200 µg/mL). Adenosine diphosphate (ADP) and anti-CD9 (ALB6), included as positive control reagents known to induce platelet activation, are added at a concentration of 10 µM and 10 µg/mL, respectively. Then, 10 µL of anti-CD41a-PE and 10 µL of anti-CD62P-APC were added and incubated for 15 min. in the dark at room temperature. Finally, 500 µL of CellFix (BD Biosciences, diluted 1/10 in water) were added and 200 µL of each sample is transferred in a U-bottom 96-well plate suitable for CytoFLEX acquisition. Platelets are identified by the CD41a-PE positive staining. Platelet activation is assessed by the expression of CD62P marker.

Figure 10:
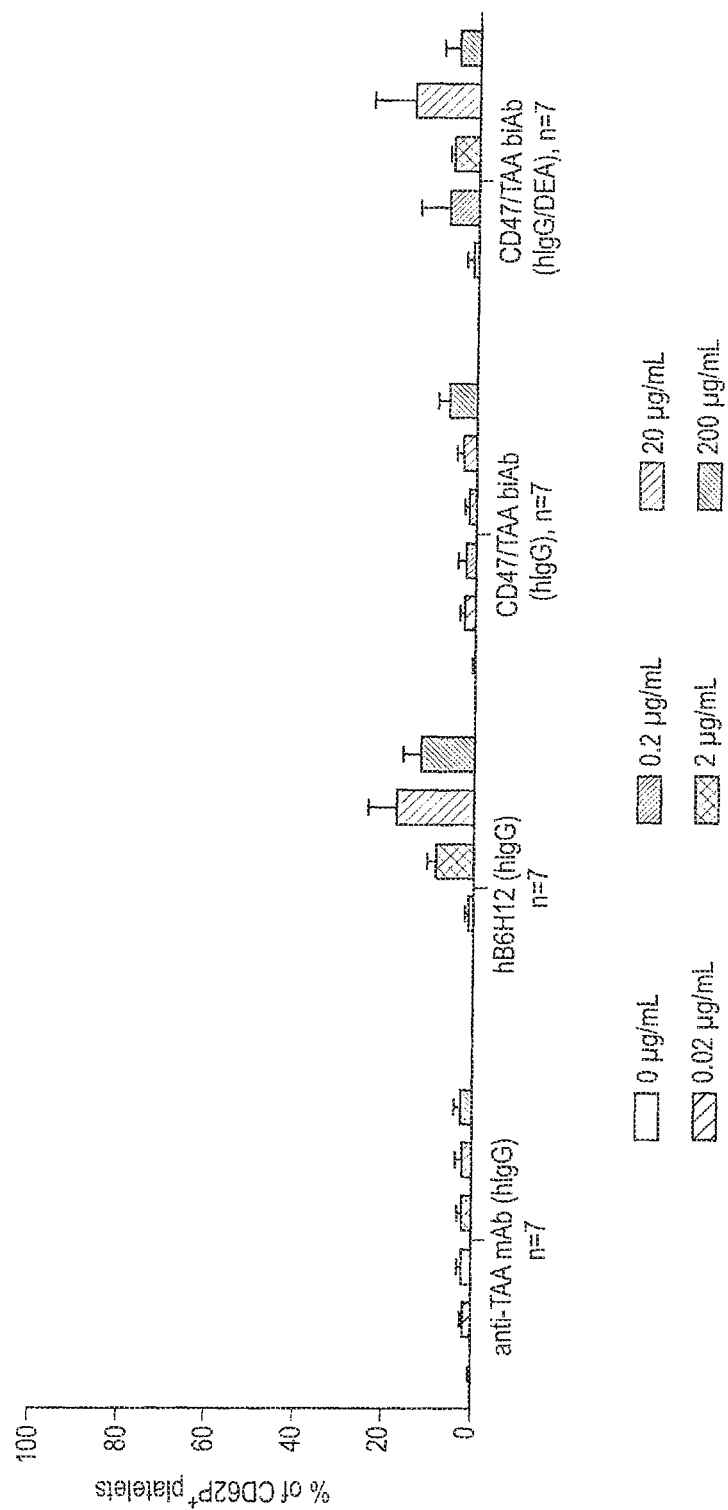
FIG. 10 shows in vitro platelet activation (assessed by flow cytometry and expressed as % CD62P expression), induced by incubation of human whole blood with antibodies as indicated at different concentrations (from 0 to 200 µg/mL). Contrary to B6H12-hIgG1 which induces platelet activation at 2 µg/ml and higher, the TAA×CD47 bispecific antibody with wild type IgG1 Fc doesn't induce platelet activation even at the highest concentration tested (200 µg/mL). The CEA×CD47 bispecific antibodies K2AC5 and K2AC22 were also tested, versions with wtIgG1 Fc as well as afucosylated versions did not show significant platelet activation up to 20 µg/mL (see example 15).

FIG. 10 shows results obtained in blood from seven volunteer donors. It was found that neither the anti-TAA monoclonal antibody nor the TAA×CD47 bispecific antibody induced relevant platelet activation (both with wt IgG1 Fc). In contrast the anti-CD47 antibody B6H12.2 with wt IgG1 Fc induced platelet activation and also the TAA×CD47 biAb with Fc carrying DEA mutations showed platelet activation.

Also the CEA×CD47 antibodies K2AC5 and K2AC22 (with and without afucosylation) have been studied in the concentration range as shown in FIG. 10 for platelet activation in whole blood. In the blood of 6 from 7 donors no significant platelet activation was seen, like shown for TAA×CD47 in FIG. 10. One donor showed already with positive control agents uncommon platelet activation and then also some platelet activation with K2AC5 and 22. Results of this one donor were disregarded due to uncommon platelet activation.

According to the knowledge of the inventors, the potential for aggregation in the presence of CD47/CEA bispecific antibody could be assessed on platelet rich plasma (PRP). PRP is challenged with ADP at 10 µM and 5 µM or with the test articles at 200, 100, 20, 25, and 12.5 µg/mL, as well as with saline or the isotype control. Platelet aggregation can be evaluated throughout platelet stimulation (i.e. 10 min) with a Thrombo-aggregometer TA 4V under constant stirring. Thrombosoft 1.6 software (SD Innovation, Frouard, France) can be used for analysis of the data.

Example 16: Hematology Assessment in Cynomolgus Examples

According to the knowledge of the inventors cynomolgus monkey cross-reactive antibodies could be tested in vivo in Cynomolgus Monkeys for any effect on hematology parameters (including RBC and platelets). An antibody according to the invention is e.g. given to cynomolgus monkeys per intravenous route, at doses up to 100 mg/kg, on a weekly basis. Hematology parameters, including red blood cell and platelet counts, are monitored over time and compared to control values in monkeys (pre-dose values). Hematology parameters are determined by routine methods.

Figure 9:
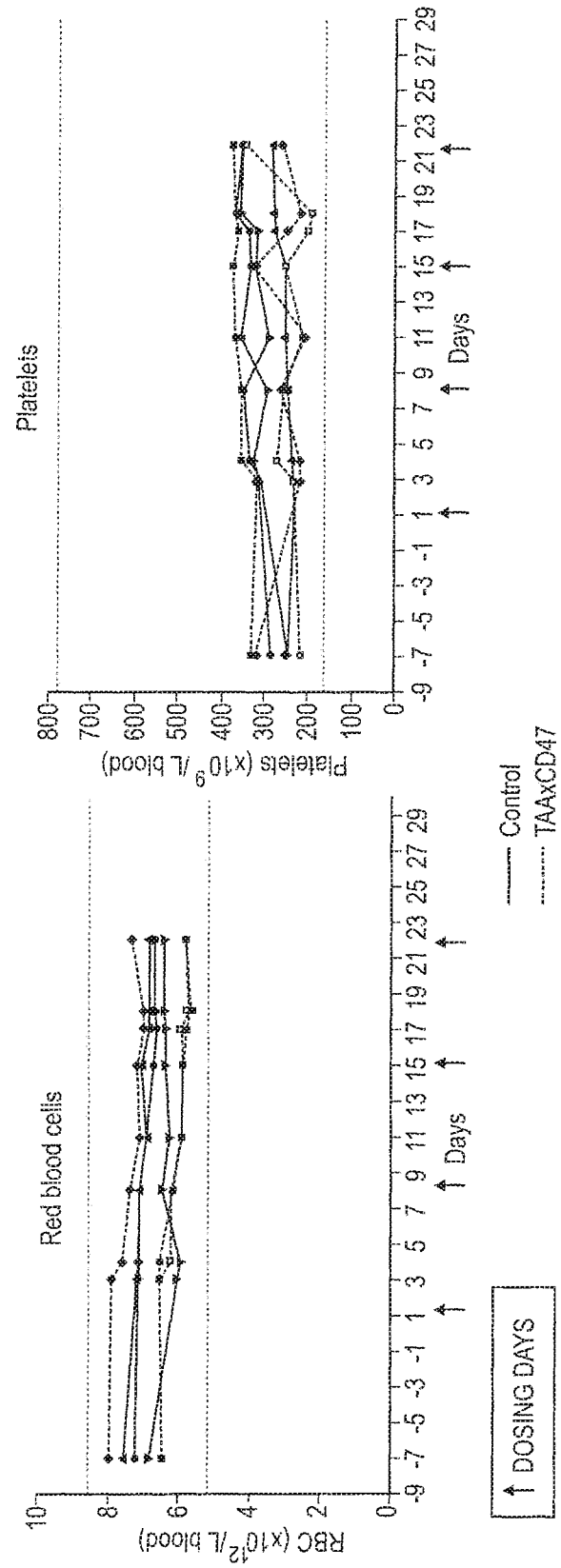
FIG. 9 shows red blood cell counts and platelet counts in Non Human Primate (NHP; cynomolgus monkeys) that received four weekly iv infusions of either control hIgG1 antibody or TAA×CD47 bispecific antibody (30 mg/kg for the first two weeks and 100 mg/kg for the last two weeks). No significant decrease in hematology counts was observed with the TAA×CD47 bispecific antibody in spite of high exposure (TAA×CD47 bispecific antibody plasma concentration at the end of the second dosing, at 30 mg/kg, was approx. 500 nM).

Results in FIG. 9 have been obtained with an IgG1 TAA×CD47 (not CEA×CD47) κλ bispecific antibody containing the CD47 binding arm of the CEA×CD47 bispecific antibodies according to this invention. Despite the repeated dosing with high doses there is no significant difference between control animals and treated animals regarding RBC counts and platelet counts. This is in contrast to published results with the IgG4 anti-CD47 antibody hu5F9-G4 (Jie Liu et al (Open access article, PLOS ONE 10(9) September 2015)) showing dose dependent decrease of hemoglobin starting already at single doses around 1 mg/kg. IgG4 format was used to minimize effects on red blood cells and platelets, compared to IgG1 format. Despite of this measure even at already rather low doses of 1 mg/kg and less, dose dependent reductions of e.g. hemoglobin are observed in cynomolgus monkeys.

Example 17: Determination of Pharmacokinetics Properties in Cynomolgus Monkeys According to the knowledge of the inventors in single dose pharmacokinetic studies, animals can be randomized to 2 to 5 treatment groups of n=2 to 4 monkeys per group (including males and females). Animals are administered with single IV doses of the bispecific antibodies of this invention (infusion over 15 to 30 minutes). Doses in the treatment groups are ranging from 0.01 mg/kg to 100 mg/kg. Administration volumes are up to 5 mL/kg. Blood withdrawals are scheduled according to the experimental protocol at multiple time points, e,g, 0.25, 1, 4, 8, 24, 48, 72, 96, 120, 168, 240, 336, 504 (day 22), 672 (day 29), 840 (day 36), 1008 (day 43), 1176 (day 50) and 1344 h (day 57) after the intravenous administration of the bispecific antibody. Blood samples of approximately 2 mL per animal and time-point are collected. Concentrations of the antibodies were either measured in serum or in plasma. An ELISA test is developed and validated to measure the concentrations. Each sample is measured in duplicates.

From the concentration time curves PK parameters like Cmax, clearance, elimination half-life, area under the curve etc. can be determined by using industry standard software (Phoenix WinNonlin; non-compartmental analysis).

Elimination half-lives of the CEA×CD47 kappa-lambda bispecific antibodies are expected to be in the range of 3 to 14 days, suggesting q1w or q2w or $q$3w or $q$4w administrations to patients.

Example 18: ADCP Mediated by Bispecific Antibodies in Presence of Shed CEA

MKN45 cells used as target cells are stained with calcein AM. In parallel, concentrations of tested antibodies are incubated or not with a fixed dose (200 ng/mL) of commercial shed CEA (BioRad). After this incubation the stained MKN-45 are opsonized for 20 minutes at room temperature with the antibodies previously mixed with shed CEA. Then macrophages (stained with calcein red orange) adhering to microplate wells are co-incubated with the opsonized labeled target tumor cells at an effector:target cells ratio of 1:3 for 2.5 hours at 37° C. The ADCP is performed in a presence of 1 mg/mL of human IgG. At the end of the incubation period, supernatants are replaced by complete culture medium and the microplates are imaged with the CellInsight™ CX5 High Content Screening Platform. 1500 macrophages are acquired and analyzed per well. Phagocytosis is evidenced as double-positive events (macrophage+engulfed target tumor cell) and the phagocytosis indexes are calculated by the CellInsight™ manufacturers' software. Results are shown in FIG. 20B.

Example 19: ADCP Mediated by Bispecific Antibodies in Presence of CEA-TCB and CEA-TCB1

Calcein AM-labeled MKN45 cells used as target cells are pre incubated or not with a fixed dose of CEA-TCB (300 nM) or CEA-TCB1 (30 nM) for 20 min at RT. After this incubation different concentrations of tested antibody are added in appropriate well for 20 min Then macrophages (stained with calcein red orange) adhering to microplate wells are co-incubated with the opsonized labeled target tumor cells at an effector:target cells ratio of 1:3 for 2.5 hours at 37° C. The ADCP is performed in a presence of 1 mg/mL of human hIgG. At the end of the incubation period, supernatants are replaced by complete culture medium and the microplates are imaged with the CellInsight™ CX5 High Content Screening Platform. 1500 macrophages are acquired and analyzed per well. Phagocytosis is evidenced as double-positive events (macrophage+engulfed target tumor cell) and the phagocytosis indexes are calculated by the CellInsight™ manufacturers' software.

FIG. 18 shows that neither CEA-TCB nor CEA-TCB1 added decreases phagocytosis induced by K2AC22. Surprisingly phagocytosis of K2AC22 was even slightly increased by the addition of 30 nM CEA-TCB1.

Example 20: Killing Assay by Combination of CD47×CEA and CEA×CD3

Human peripheral blood mononuclear cells (PBMCs) were isolated from buffy coats. Part of these PBMCs were frozen in freezing medium (90% FCS 10% DMSO) (in order to be used as source of T cells) and part were used to prepare macrophages (as explained in Phagocytosis section). After 6 days of macrophage differentiation, cells were plated in 96 well-plates and incubated at 37° C. On the day of the assay (2 days after macrophage plating), frozen PBMCs from the corresponding macrophage donor were thawed and added to the macrophage plates. Target cells (MKN45 engineered to express Luciferase) were opsonized with a combination of antibodies, i.e. with a CEA×CD3 T-cell bispecific antibody at certain concentrations together with certain concentrations of of a CEA×CD47 bispecific antibody. Opsonized targets were added to the plates containing macrophages and autologous PBMCs; and the plates were incubated at 37° C. for 48 h. After 48 h, half of the well medium was removed and a solution of 2× Luciferin was added to the plates to obtain a final concentration of 150 µg/mL. After 5 minutes incubation at RT, plates were read using a Synergy NEO. Percentage of viability was calculated dividing the luminescence value (minus background) by the control containing only target cells and multiplying by 100. Percentage of killing was then extrapolated by subtracting the percentage of viability to 100.

Figure 19A:
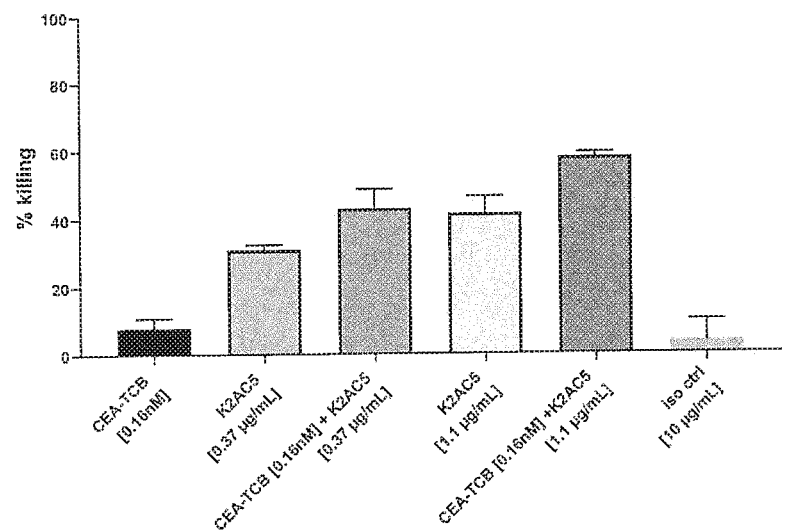
FIGS. 19A and 19B shows the killing (assessed by luminescence and expressed as % of killing) of MKN45 cancer cells in a mixed assay (with PBMCs and macrophages added, obtained from same human volunteer donor) by 2 selected CD47×CEA bispecific antibodies of the invention (K2AC5 (FIG. 19A) and K2AC22 (FIG. 19B) at two doses (i.e. 0.37 µg/mL or 1.1 µg/mL) alone, or in combination with CEA-TCB at 0.16 nM or 0.8 nM, and compared to the CEA-TCB alone or to an irrelevant hIgG1 control. (A) At least additive effect of the combination of the CEA×CD3 bispecific antibody CEA-TCB (SEQ ID NO:96 to 99) and the CEA×CD47 bispecific antibody K2AC5; (B) At least additive effects also for CEA-TCB+K2AC22.
Figure 19A:
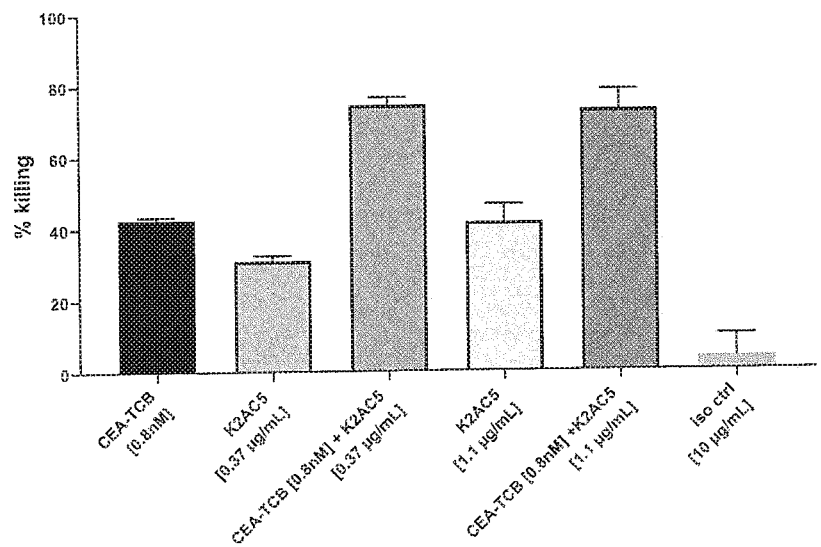
Figure 19B:
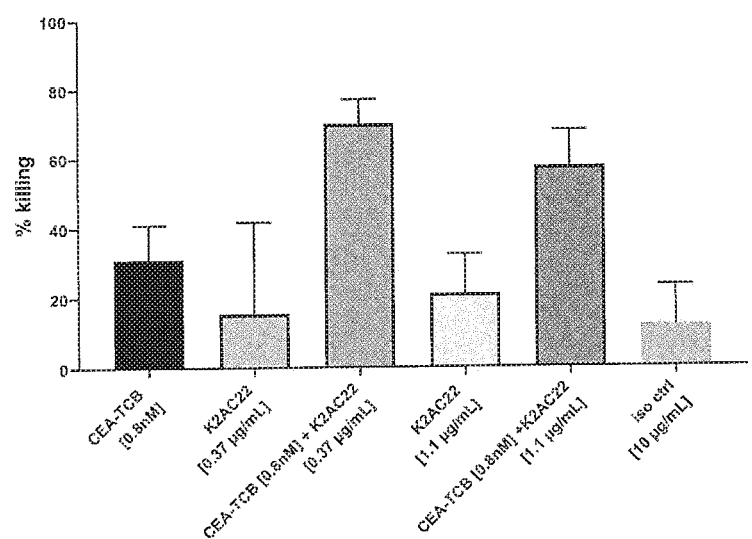

FIGS. 19A and B show results obtained with combinations of CEA-TCB and K2AC5 and K2AC22 at various concentrations.

All publications, patents, patent applications, internet sites, and accession numbers/database sequences including both polynucleotide and polypeptide sequences cited herein are hereby incorporated by reference herein in their entirety for all purposes to the same extent as if each individual publication, patent, patent application, internet site, or accession number/database sequence were specifically and individually indicated to be so incorporated by reference.

The invention claimed is:

1. A bispecific antibody comprising a first binding part specifically binding to human CEACAM5, and a second binding part specifically binding to human CD47, wherein
   a) the first binding part comprises a first heavy chain variable region comprising as CDRs a CDRH1 of SEQ ID NO: 25, a CDRH2 of SEQ ID NO: 26 and a CDRH3 of SEQ ID NO: 27 and a first light chain variable region comprising a combination of CDRL1, CDRL2 and CDRL3 selected from the group consisting of SEQ ID NOs: 31, 32 and 33; SEQ ID NOs: 34, 35, and 36; SEQ ID NOs: 37, 38, and 39; SEQ ID NOs: 40, 41, and 42; SEQ ID NOs: 43, 44, and 45; SEQ ID NOs: 46, 47, and 48; SEQ ID NOs: 49, 50, and 51; SEQ ID NOs: 52, 53, and 54; SEQ ID NOs: 55, 56, and 57; SEQ ID NOs: 58, 59, and 60; SEQ ID NOs: 61, 62, and 63; and SEQ ID NO: 112, 113, and 114; and
   b) the second binding part comprises a second heavy chain variable region comprising as CDRs a CDRH1 of SEQ ID NO: 25, CDRH2 of SEQ ID NO: 26 and CDRH3 of SEQ ID NO: 27 and a second light chain variable region comprising as CDRs a CDRL1 of SEQ ID NO: 28, CDRL2 of SEQ ID NO: 29, and CDRL3 of SEQ ID NO: 30.

2. The bispecific antibody of claim 1, wherein
   a) the first binding part comprises a heavy chain variable region (VH) of SEQ ID NO: 4 and a light chain variable region (VL) selected from the group of VLs included in the light chain sequences SEQ ID NOs: 64-74 and 115; and
   b) the second binding part comprises a heavy chain variable region of SEQ ID NO: 4 and a light chain variable region of SEQ ID NO: 10.

3. The bispecific antibody of claim 1, wherein the first binding part specific for CEACAM5 comprises a lambda light chain variable domain and a lambda light chain constant domain and wherein the binding part specific for CD47 comprises a kappa light chain variable domain and a kappa light chain constant domain or wherein the first binding part specifically binding to CEACAM5 comprises a kappa light chain variable domain and a lambda light chain constant domain and wherein the second binding part specifically binding to CD47 comprises a kappa light chain variable domain and a kappa light chain constant domain.

4. The bispecific antibody of claim 1, wherein each binding part of the bispecific antibody comprises a common heavy chain (cHC).

5. The bispecific antibody of claim 1, wherein the EC50 for the phagocytosis index curve of MKN-45 cells of the bispecific antibody in the presence of human macrophages, as measured by imaging, with an E:T ratio of 1:3 human macrophages:target tumor cells, is not shifted by more than a factor of 4 towards higher concentrations in the presence of 200 ng/ml soluble CEACAM5 compared to the EC50 measured without soluble CEACAM5 and/or that the maximum of the phagocytosis index curve is not reduced by 20% or more by addition of 200 ng/mL CEACAM5.

6. The bispecific antibody of claim 5, wherein the EC50 for the binding curve to MKN-45 cells of the bispecific antibody is not shifted by more than a factor of 2 towards higher concentrations in the presence of 200 ng/ml soluble CEACAM5 compared to the EC50 measured without soluble CEACAM5.

7. The bispecific antibody of claim 1, wherein the antibody does not cross-react with human CEACAM1.

8. The bispecific antibody of claim 1, wherein the bispecific antibody binds to human CEACAM6 expressed on recombinant CHO cells CHO-K1 with an EC50 of 1 to 50 nM.

9. The bispecific antibody of claim 1, wherein the bispecific antibody inhibits the interaction between CD47 and signal-regulatory protein alpha (SIRPα; CD172a; UniProtKB P78324) on MKN-45 cells with an IC50 of 0.1 to 10 nM.

10. The bispecific antibody of claim 1, wherein the bispecific antibody has a Fc region that has been modified to have a reduced number of fucose residues in N-linked oligosaccharides as compared to the bispecific antibody that has not been modified.

11. The bispecific antibody of claim 10, wherein 50% to 100% of the N-linked oligosaccharides are nonfucosylated.

12. A pharmaceutical composition comprising a bispecific antibody of claim 1 and a pharmaceutically acceptable excipient or carrier.

13. A method of treating a CEACAM5-expressing cancer, comprising administering the bispecific antibody of any of claims 1-11 to a patient in need thereof.

14. The method of claim 13, wherein the EC50 of the phagocytosis index curve of the bispecific antibody in the presence of 1 mg/mL human IgG is in the range of 0.1 to 3 times the EC50 of reference antibody K2AC22 under the same experimental conditions.

15. The method of claim 13, wherein the cancer is a colorectal cancer, NSCLC (non-small cell lung cancer), gastric cancer, pancreatic cancer, breast cancer, or another cancer comprising tumor cells that express CEACAM5.

16. The method of claim 13, wherein the bispecific antibody is administered in simultaneous, separate, or sequential combination with a second bispecific antibody comprising a first binding part specifically binding to human CEACAM5, and a second binding part specifically binding to human CD3F in the treatment of the patient having said CEACAM5-expressing cancer.

17. The method of claim 13, wherein the bispecific antibody is administered in simultaneous, separate, or sequential combination with CEA-TCB and/or CEA-TCB1.

18. A method of inducing cell lysis of a CEACAM5-expressing tumor cell comprising contacting the tumor cell with the bispecific antibody of any of claims 1-11.

19. The method of claim 18, wherein the tumor cell is in a patient.

20. A polynucleotide encoding the bispecific antibody of any of claims 1-11.

21. An expression vector comprising the polynucleotide of claim 20.

22. A host cell comprising the polynucleotide of claim 20 or the vector of claim 21.

23. A method for the production of a bispecific antibody, comprising:
   a) culturing a host cell comprising the expression vector of claim 21 under conditions which permit the production of the encoded bispecific antibody; and
   b) isolating the bispecific antibody.

* * * * *